United States Patent
Fuchss et al.

(10) Patent No.: US 10,383,874 B2
(45) Date of Patent: *Aug. 20, 2019

(54) ARYLQUINAZOLINES

(71) Applicant: Merck Patent GmbH, Darmstadt (DE)

(72) Inventors: Thomas Fuchss, Bensheim-Auerbach (DE); Ulrich Emde, Darmstadt (DE); Hans-Peter Buchstaller, Griesheim (DE); Werner Mederski, Zwingenberg (DE)

(73) Assignee: Merk Patent GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/189,113

(22) Filed: Nov. 13, 2018

(65) Prior Publication Data

US 2019/0142833 A1 May 16, 2019

Related U.S. Application Data

(60) Continuation of application No. 15/633,064, filed on Jun. 26, 2017, now Pat. No. 10,172,859, which is a division of application No. 14/890,214, filed as application No. PCT/EP2014/001236 on May 8, 2014, now Pat. No. 9,732,094.

(30) Foreign Application Priority Data

May 11, 2013 (DE) .................. 10 2013 008 118

(51) Int. Cl.
| | | |
|---|---|---|
| *C07D 237/14* | (2006.01) | |
| *C07D 239/72* | (2006.01) | |
| *C07D 239/74* | (2006.01) | |
| *C07D 265/30* | (2006.01) | |
| *C07D 285/01* | (2006.01) | |
| *C07D 401/10* | (2006.01) | |
| *C07D 403/10* | (2006.01) | |
| *C07D 403/14* | (2006.01) | |
| *C07D 405/14* | (2006.01) | |
| *C07D 417/10* | (2006.01) | |
| *C07D 471/04* | (2006.01) | |
| *C07D 473/00* | (2006.01) | |
| *C07D 487/04* | (2006.01) | |
| *C07D 491/048* | (2006.01) | |
| *C07D 495/04* | (2006.01) | |
| *C07D 498/08* | (2006.01) | |
| *C07D 513/04* | (2006.01) | |
| *A61K 31/519* | (2006.01) | |
| *C07C 25/02* | (2006.01) | |
| *A61K 31/5377* | (2006.01) | |
| *A61K 31/5386* | (2006.01) | |
| *A61K 45/06* | (2006.01) | |
| *C07D 417/14* | (2006.01) | |
| *C07D 405/04* | (2006.01) | |

(52) U.S. Cl.
CPC ........ *A61K 31/519* (2013.01); *A61K 31/5377* (2013.01); *A61K 31/5386* (2013.01); *A61K 45/06* (2013.01); *C07C 25/02* (2013.01); *C07D 237/14* (2013.01); *C07D 239/72* (2013.01); *C07D 239/74* (2013.01); *C07D 265/30* (2013.01); *C07D 285/01* (2013.01); *C07D 401/10* (2013.01); *C07D 403/10* (2013.01); *C07D 403/14* (2013.01); *C07D 405/04* (2013.01); *C07D 405/14* (2013.01); *C07D 417/10* (2013.01); *C07D 417/14* (2013.01); *C07D 471/04* (2013.01); *C07D 473/00* (2013.01); *C07D 487/04* (2013.01); *C07D 491/048* (2013.01); *C07D 495/04* (2013.01); *C07D 498/08* (2013.01); *C07D 513/04* (2013.01)

(58) Field of Classification Search
CPC .. C07D 237/14; C07D 239/72; C07D 239/74; C07D 265/30; C07D 285/01; C07D 401/10; C07D 403/10; C07D 403/14; C07D 405/14; C07D 417/10; C07D 417/14; C07D 471/04; C07D 473/00; C07D 487/04; C07D 491/048; C07D 495/04; C07D 498/08; C07D 513/04
See application file for complete search history.

(56) References Cited

U.S. PATENT DOCUMENTS

| | | |
|---|---|---|
| 9,126,952 B2 | 9/2015 | Mederski et al. |
| 2012/0184572 A1 | 7/2012 | Song et al. |
| 2013/0012489 A1 | 1/2013 | Mederski et al. |

FOREIGN PATENT DOCUMENTS

| | | |
|---|---|---|
| WO | WO-1992007844 A1 | 5/1992 |
| WO | WO-2000061186 A1 | 10/2000 |
| WO | WO-2005113560 A2 | 12/2005 |
| WO | WO-2006046031 A1 | 5/2006 |
| WO | WO-2010008739 A2 | 1/2010 |
| WO | WO-2010048149 A2 | 4/2010 |

(Continued)

OTHER PUBLICATIONS

Alessi et al., "Molecular basis for the substrate specificity of protein kinase B; compassion with MAPLAP kinase-1 and p70 S6 kinase," Federation of European Biochemical Societies Letter, vol. 399, no Month Listed 1996 (pp. 333-338).

(Continued)

*Primary Examiner* — Rebecca L Anderson
(74) *Attorney, Agent, or Firm* — Andrea L. C. Reid; Dechert LLP

(57) ABSTRACT

The invention relates to novel compounds of the formula (I) which can be used for the inhibition of serine-threonine protein kinases and for the sensitization of cancer cells to anticancer agents and/or ionizing radiation.

9 Claims, No Drawings

(56) References Cited

FOREIGN PATENT DOCUMENTS

| WO | WO-2010075273 A1 | 7/2010 |
|----|----|----|
| WO | WO-2010107768 A1 | 9/2010 |
| WO | WO-2011113512 A1 | 9/2011 |
| WO | WO-2012016133 A2 | 2/2012 |
| WO | WO-2012019315 A1 | 2/2012 |
| WO | WO-2013178816 A1 | 12/2013 |
| WO | WO-2014039714 A2 | 3/2014 |
| WO | WO-2014183850 A1 | 11/2014 |
| WO | WO-2015011284 A2 | 1/2015 |
| WO | WO-2013072015 A1 | 5/2015 |

OTHER PUBLICATIONS

Bhide et al., "Recent Advances in Radiotherapy," BMC Medicine, vol. 8, No. 25, No Month Listed 2010 (5 pages).
Campos-González et al., "Tyrosine Phosphorylation of Mitogen-activated Protein Kinase in Cells with Tyrosine Kinase-negative Epidermal Growth Factor Receptors," The Journal of Biological Chemistry, vol. 267, No. 21, Jul. 25, 1992 (pp. 14535-14538).
Choi et al., "Technological Advances in Radiation Therapy for Prostate Cancer," Current Urology Reports, vol. 11, No Month Listed 2010 (pp. 172-179).
Damstrup, "M3814, a DNA-dependent protein kinase inhibitor (DNA-PKi), potentiates the effect of ionizing radiation in xenotransplanted tumors in nude mice," Poster, Multidisciplinary Head and Neck Center Symposium, Feb. 18-20, 2016, No. 280, Abstract (1 page).
Daniel et al., "A Role for DNA-PK in Retroviral DNS Integration," Science, vol. 284, No. 5414, Apr. 23, 1999 (pp. 644-647).
Davies et al., "Specificity and mechanism of action and some commonly used protein kinase inhibitors," Biochemical Journal, vol. 351, no Month Listed 2000 (pp. 95-105).
Ebert et al., "Therapeutic effects of DNA-Proteinkinase—Inhibitor in combination with irradiation," Presentation, DEGRO, No Month Listed 2018 (10 pages).
Ebert et al., "Therapeutischer Effekte einer kombinierten Strahlentherapie und DNA-Proteinkinase-Inhibitor," Presentation, DEGRO, No Month Listed 2017 (11 pages).
Ebert et al., "Therapeutischer Effekte einer kombinierten Strahlentherapie und DNA-Proteinkinase-Inhibitor," Presentation, DEGRO, Strahlenther Onkol, vol. 193, Supplemental S1-S194, No Month Listed 2017 (11 pages).
Fuchss et al., "Highly potent and selective DNA-PK inhibitor M3814 with sustainable anti-tumor activity in combination with radiotherapy," American Association for Cancer Research, vol. 58, Supplemental No. 13, Abstract #4198, Apr. 2017 (1 page).
Fuchss, "DNA-PK Inhibitor M3814: DNA Repair Inhibition in Cancer Therapy," EFMC-ASMC 2017, EFMC International Symposium on Advances in Synthetic and Medicinal Chemistry, Vienna, Austria, Aug. 27-31, 2017 (28 pages).
Fuchss, "DNA-PK Inhibitor M3814; Highly Potent and Selective DNA-PK Inhibitor M3814 with Sustainable Anti-Tumour Activity in Combination with Radiotherapy," SMR—The Society for Medicines Research, London, Jan. 2016 (22 pages).
Fuchss, "Highly Potent and Selective DNA-PK Inhibitor M3814 with Sustainable Anti-Tumour Activity in Combination with Radiotherapy," AACR—American Association for Cancer Research Annual Meeting, Washington, D.C., Apr. 1-5, 2017 (Abstract No. 4198).
Fuchss, "Highly Potent and Selective DNA-PK Inhibitor M3814 with Sustainable Anti-Tumour Activity in Combination with Radiotherapy," AACR—American Association for Cancer Research Annual Meeting, Washington, D.C., Apr. 1-5, 2017 (abstract).
Goytisolo et al., "The absence of the DNA-Dependent Protein Kinase Catalytic Subunit in Mice Results in Anaphase Bridges and in Increased Telomeric Fusions with Normal Telomere Length and G-Strand Overhang," Molecular and Cellular Biology, vol. 21, No. 11, Jun. 2011 (pp. 3642-3651).
Guo et al., "Pharmacological DNA-PK Inhibition Induces ATM/p53 Dependent Premature Senescence with Immunomodulatory Phenotype in Irradiated Cancer Cells," AACR—American Association for Cancer Research Annual Meeting, Chicago, Illinois, Apr. 14-18, 2018 (1 page).
Haines et al., "Selective DNA-PK inhibitor, M3814, boosts p53 apoptotic response to DNA double-strand breaks and effectively kills acute leukemia cells: implications for acute myeloid leukemia therapy," Poster, Annual AACR Meeting, Chicago, Illinois, No Month Listed 2018 (1 page).
Hardcastle et al., "Discovery of Potent Chromen-4-one Inhibitors of the DNA-Dependent Protein Kinase (DNA-PK) Using a Small-Molecular Library Approach," Journal of Medicinal Chemistry, vol. 48, No. 24, Oct. 2005 (pp. 7829-7846).
Hartley et al., "DNA-Dependent Protein Kinase Catalytic Subunit: A Relative of Phosphatidylinositol 3-Kinase and the Ataxia Telangiectasis Gene Product," Cell, vol. 82, Sep. 8, 1995 (pp. 849-856).
Hermann et al., "Klinische Strahlenbiologic [Clinical Radiation Biology]," Elsevier Munich, $4^{th}$ Edition, No Month Listed 2006 (pp. 67-68).
International Search Report issued by the European Patent Office as International Searching Authority for International Patent Application No. PCT/EP2014/001236 dated Jul. 7, 2014 (2 pages).
Izzard et al., "Competitive and Noncompetitive Inhibition of the DNA-dependent Protein Kinase," Cancer Research, vol. 59, Jun. 1, 1999 (pp. 2581-2586).
Kashishian et al., "DNA-dependent protein kinase inhibitors as drug candidates for the treatment of cancer," Molecular Cancer Therapeutics, vol. 2, No. 12, No Month Listed 2003 (pp. 1257-1264).
Khwaja et al., "Matric adhesion and Ras transformation bother activate a phosphoinositide 3-OH kinase and protein kinase B/Akt cellular survival pathway," The EMBO Journal, vol. 16, No. 10, No Month Listed 1997 (pp. 2783-2793).
Klein et al., "Overcoming hypoxia-induced tumor radioresistance in non-small cell lung cancer by targeting DNA-dependent protein kinase in combination with carbon ion irradiation," Radiation Oncology, vol. 12, No. 208, Dec. 2017 (8 pages).
Lempiäinen et al., "Emerging common themes in regulation of PIKKs and PI3Ks," The EMBO Journal, vol. 28, No. 20, No Month Listed 2009 (pp. 3067-3073).
Mardin, "From DNA replication to repair: Novel strategies for synthetic lethality," Abstract, Presented at CRUK, No Month Listed 2018 (1 page).
Mardin, "From DNA replication to repair: Novel strategies for synthetic lethality," Presentation, Manchester CRUK, Jun. 2018 (17 pages).
Massimini et al., "DNA damage response pathway inhibition—a pipeline and the phase I experience," Abstract, WIN Consortium Symposium, Paris, France, Jun. 26, 2017 (3 pages).
Massimini et al., "DNA damage response pathway inhibition—a pipeline and the phase I experience," Presentation, WIN Consortium Symposium, Paris, France, Jun. 26, 2017 (32 pages).
Roidos et al., "Colour Assay Tracing Repair (CAT-R) to study DNA double strand break repair," Presentation, GRC, No Month Listed 2018 (1 page).
Rosenzweig et al., "Radiosensitization of Human Tumor Cells by the Phosphatidylinositol 3-Kinase Inhibitors Wortmannin and LY294002 Correlates with Inhibition of DNA-dependent Protein Kinase and Prolonged G2-M Delay," Clinical Cancer Research, vol. 3, Jul. 1997 (pp. 1149-1156).
Sills et al., "Comparison of Assay Technologies for a Tyrosine Kinase Assay Generates Different Results in High Throughput Screening," Journal of Biomolecular Screening, vol. 7, No. 3, No Month Listed 2002 (pp. 194-214).
Sirrenberg et al., "A novel selective DNA-PK inhibitor, M3814, as a potential combination partner of Etoposide and Cisplatin in the therapy of lung cancer," American Association for Cancer Research, vol. 58, Supplemental No. 13, Abstract #4138, Apr. 2017 (1 page).
Smith et al., "The DNA-dependent protein kinase," Genes and Development, vol. 13, No Month Listed 1999 (pp. 916-934).
Sorg et al., "Automated High Throughput Screening for Serine Kinase Inhibitors Using a LEADSeeker™ Scintillation Proximity

(56) References Cited

OTHER PUBLICATIONS

Assay in the 1536-Well Format," Journal of Biomolecular Screening, vol. 7, No. 1, No Month Listed 2002 (pp. 11-19).
Sun et al., "TP53 Status Determines the Fate of Cancer Cells Exposed to Ionizing Radiation and DNA-PK Inhibitor, M3814," AACR—American Association for Cancer Research Annual Meeting, Chicago, Illinois, Apr. 14-18, 2018 (1 page).
Van Bussel et al., "A Multicenter Phase I Trial of the DNA-Dependent Protein Kinase (DNA-PK) Inhibitor M3814 in Patients with Solid Tumors," Abstract, 53rd ASCO Annual Meeting, Chicago, Illinois, Jun. 2017 (1 page).
Van Triest et al., "A phase Ia/Ib trial of the DNA-dependent protein kinase inhibitor (DNA-PKi) M3814 in combination with radiotherapy in patients with advanced solid tumors," Abstract, 53rd ASCO Annual Meeting, Chicago, Illinois, Jun. 2017 (1 page).
Van Triest et al., "A phase Ia/Ib trial of the DNA-PK inhibitor M3814 in combination with radiotherapy (RT) in patients (pts) with advanced solid tumors: dose-escalation results," Abstract, 54th ASCO Annual Meeting, Chicago, Illinois, Jun. 2018 (2 pages).
Vassilev, "Pharmacological Intervention in p53 Regulation by Inhibitors of MDM2 and ATM," AACR—American Association for Cancer Research Annual Meeting, Miami, Florida, May 16-19, 2016 (40 pages).
White et al., "Mammary epithelial-specific expression of the integrin-linked kinase (ILK) results in the induction of mammary gland hyperplasias and tumors in transgenic mice," Oncogene, vol. 20, No Month Listed 2001 (pp. 7064-7072).
Williams et al., "Telomere Dysfunction and DNA-PKcs Deficiency: Characterization and Consequence," Cancer Research, vol. 69, No. 5, Mar. 1, 2009 (pp. 2100-2107).
Yoshida et al., "Study of biodegradable copoly(1-lactic acid/glycolic acid) formulations with controlled release of Z-100 for application in radiation therapy," International Journal of Pharmaceutics, vol. 115, No Month Listed 1995 (pp. 61-67).
Zenke et al., "M3814, a novel investigational DNA-PK inhibitor enhancing the effect of fractionated radiotherapy leading to complete regression of tumors in mice," Poster, Presented at American Association of Cancer Research, New Orleans, Louisiana, Apr. 16-20, 2016 (1 page).
Zenke, "DNA-PK Inhibitor M3814," International Congress on Targeted Anticancer Therapies, Jun. 2018 (18 pages).
Zenke, "Overview on DDR Projects at Merck," Minisymposium DNA-Damage & Repair UCT Mainz, Oct. 2017 (22 pages).

ARYLQUINAZOLINES

The present application is a continuation of U.S. application Ser. No. 15/633,064, filed Jun. 26, 2017, now U.S. Pat. No. 10,172,859, which is a divisional of U.S. application Ser. No. 14/890,214, filed Nov. 10, 2015, now U.S. Pat. No. 9,732,094, which is a continuation of international PCT Application, PCT/EP2014/001236, filed May 8, 2014, which claims priority to DE Application No. 102013008118.1, filed on May 11, 2013.

The invention relates to compounds of the formula (I)

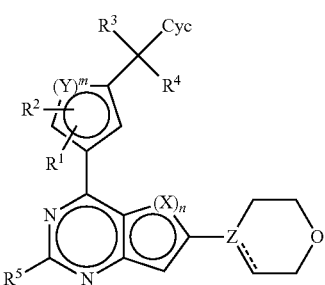

in which
X is CH, CF, S or N,
Y is CH, S or N,
Z is C or N,
- - - - forms, if Z=C, a double bond together with the single bond,
  is absent if Z=N,
n is 1 or 2, where
  if n=1, X=S,
  and if n=2, both X=CH, or the X linked to the pyrimidine ring is CF and the X not linked to the pyrimidine ring is CH, or one X is CH and the other X is N;
m is 1 or 2, where
  if m=1, Y=S,
  and if m=2, both Y=CH, or one Y is CH and the other Y is N;
$R^1$, $R^2$, $R^3$, $R^4$, independently of one another, are H, Hal, CN, OH, $CONH_2$, CONH(LA) or LA;
$R^5$ is H, Hal, CN or C≡CH;
Cyc is phenyl, which may be unsubstituted or mono- or disubstituted, independently of one another, by $R^6$, or is $Het^1$;
$Het^1$ is a mono- or bicyclic, 5-10-membered heterocycle, having 1-3 N, O and/or S atoms, or 1-4 N atoms, which may be unsubstituted or mono-, di- or trisubstituted, independently of one another, by $R^6$, or may be monosubstituted by $Het^2$;
$R^6$ is Hal, LA, oxo, CN, or $NH_2$;
LA is unbranched or branched alkyl having 1-5 C atoms, which may be saturated or partially unsaturated, in which 1-3 H atoms may be replaced by Hal, and/or one H atom may be replaced by CN or $Het^2$, and/or one or two $CH_2$ groups may be replaced by O, NH, $NH_2$, $N(CH_3)$ or CO;
$Het^2$ is a 3-5-membered aliphatic homo- or heterocycle having 0, 1, 2 or 3 N, O and/or S atoms, which is unsubstituted;
Hal is F, Cl, Br or I;
and/or physiologically acceptable salts, tautomers and/or stereoisomers thereof, including mixtures thereof in all ratios.

The compounds of the formula (I) can be used for the inhibition of serine/threonine protein kinases and for the sensitisation of cancer cells to anticancer agents and/or ionising radiation. The invention also relates to the use of the compounds of the formula (I) in the prophylaxis, therapy or progress control of cancer, tumours or metastases, in combination with radiotherapy and/or an anticancer agent. The invention furthermore relates to a process for the preparation of the compounds of the formula (I) by reaction of compounds of the formulae (IV) and (V) and optionally conversion of a base or acid of the compounds of the formula (I) into a salt thereof.

DNA-dependent protein kinase (DNA-PK) is a serine/threonine protein kinase which is activated in conjunction with DNA. Biochemical and genetic data show that DNA-PK consists (a) of a catalytic sub-unit, which is called DNA-PKcs, and (b) two regulatory components (Ku70 and Ku80). In functional terms, DNA-PK is a crucial constituent on the one hand of the repair of DNA double-strand breaks (DSBs) and on the other hand of somatic or V(D)J recombination. In addition, DNA-PK and its components are connected with a multiplicity of further physiological processes, including modulation of the chromatin structure and telomeric maintenance (Smith & Jackson (1999) Genes and Dev 13: 916; Goytisolo et al. (2001) Mol. Cell. Biol. 21: 3642; Williams et al. (2009) Cancer Res. 69: 2100).

Human genetic material in the form of DNA is constantly subjected to attack by reactive oxygen species (ROSs), which are formed principally as by-products of oxidative metabolism. ROSs are capable of causing DNA damage in the form of single-strand breaks. Double-strand breaks can arise if prior single-strand breaks occur in close proximity. In addition, single- and double-strand breaks may be caused if the DNA replication fork encounters damaged base patterns. Furthermore, exogenous influences, such as ionising radiation (for example gamma or particle radiation), and certain anticancer medicaments (for example bleomycin) are capable of causing DNA double-strand breaks. DSBs may furthermore occur as intermediates of somatic recombination, a process which is important for the formation of a functional immune system of all vertebrates. If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining, in which the DNA-dependent protein kinase adopts the key role. Biochemical investigations have shown that DNA-PK is activated most effectively by the occurrence of DNA-DSBs. Cell lines whose DNA-PK components have mutated and are non-functional prove to be radiation-sensitive (Smith and Jackson, 1999).

Owing to its catalytic domain, which is in the C-terminal catalytic sub-unit (DNA-PKcs), which numbers about 500 amino acids, DNA-PK belongs to the family of phosphatidylinositol-3-kinase-related kinases (PIKKs), where DNA-PK is not a lipid kinase (Hartley et al. (1995) Cell 82: 849; Smith & Jackson (1999) Genes and Dev 13: 916; Lempiäinen & Halazonetis (2009) EMBO J. 28: 3067).

It has been described by Izzard et al. (1999) Cancer Res. 59: 2581, that the PI3 kinase inhibitor LY294002 inhibits the function of DNA-PK in in-vitro experiments. The $IC_{50}$ value (concentration at which 50% of the enzyme activity is inhibited) is at a relatively ineffective 1.25 µM (5.0 mM ATP). Although the evidence that the inhibitor LY294002 allows mammal cells to become more radiation-sensitive, i.e. the cytotoxicity of ionising radiation is increased, in principle implies use in the irradiation therapy of, for example, solid cancer tumours, only a weak increase in sensitivity to ionising irradiation has been demonstrated for LY294002 in cellular terms (Rosenzweig et al. (1999) Clin. Cancer Res. 3: 1149). KuDOS Pharmaceuticals Ltd. have optimised the lead structure LY294002 and presented various DNA-PK inhibitors. The introduction of a dibenzothiophenyl group led to the inhibitor NU-7441, an ATP-competitive compound having an $IC_{50}$ value of 20.0 nM (Hardcastle et al. (2005) J. Med. Chem. 48: 7829). KU-0060648 combines inhibitory properties with respect to DNA-PK with an improved solubility profile in aqueous medium, but the kinases of the PI3K isoenzyme family are likewise potently inhibited by KU-0060648. The long-existing need for a potent and selective DNA-PK inhibitor has consequently not been satisfied to date.

The invention is based on the object of overcoming the disadvantages indicated in the prior art and of developing effective inhibitors of DNA-PK which are selective with respect to the related kinases of the PIKK family and are of low molecular size and, in particular, enable effective application in cancer therapy as radio- and chemosensitisers—with the aim of improving the therapeutic efficacy with a simultaneous reduction in side effects.

The object of the invention is achieved in accordance with the independent claims. The subclaims contain preferred embodiments. In accordance with the invention, compounds of the formula (I) are provided.

Surprisingly, it has been found that the compounds according to the invention are provided with inhibiting properties for serine/threonine protein kinases. The compounds of the formula (I) are designed in such a way that potent and selective inhibition of DNA-PK occurs. The compounds according to the invention thus open up entirely new possibilities with respect to the anticarcinogenic action of anticancer agents. The compounds of the formula (I) play a therapeutic role here as radio- and chemosensitisers through specific inhibition of the repair of DNA double-strand breaks (non-homologous end-joining) in the treatment of cancer.

To date, it is known from WO 1992/07844 that 2,4-diaminoquinazoline derivatives are enhancers of chemotherapeutic agents in the treatment of cancer. The derivatives address the multiple resistance of tumour cells as a consequence of overexpression of the mdr1 gene, whose gene product of an efflux P glycoprotein pump keeps the intracellular active-compound concentration low. Neither are physicochemical or pharmacological data disclosed, nor is a marketed medicament is known. Other quinazoline derivatives as DNA-PK inhibitors are disclosed in WO 2011/113512.

The present invention provides a new generation of DNA-PK inhibitors which are not only capable of specific inhibition, which arises, in particular, in the case of cellular assays. In addition, they are also distinguished by the absence of the frequently observed, undesired inhibition of cardiac ion channels, in particular of Kv1.11 hERG, the blockade of which may result in life-threatening arrhythmia.

The compounds according to the invention and salts thereof consequently have valuable pharmacological properties while at the same time being well tolerated.

For the purposes of the invention, the compounds of the formula (I) are defined in such a way that they are also taken to mean pharmaceutically usable derivatives, salts, solvates, solvates of salts, precursors of the compounds, tautomers and optically active forms (such as, for example, stereoisomers, diastereomers, enantiomers, racemates). Solvates of the compounds are taken to mean adductions of inert solvent molecules onto the compounds, which form owing to their mutual attractive force. Solvates are, for example, mono- or dihydrates or alcoholates. Pharmaceutically usable derivatives are taken to mean, for example, the salts of the compounds according to the invention and so-called precursors of the compounds. Precursors are taken to mean, for example, compounds of the formula (I) modified by means of alkyl or acyl groups, sugars or oligopeptides, which are rapidly cleaved in the organism to give the effective compounds according to the invention. These also include biodegradable polymer derivatives of the compounds according to the invention, as described, for example, in Int. J. Pharm. 115, 61-67 (1995). Any compound which can be converted in vivo into a bioactive agent, i.e. compounds of the formula (I), is a precursor in the sense of this invention. Any biologically active compound which results from the in-vivo metabolisation of a compound according to the invention is a metabolite in the sense of the present invention. The compounds of the formula (I) can have one or more chiral centres and therefore occur in various stereoisomeric forms. The formula (I) encompasses all these forms.

The invention also relates to the use of mixtures of the compounds of the formula (I), for example mixtures of two diastereomers, for example in the ratio 1:1, 1:2, 1:3, 1:4, 1:5, 1:10, 1:100 or 1:1000. Particular preference is given here to mixtures of stereoisomeric compounds.

Above and below, the radicals X, Y, $R^1$, $R^2$, $R^3$, $R^4$, $R^5$, $R^6$, LA, Cyc, $Het^1$, $Het^2$ and Hal as well as m and n have the meanings indicated for the formula (I), unless expressly indicated otherwise. If individual radicals occur a number of times within a compound or radical, the radicals adopt, independently of one another, the meanings indicated, unless expressly indicated otherwise. The terms used here for the definition of the compounds are generally based on the rules of the IUPAC organisation for chemical compounds and in particular organic compounds. The terms for explanation of the above-mentioned compounds of the invention always have the following meanings, unless indicated otherwise in the description or claims.

"LA" in the sense of the invention denotes a saturated or partially unsaturated hydrocarbon radical which is unbranched (linear) or branched and has 1, 2, 3, 4 or 5 C atoms. Examples of LA are methyl, ethyl, propyl, isopropyl, 1,1-, 1,2- or 2,2-dimethylpropyl, 1-ethylpropyl, butyl, isobutyl, sec-butyl, tert-butyl. However, the hydrocarbon radical may also be substituted in such a way that 1-3 H atoms may be replaced by Hal, and/or one H atom may be replaced by CN or $Het^2$, and/or one or two $CH_2$ groups may be replaced by O, NH, $N(CH_3)$ or CO. Examples thereof are methoxy, methylsulfanyl, ethoxy, cyanomethoxy, 2-propionitriloxy, oxetan-3-yloxy, N-methylaminocarbonyl, carboxamido, 2-methoxyethoxy, 2,2,2-trifluoroethoxy, or 2-hydroxyethoxy.

"$Het^1$" in the sense of the invention denotes a mono- or bicyclic aliphatic or aromatic hydrocarbon heterocycle having 3, 4, 5, 6, 7, 8, 9 or 10 C atoms and 0, 1, 2 or 3 N, O and/or S atoms, which may be substituted. Examples of suitable "Cyc" are phenyl, pyridine, pyrazine, pyridazine, pyrazolo[1,5-a]pyrimidinyl, or imidazo[1,2-b]pyridazinyl.

"Het²" in the sense of the invention denotes a 3-5-membered aliphatic homo- or heterocycle having 0, 1, 2 or 3 N, O or S atoms. Examples of Het² are oxetane, pyrrolidine or cyclopropyl.

In a preferred embodiment of the present invention, arylquinazoline derivatives of the formula (Ia) are provided

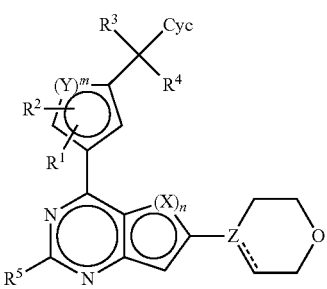

(Ia)

in which
X, Y, independently of one another, are CH, S or N,
Z is C or N,
- - - - forms, if Z=C, a double bond together with the single bond,
  is absent if Z=N,
n is 1 or 2, where
  if n=1, X=S,
  and if n=2, both X=CH, or the X linked to the pyrimidine ring is CH and the X not linked to the pyrimidine ring is N;
m is 1 or 2, where
  if m=1, Y=S,
  and if m=2, both Y=CH, or one Y is CH and the other Y is N;
$R^1$, $R^2$, $R^3$, $R^4$, independently of one another, are H, Hal, CN, OH, $CONH_2$ or LA;
$R^5$ is H, Hal, CN or C≡CH;
Cyc is phenyl, which may be unsubstituted or mono- or disubstituted, independently of one another, by $R^6$, or $Het^1$;
$Het^1$ is a mono- or bicyclic, 5-10-membered heterocycle, having 1-3 N, O and/or S atoms, which may be unsubstituted or mono- or disubstituted, independently of one another, by $R^6$;
$R^6$ is Hal, LA, oxo, CN, $NH_2$ or $Het^2$;
LA is unbranched or branched alkyl having 1-5 C atoms, which may be saturated or partially unsaturated, in which 1-3 H atoms may be replaced by Hal, and/or one H atom may be replaced by CN or $Het^2$, and/or one or two $CH_2$ groups may be replaced by O, NH, $NH_2$, $N(CH_3)$ or CO;
$Het^2$ is a 3-5-membered aliphatic homo- or heterocycle having 0, 1, 2 or 3 N, O and/or S atoms, which is unsubstituted;
Hal is F, Cl, Br or I;
Furthermore preferred arylquinazoline derivatives conform to the formula (Ib)

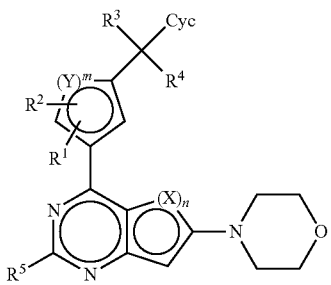

(Ib)

in which all substituents have the meaning indicated for the formulae (I) or (Ia), and/or physiologically acceptable salts, tautomers and/or stereoisomers thereof, including mixtures thereof in all ratios.

In a furthermore preferred embodiment of the present invention, arylquinazoline derivatives of the formula (II) are provided

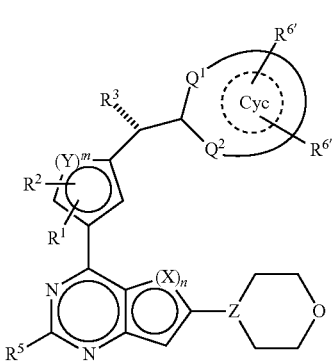

(II)

in which
$R^3$ is Hal, CN, OH, $CONH_2$, CONH(LA) or LA;
$R^{6'}$, $R^{6''}$, independently of one another, are H, Hal, LA, oxo, CN, $NH_2$ or $Het^2$;
$Q^1$, $Q^2$, independently of one another, are CH, N or NH and are in each case unsubstituted;
- - - - denotes the presence or absence of double bonds in Cyc;
and the other substituents have the meaning indicated for the formula (I),
and/or physiologically acceptable salts, tautomers and/or stereoisomers thereof,
including mixtures thereof in all ratios.

It has namely been found that the activity of the compounds according to the invention is particularly high if $R^3$ has the configuration depicted in the formula (II) and Q carries no substituent.

In a furthermore preferred embodiment of the present invention, arylquinazoline derivatives of the formula (III) are provided

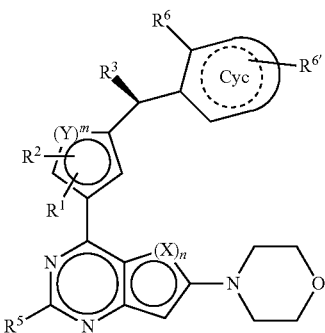

(III)

in which
R³ is Hal, CN, OH, CONH₂, CONH(LA) or LA;
R⁶ is Hal, LA, oxo, CN, NH₂ or Het²;
R⁶" is H, Hal, LA, oxo, CN, NH₂ or Het²;
- - - - denotes the presence or absence of double bonds in Cyc;
and the other substituents have the meaning indicated for the formula (I),
and/or physiologically acceptable salts, tautomers and/or stereoisomers thereof,
including mixtures thereof in all ratios.

It has namely been found that the activity of the compounds according to the invention is particularly high if R³ has the configuration depicted in the formula (III) and Cyc is substituted in the ortho-position by R⁶.

Very particular preference is given to the sub-formulae (IIa), (IIb), (IIIa) and (IIIb) of the formulae (II) and (III):

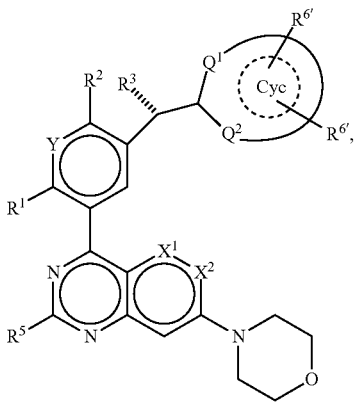

(IIa)

in which
R², R³, independently of one another, are Hal, CN, OH, CONH₂, CON(LA) or LA;
R⁶', R⁶", independently of one another, are H, Hal, LA, oxo, CN, NH₂ or Het²;
Q¹, Q² independently of one another, are CH, N or NH and are in each case unsubstituted;
X¹ is CH, CF or N;
X² is CH or N,
where X¹, X² are not simultaneously N;
Y is CH or N;
- - - denotes the presence or absence of double bonds in Cyc;
and the other substituents have the meaning indicated for the formula (I),
and/or physiologically acceptable salts, tautomers and/or stereoisomers thereof, including mixtures thereof in all ratios;

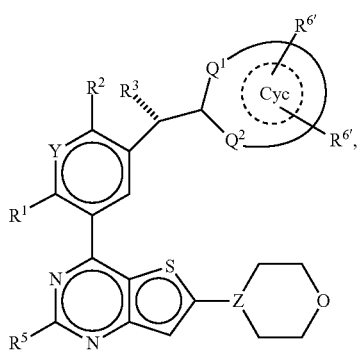

(IIb)

in which
R², R³, independently of one another, are Hal, CN, OH, CONH₂, CON(LA) or LA;
R⁶', R⁶", independently of one another, are H, Hal, LA, oxo, CN, NH₂ or Het²;
Q¹, Q² independently of one another, are CH, N or NH and are in each case unsubstituted;
Y is CH or N,
- - - - denotes the presence or absence of double bonds in Cyc;
and all other substituents have the meaning indicated for the formula (I),
and/or physiologically acceptable salts, tautomers and/or stereoisomers thereof,
including mixtures thereof in all ratios;

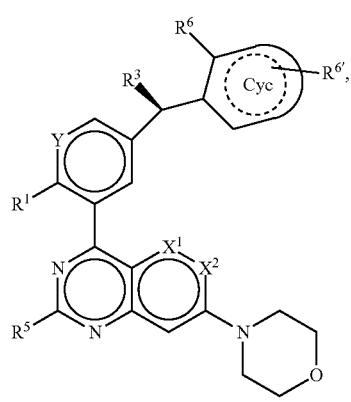

(IIIa)

in which
R³ is Hal, CN, OH, CONH₂, CON(LA) or LA;
R⁶ is Hal, LA, oxo, CN, NH₂ or Het²;
R⁶" is H, Hal, LA, oxo, CN, NH₂ or Het²;
X¹ is CH, CF or N;
X² is CH or N,
where X¹, X² are not simultaneously N;
Y is CH or N;
- - - denotes the presence or absence of double bonds in Cyc;
and the other substituents have the meaning indicated for the formula (I),
and/or physiologically acceptable salts, tautomers and/or stereoisomers thereof, including mixtures thereof in all ratios;

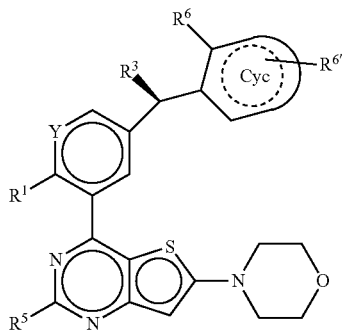

(IIIb)

in which
R³ is Hal, CN, OH, CONH₂, CON(LA) or LA;
R⁶ is Hal, LA, oxo, CN, NH₂ or Het²;
R⁶" is H, Hal, LA, oxo, CN, NH₂ or Het²;
Y is CH or N,
- - - - denotes the presence or absence of double bonds in Cyc;
and all other substituents have the meaning indicated for the formula (I),
and/or physiologically acceptable salts, tautomers and/or stereoisomers thereof,
including mixtures thereof in all ratios.

Furthermore preferred sub-groups of compounds of the formula (IIa) can be expressed by the following sub-formulae (IIa-A) to (IIa-O), which conform to the formula (IIa), but in which
in the case of the sub-formula (IIa-A)
X¹ is CH,
R¹ is F or Cl,
R² is F or Cl,
in the case of the sub-formula (IIa-B)
R¹ is F,
R² is F or Cl,
in the case of the sub-formula (IIa-C)
X¹, X² is CH,
in the case of the sub-formula (IIa-D)
X¹ is CH,
R⁵ is H,
in the case of the sub-formula (IIa-E)
R³ is H, OH,
in the case of the sub-formula (IIa-F)
X¹ is CH,
R³ is OH,
in the case of the sub-formula (IIa-G)
X¹ is CH,
Y is CH,
in the case of the sub-formula (IIa-H)
X¹ is CH,
Cyc is pyridine, pyrazine or pyridazine, or pyrazolo[1,5-a]pyrimidinyl or imidazo[1,2-b]pyridazinyl,
in the case of the sub-formula (IIa-J)
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}pyridazinyl, thieno[2,3-d}-pyrimidinyl or imidazo[4,5-c]pyridinyl, each of which may be unsubstituted, or may be mono- or disubstituted by methoxy, methyl, oxo, Cl or CHF₂O, in the case of the sub-formula (IIa-K)
R¹ is F or Cl,
R² is F or Cl,
R³ is OH,
R⁵ is H,
X¹, X² is CH,
in the case of the sub-formula (IIa-L)
R¹ is F,
R² is F or Cl,
R³ is H or OH,
R⁵ is H,
in the case of the sub-formula (IIa-M)
R¹ is F or Cl,
R² is F or Cl,
R³ is OH,
R⁵ is H,
X¹, X² is CH,
Cyc is pyridine, pyrazine or pyridazine, or pyrazolo[1,5-a]pyrimidinyl or imidazo[1,2-b]pyridazinyl,
in the case of the sub-formula (IIa-N)
R¹ is F,
R² is F or Cl,
R³ is H or OH,
R⁵ is H,
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}pyridazinyl, thieno[2,3-d}-pyrimidinyl or imidazo[4,5-c]pyridinyl, each of which may be unsubstituted, or may be mono- or disubstituted by methoxy, methyl, oxo, Cl or CHF₂O,
in the case of the sub-formula (IIa-O)
R¹ is F,
R² is F or Cl,
R³ is H or OH,
R⁵ is H,
Cyc is 5-methoxypyridazin-3-yl, imidazo[1,2-b]pyridazin-6-yl, 3-chloro-6-methoxypyrazin-2-yl, 3-chloropyrazin-2-yl, pyridazin-4-yl, 3-methoxypyrazin-2-yl, 6-methoxypyridazin-3-yl, 3-difluoromethoxypyridin-2-yl, 3-methylpyrazin-2-yl, thieno[2,3-d}pyrimidin-4-yl, 1-methyl-1H-pyridin-2-one-6-yl, 1H-pyridazin-6-one-3-yl, furo[2,3-d}pyridazin-7-yl, thieno[2,3-d}pyridazin-7-yl, 3,5-dimethylpyrazin-2-yl, furo[2,3-d}pyrimidin-4-yl, 3-methyl-3H-imidazo[4,5-c]pyridin-4-yl,
and/or physiologically acceptable salts, tautomers and/or stereoisomers thereof, including mixtures thereof in all ratios.

Furthermore preferred sub-groups of compounds of the formula (IIIa) can be expressed by the following sub-formulae (IIIa-B) to (IIIa-O), which conform to the formula (IIIa), but in which in the case of the sub-formula (IIIa-B)
R¹ is F,
in the case of the sub-formula (IIIa-C)
X¹, X² is CH,
in the case of the sub-formula (IIIa-D)
X¹ is CH,
R⁵ is H,
in the case of the sub-formula IIIa-(E)
R³ is H, OH,
in the case of the sub-formula (IIIa-F)
X¹ is CH,
R³ is OH,
in the case of the sub-formula (IIIa-G)
X¹ is CH,
Y is CH,
in the case of the sub-formula (IIIa-H)
X¹ is CH,
Cyc is pyridine, pyrazine or pyridazine, or pyrazolo[1,5-a]pyrimidinyl or imidazo[1,2-b]-pyridazinyl, in the case of the sub-formula (IIIa-J)
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}pyridazinyl, thieno[2,3-d}-pyrimidinyl or imidazo[4,5-c]pyridinyl, each of which may be unsubstituted, or may be mono- or disubstituted by methoxy, methyl, oxo, Cl or $CHF_2O$,
in the case of the sub-formula (IIIa-K)
$R^1$ is F or Cl,
$R^3$ is OH,
$R^5$ is H,
$X^1$, $X^2$ is CH,
in the case of the sub-formula (IIIa-L)
$R^1$ is F,
$R^3$ is H or OH,
$R^5$ is H,
in the case of the sub-formula (IIIa-M)
$R^1$ is F or Cl,
$R^3$ is OH,
$R^5$ is H,
$X^1$, $X^2$ is CH,
Cyc is pyridine, pyrazine or pyridazine, or pyrazolo[1,5-a]pyrimidinyl or imidazo[1,2-b]-pyridazinyl,
in the case of the sub-formula (IIIa-N)
$R^1$ is F,
$R^3$ is H or OH,
$R^5$ is H,
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}pyridazinyl, thieno[2,3-d}-pyrimidinyl or imidazo[4,5-c]pyridinyl, each of which may be unsubstituted, or may be mono- or disubstituted by methoxy, methyl, oxo, Cl or $CHF_2O$,
in the case of the sub-formula (IIIa-O)
$R^1$ is F,
$R^3$ is H or OH,
$R^5$ is H,
Cyc is 5-methoxypyridazin-3-yl, imidazo[1,2-b]pyridazin-6-yl, 3-chloro-6-methoxypyrazin-2-yl, 3-chloropyrazin-2-yl, pyridazin-4-yl, 3-methoxypyrazin-2-yl, 6-methoxypyridazin-3-yl, 3-difluoromethoxypyridin-2-yl, 3-methylpyrazin-2-yl, thieno[2,3-d}pyrimidin-4-yl, 1-methyl-1H-pyridin-2-one-6-yl, 1H-pyridazin-6-one-3-yl, furo[2,3-d}pyridazin-7-yl, thieno[2,3-d}pyridazin-7-yl, 3,5-dimethylpyrazin-2-yl, furo[2,3-d}pyrimidin-4-yl, 3-methyl-3H-imidazo[4,5-c]pyridin-4-yl,
and/or physiologically acceptable salts, tautomers and/or stereoisomers thereof, including mixtures thereof in all ratios.

Furthermore preferred sub-groups of compounds of the formula (IIb) can be expressed by the following sub-formulae (IIb-Q) to (IIb-U), which conform to the formula (IIb), but in which
in the case of the sub-formula (IIb-Q)
$R^1$ is F or Cl,
$R^2$ is F or Cl,
$R^3$ is OH,
$R^5$ is H,
Y is CH,
in the case of the sub-formula (IIb-R)
$R^1$ is F,
$R^2$ is F or Cl,
$R^3$ is OH,
$R^5$ is H,
Y is CH,
in the case of the sub-formula (IIb-S)
Cyc is pyridine, pyrazine or pyridazine,
in the case of the sub-formula (IIb-T)
$R^1$ is F or Cl,
$R^2$ is F or Cl,
$R^3$ is OH,
$R^5$ is H,
Cyc is pyridine, pyrazine or pyridazine,
in the case of the sub-formula (IIb-U)
$R^1$ is F,
$R^2$ is F or Cl,
$R^3$ is OH,
$R^5$ is H,
Cyc is pyridine, pyrazine, pyridazine or 3-methylpyrazin-2-yl,
and/or physiologically acceptable salts, tautomers and/or stereoisomers thereof, including mixtures thereof in all ratios.

Furthermore preferred sub-groups of compounds of the formula (IIIb) can be expressed by the following sub-formulae (IIIb-Q) to (IIIb-U), which conform to the formula (IIIb), but in which
in the case of the sub-formula (IIIb-Q)
$R^1$ is F or Cl,
$R^3$ is OH,
$R^5$ is H,
Y is CH,
in the case of the sub-formula (IIIb-R)
$R^1$ is F,
$R^3$ is OH,
$R^5$ is H,
Y is CH,
in the case of the sub-formula (IIIb-S)
Cyc is pyridine, pyrazine or pyridazine,
in the case of the sub-formula (IIIb-T)
$R^1$ is F or Cl,
$R^3$ is OH,
$R^5$ is H,
Cyc is pyridine, pyrazine or pyridazine,
in the case of the sub-formula (IIIb-U)
$R^1$ is F,
$R^3$ is OH,
$R^5$ is H,
Cyc is pyridine, pyrazine, pyridazine or 3-methylpyrazin-2-yl,
and/or physiologically acceptable salts, tautomers and/or stereoisomers thereof, including mixtures thereof in all ratios.

Very particular preference is given to those compounds of the formulae (I) and sub-formulae thereof, and/or physiologically acceptable salts, tautomers and/or stereoisomers thereof, including mixtures thereof in all ratios, that are compiled in Tables 1-8.

The compounds of the formula (I) and also the starting materials for their preparation are prepared by methods known per se, as are described in the literature (for example in standard works, such as Houben-Weyl, Methoden der organischen Chemie [Methods of Organic Chemistry], Georg-Thieme-Verlag, Stuttgart) and/or are known person skilled in the art, and under reaction conditions which are known and suitable for the said reactions. Use can also be made here of variants known per se which are not mentioned here in greater detail. Depending on the conditions used, the reaction time is between a few min and 14 days, the reaction temperature is between −70° C. and 150° C., normally between −50° C. and 100° C., particularly preferably between −10° C. and 70° C.

The reaction is carried out in an inert solvent and generally in the presence of an acid-binding agent, preferably an organic base, such as DIPEA, triethylamine, dimethylaniline, pyridine, quinoline, piperidine or diethanolamine. The addition of an alkali-metal or alkaline-earth metal hydroxide, carbonate or bicarbonate or another salt of a weak acid of the alkali or alkaline-earth metals, preferably of potassium, sodium, calcium or caesium, may also be favourable. Suitable bases are metal oxides, such as, for example, aluminium oxide, alkali-metal hydroxides (including potassium hydroxide, sodium hydroxide and lithium hydroxide), alkaline-earth metal hydroxides (for example barium hydroxide and calcium hydroxide) and alkali-metal alkoxides (for example potassium ethoxide and sodium propoxide).

Suitable inert solvents are, inter alia, hydrocarbons, such as cyclohexane, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, methyl tert-butyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to DMF, methanol, dichloromethane, THF, acetic acid and acetonitrile.

The process and the subsequent work-up of the reaction mixture can basically be carried out as a batch reaction or in a continuous reaction procedure. The continuous reaction procedure comprises, for example, reaction in a continuous stirred-kettle reactor, a stirred-kettle cascade, a loop or cross-flow reactor, a flow tube or in a microreactor. The reaction mixtures are optionally worked up, as needed, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

The compounds of the formula (I) can preferably be obtained by reacting compounds of the formulae (V) and (VI). The present invention thus also relates to a process for the preparation of compounds of the formula (I), sub-formulae thereof and/or physiologically acceptable salts, tautomers and/or stereoisomers thereof, including mixtures thereof in all ratios, having the following steps:

(a) reaction of a compound of the formula (V)

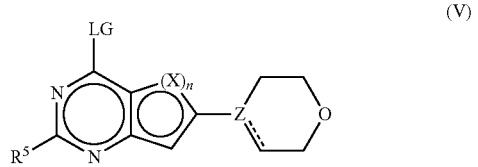

in which LG is a conventional leaving group, such as Hal, with a compound of the formula (IV)

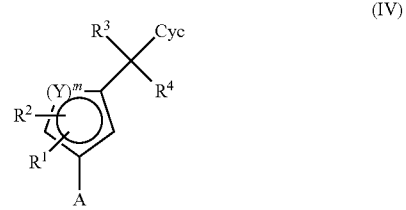

in which A is boronic acid or a boronic acid ester,
to give the compounds of the formula (I) and optionally
(b) conversion of a base or acid of the compounds of the formula (I) into one of their salts.

The starting compounds are generally known. If they are novel, they can be prepared by methods known per se. The compounds of the formulae (I), (Ia), (Ib), (II), (IIa), (IIb), (III), (IIIa), (IIIb), (IV) and (V) can be prepared by known methods. If desired, the starting materials can be formed in situ, so that they are not isolated from the reaction mixture, but instead are immediately converted further into the compounds according to the invention. It is likewise possible to carry out the reaction stepwise.

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula (I) and sub-formulae thereof are for the most part prepared by conventional methods. If the compounds contain a carboxyl group, one of its suitable salts can be formed by reacting the compound with a suitable base to give the corresponding base-addition salt. Such bases are, for example, alkali-metal hydroxides (for example potassium hydroxide, sodium hydroxide and lithium hydroxide), alkaline-earth metal hydroxides (for example barium hydroxide and calcium hydroxide), alkali-metal alkoxides (for example potassium ethoxide and sodium propoxide) and various organic bases, such as piperidine, diethanolamine and N-methylglutamine. A base of the formula (I) and sub-formulae thereof can be converted into the associated acid-addition salt using an acid, for example by reaction of equivalent amounts of the base and the acid in an inert solvent, such as, for example, ethanol, with subsequent evaporation. Suitable acids for this reaction are, in particular, those which give physiologically acceptable salts, such as, for example, hydrogen halides (for example hydrogen chloride, hydrogen bromide or hydrogen iodide), other mineral acids and corresponding salts thereof (for example sulfate, nitrate or phosphate and the like), alkyl- and mono-arylsulfonates (for example ethanesulfonate, toluenesulfonate and benzenesulfonate) and other organic acids and corresponding salts thereof (for example acetate, trifluoroacetate, tartrate, maleate, succinate, citrate, benzoate, salicylate, ascorbate and the like. Salts with physiologically unacceptable acids, for example picrates, can be used for the isolation and/or purification of the compounds of the formula (I).

With regard to that stated above, it can be seen that the expression "pharmaceutically acceptable salt" in the present connection is taken to mean an active compound which comprises a compound of the formula (I) in the form of one of its salts, in particular if this salt form imparts improved pharmacokinetic properties on the active compound compared with the free form of the active compound. The pharmaceutically acceptable salt form of the active compound can also provide this active compound for the first time with a desired pharmacokinetic property and can even have a positive influence on the pharmacodynamics of this active compound with respect to its therapeutic efficacy in the body.

Compounds according to the invention may be chiral owing to their molecular structure and may accordingly occur in various enantiomeric forms. They may therefore be in racemic or optically active form. Since the pharmaceutical efficacy of the racemates or stereoisomers of the compounds of the formula (I) may differ, it may be desirable to use the enantiomers. In these cases, the end product, or even the intermediate, may be separated into enantiomeric compounds by chemical or physical measures known to the person skilled in the art or already employed as such in the synthesis.

It is generally known that atoms can have atomic masses or mass numbers which can differ from the atomic masses or mass numbers usually occurring naturally. Examples of isotopes which are commercially available and which can be incorporated into a compound according to the invention by known methods are isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl. The incorporation of heavier isotopes, in particular deuterium ($^2$H) into a compound according to the invention has therapeutic advantages due to the higher metabolic stability of this isotope-labelled compound. Higher metabolic stability results directly in an increased in vivo half life, which enables a lower dosage.

The definitions of the atoms H, C, N, etc., as used in the compounds according to the invention, generally also relate to the heavier isotopes of these atoms.

Particular preference is given in accordance with the invention to the use of D (deuterium, $^2$H) instead of hydrogen ($^1$H).

It has been found that the compounds according to the invention cause specific inhibition of serine/threonine protein kinases. The invention therefore furthermore relates to the use of compounds of the formula (I) or sub-formulae thereof and/or physiologically acceptable salts, tautomers and/or stereoisomers thereof, including mixtures thereof in all ratios, for the inhibition of serine/threonine protein kinases, preferably PIKK, particularly preferably DNA-PK. Especial preference is given to the inhibition of the above-mentioned serine/threonine protein kinases ex vivo or in vitro. The term "inhibition" relates to any reduction in the activity which is based on the action of the specific compounds according to the invention in that the latter are capable of interacting with the target molecule in such a way that recognition, binding and blocking is made possible. The compounds are distinguished by high affinity to at least one serine/threonine protein kinases, ensuring reliable binding and preferably complete blocking of the kinase activity. The compounds are particularly preferably monospecific in order to guarantee exclusive and direct recognition of the selected kinase. The term "recognition" relates here to any type of interaction between the compound and the said target molecules, in particular covalent or non-covalent bonds, such as, for example, a covalent bond, hydrophobic/hydrophilic interactions, van der Waals forces, ion attraction, hydrogen bonds, ligand/receptor interactions, base pairs of nucleotides or interactions between epitope and antibody binding site.

The compounds according to the invention exhibit an advantageous biological activity which can be demonstrated in the tests described herein, such as, for example, enzyme-based assays. Measurement of the kinase activity is a technique which is well known to the person skilled in the art. Generic test systems for the determination of the kinase activity using substrates, for example histone (Alessi et al. (1996) FEBS Lett. 399(3): 333) or the basic myelin protein, are described in the literature (Campos-González & Glenney (1992) JBC 267: 14535). Various assay systems are available for the identification of kinase inhibitors. In the scintillation proximity assay (Sorg et al. (2002) J Biomolecular Screening 7: 11) and the flash-plate assay, the radioactive phosphorylation of a protein or peptide as substrate are measured using ATP. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are useful as assay methods (Sills et al. (2002) J Biomolecular Screening 191). Other non-radioactive ELISA methods use specific phospho-antibodies (phospho-ABs). The phospho-AB binds only the phosphorylated substrate. This binding can be detected by chemiluminescence using a second peroxidase-conjugated anti-sheep antibody.

The above-mentioned use of the compounds can take place in in-vitro or in-vivo models. The susceptibility of a particular cell to treatment with the compounds according to the invention can be determined by testing in vitro. Typically, a culture of the cell is incubated with a compound according to the invention at various concentrations for a period of time which is sufficient to enable the active agents to induce cell death or to inhibit cell proliferation, cell vitality or migration, usually between about one hour and up to 9 days. For testing in vitro, cultivated cells from a biopsy sample can be used. The amount of cells remaining after the treatment is then determined. The use in vitro takes place, in particular, on samples of mammal species which are suffering from cancer, tumours or metastases. The host or patient can belong to any mammal species, for example a primate species, in particular humans, but also rodents (including mice, rats and hamsters), rabbits, horses, cows, dogs, cats, etc. Animal models are of interest for experimental investigations, providing a model for the treatment of a human disease.

The testing of a plurality of specific compounds enables the selection of the active compound which appears the most suitable for the treatment of the patient. The in-vivo dose of the selected compound is advantageously matched to the susceptibility of the kinase and/or severity of the disease of the patient taking into account the in-vitro data, as a result of which the therapeutic efficacy is noticeably increased. The dose varies depending on the specific compound used, the specific disease, the patient status, etc. A therapeutic dose is typically sufficient considerably to reduce the undesired cell population in the target tissue, while the viability of the patient is maintained. The following teaching of the invention and embodiments thereof relating to the use of compounds of the formula (I) for the preparation of a medicament for the prophylaxis, therapy and/or progress control is valid and can be applied without restrictions to the use of the compounds for the inhibition of the kinase activity, if it appears appropriate.

The treatment is generally continued until a considerable reduction has occurred, for example at least about 50% reduction of the cell load, and can be continued until essentially no more undesired cells are detected in the body. In tests of this type, the compounds according to the invention exhibit and cause an inhibiting effect, which is usually documented by $IC_{50}$ values in a suitable range, preferably in the micromolar range and more preferably in the nanomolar to picomolar range. The kinase is inhibited, in particular, to the extent of 50% if the concentration of the compounds is less than 1 µM, preferably equal to or less than 0.5 µM, particularly preferably less than 0.1 µM. This concentration is called the $IC_{50}$ value.

The invention also relates to a medicament comprising at least one compound of the formula (I) or sub-formulae thereof and/or physiologically acceptable salts, tautomers and/or stereoisomers thereof, including mixtures thereof in all ratios. The invention also relates to a pharmaceutical composition comprising, as active compound, an effective amount of at least one compound of the formula (I) or sub-formulae thereof and/or physiologically acceptable salts, tautomers and/or stereoisomers thereof, including mixtures thereof in all ratios, together with pharmaceutically tolerated assistants.

A "medicament", "drug" and a "pharmaceutical composition" or "pharmaceutical formulation" here is any composition which can be employed in the prophylaxis, therapy, progress control or aftertreatment of patients who, at least temporarily, exhibit a pathogenic modification of the overall condition or the condition of individual parts of the patient organism, preferably as a consequence of cancer, tumours, or metastases.

In order to increase the protective or therapeutic action of the compounds according to the invention, pharmaceutically tolerated adjuvants can be added. For the purposes of the invention, any substance which facilitates, enhances or modifies an effect with the compounds in accordance with the invention is an "adjuvant". Known adjuvants are, for example, aluminium compounds, such as, for example, aluminium hydroxide or aluminium phosphate, saponins, such as, for example, QS 21, muramyl dipeptide or muramyl tripeptide, proteins, such as, for example, gamma-interferon or TNF, MF 59, phosphatdibylcholine, squalene or polyols. The co-application of egg albumin in complete Freund's adjuvant can likewise cause increased cell-mediated immunity and thus support the action of neutralising antibodies formed. Furthermore, DNA, which has an immunostimulatory property, or which encodes a protein with an adjuvant effect, such as, for example, a cytokine, can be applied in parallel or in a construct.

The introduction of the pharmaceutical composition into a cell or organism can be carried out in accordance with the invention in any manner which enables the kinases to be brought into contact with the compounds present in the composition, as a consequence of which a response is induced. The pharmaceutical composition of the present invention can be administered orally, transdermally, transmucosally, transurethrally, vaginally, rectally, pulmonarily, enterally and/or parenterally. The type of administration selected depends on the indication, the dose to be administered, individual-specific parameters, etc. In particular, the various types of administration facilitate site-specific therapy, which minimises side effects and reduces the active-compound dose. Very particularly preferred injections are intradermal, subcutaneous, intramuscular or intravenous injection. The administration can be carried out, for example, with the aid of so-called vaccination guns or by means of syringes. It is also possible to prepare the substance as an aerosol, which is inhaled by the organism, preferably a human patient.

The administration forms of the pharmaceutical composition are prepared corresponding to the desired type of administration in a suitable dosage and in a manner known per se using the conventional solid or liquid vehicles and/or diluents and the assistants usually employed. Thus, pharmaceutically acceptable excipients known to the person skilled in the art can basically form part of the pharmaceutical composition according to the invention, where the amount of excipient material which is combined with the active compound in order to prepare a single dose varies depending on the individual to be treated and the type of administration. These pharmaceutically tolerated additives include salts, buffers, fillers, stabilisers, complexing agents, antioxidants, solvents, binders, lubricants, tablet coatings, flavours, dyes, preservatives, adjusters and the like. Examples of excipients of this type are water, vegetable oils, benzyl alcohols, alkylene glycol, polyethylene glycol, Kolliphor, glycerol triacetate, gelatine, hydroxypropylmethylcellulose (HPMC), carbohydrates, such as, for example, lactose or starch, magnesium stearate, talc and Vaseline.

The pharmaceutical formulation can be in the form of a tablet, film tablet, dragee, lozenge, capsule, pill, powder, granules, syrup, juice, drops, solution, dispersion, suspension, suppository, emulsion, extrudate, implant, cream, gel, ointment, paste, lotion, serum, oil, spray, aerosol, adhesive, plaster or bandage. Oral administration forms which are prepared are preferably tablets, film tablets, dragees, lozenges, capsules, pills, powders, granules, syrups, juices, drops, solutions, dispersions or suspensions—including as depot form. Furthermore, parenteral medicament forms, such as, for example, suppositories, suspensions, emulsions, implants or solutions, should be considered, preferably oily or aqueous solutions. For topical application, the medicament active compound is formulated in a conventional manner with at least one pharmaceutically acceptable vehicle, such as, for example, microcrystalline cellulose, and optionally further assistants, such as, for example, moisturisers, to give solid formulations which can be applied to the skin, such as, for example, creams, gels, ointments, pastes, powders or emulsions, or to give liquid formulations which can be applied to the skin, such as, for example, solutions, suspensions, lotions, sera, oils, sprays or aerosols. The pharmaceutical composition is preferably in the form of an injection solution. For the preparation of the injection solution, aqueous media, such as, for example, distilled water or physiological salt solutions, can be used, where the latter include acidic and basic addition salts. The pharmaceutical composition may also be in the form of a solid composition, for example in the lyophilised state, and can then be prepared before use by addition of a dissolving agent, such as, for example, distilled water. The person skilled in the art is familiar with the basic principles of the preparation of lyophilisates.

The concentration of the active compound in the formulation can be 0.1 to 100 percent by weight. It is crucial that the pharmaceutical composition comprises, as active compound, an effective amount of the compound together with the pharmaceutically tolerated assistants. The terms "effective amount" or "effective dose" are used interchangeably herein and denote an amount of the pharmaceutical active compound which has a prophylactically or therapeutically relevant action on a disease or pathological change in cell, tissue, organ or mammal. A "prophylactic action" prevents the outbreak of a disease or even infection with a pathogen after ingress of individual representatives in such a way that subsequent spread thereof is greatly reduced or they are even completely deactivated. A "prophylactic action" also includes an increase in normal physiological function. Prophylaxis is advisable, in particular, if an individual has predispositions for the onset of the above-mentioned diseases, such as, for example, a family history, a gene defect or a recently survived disease. A "therapeutically relevant action" frees in part or full from one, more than one or all disease symptoms or results in the partial or complete reversal of one, more than one or all physiological or biochemical parameters which are associated with or causally involved in the disease or pathological change into the normal state. Progress control is also taken to be a type of therapeutic treatment if the compounds are administered at certain time intervals, for example in order completely to eliminate the symptoms of a disease. The respective dose or dose range for the administration of the compounds according to the invention is sufficiently large to achieve the desired prophylactic or therapeutic effect of induction of a biological or medical response. In general, the dose will vary with the age, constitution and gender of the patient, and the severity of the disease will be taken into account. It goes without saying that the specific dose, frequency and duration of administration are, in addition, dependent on a multiplicity of factors, such as, for example, the targeting and binding ability of the compounds, feeding habits of the individual to be treated, type of administration, excretion rate and combination with other drugs. The individual dose can be adjusted both with respect to the primary disease and also with respect to the occurrence of any complications. The precise dose can be established by a person skilled in the art using known means and methods. This teaching of the invention is valid and can be applied without restrictions to the pharmaceutical composition comprising the compounds of the formula (I), if it appears appropriate.

In an embodiment of the invention, the compounds are administered in a dose of 0.01 mg to 1 g per dosage unit, preferably between 1 to 700 mg, particularly preferably 5 to 200 mg. The daily dose is in particular between 0.02 and 100 mg/kg of body weight.

In order to support the medical effect, the pharmaceutical composition may, in an embodiment of the invention, also comprise one or more further active compounds, where simultaneous or successive administration is conceivable. The therapeutic effect of the pharmaceutical composition according to the invention can consist, for example, in certain anticancer agents having a better action through the inhibition of DNA-PK as a desired side effect or in the number of side effects of these medicaments being reduced by the reduction in the dose.

In a preferred embodiment of the invention, the pharmaceutical composition according to the invention is combined with an anticancer agent. As used here, the term "anticancer agent" relates to any agent which is administered to a patient with cancer, tumours or metastases for the purpose of treatment of the cancer. Anticancer agents which are preferred in accordance with the invention are those which damage the DNA of tumour cells and thus engage in DNA replication, DNA transcription or gene expression. The following, in particular, are suitable for this purpose:
  alkylating agents, such as altretamine, bendamustine, busulfan, carmustine, chloroambucil, chloromethine, cyclophosphamide, dacarbazine, ifosfamide, improsulfan tosylate, lomustine, melphalan, mitobronitol, mitolactol, nimustine, ranimustine, temozolomide, thiotepa, treosulfan, mechloroetamine, carboquone, apaziquone, fotemustine, glufosfamide, palifosfamide, pipobroman, trofosfamide, uramustine;
  platinum compounds, such as carboplatin, cisplatin, eptaplatin, miriplatin hydrate, oxaliplatin, lobaplatin, nedaplatin, picoplatin, satraplatin;
  topoisomerase inhibitors, such as etoposide, irinotecan, razoxane, sobuzoxane,
  DNA-modifying agents, such as amrubicin, bisantrene, decitabine, mitoxantrone, procarbazine, trabectedine, clofarabine, amsacrine, brostallicin, pixantrone, laromustine;
  anticancer antibiotics, such as bleomycin, dactinomycin, doxorubicin, epirubicin, idarubicin, levamisol, miltefosine, mitomycin C, romidepsin, streptozocin, valrubicin, zinostatin, zorubicin, daunurobicin, plicamycin, aclarubicin, peplomycin, pirarubicin;
  alpha emitters, such as alpharadin ($^{223}$Ra dichloride, Xofgio), $^{211}$At, $^{213}$Bi, $^{225}$Ac, $^{227}$Th; particular preference is given to bleomycin and alpharadin.

The invention can also be practised as a kit which comprises the compounds according to the invention. The kit consists of separate packs of (a) an effective amount of a compound of the formula (I) and/or physiologically acceptable salts, tautomers and/or stereoisomers thereof, including mixtures thereof in all ratios, and (b) an effective amount of an anticancer agent. The kit comprises suitable containers, such as, for example, boxes or cartons, individual bottles, bags or ampoules. The kit may, for example, comprise separate ampoules, each containing an effective amount of a compound of the formula (I) and/or pharmaceutically usable salts, tautomers and/or stereoisomers thereof, including mixtures thereof in all ratios, and an effective amount of an anticancer agent in dissolved or lyophilised form. The kit of the invention may also contain an article which contains written instructions or points the user towards written instructions which explain the handling of the compounds of the invention.

In accordance with the invention, the compounds of the formula (I) or sub-formulae thereof and/or physiologically acceptable salts, tautomers and/or stereoisomers thereof, including mixtures thereof in all ratios, are used for the prophylaxis, therapy and/or progress control of diseases which are caused, promoted and/or spread by the activity of serine/threonine protein kinases. The present invention therefore also relates to the use of compounds of the formula (I) or sub-formulae thereof and/or physiologically acceptable salts, tautomers and/or stereoisomers thereof, including mixtures thereof in all ratios, for the preparation of a medicament for the prophylaxis, therapy and/or progress control of diseases which are caused, promoted and/or spread by the activity of serine/threonine protein kinases. In accordance with the invention, compounds of the formula (I) or sub-formulae thereof and/or physiologically acceptable salts, tautomers and/or stereoisomers thereof, including mixtures thereof in all ratios, are suitable for use in the prophylaxis, therapy and/or progress control of diseases which are caused, promoted and/or spread by activity of serine/threonine protein kinases. For the identification of a corresponding signalling pathway and in order to detect interactions between various signalling pathways, suitable models or model systems have been developed, for example cell culture models (Khwaja et al. (1997) EMBO 16: 2783) and models of transgenic animals (White et al. (2001) Oncogene 20: 7064). In order to determine certain stages in the signalling cascade, interacting compounds can be used in order to modulate the signal (Stephens et al. (2000) Biochemical J 351: 95). In addition, the compounds according to the invention can also be used as reagents for testing kinase-dependent signalling pathways in animals and/or cell culture models or in the clinical diseases mentioned in this application. As discussed herein, these signalling pathways are relevant for various diseases. Accordingly, the compounds according to the invention are useful in the prophylaxis, therapy and/or progress control of diseases which are dependent on signalling pathways with participation by serine/threonine protein kinases.

In accordance with the invention, the compounds of the formula (I) or sub-formulae thereof and/or physiologically acceptable salts, tautomers and/or stereoisomers thereof, including mixtures thereof in all ratios, are suitable for use in the prophylaxis, therapy and/or progress control of cancer, tumours and/or metastases.

The tumour is selected, in particular, from the group of malignant diseases of bladder, stomach, kidneys, head, neck, oesophagus, cervix, thyroid, intestine, liver, brain, prostate, urogenital tract, lymphatic system, larynx, lung, skin, blood, bones and immune system, and/or the cancer is selected from the group of monocytic leukaemia, non-small-cell lung carcinoma, small-cell lung carcinoma, pancreatic cancer, glioblastoma, colorectal carcinoma, breast carcinoma, acute myeloid leukaemia, chronic myeloid leukaemia, acute lymphatic leukaemia, chronic lymphatic leukaemia, Hodgkin's lymphoma and non-Hodgkin's lymphoma.

A further embodiment of the present invention relates to the compounds according to the invention in combination with radiotherapy and/or with at least one further active compound, preferably in combination with radiotherapy and/or an anticancer agent. Industrial irradiation methods which are used clinically preferably include photon irradiation (classical, electromagnetic X-ray/gamma radiation), proton irradiation, heavy-ion irradiation (ionised carbon) and neutron irradiation, without being restricted thereto. In addition, brachytherapy is used clinically with the aid of a suitable radiation source (for example alpha emitters) in the form of surface application and intracavitary and interstitial administration. These radiotherapies and other suitable irradiation therapies in the sense of the invention are known to the person skilled in the art, such as, for example, from Herrmann et al. (2006) Klinische Strahlenbiologie [Clinical Radiation Biology], Elsevier Munich, 4th Edition, 67-68; Bhide & Nutting (2010) BMC Medicine 8: 25; Choi & Hung (2010) Current Urology Reports 11(3): 172. As the most frequent application, photon irradiation has been refined technically by the IMRT (intensity-modulated radiotherapy) method and by imaging methods (three-dimensional conformal radiotherapy) in irradiation planning and performance for the most precise focusing possible. The compounds according to the invention achieve synergistic effects in existing cancer chemotherapies and irradiations and/or restore the efficacy of existing cancer therapies and irradiations.

Still a further embodiment of the invention relates to the use of at least one compound of the formula (I) and/or physiologically acceptable salts, tautomers and/or stereoisomers thereof, including mixtures thereof in all ratios, for the sensitisation of cancer cells to an anticancer agent and/or ionising radiation, with the proviso that the sensitisation does not take place in vivo on the human or animal body. The sensitisation preferably takes place ex vivo or in vitro by administering the compounds to cells, cell cultures, tissues or organs which comprise serine/threonine protein kinases. The ex-vivo use is used, in particular, in the case of animal cells which originate from an animal organism which is affected by a disease which is selected from the group of cancer, tumours or metastases. The cells treated ex vivo can either continue to be kept in culture for subsequent investigations or transferred into an animal, which can be the host animal or another animal. The ex-vivo sensitisation according to the invention is particularly advantageous for testing the specific action of the compounds, so that the in-vivo dose can be pre-adjusted correspondingly with evaluation of these ex-vivo data. As a result thereof, the therapeutic effect is increased significantly. Alternatively, the invention is also designed for use in vivo and relates to at least one compound of the formula (I) and/or physiologically acceptable salts, tautomers and/or stereoisomers thereof, including mixtures thereof in all ratios, for use for the sensitisation of cancer cells to an anticancer agent and/or ionising radiation.

The invention furthermore teaches a method for the prophylaxis, therapy and/or progress control of cancer, tumours or metastases in which an effective amount of at least one compound according to the invention and/or physiologically acceptable salts, tautomers and/or stereoisomers thereof, including mixtures thereof in all ratios, is administered to a subject to be treated. Preferred subjects in the sense of the invention are humans or animals, particularly preferably humans. It is known to the person skilled in the art here that he can administer the compounds according to the invention, which can of course also be used as the pharmaceutical composition according to the invention, in various doses to an organism, in particular a human patient. The effective amount and the type of administration can be determined by the person skilled in the art by routine experiments. The previous teaching of the invention and embodiments thereof are valid and can be applied without restrictions to the treatment method, if it appears appropriate.

All said and further constituents or components are familiar to the person skilled in the art and can experience a specific embodiment for the teaching according to the invention in routine experiments. All documents cited in the description are hereby intended to be incorporated in their entirety into the disclosure of the present invention as reference.

As part of the invention presented here, novel arylquinazoline compounds of the formula (I) were provided for the first time. The compounds according to the invention control serine/threonine protein kinases, in particular DNA-PK, affinitively and/or selectively. The compounds from formula (I) and derivatives thereof are distinguished by high specificity and stability, low preparation costs and easy handling. These properties form the basis for a reproducible mode of action, and reliable and safe interaction with the corresponding target structures. The invention also includes the use of the present arylquinazoline derivatives for the inhibition, regulation and/or modulation of the signalling cascade of serine/threonine protein kinases, in particular DNA-PK, and thus offers novel tools for research and/or diagnostics.

Medicaments and pharmaceutical compositions which comprise the said compounds and the use of these compounds for the treatment of kinase-promoted disorders are, in addition, a highly promising approach for a broad spectrum of therapies, enabling direct and immediate alleviation of symptoms to be achieved in humans and animals. This is particularly advantageous for effective combating of severe diseases, such as cancer, either as monotherapy or in combination with other antineoplastic therapies. The key participation by DNA-PK in DNA repair processes and the evidence that the DNA-PK inhibitors allows mammal cells to become more radiation-sensitive enable therapeutic use of the DNA-PK-specific inhibitors as part of the treatment of, for example, solid cancer tumours by radiotherapy and/or chemotherapy aimed at DNA-DSBs.

The compounds of the formula (I), salts, isomers, tautomers, enantiomers, diastereomers, racemates, derivatives, prodrugs and/or metabolites thereof are effective not only in the case of the said clinical disease pictures, but likewise in the diagnosis and therapy of all diseases in connection with the DNA-PK signalling cascade, in particular with respect to the inhibition of cell proliferation and migration. In addition, the inhibitors according to the invention can be used in the treatment of retroviral diseases by suppression of retroviral integration (R. Daniel (1999) Science 284: 644). Finally, the inhibitors according to the invention can be employed as immunomodulators and modulators of telomeric maintenance. The low-molecular-weight inhibitors are used individually and/or in combination with other treatment measures, such as, for example, surgical interventions, immunotherapy, radiotherapy and/or chemotherapy. The latter relate to targeted therapy with any desired NME (i.e. NCE and/or NBE) as monotherapy and/or on-target/off-target combination therapy.

Owing to their surprisingly strong and/or selective inhibition of enzymes which regulate cellular processes via the repair of dsDNA, the compounds of the invention can be administered in advantageously low dose, while they achieve a similar or even superior biological efficacy compared with the less-potent or less-selective inhibitors of the prior art. The reduced dose is also accompanied by reduced or no medical side effects. In addition, the highly selective inhibition by the compounds according to the invention is also accompanied by a reduction in undesired side effects, which is independent of the dose. In particular, the compounds according to the invention have no physiologically relevant inhibitions or blockades of the Kv 11.1 hERG potassium ion channel It goes without saying that this invention is not restricted to the specific compounds, pharmaceutical compositions, uses and methods as described herein, since such things can be varied. It furthermore goes without saying that the terminology used here serves exclusively the purpose of description of particular embodiments and is not intended to restrict the scope of protection of the invention. As used here in the specification, including the appended claims, word forms in the singular, such as, for example, "a" or "the", include the equivalent in the plural, so long as the context does not specifically indicate otherwise. For example, the reference to "a compound" includes a single compound or a plurality of compounds, which may in turn be identical or different, or the reference to "a method" includes equivalent steps and methods which are known to the person skilled in the art.

The invention is explained in greater detail below with reference to non-limiting examples of specific embodiments. The examples should, in particular, be interpreted as not being restricted to the feature combinations specifically illustrated, but instead the illustrative features can in turn be freely combined so long as the object of the invention is achieved.

EXAMPLES

An overview of the working examples is given by Tables 1-7.

The following ranges apply to the biological data reproduced therein:
DNA-PK (enzymatic):
A: $IC_{50} < 3$ nM
B: $3$ nM $\leq IC_{50} < 7$ nM
C: $7$ nM $\leq IC_{50} < 30$ nM
D: $30$ nM $\leq IC_{50}$
pDNA-PK (cellular):
A: $IC_{50} < 0.5$ μM
B: $0.5$ μM $\leq IC_{50} \leq 5$ μM
C: $5$ μM $\leq IC_{50} < 10$ μM
D: $10$ μM $\leq IC_{50} < 30$ μM
Kv11.1 hERG:
A: $K_i > 25$ WI
B: $25$ μM $\geq K_i > 15$ μM
C: $15$ μM $\geq K_i > 10$ μM
D: $10$ μM $\geq K_i$
Analysis NMR ($^1$H) was carried out with the following parameters.
Instruments: Bruker Avance DRX 500, Bruker Avance 400, Bruker DPX 300
Reference: TMS
TD (time domaine=number of data points or digital resolution): 65536
Solvent: DMSO-d6
NS (number of scans=frequency of scanning): 32
SF (spectrometer frequence=transmission frequency): 400 or 500 MHz
TE (temperature): 303 K, 363 K or 393 K
Coupling constants (J) are indicated in hertz (Hz)
HPLC: high performance chromatography with UV detector
LC-MS: high performance chromatography with UV and MS detector
SFC: supercritical fluid chromatography with UV detector
Identification of Synthesis Intermediates and Synthesis Final Products by Means of LC-MS:
LC-MS method A:
Column: Chromolith SpeedROD RP-18e 50-4.6 mm, flow rate: 2.4 ml/min., wavelength: 220 nm, eluent A: water+0.05% by vol. of formic acid, eluent B: acetonitrile+0.4% by vol. of formic acid, gradient: 4% by vol.-100% by vol. of eluent B in 2.8 min, then 100% of eluent B for a period of 0.5 min.
LC-MS method B:
Column: Chromolith SpeedROD RP-18e 50-4.6 mm, flow rate: 2.4 ml/min., wavelength: 220 nm, eluent A: water+0.1% by vol. of trifluoroacetic acid, eluent B: acetonitrile+0.1% by vol. of trifluoroacetic acid, gradient: 4% by vol.-100% by vol. of eluent B in 2.8 min, then 100% by vol. of eluent B for a period of 0.5 min.
Separation of Stereoisomeric Mixtures by Means of HPLC and SFC:
HPLC: firstly, a column screening is carried out for each stereoisomeric mixture, with the following columns: Chiralpak AD-H, Chiralpak AS-H, Chiralpak IA, Chiralpak IB, Chiralpak IC, Chiralcel OD-H, Chiralcel OJ-H, Lux Cellulose-2, Lux-Amylose-2, all columns: 250-4.6 mm.

The most suitable column is used for the further measurements (for example determination of the enantiomeric ratio). Flow rate: 0.8 ml/min, wavelength: variable, is adapted corresponding to the extinction maximum and the eluents used. Eluent: the following solvents or solvent mixtures are used for the eluents: n-heptane, n-hexane, ethanol, methanol, 2-propanol, acetonitrile, ethyl acetate, dichloromethane; the following can be used as eluent additive: 0.01-0.5% by vol. of formic acid, 0.01-0.5% by vol. of diethylamine; gradients or isocratic measurement conditions are used as required.

SFC: firstly, a column screening is carried out for each stereoisomeric mixture, with the following columns: Chiralpak AD-H, Chiralpak AS-H, Chiralpak IA, Chiralpak IB, Chiralpak IC, Chiralcel OD-H, Chiralcel OJ-H, Lux Cellulose-2, Lux-Amylose-2, all columns: 250-4.6 mm. The most suitable column is used for the further measurements (for example determination of the enantiomeric ratio). Flow rate: 5 ml/min, wavelength: variable, is adapted corresponding to the extinction maximum and the eluents used. Eluent: liquid carbon dioxide (>70 bar), co-eluent: the following solvents or solvent mixtures are used for the co-eluents: ethanol, methanol, isopropanol, acetonitrile, ethyl acetate, dichloromethane. The following can be used as eluent additive: 0.01-0.5% by vol. of formic acid, 0.01-0.5% by vol. of diethylamine. Gradients or isocratic measurement conditions are used as required.

Biological Testing

A) DNA-PK Assay (Biochemical)

The kinase assay was carried out in streptavidin-coated 348-well microtitre flashplates. To this end, 1.5 µg of DNA-PK/protein complex and 100 ng of biotinylated substrate, such as, for example, PESQEAFADLWKK-biotin-NH2 ("biotin-DNA-PK peptide"), were incubated for 90 min at room temperature in a total volume of 36.5 µl (34.25 mM HEPES/KOH; 7.85 mM Tris HCl; 68.5 mM KCl; 5 µM ATP; 6.85 mM $MgCl_2$; 0.5 mM EDTA; 0.14 mM EGTA; 0.69 mM DTT; pH 7.4) with 500 ng of DNA from calf thymus, 0.1 µCi of 33P-ATP and 1.8% of DMSO per well with and without the test compound. The reaction was stopped using 50 µl/well of 200 mM EDTA. After incubation for a further 30 min at room temperature, the liquid was removed. Each well was washed three times with 100 µl of 0.9% saline solution. A nonspecific reaction (blank value) was determined using 10 µM of an innate kinase inhibitor. The radioactivity measurement was carried out using a TopCount. $IC_{50}$ values were calculated in RS1.

Literature: Kashishian et al. (2003) Molecular Cancer Therapeutics 1257.

B) DNA-PK Phosphorylation at Serine 2056 (Cellular)

HCT116 cells were cultivated at 37° C. and 10% CO2 in MEM alpha medium with 10% of foetal calf serum and 2 mM glutamine. The cells were detached from the base of the culture vessels with the aid of trypsin/EDTA, centrifuged off in centrifuge tubes, taken up in fresh medium, and the cell density was determined. 100,000 cells were shown in 1 ml of culture medium per cavity of a 24-well cell culture plate and cultivated overnight. Next day, 10 µM bleomycin (DNA intercalator and inductor of DNA double-strand breaks) and test substances in fresh culture medium were added to the cells, and these were cultivated for a further six hours. Cell lysis was subsequently carried out, and the cell lysates were added to a blocked 96-well ELISA plate coated with DNA-PK-specific antibodies (Sigma-Aldrich WH0005591M2: total DNA-PK; Abcam ab18192 or Epitomics EM09912: phospho-serine 2056 DNA-PK) and incubated at 4° C. overnight. The 96-well ELISA plates were subsequently treated with a detection antibody (Abcam ab79444: total DNA-PK) and a streptavidin-HRP conjugate. The development of the enzymatic reaction was carried out with the aid of a chemiluminescent reagent, the chemiluminescence was measured with the aid of a Mithras LB940. The signals with the phospho-DNA-PK-specific antibody were standardised to the signal with the antibody against the total protein DNA-PKc. The determination of IC50 values or of percentage values was carried out by referencing to the signal level of the bleomycin-treated vehicle control group (100% of the control). The DMSO control was used as blank.

C) Kv11.1 (hERG) ION Channel Activity (Patch Clamp Assay)

Method for the detection and characterisation of test substances which interfere with the Kv11.1 (hERG) channel: Kv11.1 (hERG, human ether a-go-go related gene) is a potassium channel which plays a central role for repolarisation of the cells in the ventricular cardiomyocytes.

The patch-clamp measurement was carried out at room temperature in whole-cell configuration on human embryonic kidney cells (HEK293) which have been transfected in a stable manner with the hERG gene.

The whole-cell configurations were carried out using an automated patch clamp device (Patchliner™, Nanion Technologies, Munich). This is a glass chip-based system with which automated whole-cell measurements on up to 8 cells simultaneously are possible. The glass chip has a hole of defined size to which the cell is transferred into the Gigaseal by application of a reduced pressure and brought into the whole-cell configuration. Buffer, cell suspension and test substances were added to microchannels of the chip using a Teflon-coated pipette.

The cells were clamped to a holding potential of −80 mV. For measurement of substance-promoted inhibition of the Kv11.1 channel, the following voltage protocol was applied at 10-second intervals: 51 ms/−80 mV, 500 ms/+40 mV, 500 ms/−40 mV, 200 ms/−80 mV. The leakage current is subtracted by means of the P4 method. The cells were resuspended in extracellular buffer (EC) and applied to the chip. After the cell had been collected, the seal was improved by addition of a seal enhancer buffer. As soon as the whole-cell configuration had been reached, the seal enhancer buffer was washed out and replaced by extracellular buffer. The measurement started in EC for 1.5 min. DMSO (vehicle control, 0.1% of DMSO) was then applied, and the control current was recorded for 3 min. The test substance was subsequently added twice in the same concentration, and the potassium current was measured for 3.5 min in each case.

If the measurement result of a test substance at an initial concentration of 10 µM was smaller than (−)50% effect (threshold value) (for example (−)60% effect), the test substance was, in order to determine a dose/action relationship, added cumulatively in increasing concentration, where each concentration was measured for 5 min.

The reference substance used was the Kv11.1 (hERG) ion channel blocker quinidine. The effects of test substances and quinidine were standardised to the associated vehicle control. The effect on the Kv11.1 (hERG) channel activity was assessed from the potassium current at −40 mV. For the calculation, the current was evaluated for the respective final trace. A test-substance-induced inhibition of the Kv11.1 (hERG) channel was standardised to the vehicle control (0.1% of DMSO).

During the measurement, an aliquot of the test substance was taken for concentration determination. The sample was measured immediately by HPLC, and the final concentration was determined from a calibration curve.

If the measurement result of a test substance at an initial concentration of 10 µM is greater than or equal to (−)50% effect (threshold value) (for example (−)30% effect, i.e. 30% inhibition at 10 µM), the $K_i$ is calculated in accordance with the following formula: $K_i=1.0E-5\times(100+\% \text{ effect})/(-\% \text{ effect})$, [M].

The measurement result of (−)30% effect at a test substance concentration of 10 µM gives a $K_i$ of 23 µM.

D) Kv11.1 Ion Channel Binding Assay

Kv11.1 (hERG=human ether a go-go related enzyme) is a cardiac $K^+$ channel which should if possible not interact with the test substances. This interaction is determined quantitatively with the aid of the Predictor™ hERG Fluorescence Polarizations (FP) Assays from Life Technologies. In the case of this assay principle, cardiomyocyte cell membranes having a certain proportion of Kv11.1 channels are isolated.

A dye-labelled Kv11.1 binding partner gives a high fluorescence polarisation signal by interaction with the Kv11.1. In the case of displacement of the dye, a reduction in the fluorescence polarisation signal occurs.

The assay is carried out automatically as follows: 15 nl of the test substances (highest concentration: 10 mM, 10 concentrations: dilution factors 1:3.16, DMSO) are transferred into an empty microtitre plates having 384 wells by means of an acoustic pipetter. 3 µl of the isolated membranes are subsequently added. Membranes and test substances are incubated at 22° C. for 15 min (+/−5 min). In the next step, the dye-labelled binding partner is added, followed by incubation at 22° C. After incubation for two hours, the measurement of the fluorescence polarisation is carried out on an Envision multimode Reader. Measured raw data are standardised with the aid of Genedata Assay Analyzer. The IC50 and % effect values are calculated in Genedata Condoseo.

Chemical Synthesis

Above and below, all temperatures are indicated in ° C.

The stereochemical configuration assignments of enantiomeric Examples 27, 72, 82, 83, 135, 136, 185, 234, 251, 455 and 456 were confirmed by X-ray structural analyses. For Examples 234 and 251, the identification was carried out by crystallisation and X-ray structural analysis of a precursor.

The other compounds denoted as chiral in the tables (asterisk on the asymmetrical C atom) were obtained by chromatography on a chiral solid phase. The enantiomer eluted first under the respective conditions was given the name "Ena1", the enantiomer eluted second was given the name "Ena2".

Examples 1 and 2

(3,5-Difluoropyridin-4-yl)-[4-fluoro-3-(7-morpholin-4-ylquinazolin-4-yl)phenyl]methanol (1) (4-Chloro-5-fluoropyridin-3-yl)-[4-fluoro-3-(7-morpholin-4-ylquinazolin-4-yl)phenyl]methanol (2)

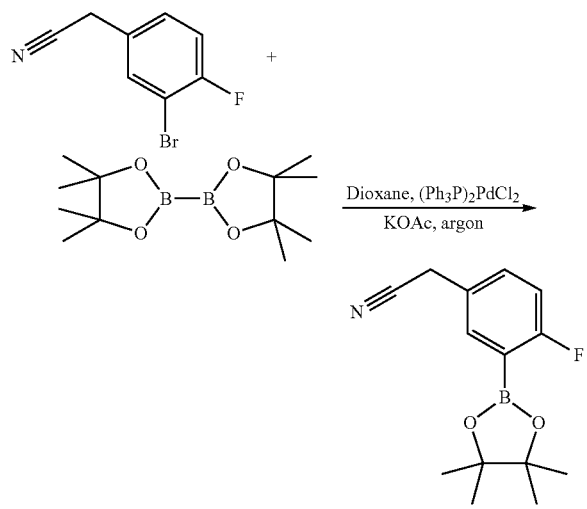

(3-Bromo-4-fluorophenyl)acetonitrile (4.00 g, 18.32 mmol), bis(pinacolato)diboron (5.22 g, 20.15 mmol), potassium acetate (55.86 mmol) and bis(triphenylphosphine)palladium(II) chloride (15.2% of Pd) (393.53 mg, 0.55 mmol) were dissolved in oxygen-free 1,4-dioxane (40 ml, max. 0.005% of water) under argon. The reaction mixture was subsequently heated at a temperature of 130° C. for 90 min. When the reaction conversion was complete, the mixture was filtered through kieselguhr. The filtrate was diluted with dichloromethane (200 ml) and water (50 ml) and extracted. The organic phase was dried over sodium sulfate, subsequently filtered and evaporated to dryness in vacuo, giving [4-fluoro-3-(4,4,5,5-tetramethyl-1,3,2-dioxaborolan-2-yl)phenyl]acetonitrile as oil (7.59 g, purity 81%, MS: 262.2 [M+H$^+$]), which was reacted further without further work-up.

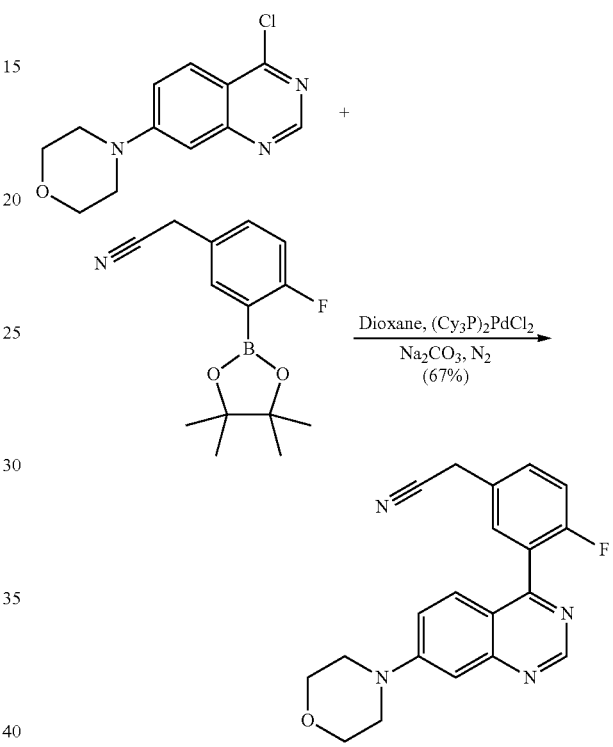

4-Fluoro-3-(4,4,5,5-tetramethyl-1,3,2-dioxaborolan-2-yl)phenyl]acetonitrile (7.60 g, 23.53 mmol), 1,4-dioxane (85.6 ml, max. 0.005% of water), 4-chloro-7-morpholin-4-ylquinazoline (5.00 g, 20.02 mmol), bis(tricyclohexylphosphine)palladium(II) dichloride (597.24 mg, 0.80 mmol) and sodium carbonate solution (2.0 M, 30 ml, 60.07 mmol) were initially introduced in a three-necked flask. The suspension obtained was heated at a temperature of 140° C. under a nitrogen atmosphere with stirring for a period of 2.5 h. When the reaction was complete, the mixture was cooled to room temperature and filtered through kieselguhr. The filtrate was diluted with ethyl acetate (250 ml) and water (100 ml) and extracted. The aqueous phase was rinsed twice with ethyl acetate (75 ml in each case). The combined organic phases were dried over sodium sulfate, subsequently filtered and evaporated to dryness in vacuo. For further work-up, the residue was suspended in methyl tert-butyl ether, filtered off and rinsed twice with further methyl tert-butyl ether (30 ml in each case). The filter cake was dried overnight in vacuo, giving [4-fluoro-3-(7-morpholin-4-ylquinazolin-4-yl)phenyl]acetonitrile (4.91 g, 13.49 mmol, MS: 349.1 [M+H$^+$], 67% yield) as yellow solid.

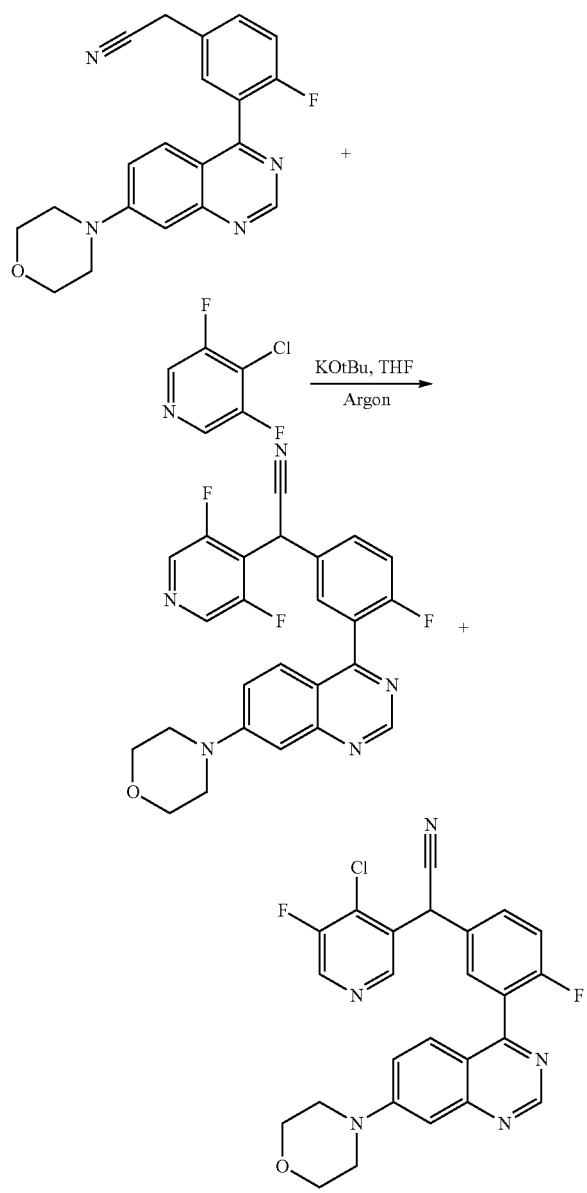

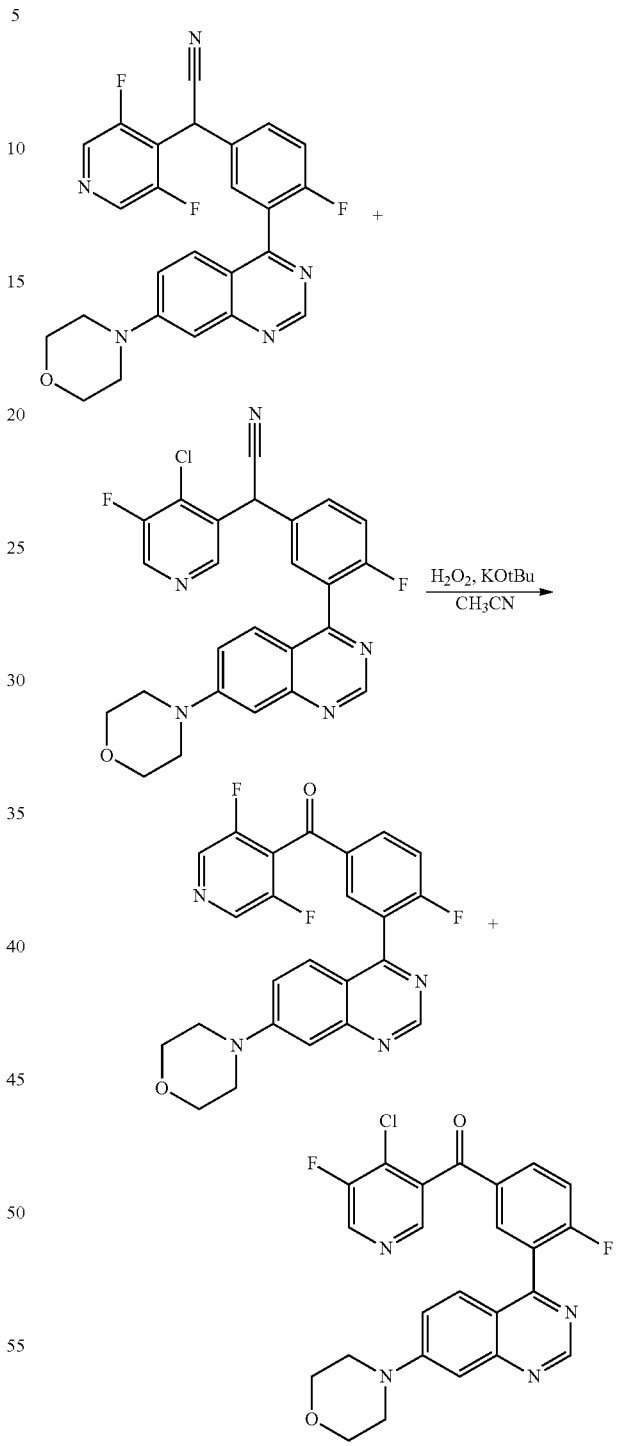

fluoro-3-(7-morpholin-4-ylquinazolin-4-yl)phenyl]acetonitrile (157 mg, 0.33 mmol, MS: 478.1/480.1 [M+H$^+$], 29% yield).

[4-Fluoro-3-(7-morpholin-4-ylquinazolin-4-yl)phenyl]acetonitrile (400 mg, 1.12 mmol), 4-chloro-3,5-difluoropyridine (189.9 mg, 1.23 mmol) were dissolved in oxygen-free, degassed tetrahydrofuran (8 ml, max. 0.0075% of water) under a dry argon atmosphere. Potassium tert-butoxide (263.9 mg, 2.35 mmol) was subsequently added to the reaction mixture, during which a dark-red solution formed, which was stirred at room temperature for a further 30 min. When the reaction was complete, the mixture was diluted with saturated ammonium chloride solution (20 ml) and water (50 ml). The aqueous phase was subsequently extracted twice with dichloromethane (60 ml in each case). The organic phase was dried over sodium sulfate, filtered off and evaporated to dryness in vacuo in a rotary evaporator. The residue was purified by flash column chromatography (gradient: dichloromethane/0-4% by vol. of ethanol), giving a mixture (420 mg, about 5:3) of the oils (3,5-difluoropyridin-4-yl)-[4-fluoro-3-(7-morpholin-4-ylquinazolin-4-yl)phenyl]acetonitrile (263 mg, 0.57 mmol, MS: 462.1 [M+H$^+$], 50% yield) and (4-chloro-5-fluoropyridin-3-yl)-[4-

The mixture (420 mg, about 5:3) of (3,5-difluoropyridin-4-yl)-[4-fluoro-3-(7-morpholin-4-ylquinazolin-4-yl)phenyl]acetonitrile and (4-chloro-5-fluoropyridin-3-yl)-[4-fluoro-3-(7-morpholin-4-ylquinazolin-4-yl)phenyl]acetonitrile was dissolved in acetonitrile (12.7 ml). Potassium tert-butoxide (80.90 mg, 0.72 mmol) was added to the reaction solution with stirring, during which a dark-red solution formed. After stirring for 15 min, the mixture was cooled to 0° C., and 30% hydrogen peroxide solution (276 µl, 2.70 mmol) was subsequently added dropwise. The cooling bath was removed after stirring for 5 min at 0°. The reaction solution was stirred at room temperature for a further 1 h. When the reaction conversion was complete, 10% sodium thiosulfate solution (5 ml) was added, and the mixture was diluted with water (25 ml). The aqueous solution was extracted twice with dichloromethane (50 ml in each case). The combined organic phases were dried over sodium sulfate, filtered off and evaporated to dryness in vacuo. The residue was purified by flash column chromatography (gradient: dichloromethane/0-4% by vol. of ethanol), giving a mixture (310 mg, about 3:1) of the oils (3,5-difluoropyridin-4-yl)-[4-fluoro-3-(7-morpholin-4-ylquinazolin-4-yl)phenyl]methanone (233 mg, 0.50 mmol, MS: 451.1 [M+H$^+$]) and (4-chloro-5-fluoropyridin-3-yl)-[4-fluoro-3-(7-morpholin-4-ylquinazolin-4-yl)phenyl]methanone (77 mg, 0.16 mmol, MS: 467.1/469.1 [M+H$^+$]).

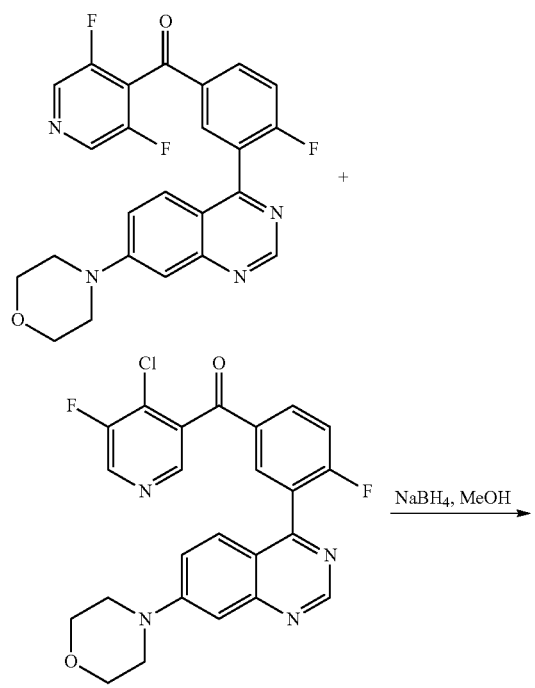

EXAMPLE 1

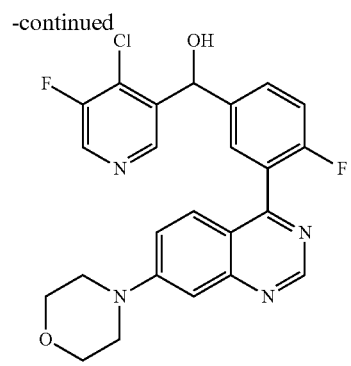

EXAMPLE 2

The mixture (310 mg, about 3:1) of (3,5-difluoropyridin-4-yl)-[4-fluoro-3-(7-morpholin-4-ylquinazolin-4-yl)phenyl]methanone and (4-chloro-5-fluoropyridin-3-yl)-[4-fluoro-3-(7-morpholin-4-ylquinazolin-4-yl)phenyl]methanone was dissolved in methanol (15 ml). Sodium borohydride (30.4 mg, 0.80 mmol) was subsequently added (evolution of gas). The reaction solution was stirred at room temperature for 45 min. When the reaction was complete, the mixture was diluted with saturated ammonium chloride solution (5 ml) and water (15 ml). The aqueous phase was subsequently extracted three times with dichloromethane (20 ml in each case). The combined organic phases were dried over sodium sulfate, filtered off and evaporated to dryness in vacuo in a rotary evaporator. The residue was dissolved in dimethyl sulfoxide (4.8 ml) and purified by chromatography by means of preparative HPLC (gradient: water/1-50% by vol. of acetonitrile over 21 min, flow rate 50 ml/min). The product fractions were combined, diluted with saturated sodium hydrogencarbonate solution (5 ml in each case) and extracted twice with dichloromethane (40 ml in each case). The organic phases were evaporated in vacuo, the residues were subsequently taken up in 1,4-dioxane (5 ml) and water (30 ml) and freeze-dried, giving pure (3,5-difluoropyridin-4-yl)-[4-fluoro-3-(7-morpholin-4-ylquinazolin-4-yl)phenyl]methanol (EXAMPLE 1, 42.50 mg, 0.09 mmol, MS: 453.1 [M+H$^+$]) and (4-chloro-5-fluoropyridin-3-yl)-[4-fluoro-3-(7-morpholin-4-ylquinazolin-4-yl)phenyl]methanol (EXAMPLE 2, 28.40 mg, 0.06 mmol, MS: 469.1/471.1 [M+H$^+$]) as solids.

Example 37

(3-Chloropyrazin-2-yl)-[4-fluoro-3-(6-morpholin-4-ylthieno[3,2-d]pyrimidin-4-yl)phenyl]-methanol (37)

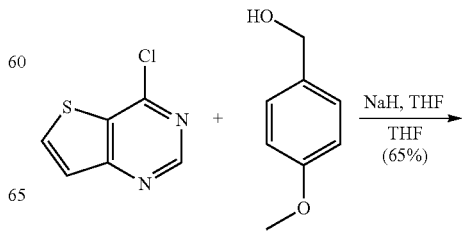

-continued

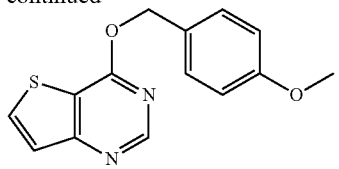

Sodium hydride (60% suspension in paraffin oil, 1.41 g, 35.0 mmol) was suspended in dry tetrahydrofuran (25 ml) under argon in a glass vessel. 4-Methoxyphenylmethanol (4.21 g, 30.0 mmol), dissolved in dry tetrahydrofuran (5 ml), was subsequently slowly added dropwise with stirring, and the mixture was stirred at room temperature for 1 h. A suspension of 4-chlorothieno[3,2-d]pyrimidine (4.00 g, 23.4 mmol) in dry tetrahydrofuran (20 ml) was then added slowly, and the mixture was stirred for a further hour. When the reaction conversion was complete, methanol (15 ml) was carefully added, the mixture was subsequently evaporated in vacuo and diluted with a mixture of water (100 ml) and ethyl acetate (150 ml). The aqueous phase was extracted three times with ethyl acetate (100 ml in each case), dried over sodium sulfate, filtered off with suction, and the filtrate was evaporated in vacuo. The solvent-free residue was taken up in ethanol (40 ml) and carefully stirred at about 5° C. for 16 h. The crystals which precipitated out overnight were filtered off with suction, rinsed with a little cold ethanol and dried at room temperature, giving 4-(4-methoxybenzyloxy)thieno [3,2-d]pyrimidine (4.15 g, 15.24 mmol, MS: 273.0 [M+H$^+$]), 65% yield) as crystalline solid.

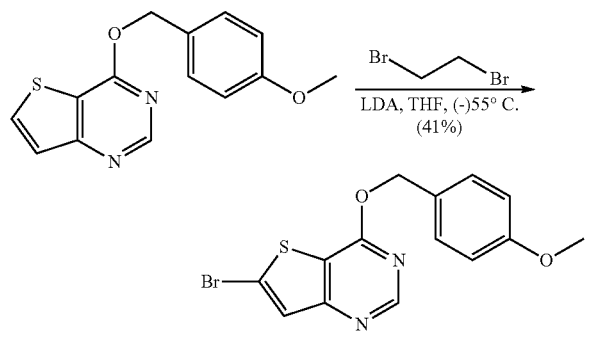

4-(4-Methoxybenzyloxy)thieno[3,2-d]pyrimidine (2.60 g, 9.55 mmol) was dissolved in dry tetrahydrofuran (35 ml) and cooled to (−)55° C. A freshly prepared lithium diisopropylamide solution (21 mmol, prepared from diisopropylamine [2.13 g, 21 mmol] and n-BuLi [15% solution from n-hexane, 13.13 ml, 21 mmol in dry tetrahydrofuran [35 ml] at [−]10° C.) was added dropwise at (−)55° C. over 10 min. The suspension obtained was stirred further. 1,2-dibromoethane (10.76 g, 6.0 mmol) was subsequently added. After a further 10 min, the mixture was warmed to (−)20° C. and stirred for 1 h. With the reaction complete, the reaction solution was added to a 50% aqueous sodium hydrogencarbonate/sodium thiosulfate solution (volume ratio 1:1, 120 ml). The aqueous phase was extracted three times with ethyl acetate. The combined organic phases were washed with saturated sodium chloride solution, subsequently dried over sodium sulfate, filtered and evaporated to dryness in a rotary evaporator. The residue was purified by means of flash column chromatography (gradient cyclohexane/0-18% by vol. of ethyl acetate, CombiFlash Rf 200, 80 g silica column, flow rate=50 ml/min., λ=220 nm), giving 6-bromo-4-(4-methoxybenzyloxy)thieno[3,2-d]pyrimidine (1.39 g, 3.95 mmol, MS: 351.0/353.0 [M+H$^+$]), 41% yield) as solid.

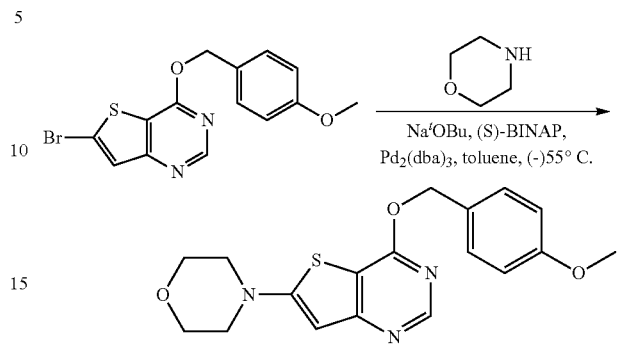

6-Bromo-4-(4-methoxybenzyloxy)thieno[3,2-d]pyrimidine (1.38 g, 3.93 mmol), morpholine (1.03 g, 11.79 mmol), sodium tert-butoxide (1.13 g, 11.79 mmol), (S)-(−)-2,2'-bis(diphenylphosphino)-1,1'-binaphtyl (S-BINAP, 122.3 mg, 0.196 mmol) and tris(dibenzylideneacetone)dipalladium (179.9 mg, 0.196 mmol) was dissolved in toluene (20 ml) under nitrogen in a microwave vessel. The reaction solution was heated at 95° C. for 4 h. The mixture was subsequently diluted with water (60 ml) and dichloromethane (60 ml). The aqueous phase was extracted three times with dichloromethane. The combined organic phases were dried over sodium sulfate and evaporated in a rotary evaporator. The residue was purified by means of flash chromatography (gradient dichloromethane/5-25% by vol. of [dichloromethane/ethanol 9:1], CombiFlash Rf 200, 80 g silica column, λ=220 nm). The suitable product fractions were combined, and the solvents were removed in a rotary evaporator, giving 4-(4-methoxybenzyloxy)-6-morpholin-4-ylthieno[3,2-d]pyrimidine (756.0 mg, 2.12 mmol, MS: 358.2 [M+H$^+$]) 54% yield) as solid.

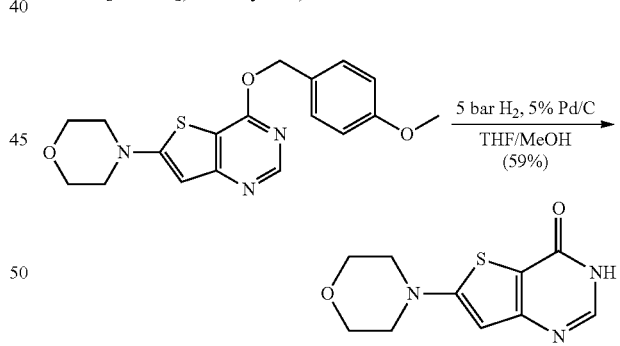

4-(4-Methoxybenzyloxy)-6-morpholin-4-ylthieno[3,2-d]pyrimidine (923 mg, 2.58 mmol) was dissolved in tetrahydrofuran (5 ml) and methanol (5 ml). Pd/C (5%, 1.9 g) was added in portions (at the beginning of the reaction, after a further 7 h and 24 h), and the mixture was hydrogenated at a maximum hydrogen pressure of 5 bar (H$_2$, purity 3.0, 57.9 g) for 36 h. The solution obtained was filtered through kieselguhr and evaporated in a rotary evaporator. The residue was purified by means of flash column chromatography (gradient: dichloromethane/10-20% by vol. of [methanol/ammonia 10:1], CombiFlash Rf 200, 24 g silica column, λ=220 nm). The suitable product fractions were combined, and the solvents were removed in a rotary evaporator, giving 6-morpholin-4-yl-3H-thieno[3,2-d}pyrimidin-4-one (361.0 mg, 1.521 mmol, MS: 238.0 [M+H⁺], 59% yield) as solid.

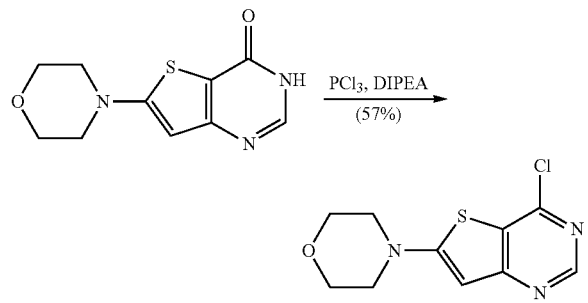

6-Morpholin-4-yl-3H-thieno[3,2-d}pyrimidin-4-one (206 mg, 0.87 mmol) was suspended in phosphoryl chloride (1.67 g, 10.89 mmol). N-Ethyldiisopropylamine (56.1 mg, 0.43 mmol) was subsequently added to the suspension. The reaction mixture was stirred overnight at room temperature. For work-up, a mixture of saturated sodium hydrogencarbonate solution (30 ml) and dichloromethane (20 ml) was added. The resultant solution was extracted three times with dichloromethane. The combined organic phases were dried over sodium sulfate, filtered and evaporated to dryness in vacuo, giving 4-chloro-6-morpholin-4-ylthieno[3,2-d}-pyrimidine (127 mg, 0.497 mmol, MS: 256.0/258.0 [M+H⁺], 57% yield) as solid.

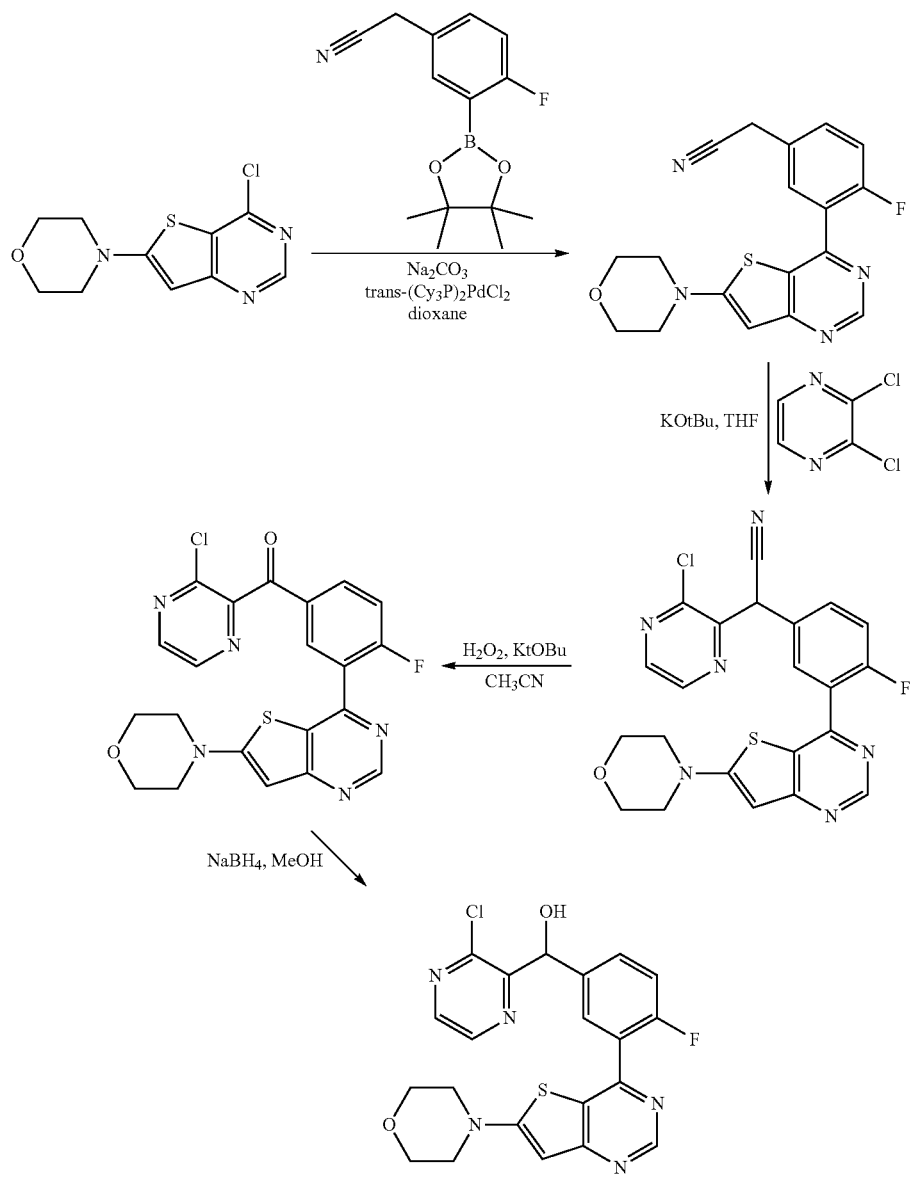

Example 37

Starting from 4-chloro-6-morpholin-4-ylthieno[3,2-d}pyrimidine, (3-chloropyrazin-2-yl)-[4-fluoro-3-(6-morpholin-4-ylthieno[3,2-d}pyrimidin-4-yl)phenyl]methanol (EXAMPLE 37) was prepared analogously to the synthesis sequence described for Examples 1 and 2.

Compounds which were prepared in accordance with Examples 1, 2 and 37 can be found in Table 1 below.

TABLE 1

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 1 | 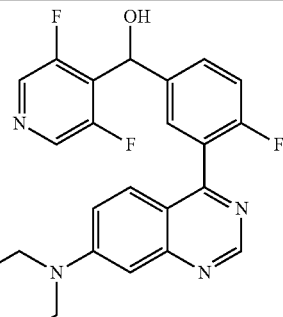<br>MS: 453.1 (M + H$^+$) | (3,5-Difluoro-pyridin-4-yl)-[4-fluoro-3-(7-morpholin-4-yl-quinazolin-4-yl)phenyl]-methanol<br><br>1H NMR (500 MHz, DMSO-d6) ppm = 9.10 (s, 1H), 8.50 (s, 2H), 7.65-7.60 (m, 2H), 7.55-7.48 (m, 2H), 7.45-7.40 (m, 1 H), 7.20 (d, J = 2.1, 1H), 6.62 d, J = 4.6, 1H), 6.23 (d, J = 4.6, 1H), 3.80-3.75 (m, (4H), 3.47-3.42 (m, 4H) | B | B | B |
| 2 | 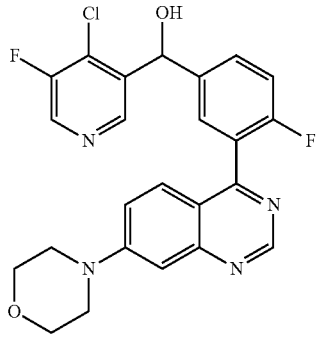 [SMILES: OC(c1ccc(F)c(-c2ncnc3cc(N4CCOCC4)ccc23)c1)c1cncc(F)c1Cl]<br>MS: 469.1/471.1 (M + H$^+$)<br>(Cl isotopy, rel. peak intensity ratio [%] 100:37) | (4-Chloro-5-fluoro-pyridin-3-yl)-[4-fluoro-3-(7-morpholin-4-yl-quinazolin-4-yl)phenyl]-methanol<br><br>1H NMR (500 MHz, DMSO-d6) ppm = 9.10 (s, 1H), 8.70 (s, 1H), 8.66 (s, 1H), 7.64-7.59 (m, 2H), 7.55-7.48 (m, 2H), 7.44-7.39 (m, 1H), 7.20 (d, J = 2.2, 1H), 6.56 (d, J = 4.4, 1H), 6.12 (d, J = 4.5, 1H), 3.81-3.74 (m, 4H), 3.47-3.40 (m, 4H) | B | A | C |
| 3 | 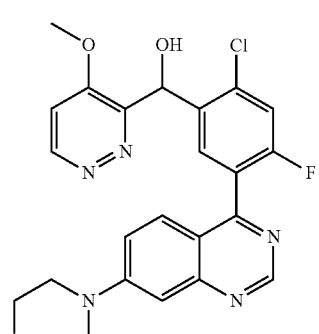<br>MS: 504.1/506.1 (M + Na$^+$)<br>(Cl isotopy, rel. peak intensity ratio [%] 100:35) | [2-Chloro-4-fluoro-5-(7-morpholin-4-yl-quinazolin-4-yl)phenyl]-(4-methoxy-pyridazin-3-yl)methanol<br><br>1H NMR (500 MHz, DMSO-d6) ppm = 9.13 (s, 1H), 8.96 (d, J = 6.0, 1H), 8.04 - 8.01 (m, 1H), 7.65 - 7.60 (m, 2H), 7.56 (dd, J = 9.4, 2.5, 1H), 7.32 (d, J = 6.0, 1H), 7.22 (d, J = 2.5, 1H), 6.46 (d, J = 6.2, 1H), 6.39 (d, J = 6.3, 1H), 3.96 (s, 3H), 3.81 - 3.75 (m, 4H), 3.50 - 3.43 (m, 4H) | B | B | A |

TABLE 1-continued

Compounds of the formula (I)

| Example | Structural formula | Name | IC₅₀ DNA-PK | IC₅₀ pDNA-PK | Kᵢ [Kv1.11 hERG] |
|---|---|---|---|---|---|
| 4 | | [2-Chloro-4-fluoro-5-(7-morpholin-4-yl-quinazolin-4-yl)phenyl]-(5-methoxy-pyridazin-3-yl)methanol | A | A | A |
| | MS: 482.1/484.1 (M + H⁺) (Cl isotopy, rel. peak intensity ratio [%] 100:34) | 1H NMR (500 MHz, DMSO-d6) ppm = 9.07 (s, 1H), 8.88 (d, J = 4.7, 1H), 7.71 (d, J = 9.5, 1H), 7.59 (dd, J = 4.7, 0.9, 1H), 7.54 (d, J = 7.6, 1H), 7.52-7.50 (m, 2H), 7.21-7.17 (m, 1H), 6.46 (d, J = 5.1, 1H), 6.15 (d, J = 5.2, 1H), 4.01 (s, 3H), 3.81-3.74 (m, 4H), 3.48-3.41 (m, 4H) | | | |
| 5 | | 3-{[4-Fluoro-3-(7-morpholin-4-yl-quinazolin-4-yl)phenyl]-hydroxymethyl}-1H-pyrazin-2-one | D | D | B |
| | MS: 434.2 (M + H⁺) | 1H NMR (500 MHz, DMSO-d6) ppm = 9.09 (s, 1H), 7.69-7.59 (m, 2H), 7.56-7.50 (m, 2H), 7.39-7.28 (m, 3H), 7.20 (d, J = 2.1, 1H), 6.00 (s, 1H), 5.87-5.75 (m, 1H), 3.81-3.74 (m, 4H), 3.44 (t, J = 5.0, 4H) | | | |
| 6 | | [2-Chloro-4-fluoro-5-(7-morpholin-4-yl-quinazolin-4-yl)phenyl]-(6-chloro-5-methoxy-pyridazin-3-yl)methanol | A | A | C |
| | MS: 516.1/518.1/520.1 (M + H⁺) (Cl₂ isotopy, rel. peak intensity ratio [%] 100:71:14) | 1H NMR (500 MHz, DMSO-d6) ppm = 9.07 (s, 1H), 7.75 (d, J = 1.0, 1H), 7.72 (d, J = 9.5, 1H), 7.56 (d, J = 7.6, 1H), 7.51 (dd, J = 9.5, 2.5, 1H), 7.47 (dd, J = 9.4, 2.9, 1H), 7.19 (d, J = 2.4, 1H), 6.59 (d, J = 5.0, 1H), 6.13-6.10 (m, 1H), 3.98 (s, 3H), 3.80-3.74 (m, 4H), 3.48-3.41 (m, 4H) | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 7 | 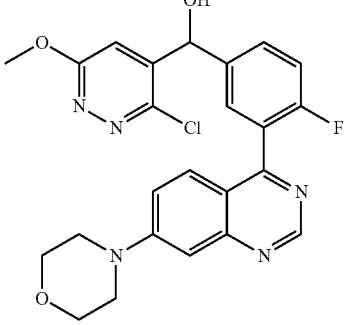 MS: 482.1/484.1 (M + H +) (Cl isotopy, rel. peak intensity ratio [%] 100:39) | (3-Chloro-6-methoxy-pyridazin-4-yl)-[4-fluoro-3-(7-morpholin-4-yl-quinazolin-4-yl)phenyl]-methanol<br><br>1H NMR (500 MHz, DMSO-d6) ppm = 9.09 (s, 1H), 7.62-7.57 (m, 2H), 7.55-7.47 (m, 3H), 7.43-7.39 (m, 1H), 7.20 (d, J = 2.4, 1H), 6.58 (d, J = 4.5, 1H), 5.88 (d, J = 4.4, 1H), 4.04(s, 3H), 3.80-3.75 (m, 4H), 3.46-3.42 (m, 4H) | B | A | B |
| 8 | 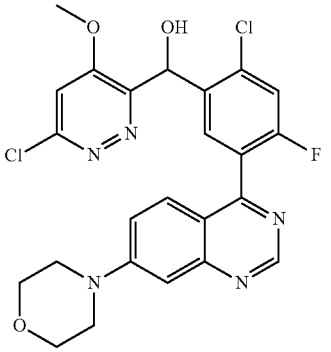 [SMILES: COc1cc(Cl)nnc1C(O)c1cc(-c2ncnc3cc(N4CCOCC4)ccc23)c(F)cc1Cl] MS: 516.1/518.1/520.1 (M + H$^+$) (Cl$_2$ isotopy, rel. peak intensity ratio [%] 100:72:16) | [2-Chloro-4-fluoro-5-(7-morpholin-4-yl-quinazolin-4-yl)phenyl]-(6-chloro-4-methoxy-pyridazin-3-yl)methanol<br><br>1H NMR (500 MHz, DMSO-d6) ppm = 9.13 (s, 1H), 8.01-7.99 (m, 1H), 7.65-7.59 (m, 3H), 7.56 (dd, J = 9.5, 2.5, 1H), 7.22 (d, J = 2.5, 1H), 6.52 (d, J = 6.2, 1H), 6.39 (d, J = 6.2, 1H), 4.02 (s, 3H), 3.80-3.76 (m, 4H), 3.48-3.44 (m, 4H) | C | B | C |
| 9 | 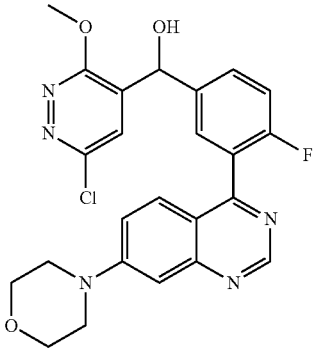 [SMILES: COc1nnc(Cl)cc1C(O)c1ccc(F)c(-c2ncnc3cc(N4CCOCC4)ccc23)c1] MS: 482.1/484.1 (M + H$^+$) (Cl isotopy, rel. peak intensity ratio [%] 100:38) | (6-Chloro-5-methoxy-pyridazin-3-yl)-[4-fluoro-3-(7-morpholin-4-yl-quinazolin-4-yl)phenyl]-methanol<br><br>1H NMR (500 MHz, DMSO-d6) ppm = 9.10 (s, 1H), 7.88 (d, J = 1.0, 1H), 7.63-7.58 (m, 2H), 7.55-7.47 (m, 2H), 7.42-7.35 (m, 1H), 7.20 (d, J = 2.3, 1H), 6.46 (d, J = 4.3, 1H), 5.85-5.82 (m, 1H), 4.00 (s, 3H), 3.81-3.74 (m, 4H), 3.48-3.41 (m, 4H) | B | A | D |

TABLE 1-continued

Compounds of the formula (I)

| Example | Structural formula | Name | IC₅₀ DNA-PK | IC₅₀ pDNA-PK | $K_i$ [Kv1.11 hERG] |
|---|---|---|---|---|---|
| 10 | (structure) MS: 482.1/484.1 (M + H⁺) (Cl isotopy, rel. peak intensity ratio [%] 100:38) | (6-Chloro-4-methoxy-pyridazin-3-yl)-[4-fluoro-3-(7-morpholin-4-yl-quinazolin-4-yl)phenyl]-methanol<br><br>1H NMR (500 MHz, DMSO-d6) ppm = 9.09 (s, 1H), 7.64-7.60 (m, 2H), 7.53-7.51 (m, 3H), 7.40-7.35 (m, 1H), 7.21-7.19 (m, 1H), 6.29 (d, J = 5.3, 1H), 6.18 (d, J = 4.3, 1H), 3.93 (s, 3H), 3.80-3.75 (m, 4H), 3.46-3.42 (m, 4H) | B | A | A |
| 11 | (structure) MS: 448.2 (M + H⁺); R_t 6.1 min (SFC, Chiracel OJ-H, CO₂/15% by vol. of methanol, 0.5% by vol. of diethylamine) | [4-Fluoro-3-(7-morpholin-4-yl-quinazolin-4-yl)phenyl]-(5-methoxy-pyridazin-3-yl)methanol (Ena 1)<br><br>see racemate | B | A | C |
| 12 | (structure) MS: 448.2 (M + H⁺); R_t 8.72 min (SFC, Chiracel OJ-H, CO₂/15% by vol. of methanol, 0.5% by vol. of diethylamine) | [4-Fluoro-3-(7-morpholin-4-yl-quinazolin-4-yl)phenyl]-(5-methoxy-pyridazin-3-yl)methanol (Ena 2)<br><br>see racemate | A | B | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 13 | MS: 490.2 (M + H$^+$) | (3-tert-Butoxy-pyrazin-2-yl)-[4-fluoro-3-(7-morpholin-4-yl-quinazolin-4-yl)phenyl]-methanol | D | D | C |
|  |  | 1H NMR (500 MHz, DMSO-d6) ppm = 9.09 (s, 1H), 8.14 (d, J = 2.7, 1H), 8.08 (d, J = 2.7, 1H), 7.63-7.56 (m, 2H), 7.54-7.47 (m, 2H), 7.40-7.35 (m, 1H), 7.21-7.18 (m, 1H), 5.97 (d, J = 6.0, 1H), 5.91 (d, J = 6.1, 1H), 3.81-3.75 (m, 4H), 3.47-3.41 (m, 4H), 1.47 (s, 9H) |  |  |  |
| 14 | MS: 487.2 (M + H$^+$) | [4-Fluoro-3-(7-morpholin-4-yl-quinazolin-4-yl)phenyl]-(3-pyrrolidin-1-yl-pyrazin-2-yl)methanol | B | B | A |
|  |  | 1H NMR (500 MHz, DMSO-d6) ppm =9.09 (s, 1H), 7.99 (d, J = 2.4, 1H), 7.80 (d, J = 2.5, 1H), 7.58-7.52 (m, 4H), 7.38-7.32 (m, 1H), 7.21-7.17 (m, 1H), 6.18-6.13 (m, 1H), 6.09-6.01 (m, 1H), 3.78 (t, J = 4.9, 4H), 3.68-3.56 (m, 4H), 3.44 (t, J = 4.9, 4H), 1.96-1.81 (m, 4H) |  |  |  |
| 15 | MS: 448.2 (M + H$^+$); Rt 19.73 min, (HPLC, Chiracel OJ-H, methanol) | [4-Fluoro-3-(7-morpholin-4-yl-quinazolin-4-yl)phenyl]-(3-methoxy-pyrazin-2-yl)methanol (Ena 2) | A | A | B |
|  |  | see racemate |  |  |  |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 16 | MS: 448.2 (M + H$^+$); R$_t$ 7.55 min, (HPLC, Chiracel OJ-H, methanol) | [4-Fluoro-3-(7-morpholin-4-yl-quinazolin-4-yl)phenyl]-(3-methoxy-pyrazin-2-yl)methanol (Ena 1)<br><br>see racemate | C | B | A |
| 17 | MS: 485.1/487.1/489.1 (M + H$^+$) (Cl$_2$ isotopy, rel. peak intensity ratio [%] 100:64:11) | (3,5-Dichloro-pyridin-4-yl)-[4-Fluoro-3-(7-morpholin-4-yl-quinazolin-4-yl)phenyl]-methanol<br><br>1H NMR (500 MHz, DMSO-d6) ppm = 9.09 (s, 1H), 8.62 (s, 2H), 7.58-7.48 (m, 4H), 7.43-7.37 (m, 1H), 7.19 (d, J = 2.2, 1H), 6.70-6.65 (m, 1H), 6.52 (d, J = 4.7, 1H), 3.81-3.74 (m, 4H), 3.48-3.40 (m, 4H) | B | B | C |
| 18 | MS: 448.1 (M + H$^+$) | [4-Fluoro-3-(7-morpholin-4-yl-quinazolin-4-yl)phenyl]-(4-methoxy-pyridazin-3-yl)methanol<br><br>1H NMR (500 MHz, DMSO-d6) ppm = 9.11-9.08 (m, 1H), 8.99-8.95 (m, 1H), 7.65-7.59 (m, 2H), 7.55-7.50 (m, 2H), 7.40-7.34 (m, 1H), 7.27 (d, J = 5.9, 1H), 7.22-7.18 (m, 1H), 6.24-6.18 (m, 2H), 3.88 (s, 3H), 3.81-3.74 (m, 4H), 3.48-3.40 (m, 4H) | A | B | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 19 | MS: 448.2 (M + H$^+$) | [4-Fluoro-3-(7-morpholin-4-yl-quinazolin-4-yl)phenyl]-(5-methoxy-pyridazin-3-yl)methanol | A | A | A |
|  |  | 1H NMR (500 MHz, DMSO-d6) ppm = 9.11-9.08 (m, 1H), 8.94-8.90 (m, 1H), 7.80-7.77 (m, 1H), 7.59-7.55 (m, 2H), 7.51 (qd, J = 9.4, 2.5, 2H), 7.41-7.35 (m, 1H), 7.20 (d, J = 2.3, 1H), 6.34-6.31 (m, 1H), 5.87 (d, J = 4.2, 1H), 4.01 (s, 3H), 3.8-3.74 (m, 4H), 3.48-3.40 (m, 4H) |  |  |  |
| 20 | MS: 475.2 (M + H$^+$); R$_t$ 15.12 min (HPLC, Chiralpak AD-H, n-heptane/2-propanol, 1:9 vol./vol.) | [2,4-Difluoro-5-(7-morpholin-4-yl-quinazolin-4-yl)phenyl]-imidazo[1,2-b]pyridazin-6-ylmethanol (Ena 2) | C | C | A |
|  |  | see racemate |  |  |  |
| 21 | MS: 475.2 (M + H$^+$); R$_t$ 8.05 min (HPLC, Chiralpak AD-H, n-heptane/2-propanol, 1:9 vol./vol.) | [2,4-Difluoro-5-(7-morpholin-4-yl-quinazolin-4-yl)phenyl]-imidazo[1,2-b]pyridazin-6-ylmethanol (Ena 1) | A | A | A |
|  |  | - see racemate |  |  |  |

TABLE 1-continued

Compounds of the formula (I)

| Example | Structural formula | Name | IC₅₀ DNA-PK | IC₅₀ pDNA-PK | K$_i$ [Kv1.11 hERG] |
|---|---|---|---|---|---|
| 22 | (structure) | (2-Chloro-5-methoxy-pyridin-3-yl)-[4-fluoro-3-(7-morpholin-4-yl-quinazolin-4-yl)phenyl]-methanol | A | A | D |
| | MS: 481.2/483.2 (M + H⁺) (Cl isotopy, rel. peak intensity ratio [%] 100:30) | 1H NMR (500 MHz, DMSO-d6) ppm = 9.09 (s, 1H), 8.28 (d, J = 2.6, 1H), 7.62-7.55 (m, 3H), 7.55-7.49 (m, 2H), 7.41-7.32 (m, 1H), 7.21-7.18 (m, 1H), 6.16 (d, J = 6.1, 1H), 6.03 (d, J = 6.1, 1H), 3.85 (s, 3H), 3.80-3.75 (m, 4H), 3.47-3.42 (m, 4H) | | | |
| 23 | (structure) | (3-Chloro-pyrazin-2-yl)-[4-fluoro-3-(6-morpholin-4-yl-thieno-[3,2-d]pyrimidin-4-yl)-phenyl]methanol (Ena 1) | C | C | A |
| | MS: 458.1/460.1 (M + H⁺) (Cl isotopy, rel. peak intensity ratio [%] 100:41); R$_t$ 4.96 min (SFC, Chiracel OD-H, CO₂/30% by vol. methanol) | identical to enantiomer (24) | | | |
| 24 | (structure) | (3-Chloro-pyrazin-2-yl)-[4-fluoro-3-(6-morpholin-4-yl-thieno-[3,2-d]pyrimidin-4-yl)-phenyl]methanol (Ena 2) | A | A | B |
| | MS: 458.1/460.1 (M + H⁺) (Cl isotopy, rel. peak intensity ratio [%] 100:40); R$_t$ 7.13 min (SFC, Chiracel OD-H, CO₂/30% by vol. methanol) | 1H NMR (500 MHz, DMSO-d6) ppm = 8.88 (s, 1H), 8.68 (d, J = 2.4, 1H), 8.47 (d, J = 2.4, 1H), 7.73 (dd, J = 7.0, 2.3, 1H), 7.66-7.61 (m, 1H), 7.39 (dd, J = 10.3, 8.6, 1H), 6.52 (s, 1H), 6.39 (d, J = 5.7, 1H), 6.21 (d, J = 5.7, 1H), 3.78-3.71 (m, 4H), 3.44-3.37 (m, 4H). | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 25 | MS: 482.1/484.1 (M + H⁺) (Cl isotopy, rel. peak intensity ratio [%] 100:36) | (6-Chloro-3-methoxy-pyrazin-2-yl)44-fluoro-3-(7-morpholin-4-yl-quinazolin-4-yl)phenyl]-methanol | B | A | D |
| | 1H NMR (500 MHz, DMSO-d6) ppm = 9.11 (s, 1H), 8.30 (s, 1H), 7.65-7.60 (m, 2H), 7.57-7.51 (m, 2H), 7.43-7.36 (m, 1H), 7.22-7.19 (m, 1H), 6.18 (s, 1H), 6.06-6.02 (m, 1H), 3.94 (s, 3H), 3.81-3.75 (m, 4H), 3.47-3.43 (m, 4H) | | | | |
| 26 | MS: 482.1/484.1 (M + H + ) (Cl isotopy, rel. peak intensity ratio [%] 100:35) | (3-Chloro-6-methoxy-pyrazin-2-yl)44-fluoro-3-(7-morpholin-4-yl-quinazolin-4-yl)phenyl]-methanol | A | A | A |
| | 1H NMR (500 MHz, DMSO-d6) ppm = 9.10 (s, 1H), 8.11 (s, 1H), 7.73-7.68 (m, 2H), 7.54-7.50 (m, 2H), 7.44-7.38(m, 1H), 7.21-7.19 (m, 1H), 6.31 (d, J = 5.7, 1H), 6.11 (d, J = 5.8, 1H , 3.89 (s, 3H), 3.80-3.75 (m, 4H), 3.47-3.41 (m, 4H) | | | | |
| 27 | MS: 452.1/454.1 (M + H⁺) (Cl isotopy, rel. peak intensity ratio [%] 100:40); R$_t$ 67.12 min, (HPLC, ChiralPak AD-H, ethanol) | (R)-(3-Chloro-pyrazin-2-yl)-[4-fluoro-3-(7-morpholin-4-yl-quinazolin-4-yl)phenyl]-methanol | A | A | A |
| | see racemate | | | | |

TABLE 1-continued

Compounds of the formula (I)

| Example | Structural formula | Name | IC50 DNA-PK | IC50 pDNA-PK | Ki [Kv1.11 hERG] |
|---|---|---|---|---|---|
| 28 | 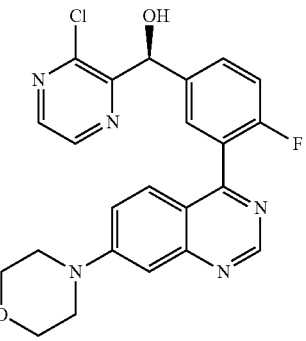<br>MS: 452.1/454.1 (M + H+) (Cl isotopy, rel. peak intensity ratio [%] 100:40); R, 37.09 min, (HPLC, ChiralPak AD-H, ethanol) | (S)-(3-Chloro-pyrazin-2-yl)-[4-fluoro-3-(7-morpholin-4-yl-quinazolin-4-yl)phenyl]-methanol<br><br>see racemate | C | C | B |
| 29 | 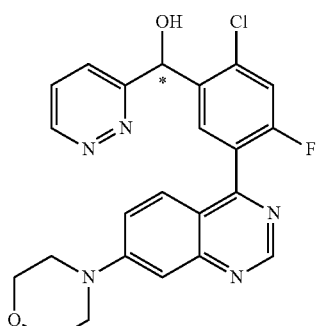<br>MS: 452.1/454.0 (M + H+) (Cl isotopy, rel. peak intensity ratio [%] 100:35); R, 5.61 mm (SFC, ChiralPak IA, CO2/40% by vol. of 2-propanol, 0.5% by vol. of diethylamine) | [2-Chloro-4-fluoro-5-(7-morpholin-4-yl-quinazolin-4-yl)phenyl]-pyridazin-3-ylmethanol (Ena 2)<br><br>1H NMR (500 MHz, DMSO-d6) ppm = 9.14 (dd, J = 4.9, 1.7, 1H), 9.11 (s, 1H), 7.88 (d, J = 7.7, 1H), 7.80 (dd, J = 8.6, 1.7, 1H), 7.72-7.66 (m, 2H), 7.58 (dd, J = 9.4, 3.3, 1H), 7.53 (dd, J = 9.5, 2.5, 1H), 7.21 (d, J = 2.4, 1H), 6.71 (d, J = 5.0, 1 H), 6.32 (d, J = 4.9, 1H), 3.80-3.75 (m, 4H), 3.47-3.43 (m, 4H) | C | D | B |
| 30 | 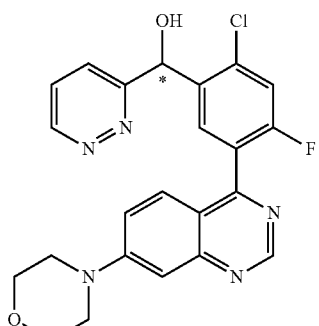<br>MS: 474.1/476.1 (M + Na+) (Cl isotopy, rel. peak intensity ratio [%] 100:34); R, 2.87min (SFC, ChiralPak IA, CO2/40% by vol. of 2-propanol, 0.5% by vol. of diethylamine) | [2-Chloro-4-fluoro-5-(7-morpholin-4-yl-quinazolin-4-yl)phenyl]-pyridazin-3-ylmethanol (Ena 1)<br><br>1H NMR (500 MHz, DMSO-d6) ppm = 9.14 (dd, J = 4.9, 1.7, 1H), 9.11 (s, 1H), 7.88 (d, J = 7.7, 1H), 7.80 (dd, J = 8.6, 1.7, 1H), 7.73-7.66 (m, 2H), 7.58 (dd, J = 9.4, 3.3, 1H), 7.53 (dd, J = 9.5, 2.5, 1H), 7.21 (d, J = 2.4, 1H), 6.71 (d, J = 5.0, 1H), 6.32 (d, J = 4.9, 1H), 3.80-3.75 (m, 4H), 3.48-3.42 (m, 4H) | A | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 31 | 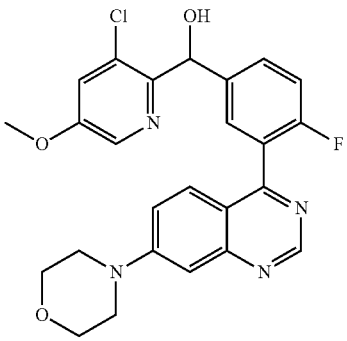 [SMILES: COc1cnc(C(O)c2ccc(F)c(-c3ncnc4cc(N5CCOCC5)ccc34)c2)c(Cl)c1] MS: 481.1/482.1 (M + H$^+$) (Cl isotopy, rel. peak intensity ratio [%] 100:30) | (3-Chloro-5-methoxy-pyridin-2-yl)-[4-fluoro-3-(7-morpholin-4-yl-quinazolin-4-yl)phenyl]-methanol  1H NMR (500 MHz, DMSO-d6) ppm = 9.09 (s, 1H), 8.28 (d, J = 2.6, 1H), 7.62-7.55 (m, 3H), 7.55-7.49 (m, 2H), 7.41-7.32 (m, 1H), 7.21-7.18 (m, 1H), 6.16 (d, J = 6.1, 1H), 6.03 (d, J = 6.1, 1H), 3.85 (s, 3H), 3.80-3.75 (m, 4H), 3.47-3.42 (m, 4H) | A | A | C |
| 32 | 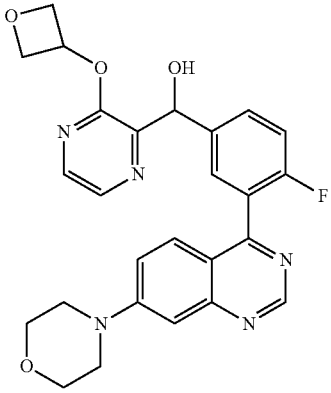 [SMILES: OC(c1ccc(F)c(-c2ncnc3cc(N4CCOCC4)ccc23)c1)c1nccnc1OC1COC1] MS: 490.2 (M + H$^+$) | [4-fluoro-3-(7-morpholin-4-yl-quinazolin-4-yl)phenyl]-[3-(oxetan-3-yloxy)-pyrazin-2-yl]methanol  1H NMR (500 MHz, DMSO-d6) ppm = 9.09 (s, 1H), 8.24 (d, J = 2.7, 1H), 8.09 (d, J = 2.8, 1H), 7.71-7.64 (m, 2H), 7.54-7.51 (m, 2H), 7.42-7.36 (m, 1H), 7.22-7.19 (m, 1H), 6.15-6.11 (m, 2H), 5.63-5.58 (m, 1H), 4.88-4.83 (m, 2H), 4.58-4.52 (m, 2H), 3.80-3.75 (m, 4H), 3.47-3.41 (m, 4H) | C | C | B |
| 33 | 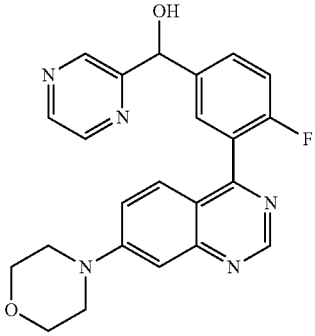 [SMILES: OC(c1ccc(F)c(-c2ncnc3cc(N4CCOCC4)ccc23)c1)c1cnccn1] MS: 418.1 (M + H$^+$) | [4-Fluoro-3-(7-morpholin-4-yl-quinazolin-4-yl)phenyl]-pyrazin-2-ylmethanol  1H NMR (400 MHz, DMSO-d6) ppm = 9.11 (s, 1H), 8.89 (d, J = 1.5, 1H), 8.59-8.53 (m, 2H), 7.71-7.65 (m, 2H), 7.57-7.50 (m, 2H), 7.44-7.37 (m, 1H), 7.21-7.19 (m, 1H), 5.94 (s, 1H), 3.81-3.75 (m, 4H), 3.49-3.44 (m, 4H) | C | D | D |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
| --- | --- | --- | --- | --- | --- |
| 34 | 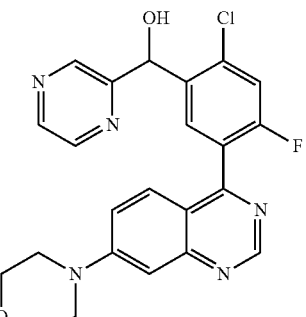 MS: 452.1/454.1 (M + H$^+$) (Cl isotopy, rel. peak intensity ratio [%] 100:36) | [2-Chloro-4-fluoro-5-(7-morpholin-4-yl-quinazolin-4-yl)phenyl]-pyrazin-2-ylmethanol  1H NMR (500 MHz, DMSO-d6) ppm = 9.11 (s, 1H), 8.86 (d, J = 1.3, 1H), 8.58-8.55 (m, 2H), 7.88 (d, J = 7.7, 1H), 7.66 (d, J = 9.5, 1H), 7.60-7.52 (m, 2H), 7.21 (d, J = 2.3, 1H), 6.62 (d, J = 4.9, 1H), 6.19 (d, J = 4.8, 1H), 3.80-3.75 (m, 4H), 3.49-3.42 (m, 4H) | C | C | B |
| 35 | 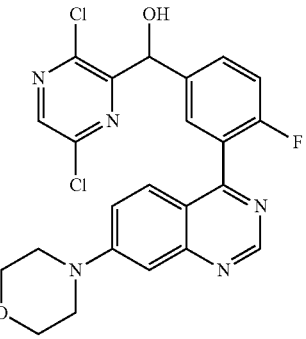 MS: 486.1/488.1/490.0 (M + H$^+$) (Cl$_2$ isotopy, rel. peak intensity ratio [%] 100:65:15) | (3,6-Dichloro-pyrazin-2-yl)-[4-fluoro-3-(7-morpholin-4-yl-quinazolin-4-yl)phenyl]-methanol  1H NMR (500 MHz, DMSO-d6) ppm = 9.10 (s, 1H), 8.63 (s, 1H), 7.68-7.64 (m, 2H), 7.55-7.51 (m, 2H), 7.45-7.40 (m, 1H), 7.20 (d J = 2.1, 1H), 6.51 (d, J = 5.5, 1H), 6.18 (d, J = 5.5, 1H , 3.81-3.75 (m, 4H), 3.48-3.41 (m, 4H) | A | A | C |
| 36 | 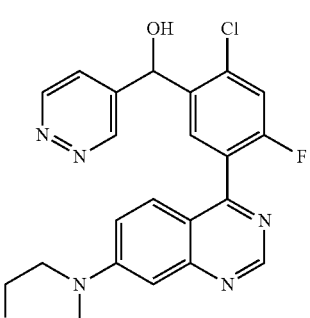 MS: 452.1/454.1 (M + H$^+$) (Cl isotopy, rel. peak intensity ratio [%] 100:33) | [2-Chloro-4-fluoro-5-(7-morpholin-4-yl-quinazolin-4-yl)phenyl]-pyridazin-4-ylmethanol  1H NMR (500 MHz, DMSO-d6) ppm = 9.27-9.25 (m, 1H), 9.19 (dd, J = 5.3, 1.2, 1H), 9.11 (s, 1H), 7.89 (d, J = 7.6, 1H), 7.72 (d, J = 9.5, 1H), 7.62-7.56 (m, 2H), 7.53 (dd, J = 9.4, 2.5, 1H), 7.21 (d, J = 2.4, 1H), 6.72 (s, 1H), 6.13 (s, 1H), 3.81-3.75 (m, 4H), 3.48-3.43 (m, 4H) | A | A | A |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 37 | 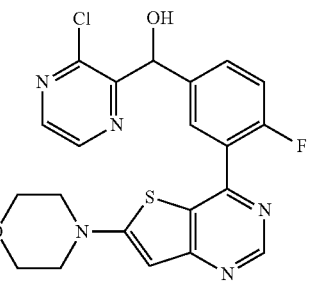 MS: 458.1/460.1 (M + H⁺) (Cl isotopy, rel. peak intensity ratio [%] 100:39) | (3-Chloro-pyrazin-2-yl)-[4-fluoro-3-(6-morpholin-4-ylthieno-[3,2-d]pyrimidin-4-yl)-phenyl]methanol  1H NMR (500 MHz, DMSO-d6) ppm = 8.88 (s, 1H), 8.68 (d, J = 2.4, 1H), 8.47 (d, J = 2.4, 1H), 7.73 (dd, J = 7.0, 2.3, 1H), 7.66-7.61 (m, 1H), 7.43-7.35 (m, 1H), 6.52 (s, 1H), 6.39 (d, J = 5.7, 1H), 6.21 (d, J = 5.6, 1H), 3.77-3.71 (m, 4H), 3.44-3.37 (m, 4H) | A | A | C |
| 38 | 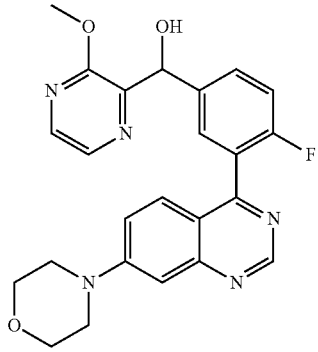 [SMILES: COc1nccnc1C(O)c1ccc(F)c(-c2ncnc3cc(N4CCOCC4)ccc23)c1] MS: 448.2 (M + H⁺) | [4-Fluoro-3-(7-morpholin-4-yl-quinazolin-4-yl)phenyl]-(3-methoxy-pyrazin-2-yl)methanol  1H NMR (500 MHz, DMSO-d6) ppm = 9.09 (s, 1H), 8.19 (d, J = 2.7, 1H), 8.15 (d, J = 2.7, 1H), 7.64-7.59 (m, 2H), 7.55-7.50 (m, 2H), 7.39-7.34 (m, 1H), 7.21-7.18 (m, 1H), 6.08 (d, J = 5.9, 1H), 6.04 (d, J = 5.9, 1H), 3.93 (s, 3H), 3.80-3.75 (m, 4H), 3.47-3.42 (m, 4H) | A | A | A |
| 39 | 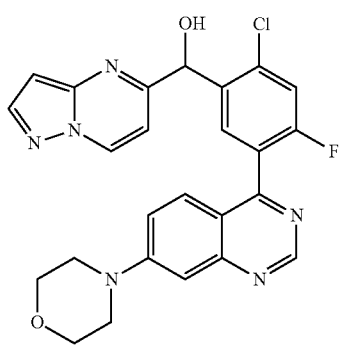 [SMILES: OC(c1ccn2nccc2n1)c1cc(-c2ncnc3cc(N4CCOCC4)ccc23)c(F)cc1Cl] MS: 491.1/493.1 (M + H⁺) (Cl isotopy, rel. peak intensity ratio [%] 100:38) | [2-Chloro-4-fluoro-5-(7-morpholin-4-yl-quinazolin-4-yl)phenyl]-pyrazolo[1,5-a]-pyrimidin-5-ylmethanol  1H NMR (500 MHz, DMSO-d6) ppm = 9.11 (s, 1H), 9.08 (dd, J = 7.2, 0.9, 1H), 8.19 (d, J = 2.4, 1H), 7.87 (d, J = 7.7, 1H), 7.69 (d, J = 9.5, 1H), 7.58 (dd, J = 9.4, 3.2, 1H), 7.52 (dd, J = 9.5, 2.5, 1H), 7.21 (d, J = 2.5, 1H), 7.17 (d, J = 7.3, 1H), 6.71 (d, J = 5.0, 1H), 6.67 (dd, J = 2.3, 0.9, 1H), 6.11 (d, J = 4.8, 1H), 3.82-3.74 (m, 4H), 3.49-3.41 (m, 4H) | B | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 40 | 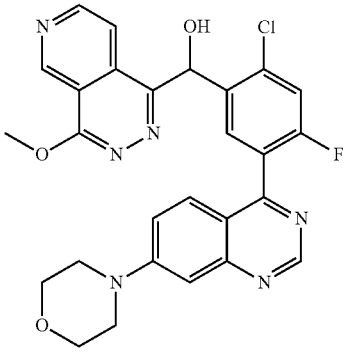 [SMILES: COc1nnc(C(O)c2cc(-c3ncnc4cc(N5CCOCC5)ccc34)c(F)cc2Cl)c2ccncc12] MS: 533.2/535.2 (M + H$^+$) (Cl isotopy, rel. peak intensity ratio [%] 100:38) | [2-Chloro-4-fluoro-5-(7-morpholin-4-yl-quinazolin-4-yl)phenyl]-(4-methoxypyrido-[3,4-d]pyridazin-1-yl)-methanol<br><br>1H NMR (400 MHz, DMSO-d6) ppm = 9.97 (s, 1H), 9.15 (s, 1H), 9.11 (d, J = 5.5, 1H), 8.10-8.02 (m, 2H), 7.73-7.62 (m, 2H), 7.57 (dd, J = 9.5, 2.5, 1H), 7.23 (d, J = 2.4, 1H), 6.95-6.87(m, 2H), 4.18 (s, 3H), 3.84-3.74 (m, 4H), 3.52-3.41 (m, 4H) | C | B | C |
| 41 | 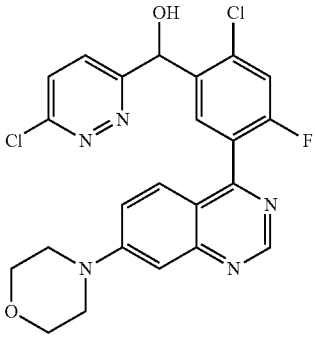 [SMILES: OC(c1ccc(Cl)nn1)c1cc(-c2ncnc3cc(N4CCOCC4)ccc23)c(F)cc1Cl] MS: 486.0/488.1/490.0 (M + H$^+$) (Cl$_2$ isotopy, rel. peak intensity ratio [%] 100:67:17) | [2-Chloro-4-fluoro-5-(7-morpholin-4-yl-quinazolin-4-yl)phenyl]-(6-chloro-pyridazin-3-yl)methanol<br><br>1H NMR (400 MHz, DMSO-d6) ppm = 9.11 (s, 1H), 7.92-7.90 (m, 2H), 7.90-7.87 (m, 1H), 7.69 (d, J = 9.5, 1H), 7.58 (dd, J = 9.4, 3.2, 1H), 7.53 (dd, J = 9.5, 2.4, 1H), 7.20 (d, J = 2.3, 1H), 6.86 (d, J = 5.0, 1H), 6.32 (d, J = 4.5, 1H), 3.81-3.74 (m, 4H), 3.48-3.43 (m, 4H) | B | A | B |
| 42 | 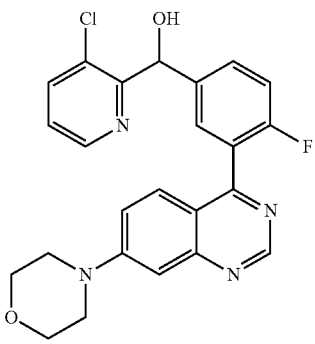 [SMILES: OC(c1ccc(F)c(-c2ncnc3cc(N4CCOCC4)ccc23)c1)c1ncccc1Cl] MS: 451.1/452.1 (M + H$^+$) (Cl isotopy, rel. peak intensity ratio [%] 100:35) | (3-Chloro-pyridin-2-yl)-[4-fluoro-3-(7-morpholin-4-yl-quinazolin-4-yl)phenyl]-methanol<br><br>1H NMR (500 MHz, DMSO-d6) ppm = 9.09 (s, 1H), 8.56 (dd, J = 4.6, 1.4, 1H), 7.92 (dd, J = 8.1, 1.4, 1H), 7.64-7.59 (m, 2H), 7.54-7.49 (m, 2H), 7.40-7.34 (m, 2H), 7.22-7.17 (m, 1H), 6.21 (s, 1H), 6.18-6.09 (m, 1H), 3.81-3.73 (m, 4H), 3.48-3.40 (m, 4H) | A | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 43 | | 6-([2-Chloro-4-fluoro-5-(7-morpholin-4-yl-quinazolin-4-yl)phenyl]-hydroxymethyl}-pyridazine-3-carboxylic acid methylamide | B | B | A |
| | MS: 531.2/533.2 (M + Na$^+$) (Cl isotopy, rel. peak intensity ratio [%] 100:39) | 1H NMR (500 MHz, DMSO-d6) ppm = 9.14 (q, J = 4.7, 1H), 9.11 (s, 1H), 8.19 (d, J = 8.7, 1H), 7.99 (d, J = 8.7, 1H), 7.87 (d, J = 7.7, 1H), 7.69 (d, J = 9.5, 1H), 7.58-7.51 (m, 2H), 7.22-7.19 (m, 1H), 6.84 (s, 1H), 6.42 (s, 1H), 3.80-3.76 (m, 4H), 3.47-3.42 (m, 4H), 2.85 (d, J = 4.7, 3H) | | | |
| 44 | | 6-{[2-Chloro-4-fluoro-5-(7-morpholin-4-yl-quinazolin-4-yl)phenyl]-hydroxymethyl}-2-methyl-2H-pyridazin-3-one (Ena 2) | C | C | B |
| | MS: 482.0/484.1 (M + H$^+$) (Cl isotopy, rel. peak intensity ratio [%] 100:35) R$_t$ 5.91 min, (SFC, Chiralcel OJ-H,CO$_2$/20% by vol. of methanol, 0.5% by vol. of diethylamine) | 1H NMR (500 MHz, DMSO-d6) ppm = 9.12 (s, 1H), 7.93 (d, J = 7.7, 1H), 7.68 (d, J = 9.5, 1H), 7.61-7.52 (m, 2H), 7.48 (d, J = 9.6, 1H), 7.21 (d, J = 2.4, 1H), 6.93 (d, J = 9.6, 1H), 6.60 (d, J = 4.8, 1H), 5.89 (d, J = 4.8, 1H), 3.80-3.75 (m, 4H), 3.59 (s, 3H), 3.48-3.43 (m, 4H) | | | |
| 45 | | 6-([2-Chloro-4-fluoro-5-(7-morpholin-4-yl-quinazolin-4-yl)phenyl]-hydroxymethyl}-2-methyl-2H-pyridazin-3-one (Ena 1) | A | A | B |
| | MS: 482.1/484.1 (M + H$^+$) (Cl isotopy, rel. peak intensity ratio [%] 100:35) ) R$_t$ 4.10 min, (SFC, Chiralcel OJ-H, CO$_2$/20% by vol. of methanol, 0.5% by vol. of diethylamine) | 1H NMR (500 MHz, DMSO-d6) ppm = 9.12 (s, 1H), 7.93 (d, J = 7.7, 1H), 7.68 (d, J = 9.5, 1H), 7.60-7.52 (m, 2H), 7.48 (d, J = 9.6, 1H), 7.21 (d, J = 2.4, 1H), 6.93 (d, J = 9.6, 1H), 6.60 (d, J = 4.9, 1H), 5.89 (d, J = 4.8, 1H), 3.81-3.75 (m, 4H), 3.59 (s, 3H), 3.48-3.42 (m, 4H) | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 46 | 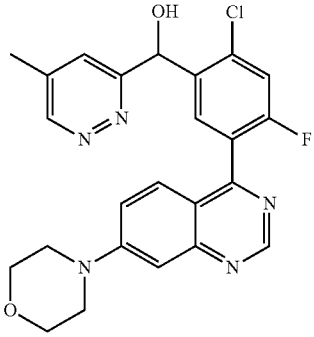 [SMILES: Cc1cnnc(C(O)c2cc(-c3ncnc4cc(N5CCOCC5)ccc34)c(F)cc2Cl)c1] MS: 488.1/490.2 (M + Na$^+$) (Cl isotopy, rel. peak intensity ratio [%] 100:32) | [2-Chloro-4-fluoro-5-(7-morpholin-4-yl-quinazolin-4-yl)phenyl]-(5-methylpyridazin-3-yl)methanol  1H NMR (500 MHz, DMSO-d6) ppm = 9.11 (s, 1H), 9.00 (d, J = 2.0, 1H), 7.87 (d, J = 7.7, 1H), 7.67 (d, J = 9.5, 1H), 7.63-7.61 (m, 1H), 7.58 (dd, J = 9.4, 3.3, 1H), 7.53 (dd, J = 9.5, 2.5, 1H), 7.21 (d, J = 2.4, 1H), 6.65 (d, J = 4.9, 1H), 6.28 (d, J = 4.9, 1H), 3.80-3.75 (m, 4H), 3.48-3.42 (m, 4H), 2.32 (s, 3H) | C | C | B |
| 47 | 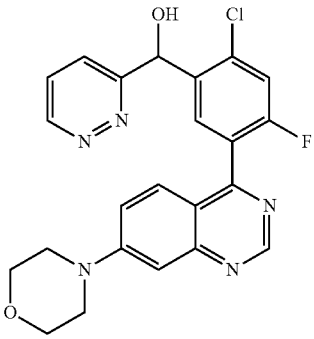 MS: 452.1/454.1 (M + H$^+$) (Cl isotopy, rel. peak intensity ratio [%] 100:39) | [2-Chloro-4-fluoro-5-(7-morpholin-4-yl-quinazolin-4-yl)phenyl]-pyridazin-3-ylmethanol  1H NMR (500 MHz, DMSO-d6) ppm = 9.16-9.12 (m, 1H), 9.12-9.09 (m, 1H), 7.91-7.86 (m, 1H), 7.81-7.77 (m, 1H), 7.73-7.65 (m, 2H), 7.61-7.56 (m, 1H), 7.55-7.51 (m, 1H), 7.23-7.19 (m, 1H), 6.72-6.69 (m, 1H), 6.34-6.30 (m, 1H), 3.81-3.75 (m, 4H), 3.48-3.42 (m, 4H) | B | A | A |
| 48 | 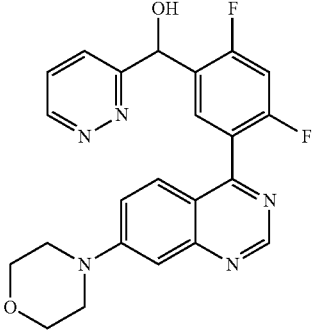 MS: 436.2 (M + H$^+$) | [2,4-Difluoro-5-(7-morpholin-4-yl-quinazolin-4-yl)phenyl]-pyridazin-3-ylmethanol  1H NMR (500 MHz, DMSO-d6) ppm = 9.14 (dd, J = 4.9, 1.6, 1H), 9.10 (s, 1H), 7.86 (dd, J = 8.5, 1.6, 1H), 7.81 (t, J = 8.1, 1H), 7.72 (dd, J = 8.5, 4.9, 1H), 7.58-7.51 (m, 2H), 7.46 (t, J = 10.1, 1H), 7.20 (d, J = 2.3, 1H), 6.66 (d, J = 4.9, 1H), 6.26 (d, J = 4.9, 1H), 3.81-3.75 (m, 4H), 3.45 (t, J = 4.9, 4H) | B | B | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 49 | | (6-Chloro-pyridazin-3-yl)-[2,4-difluoro-5-(7-morpholin-4-yl-quinazolin-4-yl)phenyl]-methanol | A | B | A |
| | MS: 470.1/471.1 (M + H$^+$) (Cl isotopy, rel. peak intensity ratio [%] 100:35) | 1H NMR (500 MHz, DMSO-d6) ppm = 9.10 (s, 1H), 7.98-7.91 (m, 2H), 7.82 (t, J = 8.1, 1H), 7.58-7.51 (m, 2H), 7.47(t, J = 10.1, 1H), 7.20 (d, J = 2.3, 1H), 6.78 (d, J = 4.9, 1H), 6.26 (d, J = 4.6, 1H), 3.82-3.74 (m, 4H), 3.48-3.41 (m, 4H) | | | |
| 50 | | 6-1[2-Chloro-4-fluoro-5-(7-morpholin-4-yl-quinazolin-4-yl)phenyl]-hydroxymethyl]-pyridazine-3-carboxylic acid dimethylamide | C | D | A |
| | MS: 523.2/525.2 (M + H$^+$) (Cl isotopy, rel. peak intensity ratio [%] 100:35) | 1H NMR (500 MHz, chloroform-d) ppm = 9.15 (s, 1H), 7.85 (d, J = 8.7, 1H), 7.79 (d, J = 7.4, 1H), 7.65 (d, J = 8.7, 1H), 7.56 (dd, J = 9.3, 3.3, 1H), 7.36 (d, J = 9.0, 1H), 7.27 (d, J = 2.5, 1H), 7.22 (d, J = 2.5, 1H), 6.54 (s, 1H), 4.99 (s, 1H), 3.92-3.87 (m, 4H), 3.46-3.42 (m, 4H), 3.22 (s, 3H), 3.19 (s, 3H) | | | |
| 51 | | [2,4-Difluoro-5-(7-morpholin-4-yl-quinazolin-4-yl)phenyl]-imidazo[1,2-b]pyridazin-6-ylmethanol | A | A | B |
| | MS: 475.2 (M + H$^+$) | 1H NMR (500 MHz, DMSO-d6) ppm = 9.12 (s, 1H), 8.26 (s, 1H), 8.12 (d, J = 9.5, 1H), 7.92 (t, J = 8.1, 1H), 7.77 (s, 1H), 7.61-7.51 (m, 2H), 7.48 (t, J = 10.1, 1H), 7.35 (d, J = 9.5, 1H), 7.21 (d, J = 2.4, 1H), 6.75 (d, J = 4.9, 1H), 6.10 (d, J = 4.7, 1H), 3.78 (t, J = 4.9, 4H), 3.45 (t, J = 4.9, 4H) | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 52 | 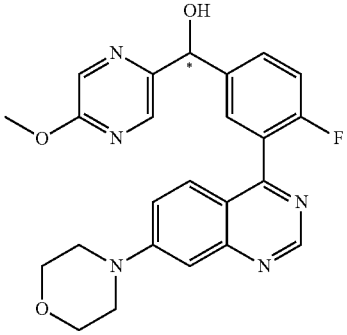 MS: 448.2 (M + H$^+$); R$_t$ 16.15 min, (HPLC, 2 × Chiralcel OJ-H, methanol) | [4-Fluoro-3-(7-morpholin-4-yl-quinazolin-4-yl)phenyl]-(5-methoxy-pyrazin-2-yl)methanol (Ena 1)  1H NMR (500 MHz, DMSO-d6) ppm = 9.09 (s, 1H), 8.39-8.38 (m, 1H), 8.23 (d, J = 1.3, 1H), 7.66-7.61 (m, 2H), 7.55-7.50 (m, 2H), 7.40-7.35 (m, 1H), 7.21-7.18 (m, 1H), 6.30 (d, J = 4.4, 1H), 5.88 (d, J = 4.4, 1H), 3.89 (s, 3H), 3.80-3.75 (m, 4H), 3.46-3.42 (m, 4H) | B | C | A |
| 53 | 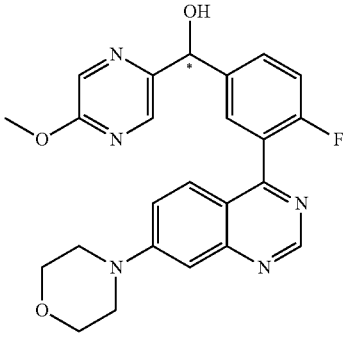 MS: 448.2 (M + H$^+$); R$_t$ 19.06 min, (HPLC, 2 × Chiralcel OJ-H, methanol) | [4-Fluoro-3-(7-morpholin-4-yl-quinazolin-4-yl)phenyl]-(5-methoxy-pyrazin-2-yl)methanol (Ena 2)  1H NMR (500 MHz, DMSO-d6) ppm = 9.09 (s, 1H), 8.39-8.38 (m, 1H), 8.23 (d, J = 1.3, 1H), 7.66-7.61 (m, 2H), 7.55-7.50 (m, 2H), 7.40-7.35 (m, 1H), 7.21-7.18 (m, 1H), 6.30 (d, J = 4.4, 1H), 5.88 (d, J = 4.4, 1H), 3.89 (s, 3H), 3.80-3.75 (m, 4H), 3.46-3.42 (m, 4H) | B | C | A |
| 54 | 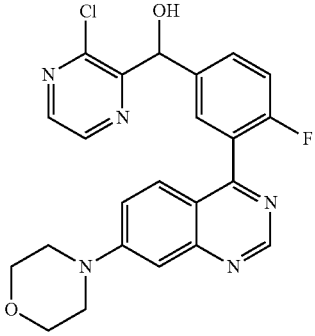 MS: 452.1/453.1 (M + H$^+$) (Cl isotopy, rel. peak intensity ratio [%] 100:35) | S(3-Chloro-pyrazin-2-yl)-[4-fluoro-3-(7-morpholin-4-yl-quinazolin-4-yl)phenyl]-methanol  1H NMR (500 MHz, DMSO-d6) ppm = 9.09 (s, 1H), 8.69 (d, J = 2.4, 1H), 8.46 (d, J = 2.4, 1H), 7.67-7.63 (m, 2H), 7.54-7.52 (m, 2H), 7.43-7.37 (m, 1H), 7.20-7.19 (m, 1H), 6.39 (d, J = 5.7, 1H), 6.23 (d, J = 5.7, 1H), 3.79-3.76 (m, 4H), 3.46-3.42 (m, 4H) | A | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 55 | 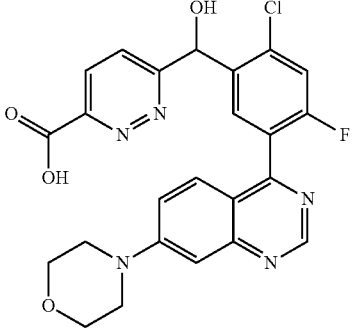 [SMILES: O=C(O)c1ccc(C(O)c2cc(-c3ncnc4cc(N5CCOCC5)ccc34)c(F)cc2Cl)nn1] MS: 496.1/498.0 (M + H$^+$) (Cl isotopy, rel. peak intensity ratio [%] 100:36) | 6-{[2-Chloro-4-fluoro-5-(7-morpholin-4-yl-quinazolin-4-yl)phenyl]-hydroxymethyl]-pyridazine-3-carboxylic acid<br><br>1H NMR (500 MHz, DMSO-d6) ppm = 13.30 (s, 1H), 9.11 (s, 1H), 8.21 (d, J = 8.7, 1H), 7.99 (d, J = 8.7, 1H), 7.87 (d, J = 7.6, 1H), 7.71 (d, J = 9.5, 1H), 7.55 (qd, J = 9.4, 2.7, 2H), 7.20 (d, J = 2.3, 1H), 7.08-6.66 (m, 1H), 6.42(s, 1H), 3.80-3.75 (m, 4H), 3.49-3.44 (m, 4H) | B | D | A |
| 56 | 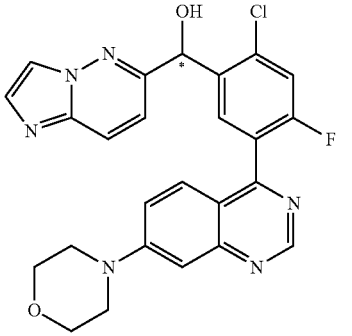 MS: 491.1/493.1 (M + H$^+$) (Cl isotopy, rel. peak intensity ratio [%] 100:34); R$_t$ 13.59 min (SFC, Chiralpak AD-H, CO$_2$/ 40% by vol. of methanol, 0.5% by vol. of diethylamine) | [2-Chloro-4-fluoro-5-(7-morpholin-4-yl-quinazolin-4-yl)phenyl]-imidazo[1,2-b]pyridazin-6-ylmethanol (Ena 2)<br><br>see racemate | B | B | C |
| 57 | 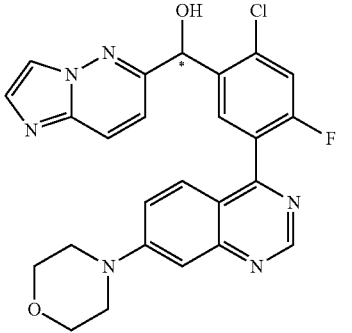 MS: 491.1/493.1 (M + H$^+$) (Cl isotopy, rel. peak intensity ratio [%] 100:36); R$_t$ 3.87 min (SFC, Chiralpak AD-H, CO$_2$/ 40% by vol. of methanol, 0.5% by vol. of diethylamine) | [2-Chloro-4-fluoro-5-(7-morpholin-4-yl-quinazolin-4-yl)phenyl]-imidazo[1,2-b]pyridazin-6-ylmethanol (Ena 1)<br><br>see racemate | A | A | C |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 58 | | 6-{[2-Chloro-4-fluoro-5-(7-morpholin-4-yl-quinazolin-4-yl)phenyl]-hydroxymethyl}-pyridazine-3-carboxylic acid methyl ester | B | C | A |
| | MS: 510.1/512.1 (M + H⁺) (Cl isotopy, rel. peak intensity ratio [%] 100:33) | 1H NMR (500 MHz, DMSO-d6) ppm = 9.11 (s, 1H), 8.23 (d, J = 8.7, 1H), 8.01 (d, J = 8.7, 1H), 7.86 (d, J = 7.6, 1H), 7.70 (d, J = 9.5, 1H), 7.55 (qd, J = 9.4, 2.8, 2H), 7.20 (d, J = 2.4, 1H), 6.94-6.81 (m, 1H), 6.42 (s, 1H), 3.94 (s, 3H), 3.81-3.75 (m, 4H), 3.48-3.42 (m, 4H) | | | |
| 59 | | 6-{[2-Chloro-4-fluoro-5-(7-morpholin-4-yl-quinazolin-4-yl)phenyl]-hydroxymethyl}-2-methyl-2H-pyridazin-3-one | A | B | B |
| | MS: 482.1/484.1 (M + H⁺) (Cl isotopy, rel. peak intensity ratio [%] 100:45) | 1H NMR (500 MHz, DMSO-d6) ppm = 9.12 (s, 1H), 7.92 (d, J = 7.7, 1H), 7.68 (d, J = 9.5, 1H), 7.59 (dd, J = 9.4, 3.1, 1H), 7.55 (dd, J = 9.4, 2.5, 1H), 7.49 (d, J = 9.6, 1H), 7.21 (d, J = 2.4, 1H), 6.95 (d, J = 9.6, 1H), 6.68 (d, J = 4.8, 1H), 5.90 (d, J = 3.6, 1H), 3.80-3.77 (m, 4H), 3.61-3.58 (m, 3H), 3.45 (s, 4H) | | | |
| 60 | | [4-Fluoro-3-(7-morpholin-4-yl-quinazolin-4-yl)phenyl]-(5-methoxypyrazin-2-yl)methanol | C | B | B |
| | MS: 448.2 (M + H⁺) | 1H NMR (500 MHz, DMSO-d6) ppm = 9.09 (s, 1H), 8.39-8.38 (m, 1H), 8.23 (d, J = 1.3, 1H), 7.66-7.61 (m, 2H), 7.55-7.50 (m, 2H), 7.40-7.35 (m, 1H), 7.21-7.18 (m, 1H), 6.30 (d, J = 4.4, 1H), 5.88 (d, J = 4.4, 1H), 3.89 (s, 3H), 3.80-3.75 (m, 4H), 3.46-3.42 (m, 4H) | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 61 |  MS: 460.2 (M + H$^+$) | [4-methoxy-3-(7-morpholin-4-yl-quinazolin-4-yl)phenyl]-(5-methoxypyrazin-2-yl)methanol<br><br>1H NMR (500 MHz, DMSO-d6) ppm = 9.04 (s, 1H), 8.36-8.35 (m, 1H), 8.20 (d, J = 1.4, 1H), 7.53 (dd, J = 8.6, 2.3, 1H), 7.44 (dd, J = 9.4, 2.5, 1H), 7.38 (d, J = 9.4, 1H), 7.35 (d, J = 2.2, 1H), 7.17 (d, J = 8.6, 1H), 7.14 (d, J = 2.5, 1H), 6.13 (d, J = 4.4, 1H), 5.79 (d, J = 4.4, 1H), 3.88 (s, 3H), 3.79-3.75 (m, 4H), 3.66 (s, 3H), 3.43-3.38 (m, 4H) | D | D | A |
| 62 | 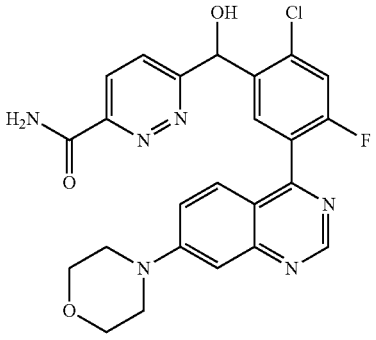 [SMILES: NC(=O)c1ccc(C(O)c2cc(-c3ncnc4cc(N5CCOCC5)ccc34)c(F)cc2Cl)nn1] MS: 495.1/497.1 (M + H$^+$) (Cl isotopy, rel. peak intensity ratio [%] 100:35) | 6-{[2-Chloro-4-fluoro-5-(7-morpholin-4-yl-quinazolin-4-yl)phenyl]-hydroxymethyl}-pyridazine-3-carboxylic acid amide<br><br>1H NMR (500 MHz, DMSO-d6) ppm = 9.11 (s, 1H), 8.49 (s, 1H), 8.20 (d, J = 8.7, 1H), 8.00 (d, J = 8.7, 1H), 7.91-7.85 (m, 2H), 7.69 (d, J = 9.5, 1H), 7.59-7.51 (m, 2H), 7.21 (d, J = 2.2, 1H), 6.84 (d, J = 5.0, 1H), 6.42 (d, J = 5.0, 1H), 3.80-3.75 (m, 4H), 3.48-3.42 (m, 4H) | B | B | A |
| 63 | 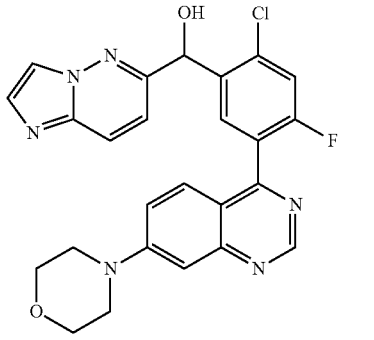 [SMILES: OC(c1ccc2nccn2n1)c1cc(-c2ncnc3cc(N4CCOCC4)ccc23)c(F)cc1Cl] MS: 491.1/493.1 (M + H$^+$) (Cl isotopy, rel. peak intensity ratio [%] 100:38) | [2-Chloro-4-fluoro-5-(7-morpholin-4-yl-quinazolin-4-yl)phenyl]-imidazo[1,2-b]pyridazin-6-ylmethanol<br><br>1H NMR (500 MHz, DMSO-d6) ppm = 9.13 (s, 1H), 8.27-8.25 (m, 1H), 8.11 (dd, J = 9.4, 0.7, 1H), 8.00 (d, J = 7.7, 1H), 7.77 (d, J = 1.2, 1H), 7.70 (d, J = 9.5, 1H), 7.61 (dd, J = 9.4, 3.3, 1H), 7.55 (dd, J = 9.4, 2.5, 1H), 7.30 (d, J = 9.5, 1H), 7.22 (d, J = 2.5, 1H), 6.81 (d, J = 4.5, 1H), 6.15 (d, J = 4.2, 1H , 3.81-3.75 (m, 4H), 3.48-3.44 (m, 4H) | A | B | C |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 64 | 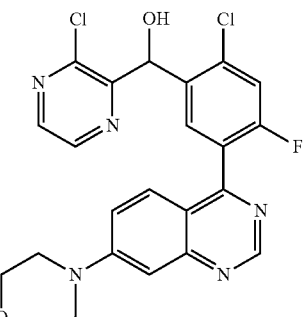<br>MS: 486.1/488.1/490.0 (M + H$^+$) (Cl$_2$ isotopy, rel. peak intensity ratio [%] 100:63:11) | [2-Chloro-4-fluoro-5-(7-morpholin-4-yl-quinazolin-4-yl)phenyl]-(3-chloropyrazin-2-yl)-methanol<br><br>1H NMR (500 MHz, DMSO-d6) ppm = 9.14(s, 1H), 8.61 (d, J = 2.4, 1H), 8.49 (d, J = 2.4, 1H), 8.00 (d, J = 7.7, 1H), 7.66 (d, J = 9.5, 1H), 7.64-7.55 (m, 2H), 7.22 (d, J = 2.4, 1H), 6.70 (d, J = 6.0, 1H), 6.42 (d, J = 6.0, 1H), 3.81-3.76 (m, 4H), 3.49-3.44 (m, 4H) | B | A | C |
| 65 | 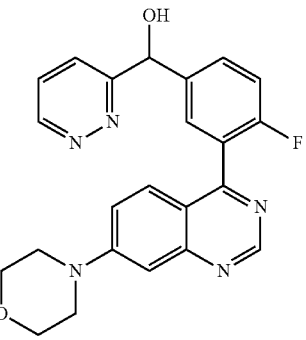<br>MS: 418.3 (M + H$^+$) | [4-Fluoro-3-(7-morpholin-4-yl-quinazolin-4-yl)phenyl]-pyridazin-3-ylmethanol<br><br>1H NMR (500 MHz, DMSO-d6) ppm = 9.12 (dd, J = 4.9, 1.7, 1H), 9.09 (s, 1H), 7.83 (dd, J = 8.6, 1.7, 1H), 7.72-7.65 (m, 3H), 7.52-7.49 (m, 2H), 7.42-7.37 (m, 1H), 7.21-7.18 (m, 1H), 6.56 (d, J = 4.3, 1H), 6.12-6.09 (m, 1H), 3.80-3.75 (m, 4H), 3.46-3.41 (m, 4H) | C | B | A |
| 66 | 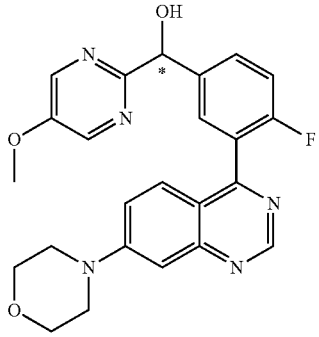<br>MS: 448.1 (M + H$^+$); R$_t$ 53.23 min, (HPLC, Chiralpak AD-H, ethanol) | [4-Fluoro-3-(7-morpholin-4-yl-quinazolin-4-yl)phenyl]-(5-methoxypyrimidin-2-yl)methanol (Ena 2)<br><br>1H NMR (500 MHz, DMSO-d6) ppm = 9.09 (s, 1H), 8.53 (s, 2H), 7.70 - 7.63 (m, 2H), 7.52 (s, 2H), 7.40-7.32 (m, 1H), 7.22-7.15 (m, 1H), 6.06 (d, J = 5.5, 1H), 5.86 (d, J = 5.5, 1H), 3.89 (s, 3H), 3.79-3.76 (m, 4H), 3.45-3.43 (m, 4H) | C | D | A |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 67 | MS: 448.1 (M + H$^+$); R$_t$ 45.79 min,(HPLC, Chiralpak AD-H,ethanol) | [4-Fluoro-3-(7-morpholin-4-yl-quinazolin-4-yl)phenyl]-(5-methoxypyrimidin-2-yl)methanol (Ena 1) | C | C | A |
|  | 1H NMR (500 MHz, DMSO-d6) ppm = 9.09 (s, 1H), 8.53 (s, 2H), 7.70-7.63 (m, 2H), 7.52 (s, 2H), 7.40-7.32 (m, 1H), 7.22-7.15 (m, 1H), 6.06 (d, J = 5.5, 1H), 5.86 (d, J = 5.5, 1H), 3.89 (s, 3H), 3.79-3.76 (m, 4H), 3.45-3.43 (m, 4H) | | | | |
| 68 | MS: 461.2 (M + H$^+$) | (6-Dimethylamino-pyridazin-3-yl)-[4-fluoro-3-(7-morpholin-4-yl-quinazolin-4-yl)phenyl]-methanol | B | C | A |
|  | 1H NMR (500 MHz, DMSO-d6) ppm = 9.09 (s, 1H), 7.65-7.56 (m, 2H), 7.55-7.48 (m, 2H), 7.43-7.34 (m, 2H), 7.24-7.17 (m, 1H), 7.07 (d, J = 9.4, 1H), 6.27 (d, J = 4.4, 1H), 5.93 (d, J = 4.4, 1H), 3.81-3.75 (m, 4H), 3.47-3.41 (m, 4H), 3.06 (s, 6H) | | | | |
| 69 | MS: 448.1 (M + H$^+$) | [4-Fluoro-3-(7-morpholin-4-yl-quinazolin-4-yl)phenyl]-(5-methoxypyrimidin-2-yl)methanol | B | C | A |
|  | 1H NMR (500 MHz, DMSO-d6) ppm = 9.09 (s, 1H), 8.53 (s, 2H), 7.70-7.63 (m, 2H), 7.52 (s, 2H), 7.40-7.32 (m, 1H), 7.22-7.15 (m, 1H), 6.06 (d, J = 5.5, 1H), 5.86 (d, J = 5.5, 1H), 3.89 (s, 3H), 3.79 - 3.76 (m, 4H), 3.45-3.43 (m, 4H) | | | | |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 70 | MS:432.1 (M + H$^+$) | [4-Fluoro-3-(7-morpholin-4-yl-quinazolin-4-yl)phenyl]-(6-methylpyridazin-3-yl)methanol<br><br>1H NMR (500 MHz, DMSO-d6) ppm = 9.09 (s, 1H), 7.72-7.61 (m, 3H), 7.58-7.47 (m, 3H), 7.43-7.33(m, 1H), 7.22-7.16 (m, 1H), 6.50 (d, J = 4.0, 1H), 6.07 (d, J = 3.8, 1H), 3.77 (t, J = 5.9, 3.9, 4H), 3.44 (t, J = 4.9, 4H), 2.58 (s, 3H) | B | B | A |
| 71 | MS: 448.1 (M + H$^+$); Rt 24.02 min, (SFC, Chiralcel OJ-H, CO$_2$/15% by vol. of 2-propanol, 0.5% by vol. of diethylamine) | (R)-[4-Fluoro-3-(7-morpholin-4-yl-quinazolin-4-yl)phenyl]-(6-methoxypyridazin-3-yl)methanol<br><br>1H NMR (500 MHz, DMSO-d6) ppm = 9.09 (s, 1H), 7.70 (d, J = 9.2, 1H), 7.66-7.61 (m, 2H), 7.53-7.50 (m, 2H), 7.42-7.37 (m, 1H), 7.22-7.19 (m, 2H), 6.48 (d, J = 4.4, 1H), 6.02 (d, J = 4.4, 1H), 4.00 (s, 3H), 3.80-3.75 (m, 4H), 3.46-3.41 (m, 4H) | A | B | A |
| 72 | MS: 448.1 (M + H$^+$); Rt 19.10 min, (SFC, Chiralcel OJ-H, CO$_2$/15% by vol. of 2-propanol, 0.5% by vol. of diethylamine) | (S)-[4-Fluoro-3-(7-morpholin-4-yl-quinazolin-4-yl)phenyl]-(6-methoxypyridazin-3-yl)methanol<br><br>1H NMR (500 MHz, DMSO-d6) ppm = 9.09 (s, 1H), 7.69 (d, J = 9.2, 1H), 7.66-7.61 (m, 2H), 7.53-7.50 (m, 2H), 7.41-7.37 (m, 1H), 7.21-7.19 (m, 2H), 6.48 (d, J = 4.4, 1H), 6.02 (d, J = 4.4, 1H), 4.00 (s, 3H), 3.79-3.76 (m, 4H), 3.46-3.42 (m, 4H) | A | B | A |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 73 | MS: 462.1 (M + H$^+$) | 4-{2-Fluoro-5-[methoxy-(6-methoxy-pyridazin-3-yl)methyl]phenyl}-7-morpholin-4-yl-quinazoline | B | B | A |
| | | 1H NMR (500 MHz, DMSO-d6) ppm = 9.10 (s, 1H), 7.69 (d, J = 9.1, 1H), 7.65-7.61 (m, 2H), 7.54-7.48 (m, 2H), 7.45-7.40 (m, 1H), 7.23 (d, J = 9.2, 1H), 7.21-7.19 (m, 1H), 5.71 (s, 1H), 4.01 (s, 3H), 3.80-3.75 (m, 4H), 3.47-3.41 (m, 4H), 3.36 (s, 3H) | | | |
| 74 | MS: 448.1 (M + H$^+$) | [4-Fluoro-3-(7-morpholin-4-yl-quinazolin-4-yl)phenyl]-(6-methoxypyridazin-3-yl)methanol | A | A | A |
| | | 1H NMR (400 MHz, DMSO-d6) ppm = 9.09 (s, 1H), 7.69 (d, J = 9.2, 1H), 7.67-7.61 (m, 2H), 7.54-7.48 (m, 2H), 7.42-7.36 (m, 1H), 7.22-7.17 (m, 2H), 6.51-6.45 (m, 1H), 6.04 - 6.00 (m, 1H), 4.00 (s, 3H), 3.80-3.74 (m, 4H), 3.47-3.41 (m, 4H) | | | |
| 75 | MS: 460.1 (M + H$^+$) | 6-({4-Fluoro-3-[7-(3-oxa-8-aza-bicyclo-[3.2.1]oct-8-yl)-quinazolin-4-yl]phenyl}-hydroxymethyl)-2H-pyridazin-3-one | D | | A |
| | | 1H NMR (500 MHz, DMSO-d6) ppm = 12.88-12.84 (m, 1H), 9.04 (s, 1H), 7.63-7.57 (m, 2H), 7.50-7.45 (m, 2H), 7.44-7.38 (m, 2H), 7.14 (d, J = 2.4, 1H), 6.87 (dd, J = 9.8, 2.2, 1H), 6.42 (d, J = 4.4, 1H), 5.68-5.64 (m, 1H), 4.55-4.46 (m, 2H), 3.69 (d, J = 10.9, 2H), 3.54 (d, J = 10.4, 2H), 2.09-1.94 (m, 4H) | | | |

TABLE 1-continued

Compounds of the formula (I)

| Example | Structural formula | Name | IC₅₀ DNA-PK | IC₅₀ pDNA-PK | K$_i$ [Kv1.11 hERG] |
|---|---|---|---|---|---|
| 76 | 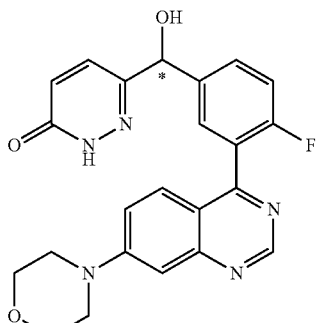 MS: 434.1 (M + H⁺); R$_t$ 16.74 min, (SFC, Chiralcel OJ-H, CO₂/15% by vol. of methanol, 0.5% by vol. of diethylamin) Ena 1 to this compound: Example 367 | 6-([4-Fluoro-3-(7-morpholin-4-yl-quinazolin-4-yl)phenyl]-hydroxymethyl}-2H-pyridazin-3-one (Ena 2)  1H NMR (400 MHz, DMSO-d6) ppm = 12.86 (s, 1H), 9.10 (s, 1H), 7.64-7.58 (m, 2H), 7.55-7.50 (m, 2H), 7.48 (d, J = 9.8, 1H), 7.45-7.38 (m, 1H), 7.23-7.16 (m, 1H), 6.87 (d, J = 9.8, 1H), 6.44 (d, J = 4.3, 1H), 5.70-5.62 (m, 1H), 3.81-3.74 (m, 4H), 3.47-3.41 (m, 4H) | A | B | A |
| 77 | 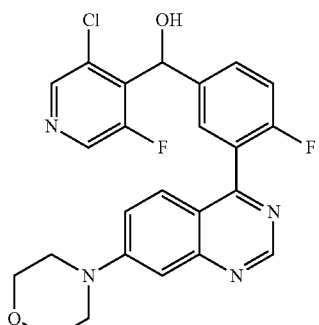 MS: 469.1/471.1 (M + H⁺) (Cl isotopy, rel. peak intensity ratio [%] 100:31) | (3-Chloro-5-fluoro-pyridin-4-yl)-[4-fluoro-3-(7-morpholin-4-yl-quinazolin-4-yl)phenyl]-methanol  1H NMR (500 MHz, DMSO-d6) ppm = 9.10 (s, 1H), 8.58-8.53 (m, 2H), 7.65-7.56 (m, 2H), 7.56-7.47(m, 2H), 7.46-7.38 (m, 1H), 7.23-7.17(m, 1H), 6.65 (d, J = 4.7, 1H), 6.33 (d, J = 4.7, 1H), 3.80-3.75 (m, 4H), 3.47-3.41 (m, 4H) | B | A | C |
| 78 | 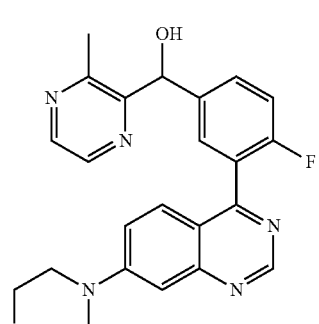 MS: 432.2 (M + H⁺) | [4-Fluoro-3-(7-morpholin-4-yl-quinazolin-4-yl)phenyl]-(3-methylpyrazin-2-yl)-methanol  1H NMR (400 MHz, DMSO-d6) ppm = 9.09 (s, 1H), 8.43 (s, 2H), 7.63-7.55 (m, 2H), 7.55-7.50 (m, 2H), 7.42-7.34 (m, 1H), 7.22-7.17 (m, 1H), 6.28 (d, J = 5.5, 1H), 6.08 (d, J = 5.4, 1H , 3.81-3.74 (m, 4H), 3.48-3.40 (m, 4H), 2.58-2.53 (m, 3H) | B | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 79 | 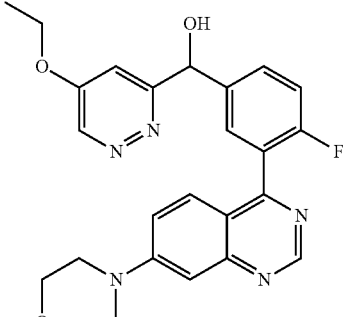<br>MS: 462.1 (M + H⁺) | (5-Ethoxypyridazin-3-yl)-[4-fluoro-3-(7-morpholin-4-yl-quinazolin-4-yl)phenyl]-methanol<br><br>1H NMR (500 MHz, DMSO-d6) ppm = 9.09 (s, 1H), 8.84 (d, J = 2.9, 1H), 7.72-7.66 (m, 2H), 7.52-7.49 (m, 2H), 7.41-7.36 (m, 1H), 7.30 (d, J = 2.9, 1H), 7.21-7.18 (m, 1H), 6.52 (d, J = 4.5, 1H), 6.04 (d, J = 4.5, 1H), 4.26-4.16 (m, 2H), 3.81-3.74 m, 4H), 3.48-3.40 (m, 4H), 1.34 (t, J = 6.9, 3H). | D | C | B |
| 80 | 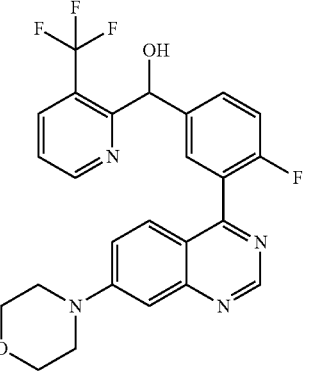<br>MS:485.2 (M + H⁺) | [4-Fluoro-3-(7-morpholin-4-yl-quinazolin-4-yl)-phenyl]-(3-trifluoro-methylpyridin-2-yl)-methanol<br><br>1H NMR (500 MHz, DMSO-d6) ppm = 9.10 (s, 1H), 8.90 - 8.85 (m, 1H), 8.20 (dd, J = 8.1, 1.6, 1H), 7.63 (dd, J = 6.9, 2.3, 1H), 7.60-7.51 (m, 4H), 7.38 (dd, J = 9.9, 8.6, 1H), 7.21-7.18 (m, 1H), 6.32 (d, J = 6.3, 1H), 6.12 (d, J = 6.0, 1H), 3.81-3.74 (m, 4H), 3.47-3.41 (m, 4H). | B | B | A |
| 81 | 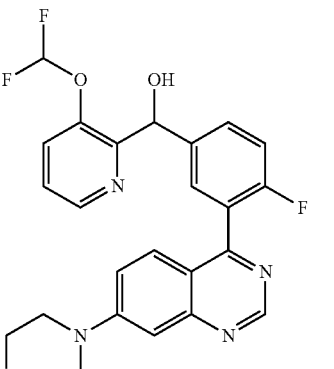<br>MS:483.2 (M + H⁺) | (3-Difluoromethoxy-pyridin-2-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 8.46 (dd, J = 4.6, 1.3, 1H), 7.67-7.64 (m, 1H), 7.62-7.57 (m, 2H), 7.54-7.49 (m, 2H), 7.42 (dd, J = 8.3, 4.6, 1H), 7.40-7.10 (m, 3H), 6.14-6.07 (m, 2H), 3.81-3.75 (m, 4H), 3.47-3.41 (m, 4H). | A | A | A |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 82 | 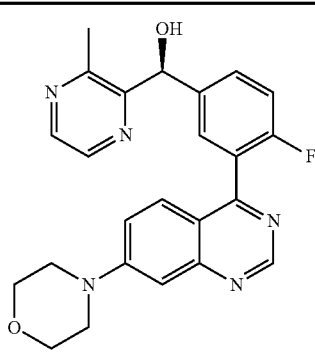<br>MS:432.2(M + H$^+$) ; ); R$_t$ 12.50 min (SFC, ChiralPak AD-H, Cl$_2$/25% by vol. of 2-propanol, 0.5% by vol. of diethylamine) | (S)-[4-Fluoro-3-(7-morpholin-4-yl-quinazolin-4-yl)-phenyl]-(3-methyl-pyrazin-2-yl)methanol<br><br>1H NMR (500 MHz, DMSO-d6) ppm = 9.10 (s, 1H), 8.44 (s, 2H), 7.64-7.51 (m, 4H), 7.44-7.35 (m, 1H), 7.20 (s, 1H), 6.31 (d, J = 5.5, 1H), 6.09 (d, J = 5.4, 1H), 3.81-3.74 (m, 4H), 3.48-3.40 (m, 4H), 2.56 (s, 3H). | C | B | A |
| 83 | 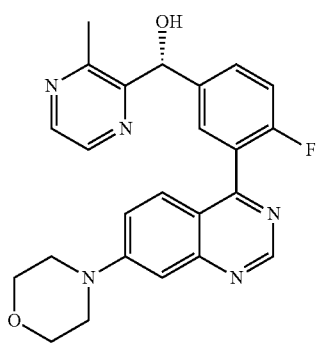 [SMILES: Cc1nccnc1[C@H](O)c1ccc(F)c(-c2ncnc3cc(N4CCOCC4)ccc23)c1]<br>MS: 432.1 (M + H$^+$); R$_t$ 19.51 min (SFC, ChiralPak AD-H, CO$_2$/25% by vol. of 2-propanol, 0.5% by vol. of diethylamine) | (R)-[4-Fluoro-3-(7-morpholin-4-yl-quinazolin-4-yl)-phenyl]-(3-methyl-pyrazin-2-yl)methanol<br><br>1H NMR (400 MHz, DMSO-d6) ppm = 9.09 (s, 1H), 8.43 (s, 2H), 7.63-7.49 (m, 4H), 7.43-7.34 (m, 1H), 7.19 (s, 1H), 6.28 (d, J = 5.5, 1H), 6.08 (d, J = 5.4, 1H), 3.82-3.73 (m, 4H), 3.48-3.40 (m, 4H), 2.55 (s, 3H). | A | A | A |
| 84 | 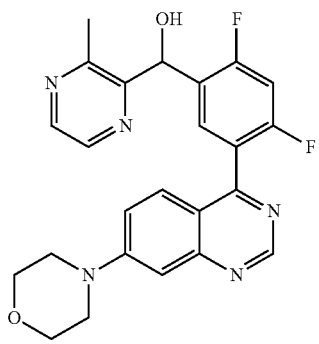 [SMILES: Cc1nccnc1C(O)c1cc(-c2ncnc3cc(N4CCOCC4)ccc23)c(F)cc1F]<br>MS: 450.2 (M + H$^+$) | [2,4-Difluoro-5-(7-morpholin-4-yl-quinazolin-4-yl)-phenyl]-(3-methyl-pyrazin-2-yl)methanol<br><br>1H NMR (500 MHz, DMSO-d6) ppm = 9.12 (s, 1H), 8.45 (d, J = 2.5, 1H), 8.39 (dd, J = 2.5, 0.8, 1H), 7.89 (t, J = 8.2, 1H), 7.61 (dd, J = 9.4, 3.2, 1H), 7.56 (dd, J = 9.4, 2.5, 1H), 7.40 (t, J = 10.1, 1H), 7.21 (d, J = 2.4, 1H), 6.39-6.35 (m, 1H), 6.27 (s, 1H), 3.81-3.75 (m, 4H), 3.49-3.43 (m, 4H), 2.67 (s, 3H). | B | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 85 | MS: 450.2 (M + H$^+$); R$_t$ 3.45 min (SFC, ChiralPak AD-H, CO$_2$/30% by vol. of methanol, 0.5% by vol. of diethylamine) | [2,4-Difluoro-5-(7-morpholin-4-yl-quinazolin-4-yl)-phenyl]-(3-methyl-pyrazin-2-yl)methanol (Ena 1) see racemate | A | B | B |
| 86 | MS: 450.2 (M + H$^+$); Rt 5.60 min (SFC, ChiralPak AD-H, CO$_2$/25% by vol. of methanol, 0.5% by vol. of diethylamine) | [2,4-Difluoro-5-(7-morpholin-4-yl-quinazolin-4-yl)-phenyl]-(3-methyl-pyrazin-2-yl)methanol (Ena 2) see racemate | A | A | A |
| 87 | MS: 448.1 (M + H$^+$) | [4-Fluoro-3-(7-morpholin-4-yl-quinazolin-4-yl)-phenyl]-(5-methoxy-pyrimidin-4-yl)-methanol<br>1H NMR (400 MHz, DMSO-d6) pp = 9.11 (s, 1H), 8.82 (s, 1H), 8.58 (s, 1H), 7.67-7.61 (m, 2H), 7.55-7.52 (m, 2H), 7.41-7.34 (m, 1H), 7.23-7.19(m, 1H), 6.13 (d, J = 6.1, 1H), 6.07 (d, J = 6.2, 1H), 3.95 (s, 3H), 3.83-3.76 (m, 4H), 3.49-3.42 (m, 4H). | A | A | B |

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 88 | MS: 464.2 (M + H$^+$) | [2,4-Difluoro-5-(7-morpholin-4-yl-quinazolin-4-yl)-phenyl]-(3,6-dimethyl-pyrazin-2-yl)methanol | A | A | B |

1H NMR (400 MHz, DMSO-d6) ppm = 9.13 (s, 1H), 8.35 (s, 1H), 7.88 (t, J = 8.2, 1H), 7.61 (dd, J = 9.4, 3.0, 1H), 7.56 (dd, J = 9.5, 2.5, 1H), 7.42 (t, J = 10.2, 1H), 7.23 (d, J = 2.4, 1H), 6.31 (d, J = 5.9, 1H), 6.22 (d, J = 5.6, 1H), 3.85-3.75 (m, 4H), 3.51-3.43 (m, 4H), 2.58 (s, 3H), 2.40 s, 3H).

| 89 | MS: 490.1/492.1 (M + H$^+$) (Cl isotopy, rel. peak intensity ratio [%] 100:43) | [2-Chloro-5-(7-morpholin-4-yl-quinazolin-4-yl)-phenyl]thieno,2-d}-pyrimidin-4-ylmethanol | B | A | C |

1H NMR (500 MHz, DMSO-d6) ppm = 9.06 (s, 1H), 9.04 (s, 1H), 8.47 (d, J = 5.6, 1H), 7.89 (d, J = 2.1, 1H), 7.76 (d, J = 9.4, 1H), 7.73 (dd, J = 8.2, 2.2, 1H), 7.69 (d, J = 8.2, 1H), 7.62 (d, J = 5.6, 1H), 7.47 (dd, J = 9.5, 2.6, 1H), 7.20-7.16 (m, 2H), 6.47 (d, J = 4.9, 1H), 3.81-3.74 (m, 4H), 3.47-3.39 (m, 4H).

| 90 | MS: 492.2 (M + H$^+$) | [2,4-Difluoro-5-(7-morpholin-4-yl-quinazolin-4-yl)-phenyl]thieno[2,3-d}-pyrimidin-4-ylmethanol | A | A | A |

1H NMR (500 MHz, DMSO-d6) ppm = 9.07 (s, 1H), 9.05 (s, 1H), 8.47 (d, J = 5.6, 1H), 7.76 (t, J = 8.0, 1H), 7.61 (d, J = 5.6, 1H), 7.55-7.46 (m, 3H), 7.20-7.17 (m, 2H), 6.32 (d, J = 4.7, 1H), 3.81-3.74 (m, 4H), 3.47-3.41 (m, 4H).

TABLE 1-continued

Compounds of the formula (I)

| Example | Structural formula | Name | IC$_{50}$ DNA-PK | IC$_{50}$ pDNA-PK | K$_i$ [Kv1.11 hERG] |
|---|---|---|---|---|---|
| 91 | MS: 447.2 (M + H$^+$) | 6-([4-Fluoro-3-(7-morpholin-4-yl-quinazolin-4-yl)-phenyl]hydroxy-methyl}-1-methyl-1H-pyridin-2-one<br><br>1H- NMR (500 MHz, DMSO-d6) ppm = 9.10 (s, 1H), 7.60-7.56 (m, 2H), 7.55-7.51 (m, 2H), 7.48-7.43 (m, 1H), 7.40 (dd, J = 9.1, 6.9, 1H), 7.21-7.19 (m, 1H), 6.52 (d, J = 5.3, 1H), 6.36 (dd, J = 9.1, 1.4, 1H), 6.25 (dd, J = 7.0, 1.4, 1H), 5.94 (d, J = 5.1, 1H), 3.80-3.75 (m, 4H), 3.47-3.41 (m, 4H), 3.38 (s, 3H). | A | A | A |

Examples 92 and 93

3-[[2-Chloro-4-fluoro-5-(7-morpholinylquinazolin-4-yl)phenyl]hydroxymethyl]-1H-pyridazin-6-one (92)

6-{[2-Chloro-4-fluoro-5-(7-morpholin-4-ylquinazolin-4-yl)phenyl]hydroxymethyl}-2-ethyl-2H-pyridazin-3-one (93)

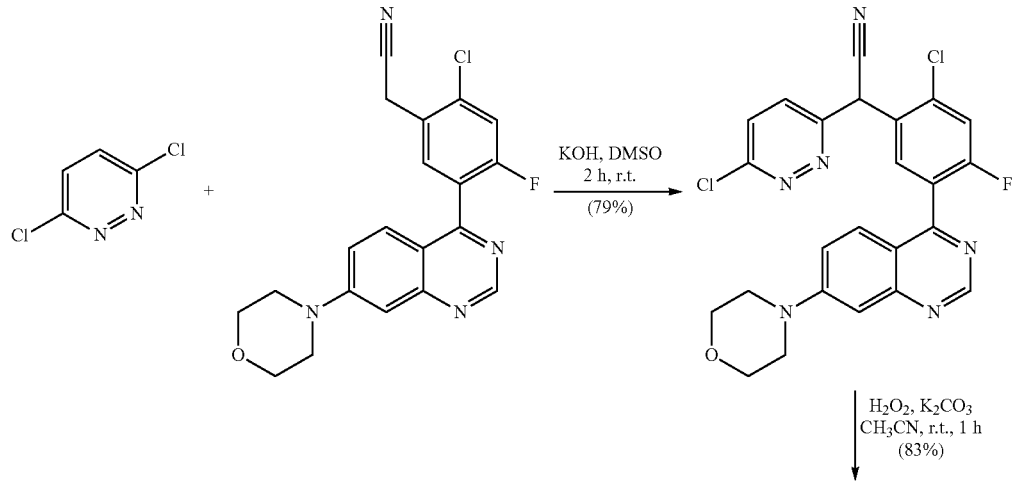

-continued

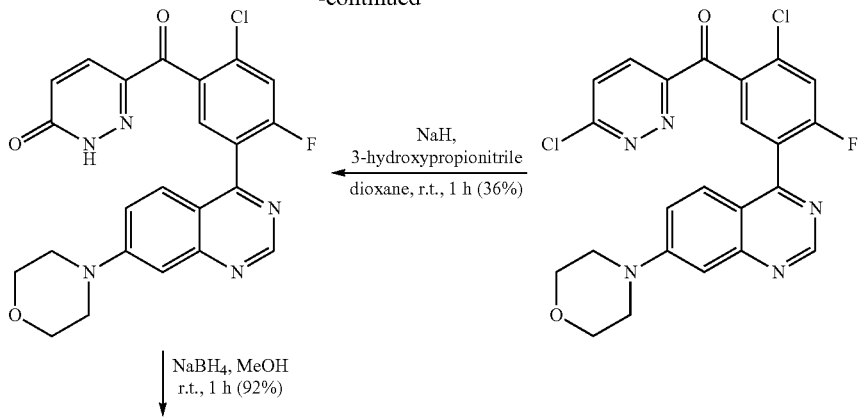

Example 92

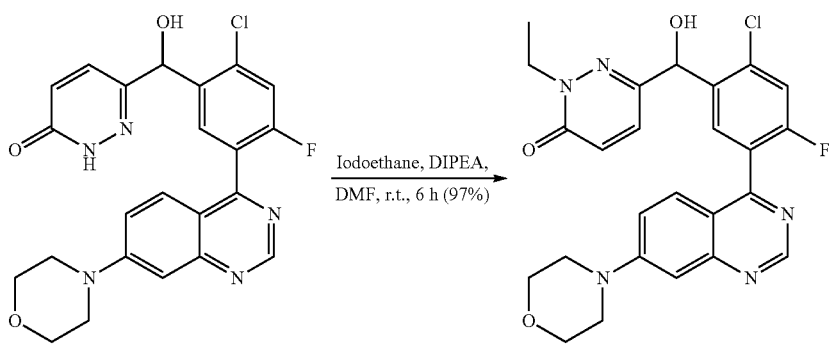

Example 93

[2-Chloro-4-fluoro-5-(7-morpholinylquinazolin-4-yl) phenyl]-(6-chloropyridazin-3-yl)methanone, starting from 2,6-dichloropyridazine and 2-[2-chloro-4-fluoro-5-(7-morpholinylquinazolin-4-yl)phenyl]acetonitrile, and 3-[[2-chloro-4-fluoro-5-(7-morpholinylquinazolin-4-yl)phenyl]-hydroxymethyl]-1H-pyridazin-6-one (EXAMPLE 92) were prepared analogously to the synthetic processes described under EXAMPLES 1 and 2.

Preparation of 3-[2-chloro-4-fluoro-5-(7-morpholinylquinazolin-4-yl)benzoyl]-1H-pyridazin-6-one from [2-chloro-4-fluoro-5-(7-morpholinylquinazolin-4-yl)phenyl]-(6-chloropyridazin-3-yl)methanone

[2-Chloro-4-fluoro-5-(7-morpholinylquinazolin-4-yl) phenyl]-(6-chloropyridazin-3-yl)methanone (2.0 g, 4.13 mmol) was dissolved in 1,4-dioxane (80 ml, max. 0.005% of water) under an argon atmosphere. 3-Hydroxypropionitrile (570 μl ml, 8.27 mmol) and sodium hydride (60% dispersion in paraffin oil) (215 mg; 5.37 mmol) were subsequently added (evolution of gas). The reaction mixture was stirred at room temperature for 2 h. After termination of the reaction, the mixture was carefully diluted with water (100 ml) and neutralised using hydrochloric acid (1.0 M). The aqueous phase was subsequently extracted twice with ethyl acetate (200 ml in each case). The combined organic phases were washed with saturated sodium chloride solution, subsequently dried over sodium sulfate, filtered and evaporated to dryness in a rotary evaporator. The residue was purified by means of flash column chromatography (dichloromethane/ 0-10% by vol. of ethanol, CombiFlash Rf 200), giving 3-[2-chloro-4-fluoro-5-(7-morpholinylquinazolin-4-yl)benzoyl]-1H-pyridazin-6-one (695 mg, 1.47 mmol, MS: 466.1/468.1 [M+H$^+$]), 36% yield) as solid.

Preparation of 6-{[2-chloro-4-fluoro-5-(7-morpholin-4-ylquinazolin-4-yl)phenyl]hydroxymethyl}-2-ethyl-2H-pyridazin-3-one (EXAMPLE 93) from 3-[[2-chloro-4-fluoro-5-(7-morpholinylquinazolin-4-yl)phenyl]hydroxymethyl]-1H-pyridazin-6-one (EXAMPLE 92)

3-[[2-Chloro-4-fluoro-5-(7-morpholinylquinazolin-4-yl) phenyl]hydroxymethyl]-1H-pyridazin-6-one (150 mg; 0.316 mmol) was dissolved in N,N-dimethylformamide (5.0 ml). Iodoethane (52 μl, 0.632 mmol) and potassium carbonate (132 mg, 0.947 mmol) were subsequently added. The reaction mixture was stirred at room temperature for 6 h. After termination of the reaction, the mixture was decanted off onto water (100 ml). The aqueous phase was subsequently extracted twice with ethyl acetate (100 ml in each case). The combined organic phases were rinsed with water (40 ml), subsequently dried over sodium sulfate, filtered us evaporated to dryness in vacuo. The residue was suspended in acetone and filtered off with suction. The filter cake was dried at room temperature in a high vacuum, giving 6-{[2-chloro-4-fluoro-5-(7-morpholin-4-ylquinazolin-4-yl)phenyl]hydroxymethyl}-2-ethyl-2H-pyridazin-3-one (EXAMPLE 93, 157 mg, 0.31 mmol, MS: 496.1/498.1 [M+H$^+$], 97% yield) as solid.

Compounds which were prepared in accordance with EXAMPLE 93 can be found in Table 2 below.

TABLE 2

Compounds of the formula (I)

| No. | Structural formula | Name | IC$_{50}$ DNA-PK | IC$_{50}$ pDNA-PK | K$_i$ [Kv1.11 hERG][ |
|---|---|---|---|---|---|
| 92 | MS: 468.1/470.0 (M + H$^+$) (Cl isotopy, rel. peak intensity ratio [%] 100:38) | 3-[[2-Chloro-4-fluoro-5-(7-morpholino-quinazolin-4-yl)phenyl]-hydroxymethyl]-1H-pyridazin-6-one | A | A | A |
| | 1H NMR (400 MHz, DMSO-d6) ppm = 12.89 (d, J = 2.4, 1H), 9.12 (s, 1H), 7.92 (d, J = 7.7, 1H), 7.68 (d, J = 9.5, 1H), 7.59-7.55 (m, 2H), 7.53 (d, J = 9.8, 1H), 7.21 (d, J = 2.2, 1H), 6.90 (dd, J = 9.8, 2.3, 1H), 6.61 (d, J = 5.1, 1H), 5.89 (d, J = 5.1, 1H), 3.81-3.76 (m, 4H), 3.48-3.44 (m, 4H) | | | | |
| 93 | MS: 496.1/498.1 (M + H$^+$) (Cl isotopy, rel. peak intensity ratio [%] 100:41) | 6-{[2-Chloro-4-fluoro-5-(7-morpholin-4-yl-quinazolin-4-yl)phenyl]-hydroxymethyl}-2-ethyl-2H-pyridazin-3-one | B | A | C |
| | 1H NMR (500 MHz, DMSO-d6) ppm = 9.13 (s, 1H), 7.94 (d, J = 7.7, 1H), 7.68 (d, J = 9.5, 1H), 7.59-7.52 (m, 2H), 7.46 (d, J = 9.6, 1H), 7.22 (d, J = 2.3, 1H), 6.92 (d, J = 9.6, 1H), 6.61 (d, J = 4.8, 1H), 5.90 (d, J = 4.8, 1H), 4.08-3.95 (m, 2H), 3.81-3.74 (m, 4H), 3.49-3.41 (m, 4H), 1.20 (t, J = 7.2 3H) | | | | |
| 94 | MS: 511.1/513.2 (M + H$^+$) (Cl isotopy, rel. peak intensity ratio [%] 100:38) | 2-(2-Amino-ethyl)-6-{[2-Chloro-4-fluoro-5-(7-morpholin-4-yl-quinazolin-4-yl)phenyl]-hydroxymethyl}-2H-pyridazin-3-one | C | D | A |
| | 1H NMR (500 MHz, DMSO-d6) ppm = 9.13 (s, 1H), 7.94 (d, J = 7.7, 1H), 7.68 (d, J = 9.5, 1H), 7.60-7.52 (m, 2H), 7.48 (d, J = 9.7, 1H), 7.21 (d, J = 2.2, 1H), 6.94 (d, J = 9.6, 1H), 6.72-6.57 (m, 1H), 5.91 (s, 1H), 4.10-3.96 (m, 2H), 3.82-3.73 (m, 4H), 3.48-3.43 (m, 4H), 2.88 (t, J = 6.6, 2H) | | | | |

TABLE 2-continued

Compounds of the formula (I)

| No. | Structural formula | Name | IC$_{50}$ DNA-PK | IC$_{50}$ pDNA-PK | K$_i$ [Kv1.11 hERG][ |
|---|---|---|---|---|---|
| 95 | | 6-{[2-Chloro-4-fluoro-5-(7-morpholin-4-yl-quinazolin-4-yl)phenyl]-hydroxymethyl}-2-cyclopropyl-2H-pyridazin-3-one | C | B | A |
| | MS: 508.1/510.1 (M + H$^+$) (Cl isotopy, rel. peak intensity ratio [%] 100:38) | 1H NMR (400 MHz, Methylenchlorid-d2) ppm = 9.04 (s, 1H), 7.71 (d, J = 7.6, 1H), 7.49 (dd, J = 9.3, 3.5, 1H), 7.26-7.20 (m, 2H), 7.18-7.14 (m, 2H), 6.74 (d, J = 9.6, 1H), 5.97 (s, 1H), 4.03-3.94 (m, 1H), 3.82-3.74 (m, 4H), 3.39-3.31 (m, 4H), 0.98-0.82 (m, 4H) | | | |
| 96 | | 6{[2-Chloro-4-fluoro-5-(7-morpholin-4-yl-quinazolin-4-yl)phenyl]-hydroxymethyl}-2-ethyl-2H-pyridazin-3-one (Ena 2) | C | B | A |
| | MS: 496.2/498.1 (M + H$^+$) (Cl isotopy, rel. peak intensity ratio [%] 100:34); R$_t$ 4.59 min (SFC, Chiracel OJ-H, CO$_2$/20% by vol. of methanol, 0.5% by vol. of diethylamine) | see racemate | | | |
| 97 | | 6-{[2-Chloro-4-fluoro-5-(7-morpholin-4-yl-quinazolin-4-yl)phenyl]-hydroxymethyl}-2-ethyl-2H-pyridazin-3-one (Ena 1) | A | B | A |
| | MS: 496.2/498.1 (M + H$^+$) (Cl isotopy, rel. peak intensity ratio [%] 100:36); R$_t$ 3.00 min (SFC, Chiracel OJ-H, CO$_2$/20% by vol. of methanol, 0.5% by vol. of diethylamine) | see racemate | | | |

TABLE 2-continued

Compounds of the formula (I)

| No. | Structural formula | Name | IC₅₀ DNA-PK | IC₅₀ pDNA-PK | $K_i$ [Kv1.11 hERG] |
|---|---|---|---|---|---|
| 98 | 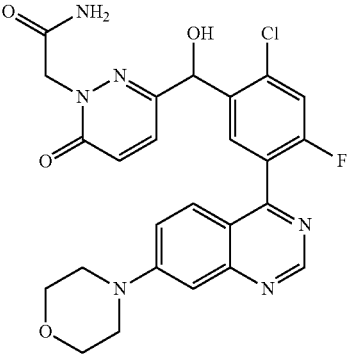 [SMILES: NC(=O)Cn1nc(C(O)c2cc(-c3ncnc4cc(N5CCOCC5)ccc34)c(F)cc2Cl)ccc1=O]<br>MS: 525.1/527.1 (M + H⁺)<br>(Cl isotopy, rel. peak intensity ratio [%] 100:36) | 2-(3-{[2-Chloro-4-fluoro-5-(7-morpholin-4-ylquinazolin-4-yl)-phenyl]hydroxymethyl}-6-oxo-6H-pyridazin-1-yl)acetamide<br><br>1H NMR (500 MHz, DMSO-d6) ppm = 9.12 (s, 1H), 7.93 (d, J = 7.7, 1H), 7.67 (d, J = 9.5, 1H), 7.58 (dd, J = 9.4, 3.0, 1H), 7.53 (dd, J = 9.5, 2.5, 1H), 7.51-7.44 (m, 2H), 7.21 (d, J = 2.4, 1H), 7.15 (s, 1H), 6.94 (d, J = 9.6, 1H), 6.62 (d, J = 4.8, 1H), 5.89 (d, J = 4.8, 1H), 4.61-4.51 (m, 2H), 3.81-3.75 (m, 4H), 3.48-3.42 (m, 4H) | B | D | A |
| 99 | 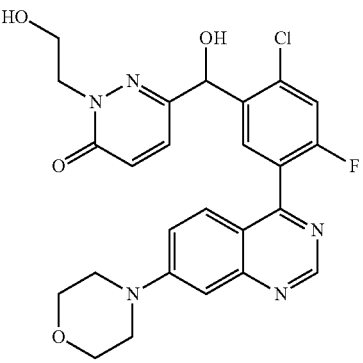 [SMILES: O=c1ccc(C(O)c2cc(-c3ncnc4cc(N5CCOCC5)ccc34)c(F)cc2Cl)nn1CCO]<br>MS: 512.2/514.2 (M + H⁺)<br>(Cl isotopy, rel. peak intensity ratio [%] 100:38) | 6-{[2-Chloro-4-fluoro-5-(7-morpholin-4-yl-quinazolin-4-yl)phenyl]-hydroxymethyl}-2-(2-hydroxy-ethyl)-2H-pyridazin-3-one<br><br>1H NMR (500 MHz, DMSO-d6) ppm = 9.13 (s, 1H), 7.94 (d, J = 7.7, 1H), 7.68 (d, J = 9.5, 1H), 7.60-7.52 (m, 2H), 7.46 (d, J = 9.6, 1H), 7.22 (d, J = 2.3, 1H), 6.92 (d, J = 9.6, 1H), 6.61 (d, J = 4.8, 1H), 5.90 (d, J = 4.8, 1H), 4.75 (t, J = 5.8, 1H), 4.11-4.00 (m, 2H), 3.82-3.74 (m, 4H), 3.65 (q, J = 6.2, 2H), 3.49-3.42 (m, 4H) | B | B | A |

Example 100

[2-Chloro-4-fluoro-5-(7-morpholin-4-ylquinazolin-4-yl)phenyl]-[6-(oxetan-3-yloxy)pyridazin-3-yl]methanol (100)

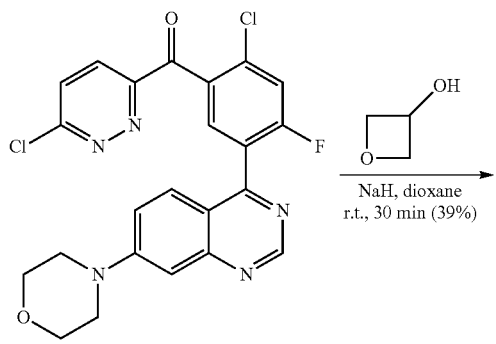

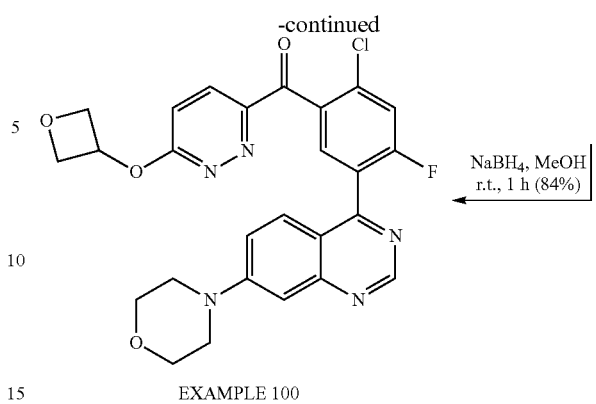

EXAMPLE 100

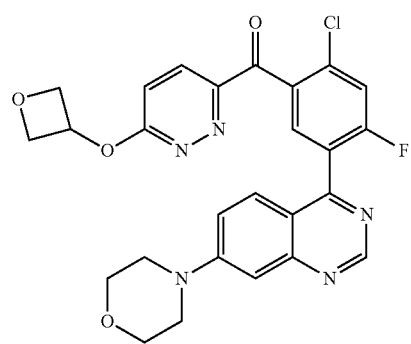 [SMILES: OC(c1ccc(OC2COC2)nn1)c1cc(-c2ncnc3cc(N4CCOCC4)ccc23)c(F)cc1Cl]

[2-Chloro-4-fluoro-5-(7-morpholin-4-ylquinazolin-4-yl)phenyl]-(6-chloropyridazin-3-yl)methanone (700 mg, 1.30 mmol) and oxetan-3-ol (112 mg, 1.43 mmol) were initially introduced dissolved in 1,4-dioxane (25 ml, max. 0.005% of water) under an argon atmosphere. Sodium hydride (60% dispersion in paraffin oil, 62 mg, 1.56 mmol) was subsequently added (evolution of gas). The reaction mixture was stirred at room temperature for 30 min. After termination of the reaction, the mixture was carefully diluted with water (80 ml) and neutralised using hydrochloric acid (1.0 M). The aqueous phase was subsequently extracted twice with ethyl acetate (80 ml in each case). The combined organic phases were rinsed with water (20 ml), subsequently dried over sodium sulfate, filtered and evaporated to dryness in a rotary evaporator. The residue was purified by means of flash column chromatography (dichloromethane/0-10% by vol. of ethanol, CombiFlash Rf 200), giving [2-chloro-4-fluoro-5-(7-morpholin-4-ylquinazolin-4-yl)phenyl]-[6-(oxetan-3-yloxy)pyridazin-3-yl]methanone (264 mg, 0.506 mmol, 522.2 [M+H$^+$]), 39% yield) as solid.

[2-Chloro-4-fluoro-5-(7-morpholin-4-ylquinazolin-4-yl)phenyl]-[6-(oxetan-3-yloxy)pyridazin-3-yl]methanol (EXAMPLE 100) was prepared analogously to the synthetic process described under EXAMPLES 1 and 2 starting from [2-chloro-4-fluoro-5-(7-morpholin-4-ylquinazolin-4-yl)phenyl]-[6-(oxetan-3-yloxy)pyridazin-3-yl]methanone.

Compounds which were prepared in accordance with EXAMPLE 100 can be found in Table 3 below.

TABLE 3

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 100 | | [2-Chloro-4-fluoro-5-(7-morpholin-4-yl-quinazolin-4-yl)-phenyl]-[6-(oxetan-3-yloxy)pyridazin-3-yl]-methanol | A | A | C |

MS: 524.2/526.1 (M + H$^+$) (Cl isotopy, rel. peak intensity ratio

1H NMR (500 MHz, DMSO-d6) ppm = 9.11 (s, 1H), 7.91 (d, J = 7.7, 1H), 7.77 (d, J = 9.2, 1H),

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| | [%] 100:39) | 7.66 (d, J = 9.4, 1H), 7.61-7.51 (m, 2H), 7.32 (d, J = 9.2, 1H), 7.21 (d, J = 2.3, 1H), 6.63 (d, J = 4.8, 1H), 6.22 (d, J = 4.8, 1H), 5.69 (p, J = 5.7, 1H), 4.94-4.87 (m, 2H), 4.62-4.56 (m, 2H), 3.80-3.76 (m, 4H), 3.48-3.43 (m, 4H) | | | |
| 101 | 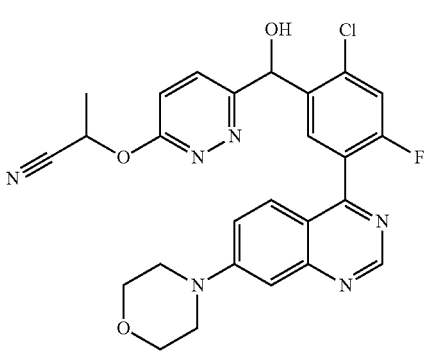 [SMILES: CC(C#N)Oc1ccc(C(O)c2cc(-c3ncnc4cc(N5CCOCC5)ccc34)c(F)cc2Cl)nn1] MS: 521.2/523.2 (M + H⁺) (Cl isotopy, rel. peak intensity ratio [%] 100:39) | 2-(6-{[2-Chloro-4-fluoro-5-(7-morpholin-4-yl-quinazolin-4-yl)-phenyl]hydroxy-methyl}pyridazin-3-yloxy)propionitrile | A | A | C |
| | | 1H NMR (500 MHz, DMSO-d6) ppm = 9.12 (d, J = 2.7, 1H), 7.93 (dd, J = 11.2, 7.7, 1H), 7.84 (dd, J = 16.3, 9.2, 1H), 7.70-7.65 (m, 1H), 7.63-7.57 (m, 1H), 7.57-7.51 (m, 1H), 7.38 (dd, J = 9.1, 3.5, 1H), 7.21 (d, J = 2.4, 1H), 6.71 (dd, J = 10.3, 5.0, 1H), 6.28 (dd, J = 9.5, 5.0, 1H), 5.95-5.87 (m, 1H), 3.81-3.74 (m, 4H), 3.48-3.42 (m, 4H), 1.76-1.70 (m, 3H) | | | |
| 102 | 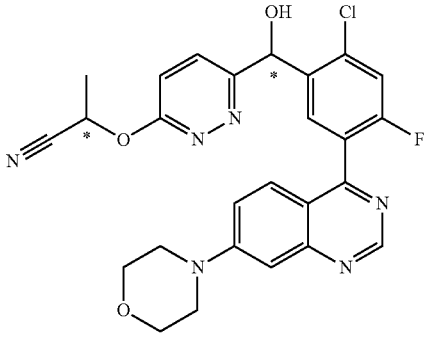 [SMILES: CC(C#N)Oc1ccc(C(O)c2cc(-c3ncnc4cc(N5CCOCC5)ccc34)c(F)cc2Cl)nn1] MS: 543.0/545.0 (M + Na⁺) (Cl isotopy, rel. peak intensity ratio [%] 100:35); R$_t$ 4.09 min (SFC, Chiralpak AS-H, CO$_2$/20% by vol. of methanol, 0.5% by vol. of diethylamine) | 2-(6-{[2-Chloro-4-fluoro-5-(7-morpholin-4-yl-quinazolin-4-yl)-phenyl]hydroxy-methyl}pyridazin-3-yloxy)propionitrile (eluate 1) | A | A | B |
| | | see also diastereomer mixture | | | |
| 103 | 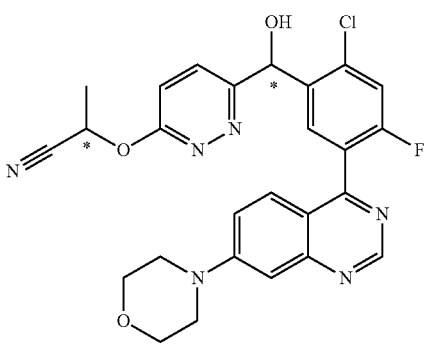 [SMILES: CC(C#N)Oc1ccc(C(O)c2cc(-c3ncnc4cc(N5CCOCC5)ccc34)c(F)cc2Cl)nn1] MS: 521.1/523.1 (M + H⁺) (Cl isotopy, rel. peak intensity ratio | 2-(6-{[2-Chloro-4-fluoro-5-(7-morpholin-4-yl-quinazolin-4-yl)-phenyl]hydroxy-methyl}pyridazin-3-yloxy)propionitrile (eluate 3) | D | D | A |
| | | see also diastereomer mixture | | | |

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| | [%] 100:38); R$_t$ 6.68 min (SFC, Chiralpak AS-H, CO$_2$/20% by vol. of methanol, 0.5% by vol. of diethylamine) | | | | |
| 104 | | 2-(6-{[2-Chloro-4-fluoro-5-(7-morpholin-4-yl-quinazolin-4-yl)-phenyl]hydroxy-methyl}pyridazin-3-yloxy)propionitrile (eluate 2) | C | B | B |
| | MS: 521.1/523.1 (M + H$^+$) (Cl isotopy, rel. peak intensity ratio [%] 100:35); R$_t$ 5.12 min (SFC, Chiralpak AS-H, CO$_2$/20% by vol. of methanol, 0.5% by vol. of diethylamine) | see also diastereomer mixture | | | |
| 105 | | 2-(3-{[4-fluoro-3-(7-morpholin-4-yl-quinazolin-4-yl)-phenyl]hydroxy-methyl}pyrazin-2-oxy)ethanol | C | D | A |
| | MS: 478.2 (M + H$^+$) | 1H NMR (500 MHz, DMSO-d6) ppm = 9.09 (s, 1H), 8.19 (d, J = 2.8, 1H), 8.12 (d, J = 2.8, 1H), 7.70-7.64 (m, 2H), 7.54-7.51 (m, 2H), 7.38-7.33 (m, 1H), 7.21-7.19 (m, 1H), 6.14 (d, J = 5.9, 1H), 6.00 (d, J = 6.0, 1H), 4.86 (t, J = 5.7, 1H), 4.34-4.30 (m, 2H), 3.80-3.75 (m, 4H), 3.74-3.69 (m, 2H), 3.46-3.42 (m, 4H) | | | |

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 106 | MS: 477.1 (M + H$^+$) | 2-(3-{[4-fluoro-3-(7-morpholin-4-yl-quinazolin-4-yl)-phenyl]hydroxy-methyl}pyrazin-2-yl-amino)ethanol | C | C | B |
| | 1H NMR (500 MHz, DMSO-d6) ppm = 9.09 (s, 1H), 7.91 (d, J = 2.7, 1H), 7.67 (d, J = 2.8, 1H), 7.63-7.58 (m, 2H), 7.55-7.49 (m, 2H), 7.41-7.35 (m, 1H), 7.20 (d, J = 2.0, 1H), 6.82-6.75 (m, 2H), 5.91 (d, J = 4.2, 1H), 4.74 (t, J = 5.1, 1H), 3.82-3.73 (m, 4H), 3.60-3.45 (m, 8H) | | | | |
| 107 | MS: 521.2/523.2 (M + H$^+$) (Cl isotopy, rel. peak intensity ratio [%] 100:39) | 3-(6-{[2-Chloro-4-fluoro-5-(7-morpholin-4-yl-quinazolin-4-yl)-phenyl]hydroxy-methyl}pyridazin-3-yl-oxy)propionitrile | B | B | A |
| | 1H NMR (500 MHz, DMSO-d6) ppm = 9.12 (s, 1H), 7.95 (d, J = 7.7, 1H), 7.67 (d, J = 9.5, 1H), 7.59 (dd, J = 9.4, 3.2, 1H), 7.55-7.49 (m, 2H), 7.21 (d, J = 2.4, 1H), 6.99 (d, J = 9.6, 1H), 6.67 (d, J = 4.9, 1H), 5.92 (d, J = 4.9, 1H), 4.31-4.17 (m, 2H), 3.81-3.75 (m, 4H), 3.49-3.42 (m, 4H), 2.99-2.88 (m, 2H) | | | | |
| 108 | MS: 498.1/500.1 (M + H$^+$) (Cl isotopy, rel. peak intensity ratio [%] 100:47) | [2-Chloro-4-fluoro-5-(7-morpholin-4-yl-quinazolin-4-yl)-phenyl]-(6-methyl-sulfanylpyridazin-3-yl)methanol | B | A | B |
| | 1H NMR (500 MHz, DMSO-d6) ppm = 9.12 (s, 1H), 7.90 (d, J = 7.7, 1H), 7.68 (d, J = 9.5, 1H), 7.66-7.60 (m, 2H), 7.60-7.56 (m, 1H), 7.54 (dd, J = 9.4, 2.5, 1H), 7.21 (d, J = 2.4, 1H), 6.68 (s, 1H), 6.25 (s, 1H), 3.80-3.76 (m, 4H), 3.47-3.43 (m, 4H), 2.61 (s, 3H) | | | | |

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 109 | | [2-Chloro-4-fluoro-5-(7-morpholin-4-yl-quinazolin-4-yl)-phenyl]-(6-methoxy-4-methylpyridazin-3-yl)methanol | D | C | A |
| | MS: 518.2/520.2 (M + Na$^+$) (Cl isotopy, rel. peak intensity ratio [%] 100:38) | 1H NMR (500 MHz, DMSO-d6) ppm = 9.14 (s, 1H), 7.99 (d, J = 7.8, 1H), 7.67-7.61 (m, 2H), 7.57 (dd, J = 9.4, 2.6, 1H), 7.23 (d, J = 2.5, 1H), 7.10 (d, J = 1.1, 1H), 6.42 (d, J = 6.4, 1H), 6.25 (d, J = 6.3, 1H), 3.96 (s, 3H), 3.82-3.75 (m, 4H), 3.50-3.42 (m, 4H), 2.49-2.46 (m, 3H) | | | |
| 110 | | [2-Chloro-4-fluoro-5-(7-morpholin-4-yl-quinazolin-4-yl)-phenyl]-(6-methoxy-5-methylpyridazin-3-yl)methanol | C | B | C |
| | MS: 496.1/498.1 (M + H$^+$) (Cl isotopy, rel. peak intensity ratio [%] 100:38) | 1H NMR (500 MHz, DMSO-d6) ppm = 9.12 (s, 1H), 7.91 (d, J = 7.8, 1H), 7.66 (d, J = 9.6, 1H), 7.59 (dd, J = 9.4, 3.3, 1H), 7.56-7.52 (m, 2H), 7.21 (d, J = 2.4, 1H), 6.54 (d, J = 4.9, 1H), 6.18 (d, J = 4.9, 1H), 4.02 (s, 3H), 3.80-3.75 (m, 4H), 3.48-3.43 (m, 4H), 2.17 (d, J = 1.0, 3H) | | | |
| 111 | | 2-(6-{[2-Chloro-4-fluoro-5-(7-morpholin-4-yl-quinazolin-4-yl)-phenyl]hydroxymethyl}pyridazin-3-yloxy)acetamide | B | C | A |
| | MS: 525.2/527.2 (M + H$^+$) (Cl isotopy, rel. peak intensity ratio [%] 100:34) | 1H NMR (500 MHz, DMSO-d6) ppm = 9.12 (s, 1H), 7.92 (d, J = 7.7, 1H), 7.74 (d, J = 9.1, 1H), 7.66 (d, J = 9.5, 1H), 7.59 (dd, J = 9.4, 3.3, 1H), 7.57-7.49 (m, 2H), 7.27 (d, J= 9.1, 1H), 7.23-7.16 (m, 2H), 6.63 (d, J = 5.0, 1H), 6.23 (d, J = 5.0, 1H), 4.81 (s, 2H), 3.81-3.75 (m, 4H), 3.49-3.43 (m, 4H) | | | |

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 112 | | [2-Chloro-4-fluoro-5-(7-morpholin-4-yl-quinazolin-4-yl)-phenyl]-[6-(2-methoxyethoxy)-pyridazin-3-yl]-methanol | A | B | B |
| | MS: 526.2/528.3 (M + H$^+$) (Cl isotopy, rel. peak intensity ratio [%] 100:38) | 1H NMR (500 MHz, DMSO-d6) ppm = 9.12 (s, 1H), 7.91 (d, J = 7.7, 1H), 7.69 (d, J = 9.2, 1H), 7.67 (d, J = 9.5, 1H), 7.59 (dd, J = 9.4, 3.3, 1H), 7.54 (dd, J = 9.5, 2.5, 1H), 7.25-7.19 (m, 2H), 6.61 (d, J = 5.0, 1H), 6.23 (d, J = 5.0, 1H), 4.54-4.50 (m, 2H), 3.80-3.75 (m, 4H), 3.71-3.67 (m, 2H), 3.48-3.43 (m, 4H), 3.29 (s, 3H) | | | |
| 113 | | (6-{[2-Chloro-4-fluoro-5-(7-morpholin-4-yl-quinazolin-4-yl)-phenyl]hydroxy-methyl}pyridazin-3-yl-oxy)acetic acid | B | D | A |
| | MS: 526.2/528.1 (M + H$^+$) (Cl isotopy, rel. peak intensity ratio [%] 100:39) | 1H NMR (500 MHz, DMSO-d6) ppm = 12.91 (s, 1H), 9.12 (s, 1H), 7.92 (d, J = 7.7, 1H), 7.75 (d, J = 9.1, 1H), 7.66 (d, J = 9.5, 1H), 7.59 (dd, J = 9.4, 3.3, 1H), 7.54 (dd, J = 9.5, 2.5, 1H), 7.31 (d, J = 9.1, 1H), 7.21 (d, J = 2.4, 1H), 6.66 (s, 1H), 6.23 (s, 1H), 4.97 (s, 2H), 3.81-3.75 (m, 4H), 3.48-3.43 (m, 4H) | | | |
| 114 | | (6-{[2-Chloro-4-fluoro-5-(7-morpholin-4-yl-quinazolin-4-yl)-phenyl]hydroxy-methyl}pyridazin-3-yl-oxy)acetic acid methyl ester | B | D | A |
| | MS: 540.2/542.2 (M + H$^+$) (Cl isotopy, rel. peak intensity ratio [%] 100:38) | 1H NMR (500 MHz, DMSO-d6) ppm = 9.12 (s, 1H), 7.92 (d, J = 7.7, 1H), 7.77 (d, J = 9.1, 1H), 7.67 (d, J = 9.5, 1H), 7.59 (dd, J = 9.3, 3.2, 1H), 7.57-7.51 (m, 1H), 7.35 (d, J = 9.1, 1H), 7.23-7.19 (m, 1H), 6.62 (s, 1H), 6.23 (s, 1H), 5.07 (s, 2H), 3.81-3.75 (m, 4H), 3.67 (s, 3H), 3.49-3.44 (m, 4H) | | | |

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 115 | | [2-Chloro-4-fluoro-5-(7-morpholin-4-yl-quinazolin-4-yl)-phenyl]-[6-(2,2,2-trifluoroethoxy)-pyridazin-3-yl]-methanol | B | B | C |

MS: 550.2/552.1 (M + H$^+$) (Cl isotopy, rel. peak intensity ratio [%] 100:40)

1H NMR (500 MHz, DMSO-d6) ppm = 9.11 (s, 1H), 7.91 (d, J = 7.7, 1H), 7.81 (d, J = 9.2, 1H), 7.66 (d, J = 9.5, 1H), 7.60-7.52 (m, 2H), 7.41 (d, J = 9.1, 1H), 7.20 (d, J = 2.3, 1H), 6.72 (d, J = 5.0, 1H), 6.26 (d, J = 4.5, 1H, 5.22-5.08 (m, 2H), 3.80-3.75 (m, 4H), 3.47-3.43 (m, 4H)

| 116 | | 2-(6-{[2-Chloro-4-fluoro-5-(7-morpholin-4-yl-quinazolin-4-yl)-phenyl]hydroxymethyl}pyridazin-3-yloxy)ethanol | A | B | A |

MS: 512.2/514.1 (M + H$^+$) (Cl isotopy, rel. peak intensity ratio [%] 100:38)

1H NMR (500 MHz, DMSO-d6) ppm = 9.12 (s, 1H), 7.91 (d, J = 7.7, 1H), 7.71-7.64 (m, 2H), 7.61-7.51 (m, 2H), 7.23-7.17 (m, 2H), 6.60 (d, J = 5.0, 1H), 6.22 (d, J = 5.0, 1H), 4.84 (t, J = 5.5, 1H), 4.44-4.39 (m, 2H), 3.81-3.76 (m, 4H), 3.74 (q, J = 5.4, 2H), 3.48-3.43 (m, 4H)

| 117 | | (3-Amino-pyrazin-2-yl)-[2-chloro-4-fluoro-5-(7-morpholin-4-yl-quinazolin-4-yl)-phenyl]methanol | B | B | B |

MS: 467.1/469.1 (M + H$^+$) (Cl isotopy, rel. peak intensity ratio [%] 100:34)

1H NMR (400 MHz, DMSO-d6) ppm = 9.14 (s, 1H), 7.91 (d, J = 7.8, 1H), 7.87 (d, J = 2.7, 1H), 7.67-7.55 (m, 4H), 7.21 (d, J = 2.5, 1H), 6.41 (s, 3H), 6.09 (s, 1H), 3.81-3.75 (m, 4H), 3.50-3.45 (m, 4H)

TABLE 3-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 118 | 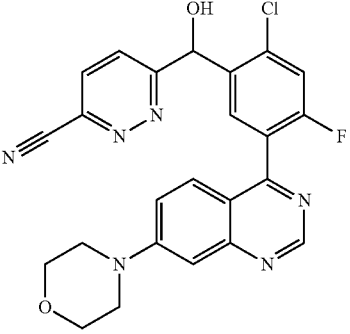 [SMILES: N#Cc1ccc(C(O)c2cc(-c3ncnc4cc(N5CCOCC5)ccc34)c(F)cc2Cl)nn1] | 6-{[2-Chloro-4-fluoro-5-(7-morpholin-4-yl-quinazolin-4-yl)-phenyl]hydroxy-methyl}pyridazine-3-carbonitrile | B | B | B |
| | MS: 477.0/479.1 (M + H⁺) (Cl isotopy, rel. peak intensity ratio [%] 100:41) | 1H NMR (500 MHz, DMSO-d6) ppm = 9.11 (s, 1H), 8.36 (d, J = 8.7, 1H), 8.13 (d, J = 8.7, 1H), 7.86 (d, J = 7.6, 1H), 7.71 (d, J = 9.5, 1H), 7.55 (qd, J = 9.4, 2.7, 2H), 7.21 (d, J = 2.3, 1H), 6.96 (d, J = 4.9, 1H), 6.43 (d, J = 4.9, 1H), 3.80-3.76 (m, 4H), 3.48-3.43 (m, 4H) | | | |
| 119 | 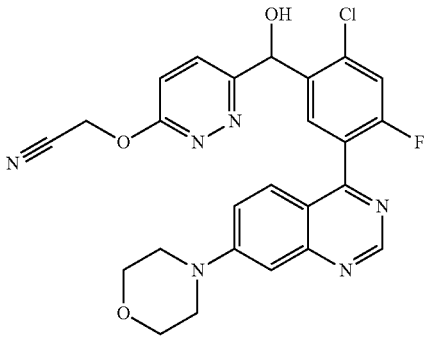 [SMILES: N#CCOc1ccc(C(O)c2cc(-c3ncnc4cc(N5CCOCC5)ccc34)c(F)cc2Cl)nn1] | (6-{[2-Chloro-4-fluoro-5-(7-morpholin-4-yl-quinazolin-4-yl)-phenyl]hydroxy-methyl}pyridazin-3-yl-oxy)acetonitrile | A | A | B |
| | MS: 507.1/509.1 (M + H⁺) (Cl isotopy, rel. peak intensity ratio [%] 100:35) | 1H NMR (400 MHz, DMSO-d6) ppm = 9.12 (s, 1H), 7.93 (d, J = 7.7, 1H), 7.85 (d, J = 9.2, 1H), 7.67 (d, J = 9.5, 1H), 7.60 (dd, J = 9.4, 3.3, 1H), 7.54 (dd, J = 9.4, 2.5, 1H), 7.40 (d, J = 9.1, 1H), 7.21 (d, J = 2.4, 1H), 6.72 (d, J = 5.0, 1H), 6.28 (d, J = 4.8, 1H), 5.38 (s, 2H), 3.81-3.75 (m, 4H), 3.48-3.42 (m, 4H) | | | |

Examples 120, 121 and 122

[2,4-Difluoro-5-(7-morpholin-4-ylquinazolin-4-yl)phenyl]-(4-methoxyphenyl)methanol (EXAMPLE 120)

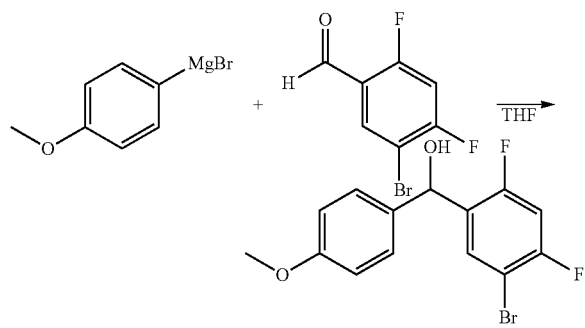

5-Bromo-2,4-difluorobenzaldehyde (280 mg, 1.27 mmol) in dry tetrahydrofuran (10 ml) was initially introduced in a three-necked flask with internal thermometer, protective-gas inlet, septum and stirrer bar which had been dried by heating. 4-Methoxyphenylmagnesium bromide (1 M in THF, 1.39 ml, 1.39 mmol) was slowly added dropwise at 5° C., and the reaction solution was stirred at room temperature for 18 h. With water (20 ml) was subsequently added to the reaction solution. The phases were separated, and the aqueous phase was extracted twice with ethyl acetate (20 ml). The combined organic phases were washed with water, dried over sodium sulfate, filtered and evaporated to dryness in a rotary evaporator, giving (5-bromo-2,4-difluorophenyl)-(4-methoxyphenyl)methanol (530 mg, 1.61 mmol, MS: 353 [M+H$^+$]) as oily crude product, which was used without further purification for the next synthesis step.

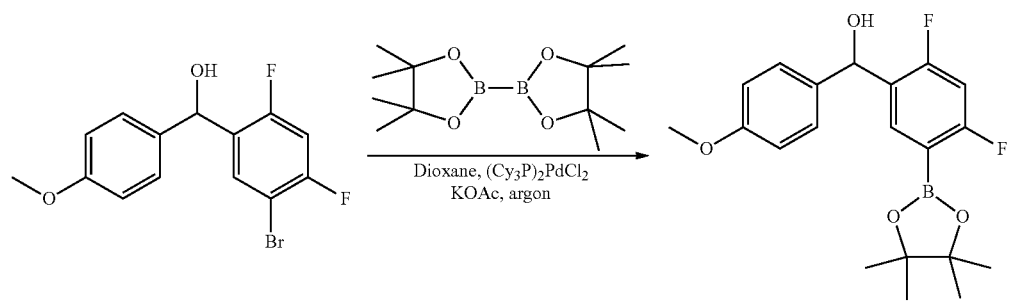

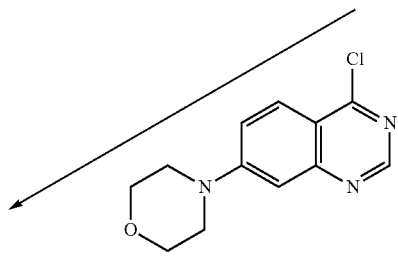

PdCl$_2$(dppf) dioxane,
aqueous Na$_2$CO$_3$ solution,
argon
(overall yield 16%)

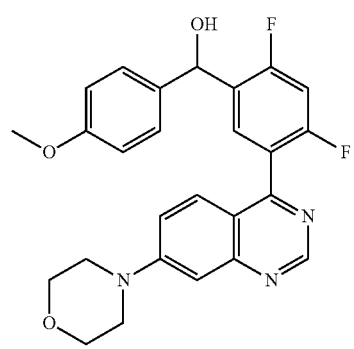

EXAMPLE 120

Starting from (5-bromo-2,4-difluorophenyl)-(4-methoxyphenyl)methanol, [2,4-difluoro-5-(7-morpholin-4-ylquinazolin-4-yl)phenyl]-(4-methoxyphenyl)methanol (EXAMPLE 120) was prepared analogously to the synthetic processes described under EXAMPLES 1 and 2.

(6-Difluoromethoxypyridazin-3-yl)-[4-fluoro-3-(7-morpholin-4-ylquinazolin-4-yl)phenyl]-methanol (EXAMPLE 121)

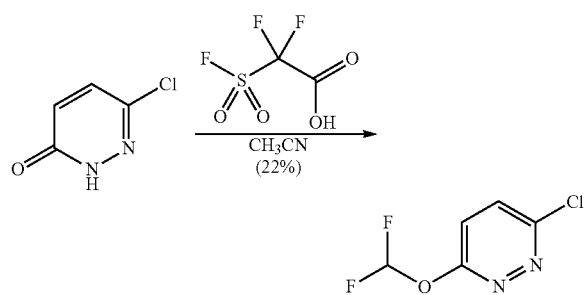

6-Chloro-2H-pyridazin-3-one (944 mg, 7.23 mmol) and difluoro(fluorosulfonyl)acetic acid (1.42 g, 7.96 mmol) were dissolved in acetonitrile (19 ml) in a vessel with stirrer bar and stirred at room temperature for 40 h. The reaction solution was then diluted with ethyl acetate (150 ml) and washed successively with water, saturated sodium hydrogencarbonate solution and again with water. The organic phase was dried using sodium sulfate, filtered and evaporated to dryness in a rotary evaporator. The residue was taken up in cyclohexane, re-filtered, and the solvent was removed in a rotary evaporator. The residue obtained was purified by means of flash column chromatography (gradient cyclohexane/0-50% by vol. of ethyl acetate, CombiFlash Rf 200). The suitable product fractions were combined, and the solvents were removed in a rotary evaporator, giving 3-chloro-6-(difluoromethoxy)pyridazine (285 mg, 1.58 mmol, MS: 181.0/183.1[M+H$^+$]), 22% yield) as colourless liquid.

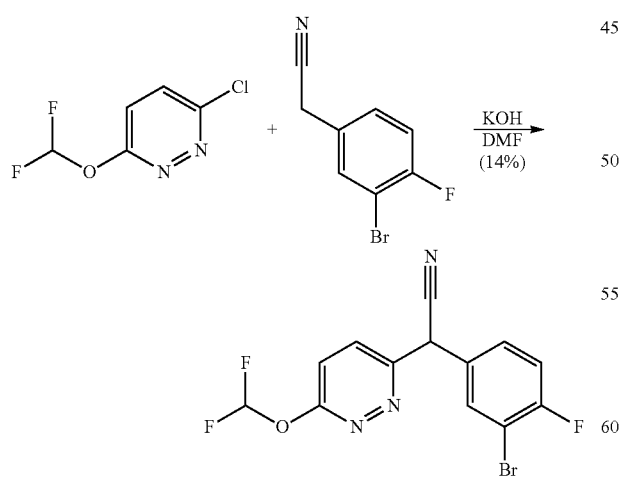

Potassium hydroxide powder (603 mg, 10.75 mmol) was suspended in dry N,N-dimethylformamide (2 ml) in a glass vessel with stirrer bar and stirred at room temperature for 30 min. (3-Bromo-4-fluorophenyl)acetonitrile (1.0 g, 4.67 mmol), dissolved in N,N'-dimethylformamide (1.3 ml), was subsequently added dropwise. The reaction mixture was stirred at room temperature for a further 30 min. (5-Bromo-2,4-difluorophenyl)-(4-methoxyphenyl)methanol (506 mg, 2.80 mmol) was then added in portions to the reaction mixture and stirred at 50° C. for 2 h under an oxygen-free argon protective-gas atmosphere. The reaction mixture was added to a mixture of water (50 ml) and saturated sodium chloride solution (35 ml) and extracted twice with ethyl acetate. The combined organic phases were dried over sodium sulfate, filtered and evaporated to dryness in a rotary evaporator. The residue was purified by means of RP column chromatography (gradient water/acetonitrile with 0.1% by vol. of formic acid, CombiFlash Rf 200). The suitable product fractions were combined, and the solvents were removed in a rotary evaporator, giving (3-bromo-4-fluorophenyl)-(6-difluoromethoxypyridazin-3-yl)acetonitrile (146 mg, 0.41 mmol, MS: 358.0/360.0[M+H$^{30}$], 14% yield) as liquid. 2-(3-Bromo-4-fluorophenyl)-2-(6-chloropyridazin-3-yl)acetonitrile is formed as by-product.

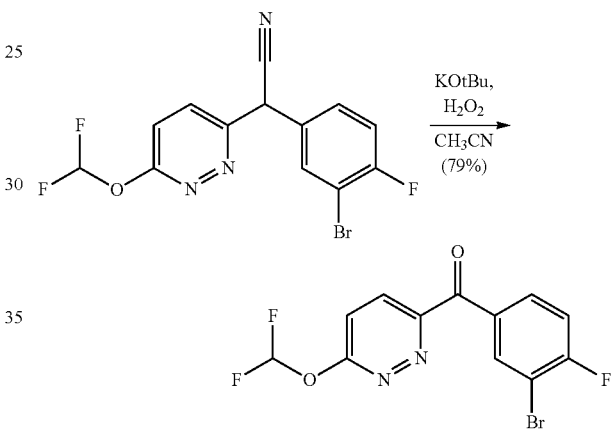

(3-Bromo-4-fluorophenyl)-(6-difluoromethoxypyridazin-3-yl)acetonitrile (146 mg, 0.41 mmol) was dissolved in dry acetonitrile (4 ml). Potassium tert-butoxide (43.6 mg, 0.388 mmol) was subsequently added, and the reaction mixture was stirred at room temperature for 25 min. The reaction solution was then cooled to 0° C. in an ice bath, hydrogen peroxide (30% in water, 92 µl, 0.90 mmol) was added dropwise, and the reaction mixture was stirred firstly at 0° C. for a further 25 min and then at room temperature for 1 h. For work-up, the reaction mixture was added to water (40 ml) and extracted twice with ethyl acetate. The combined organic phases were dried over sodium sulfate, filtered and evaporated to dryness in a rotary evaporator, giving (3-bromo-4-fluorophenyl)-(6-difluoromethoxypyridazin-3-yl)methanone (113 mg, 0.32 mmol, MS: 346.9/349.0[M+H$^+$], 79% yield) as solid.

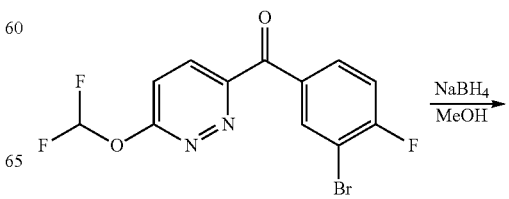

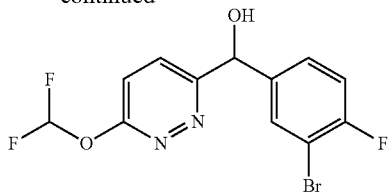

(3-Bromo-4-fluorophenyl)-(6-difluoromethoxypyridazin-3-yl)methanone (126 mg, 0.36 mmol) was dissolved in methanol (4 ml). Sodium borohydride (60.4 mg, 1.60 mmol) was subsequently added in portions, and the reaction mixture was stirred at room temperature for 1 h. After termination of the reaction, the mixture was diluted with saturated ammonium chloride solution (5 ml) and subsequently extracted twice with ethyl acetate (30 ml). The combined organic phases were washed with water, dried over sodium sulfate, filtered and evaporated to dryness in a rotary evaporator, giving (3-bromo-4-fluorophenyl)-(6-difluoromethoxypyridazin-3-yl)methanol (127 mg, MS: 349/351 [M+H$^+$]) as crude product in the form of a solid, which was used without further purification for further synthesis steps.

(6-Difluoromethoxypyridazin-3-yl)-[4-fluoro-3-(7-morpholin-4-ylquinazolin-4-yl)phenyl]-methanol (EXAMPLE 121) was obtained analogously by the synthetic process described for [2,4-difluoro-5-(7-morpholin-4-ylquinazolin-4-yl)phenyl]-(4-methoxyphenyl)methanol (EXAMPLE 120)

1-[2-Chloro-4-fluoro-5-(7-morpholin-4-ylquinazolin-4-yl)phenyl]-1-(6-methoxypyridazin-3-yl)prop-2-yn-1-ol (EXAMPLE 122)

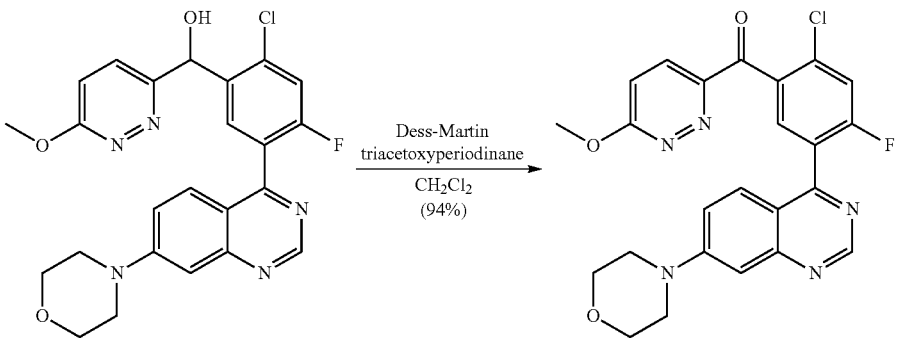

BEISPIEL 137

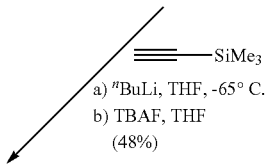

a) $^n$BuLi, THF, -65° C.
b) TBAF, THF
(48%)

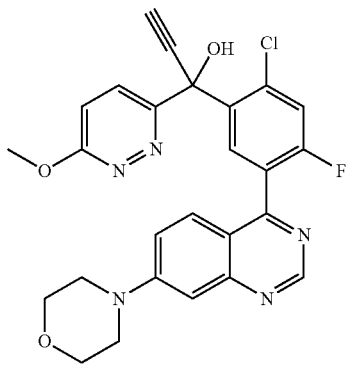

EXAMPLE 122

([2-Chloro-4-fluoro-5-(7-morpholin-4-ylquinazolin-4-yl)phenyl]-(6-methoxypyridazin-3-yl)methanol (EXAMPLE 137, 898 mg, 1.75 mmol) was dissolved in diochloromethane (15 ml). Dess-Martin triacetoxyperiodinane (15% in dichloromethane, 7.23 ml, 3.50 mmol) was subsequently added. The reaction suspension was stirred at room temperature for 1 h. For work-up, water (60 ml) and a 10%, aqueous sodium thiosulfate solution was added. The aqueous phase was extracted twice with ethyl acetate (80 ml in each case). The combined organic phases were washed with saturated sodium chloride solution (30 ml), dried over sodium sulfate, filtered, and the filtrate was evaporated to dryness in vacuo, giving 2.1 g of a crude product in the form of an oil. The residue was purified by means of flash column chromatography (gradient: dichloromethane/0-25% by vol. of dichloromethane/ethanol 9:1, CombiFlash Rf 200), giving [2-chloro-4-fluoro-5-(7-morpholin-4-ylquinazolin-4-yl)phenyl]-(6-methoxypyridazin-3-yl)methanone (792 mg, 1.65 mmol, MS: 480.1/482.1 [M+H⁺], 94% yield) as foam.

Trimethylsilylacetylene (179 µl, 125 mg, 1.25 mmol) dissolved in dry tetrahydrofuran (3 ml) was initially introduced in a glass vessel with stirrer bar and internal thermometer under argon. The reaction solution was cooled to (−)20° C., and n-butyllithium (1.6 M in n-hexane, 781 µl, 1.25 mmol) was slowly added dropwise. The reaction mixture was stirred at (−)20° C. for a further 30 min. The reaction solution was then cooled to (−)70° C., and [2-chloro-4-fluoro-5-(7-morpholin-4-ylquinazolin-4-yl)phenyl]-(6-methoxypyridazin-3-yl)methanone (200 mg, 0.417 mmol) dissolved in dry tetrahydrofuran (6 ml) was subsequently added dropwise. The temperature of the reaction mixture was increased to (−)40° C. over a period of 1 h. Water (40 ml) was subsequently added, and the phases were separated. The organic phase was extracted twice with dichloromethane. The combined organic phases were dried using sodium sulfate, filtered and evaporated to dryness in vacuo. The residue was dissolved in dry tetrahydrofuran (4 ml), and tetra-n-butylammonium fluoride trihydrate (109 mg, 0.42 mmol) was added. The mixture was subsequently stirred at room temperature for 18 h. The volatile reaction constituents were then removed in a rotary evaporator. The residue was pre-purified by means of flash column chromatography (gradient: dichloromethane/0-34% by vol. of dichloromethane/ethanol 1:1, CombiFlash Rf 200). The product fractions were combined, and the solvents were removed in vacuo in a rotary evaporator. The residue was finally purified by means of preparative RP chromatography (Chromolith RP-18e 21.2×100 mm, flow rate: 50 ml/min., wavelength: 220 nm). The volatile solvent constituents of the suitable fractions were removed by means of a vacuum centrifuge (Genevac HT-12), and the product was freeze-dried from acetonitrile/water (1:3 parts by volume), giving 1-[2-chloro-4-fluoro-5-(7-morpholin-4-ylquinazolin-4-yl)phenyl]-1-(6-methoxypyridazin-3-yl)prop-2-yn-1-ol (EXAMPLE 122, 102 mg, 0.20 mmol, MS: 506.1/508.1 [M+H⁺], 48% yield) as solid.

Compounds which were prepared in accordance with EXAMPLES 120, 121 and 122 can be found in Table 4 below.

TABLE 4

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 120 | 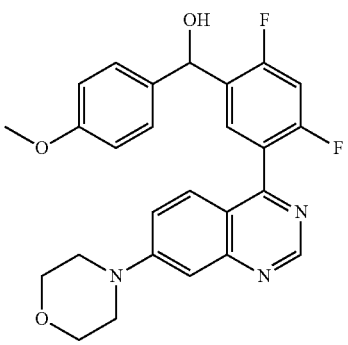 [SMILES: COc1ccc(C(O)c2cc(-c3ncnc4cc(N5CCOCC5)ccc34)c(F)cc2F)cc1]<br>MS: 464.2 (M + H⁺) | [2,4-Difluoro-5-(7-morpholin-4-yl-quinazolin-4-yl)-phenyl]-(4-methoxyphenyl)-methanol | C | B | D |

1H NMR (400 MHz, DMSO-d6) ppm = 9.09 (s, 1H), 7.61-7.47 (m, 3H), 7.36-7.30 (m, 2H), 7.27 (t, J = 9.1, 1H), 7.20 (d, J = 2.3, 1H), 6.93-6.87 (m, 2H), 6.18 (d, J = 4.6, 1H), 6.14 (d, J = 4.6, 1H), 3.81-3.75 (m, 4H), 3.73 (s, 3H), 3.48-3.41 (m, 4H)

TABLE 4-continued

Compounds of the formula (I)

| No. | Structural formula | Name | IC₅₀ DNA-PK | IC₅₀ pDNA-PK | $K_i$ [Kv1.11 hERG] |
|---|---|---|---|---|---|
| 121 | 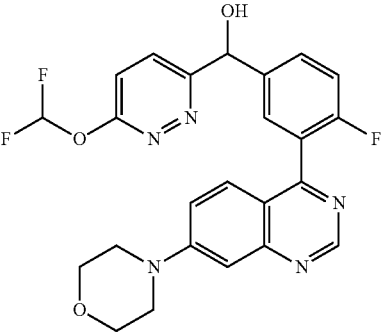 [SMILES: OC(c1ccc(F)c(-c2ncnc3cc(N4CCOCC4)ccc23)c1)c1ccc(OC(F)F)nn1]<br><br>MS: 484.1 (M + H⁺) | (6-Difluoro-methoxy-pyridazin-3-yl)-[4-fluoro-3-(7-morpholin-4-yl-quinazolin-4-yl)-phenyl]methanol<br><br>1H NMR (500 MHz, DMSO-d6) ppm = 9.10 (s, 1H), 7.96 (d, J = 9.1, 1H), 7.73-7.63 (m, 2H), 7.57-7.47 (m, 3H), 7.46-7.31 (m, 1H), 7.22-7.16 (m, 1H), 6.63 (d, J = 4.4, 1H), 6.10 (d, J = 4.4, 1H), 3.81-3.75 (m, 4H), 3.47-3.41 (m, 4H) | B | B | B |
| 122 | 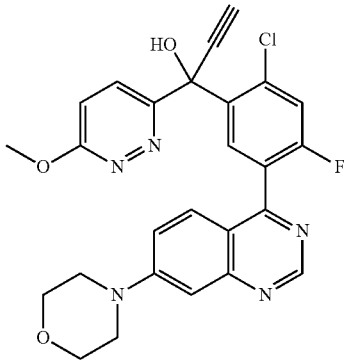 [SMILES: C#CC(O)(c1ccc(OC)nn1)c1cc(-c2ncnc3cc(N4CCOCC4)ccc23)c(F)cc1Cl]<br><br>MS: 506.1/508.1 (M + H⁺)<br>(Cl isotopy, rel. peak intensity ratio [%] 100:35) | 1-[2-Chloro-4-fluoro-5-(7-morpholin-4-yl-quinazolin-4-yl)-phenyl]-1-(6-methoxy-pyridazin-3-yl)-prop-2-yn-1-ol<br><br>1H NMR (500 MHz, DMSO-d6) ppm = 9.16 (s, 1H), 8.28 (d, J = 7.7, 1H), 7.96 (d, J = 9.2, 1H), 7.69-7.63 (m, 2H), 7.59 (dd, J = 9.5, 2.5, 1H), 7.50 (s, 1H), 7.30 (d, J = 9.2, 1H), 7.23 (d, J = 2.5, 1H), 4.02 (s, 3H), 3.94 (s, 1H), 3.81-3.76 (m, 4H), 3.50-3.44 (m, 4H) | C | B | C |
| 123 | 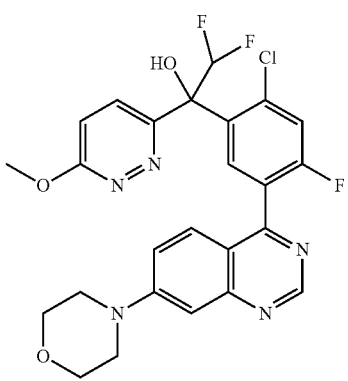 [SMILES: COc1ccc(C(O)(c2cc(-c3ncnc4cc(N5CCOCC5)ccc34)c(F)cc2Cl)C(F)F)nn1]<br><br>MS: 532.1/534.1 (M + H⁺)<br>(Cl isotopy, rel. peak intensity ratio [%] 100:40) | 1-[2-Chloro-4-fluoro-5-(7-morpholin-4-yl-quinazolin-4-yl)-phenyl]-2,2-difluoro-1-(6-methoxy-pyridazin-3-yl)-ethanol<br><br>1H NMR (500 MHz, DMSO-d6) ppm = 9.15 (s, 1H), 8.17 (d, J = 7.7, 1H), 7.67-7.61 (m, 3H), 7.57 (dd, J = 9.5, 2.5, 1H), 7.32 (s, 1H, 7.26 (d, 1H), 7.25-7.22 (m, 1H), 7.22-6.96 (m, 2H), 4.05 (s, 3H), 3.81-3.75 (m, 4H), 3.50-3.45 (m, 4H). | C | D | A |

TABLE 4-continued

Compounds of the formula (I)

| No. | Structural formula | Name | IC₅₀ DNA-PK | IC₅₀ pDNA-PK | $K_i$ [Kv1.11 hERG] |
|---|---|---|---|---|---|
| 124 | MS: 582.1 (M + H⁺) | [2,4-Difluoro-5-(7-morpholin-4-yl-quinazolin-4-yl)-phenyl]-(2-fluoro-4-methoxy-phenyl)methanol | C | B | D |

1H NMR (400 MHz, DMSO-d6) ppm = 9.09 (s, 1H), 7.70 (t, J = 8.8, 1H), 7.62-7.44 (m, 3H), 7.25 (t, J = 9.2, 1H), 7.20 (d, J = 2.4, 1H), 6.82 (dd, J = 8.6, 2.5, 1H), 6.74 (dd, J = 12.6, 2.5, 1H), 6.34 (d, J = 4.6, 1H), 6.28 (d, J = 4.6, 1H), 3.82-3.71 (m, 7H), 3.49-3.41 (m, 4H)

| 125 | MS: 496.1/498.1 (M + H⁺) (Cl isotopy, rel. peak intensity ratio [%] 100:35) | 1-[2-Chloro-4-fluoro-5-(7-morpholin-4-yl-quinazolin-4-yl)-phenyl]-1-(6-methoxy-pyridazin-3-yl)-ethanol | B | D | B |

1H NMR (500 MHz, DMSO-d6) ppm = 9.15 (s, 1H), 8.20 (d, J = 7.9, 1H), 7.67 (dd, J = 9.4, 3.4, 1H), 7.60-7.54 (m, 3H), 7.23 (d, J = 2.5, 1H), 7.18 (d, J = 9.2, 1H), 6.39 (s, 1H), 4.03 (s, 3H), 3.82-3.75 (m, 4H), 3.49-3.45 (m, 4H), 2.02 (s, 3H)

| 126 | MS: 488.1/490.1 (M + H⁺) (Cl isotopy, rel. peak intensity ratio [%] 100:39); R_f 16.85 min (SFC, Chiracel OD-H, CO₂/15% by vol. of methanol, 0.5% by vol. of diethylamine) | [2-Chloro-4-fluoro-5-(6-morpholin-4-ylthieno[3,2-d]-pyrimidin-4-yl)-phenyl]-(6-methoxy-pyridazin-3-yl)-methanol (Ena 2) | A | A | C |

1H NMR (500 MHz, DMSO-d6) ppm = 8.90 (s, 1H), 8.00 (d, J = 7.9, 1H), 7.69 (d, J = 9.2, 1H), 7.66 (d, J = 10.0, 1H), 7.22 (d, J = 9.2, 1H), 6.62 (d, J = 4.9, 1H), 6.54 (s, 1H), 6.22 (d, J = 4.9, 1H), 3.99 (s, 3H), 3.77-3.72 (m, 4H), 3.45-3.39 (m, 4H)

TABLE 4-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 127 | 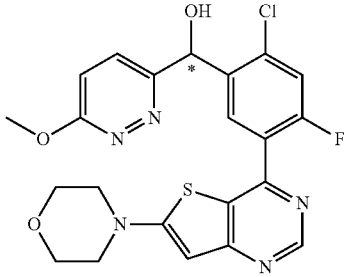 [SMILES: COc1ccc(C(O)c2cc(-c3ncnc4cc(N5CCOCC5)sc34)c(F)cc2Cl)nn1] MS: 488.1/490.1 (M + H$^+$) (Cl isotopy, rel. peak intensity ratio [%] 100:40); R$_t$ 14.73 min (SFC, Chiracel OD-H, CO$_2$/15% by vol. of methanol, 0.5% by vol. of diethylamine) | [2-Chloro-4-fluoro-5-(6-morpholin-4-ylthieno[3,2-d]-pyrimidin-4-yl)-phenyl]-(6-methoxy-pyridazin-3-yl)-methanol (Ena 1) 1H NMR (500 MHz, DMSO-d6) ppm = 8.90 (s, 1H), 8.00 (d, J = 7.9, 1H), 7.69 (d, J = 9.2, 1H), 7.66 (d, J = 10.0, 1H), 7.22 (d, J = 9.1, 1H), 6.61 (d, J = 5.0, 1H), 6.54 (s, 1H), 6.21 (d, J = 4.9, 1H), 3.99 (s, 3H), 3.77-3.72 (m, 4H), 3.45-3.40 (m, 4H) | B | C | C |
| 128 | 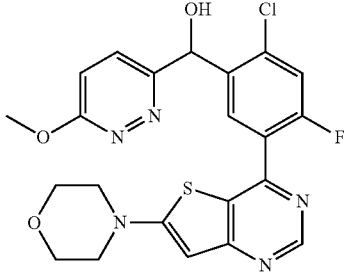 [SMILES: COc1ccc(C(O)c2cc(-c3ncnc4cc(N5CCOCC5)sc34)c(F)cc2Cl)nn1] MS: 488.1/490.1 (M + H$^+$) (Cl isotopy, rel. peak intensity ratio [%] 100:41) | [2-Chloro-4-fluoro-5-(6-morpholin-4-ylthieno[3,2-d]-pyrimidin-4-yl)-phenyl]-(6-methoxy-pyridazin-3-yl)-methanol 1H NMR (500 MHz, DMSO-d6) ppm = 8.90 (s, 1H), 8.00 (d, J = 7.9, 1H), 7.69 (d, J = 9.2, 1H), 7.66 (d, J = 10.0, 1H), 7.22 (d, J = 9.1, 1H), 6.61 (d, J = 4.9, 1H), 6.54 (s, 1H), 6.22 (d, J = 4.9, 1H), 3.99 (s, 3H), 3.77-3.73 (m, 4H), 3.44-3.40 (m, 4H) | A | B | B |
| 129 | 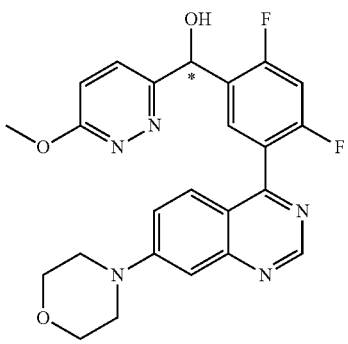 MS: 466.2 (M + H$^+$); R$_t$ 4.13 min, (SFC, Chiralpak AS-H, CO$_2$/18% by vol. of methanol, 0.5% by vol. of diethylamine) | [2,4-Difluoro-5-(7-morpholin-4-yl-quinazolin-4-yl)-phenyl]-(6-methoxy-pyridazin-3-yl)-methanol (Ena 2) see racemate | C | C | B |

TABLE 4-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 130 | 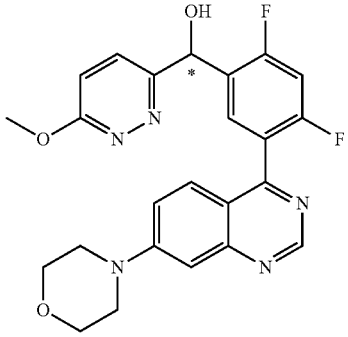<br>MS: 466.2 (M + H$^+$); R$_t$ 2.79 min, (SFC, Chiralpak AS-H, CO$_2$/ 18% by vol. of methanol, 0.5% by vol. of diethylamine) | [2,4-Difluoro-5-(7-morpholin-4-yl-quinazolin-4-yl)-phenyl]-(6-methoxy-pyridazin-3-yl)-methanol (Ena 1)<br><br>see racemate | A | A | A |
| 131 | 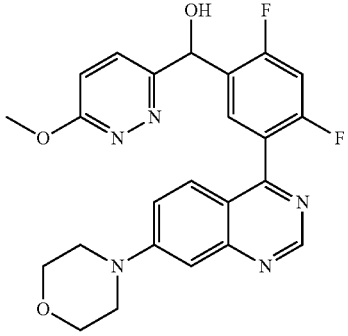<br>MS: 466.2 (M + H$^+$) | [2,4-Difluoro-5-(7-morpholin-4-yl-quinazolin-4-yl)-phenyl]-(6-methoxy-pyridazin-3-yl)-methanol<br><br>1H NMR (500 MHz, DMSO-d6) ppm = 9.11 (s, 1H), 7.83 (t, J = 8.1, 1H), 7.75 (d, J = 9.2, 1H), 7.56 (qd, J = 9.4, 2.8, 2H), 7.45 (t, J = 10.1, 1H), 7.25-7.19 (m, 2H), 6.59-6.57 (m, 1H), 6.20-6.16 (m, 1H), 4.00 (s, 3H), 3.81-3.75 (m, 4H), 3.48-3.42 (m, 4H) | B | B | B |
| 132 | 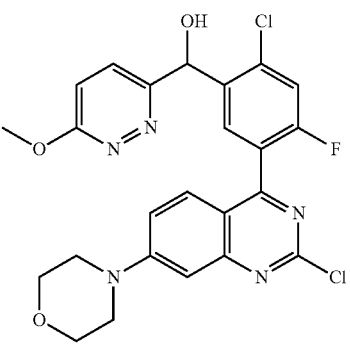 [SMILES: COc1ccc(C(O)c2cc(-c3nc(Cl)nc4cc(N5CCOCC5)ccc34)c(F)cc2Cl)nn1]<br>MS: 516.1/518.1/520.0 (M + H$^+$) (Cl$_2$ isotopy, rel. peak intensity ratio [%] 100:69:12) | [2-Chloro-5-(2-chloro-7-morpholin-4-yl-quinazolin-4-yl)-4-fluorophenyl]-(6-methoxy-pyridazin-3-yl)-methanol<br><br>1H NMR (500 MHz, DMSO-d6) ppm = 7.94 (d, J = 7.7, 1H), 7.72-7.65 (m, 2H), 7.63-7.49 (m, 2H), 7.21 (d, J = 9.1, 1H), 7.15 (d, J = 2.4, 1H), 6.22 (s, 1H), 4.00 (s, 3H), 3.79-3.73 (m, 4H), 3.53-3.47 (m, 4H) | B | B | A |

TABLE 4-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 133 | 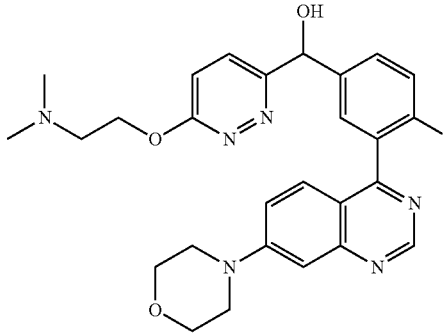<br><br>MS: 505.3 (M + H$^+$) | [6-(2-Dimethyl-amino-ethoxy)-pyridazin-3-yl]-[4-fluoro-3-(7-morpholin-4-yl-quinazolin-4-yl)-phenyl]methanol<br><br>1H NMR (500 MHz, DMSO-d6) ppm = 9.09 (s, 1H), 7.69 (d, J = 9.2, 1H), 7.67-7.61 (m, 2H), 7.55-7.47 (m, 2H), 7.44-7.36 (m, 1H), 7.24-7.15 (m, 2H), 6.49 (d, J = 4.0, 1H), 6.04-5.98 (m, 1H), 4.56-4.41 (m, 2H), 3.80-3.74 (m, 4H), 3.47-3.41 (m, 4H), 2.64 (t, J = 5.8, 2H), 2.19 (s, 6H) | C | C | A |
| 134 | 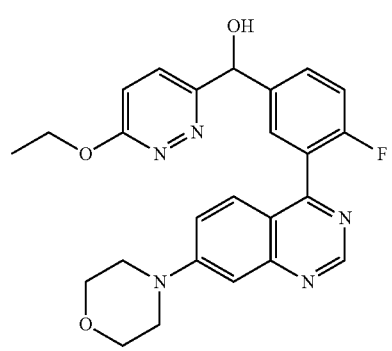 [SMILES: CCOc1ccc(C(O)c2ccc(F)c(-c3ncnc4cc(N5CCOCC5)ccc34)c2)nn1]<br><br>MS: 462.1 (M + H$^+$) | (6-Ethoxy-pyridazin-3-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 7.68 (d, J = 9.2, 1H), 7.66-7.61 (m, 2H), 7.53-7.50 (m, 2H), 7.43-7.35 (m, 1H), 7.21-7.19 (m, 1H), 7.17 (d, J = 9.1, 1H), 6.47 (d, J = 4.4, 1H), 6.01 (d, J = 4.3, 1H), 4.52-4.38 (m, 2H), 3.82-3.73 (m, 4H), 3.46-3.41 (m, 4H), 1.36 (t, J = 7.0, 3H) | C | B | C |
| 135 | 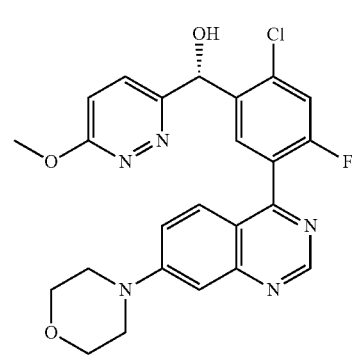 [SMILES: COc1ccc([C@H](O)c2cc(-c3ncnc4cc(N5CCOCC5)ccc34)c(F)cc2Cl)nn1]<br><br>MS: 482.1/484.1 (M + H$^+$) (Cl isotopy, rel. peak intensity ratio [%] 100:36); R$_t$ 5.34 min (SFC, Chiralpak AD-H, CO$_2$/40% by vol. of methanol, 0.5% by vol. of diethylamine) | (R)-[2-Chloro-4-fluoro-5-(7-morpholin-4-yl-quinazolin-4-yl)-phenyl]-(6-methoxy-pyridazin-3-yl)-methanol<br><br>1H NMR (500 MHz, DMSO-d6) ppm = 9.12 (s, 1H), 7.91 (d, J = 7.7, 1H), 7.69 (d, J = 9.2, 1H), 7.67 (d, J = 9.5, 1H), 7.62-7.51 (m, 2H), 7.24-7.18 (m, 2H), 6.61 (d, J = 4.8, 1H), 6.23 (d, J = 4.8, 1H), 4.00 (s, 3H), 3.81-3.75 (m, 4H), 3.48-3.42 (m, 4H) | C | D | A |

TABLE 4-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 136 | | (S)-[2-Chloro-4-fluoro-5-(7-morpholin-4-yl-quinazolin-4-yl)-phenyl]-(6-methoxy-pyridazin-3-yl)-methanol | A | A | A |
| | MS: 482.1/484.1 (M + H$^+$) (Cl isotopy, rel. peak intensity ratio [%] 100:36); R$_t$ 3.38 min (SFC, Chiralpak AD-H, CO$_2$/40% by vol. of methanol, 0.5% by vol. of diethylamine) | 1H NMR (500 MHz, DMSO-d6) ppm = 9.12 (s, 1H), 7.91 (d, J = 7.7, 1H), 7.69 (d, J = 9.2, 1H), 7.66 (d, J = 9.5, 1H), 7.61-7.52 (m, 2H), 7.24-7.19 (m, 2H), 6.61 (d, J = 5.0, 1H), 6.23 (d, J = 4.9, 1H), 4.00 (s, 3H), 3.81-3.75 m, 4H), 3.48-3.43 (m, 4H) | | | |
| 137 | | [2-Chloro-4-fluoro-5-(7-morpholin-4-ylquinazolin-4-yl)-phenyl]-(6-methoxy-pyridazin-3-yl)-methanol | A | B | C |
| | MS: 482.1/484.1 (M + H$^+$) (Cl isotopy, rel. peak intensity ratio [%] 100:36) | 1H NMR (400 MHz, DMSO-d6) ppm = 9.12 (s, 1H), 7.91 (d, J = 7.7, 1H), 7.69 (d, J = 9.1, 1H), 7.66 (d, J = 9.5, 1H), 7.62-7.51 (m, 2H), 7.24-7.17 (m, 2H), 6.60 (d, J = 4.9, 1H), 6.23 (d, J = 3.5, 1H), 4.00 (s, 3H), 3.82-3.74 (m, 4H), 3.49-3.42 (m, 4H) | | | |

Example 138

1-[5-(7-Morpholin-4-ylquinazolin-4-yl)pyridin-3-yl]-1-thiazol-2-ylethanol (EXAMPLE 138)

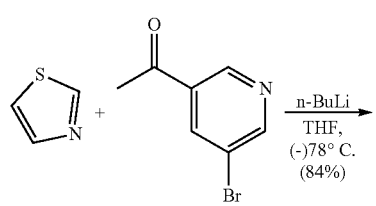

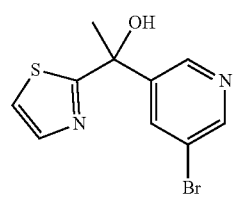

Thiazole (143 µl, 2.0 mmol) in dry tetrahydrofuran (10 ml) was initially introduced in a three-necked flask which had been dried by heating. The reaction solution was cooled to (−)78° C. by means of acetone/dry-ice bath. n-Butyl-lithium (15% solution in n-hexane, 1.63 ml, 2.6 mmol) was added dropwise over a period of 10 min at constant temperature. The reaction mixture was stirred for a further 10 min. The suspension was was subsequently warmed to (−)30° C. and re-cooled to (−)55° C., and 1-(5-bromopyridin-3-yl)ethanone (380 mg, 1.90 mmol), dissolved in dry tetrahydrofuran (6 ml), was added dropwise at (−)40° C. The reaction temperature is allowed to rise to (−)10° C. over 1.5 h. After termination of the reaction (HPLC check), saturated ammonium chloride solution was added, and the mixture was stirred at room temperature for 30 min. The reaction mixture was added to a two-phase solution of water (60 ml) and ethyl acetate (80 ml) and extracted three times with ethyl acetate. The combined organic phases were washed with saturated sodium chloride solution, dried over sodium sulfate, filtered and evaporated in a rotary evaporator. The oily crude product was purified by means of flash column chromatography (solvent: dichloromethane/2.0% by vol. of methanol, then dichloromethane/3.0% by vol. of methanol+ 1.0% by vol. of ammonia, amount of flash silica gel 30 g). The product fractions were combined, and the solvents were removed in vacuo in a rotary evaporator, giving 1-(5-bromopyridin-3-yl)-1-thiazol-2-ylethanol (479 mg, 1.68 mmol, MS: 285.0/287.0 [M+H$^+$], 84% yield) as oil.

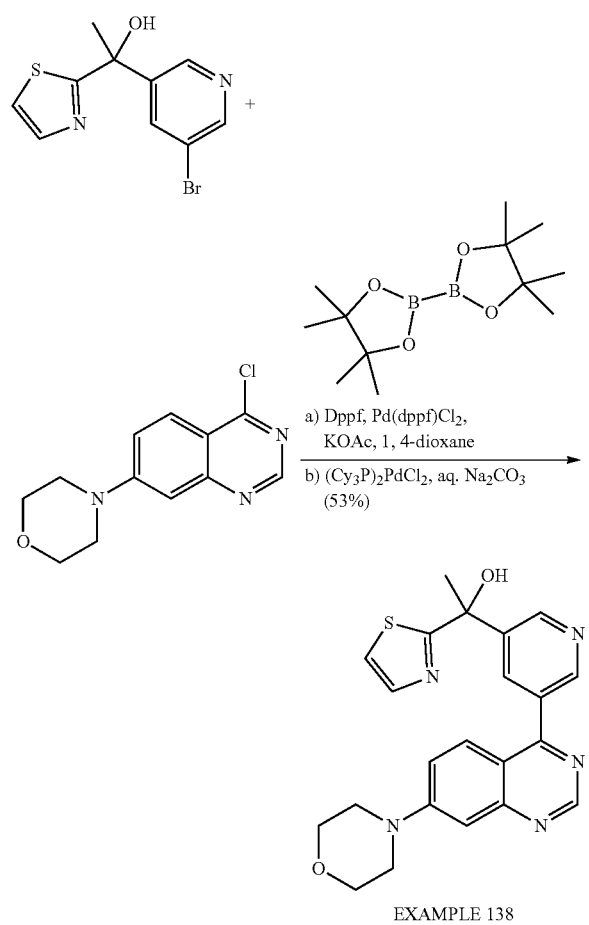

EXAMPLE 138

1-(5-Bromopyridin-3-yl)-1-thiazol-2-ylethanol (162 mg, 0.55 mmol), bis(pinacolato)diboron (140 mg, 0.55 mmol), 1,1′-bis(diphenylphosphino)ferrocene (Dppf, 7.1 mg, 0.013 mmol), 1,1′-bis(diphenylphosphino)ferrocenepalladium(II) dichloride [Pd(dppf)Cl$_2$, 10.4 mg, 0.013 mmol] and potassium acetate (167 mg, 1.7 mmol) were suspended in dry, oxygen-free 1,4-dioxane in a glass vessel with stirrer bar. The glass vessel was sealed using a septum. The reaction solution was stirred and heated at 115° C. for 2.5 h. The reaction monitoring is carried out by means of HPLC. 4-Chloro-7-morpholin-4-ylquinazoline (106 mg, 0.43 mmol), bis(tricyclohexylphosphine)palladium(II) dichloride (9.4 mg, 0.013 mmol) and 2.0 M sodium carbonate solution (531 μl) were added to the reaction solution. The reaction mixture was subsequently stirred at a temperature of 125° C. for 1.5 h. The mixture was decanted into water/dichloromethane (1:1 parts by volume, 40 ml), and the resultant solution was extracted three times with dichloromethane. The combined organic phases were dried over sodium sulfate, filtered and evaporated in a rotary evaporator. The residue was purified by means of flash chromatography [gradient: dichloromethane/20-58% by vol. of a solvent mixture of dichloromethane/methanol 9:1 (parts by volume), CombiFlash Rf 200]. The suitable product fractions were combined, and the solvents were removed in a rotary evaporator, giving 1-[5-(7-morpholin-4-ylquinazolin-4-yl)pyridin-3-yl]-1-thiazol-2-ylethanol (EXAMPLE 138, 95 mg, 0.23 mmol, MS: 420.2 [M+H$^+$], 53% yield) as oil.

Example 139

{3-[7-(3,6-Dihydro-2H-pyran-4-yl)quinazolin-4-yl]-4-fluorophenyl}thiazol-2-ylmethanol (139)

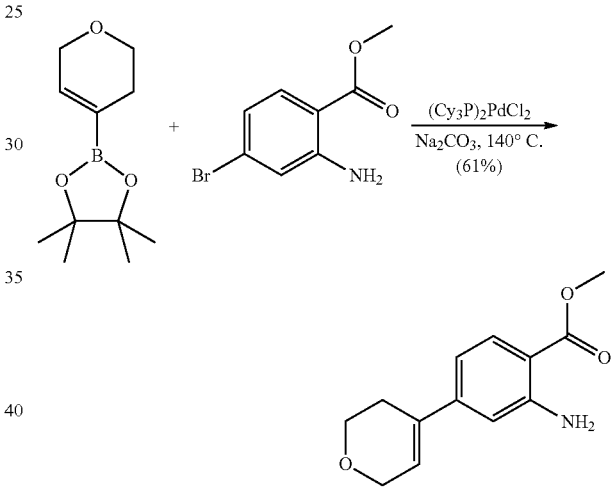

4-(4,4,5,5-Tetramethyl-1,3,2-dioxaborolan-2-yl)-3,6-dihydro-2H-pyran (575 mg, 2.74 mmol), methyl 2-amino-4-bromobenzoate (600 mg, 2.61 mmol), bis(tricyclohexylphosphine)palladium(II) dichloride (57.8 mg, 0.078 mmol) and oxygen-free 2.0 M sodium carbonate solution (3.26 ml, 6.52 mmol) in degassed, oxygen-free 1,4-dioxane (12 ml) were initially introduced in a microwave glass vessel with stirrer bar. The substance mixture was heated at 135° C. for a period of 55 min in a Personal Chemistry Microwave Synthesiser at 100 watts. The reaction solution was subsequently decanted off into a mixture of water (40 ml) and ethyl acetate (30 ml) mixture. The resultant solution was extracted three times with ethyl acetate. The combined organic phases were washed with saturated sodium chloride solution, dried over sodium sulfate, filtered and evaporated in vacuo in a rotary evaporator. The residue was purified by means of flash chromatography [gradient: dichloromethane/ 0-10% by vol. of a solvent mixture of dichloromethane/ methanol 10:1 (parts by volume), CombiFlash Rf 200]. The suitable product fractions were combined, and the solvents were removed in a rotary evaporator, giving methyl 2-amino-4-(3,6-dihydro-2H-pyran-4-yl)benzoate (371.1 mg, 1.59 mmol, MS: 234.2 [M+H$^+$], 61% yield) as solid

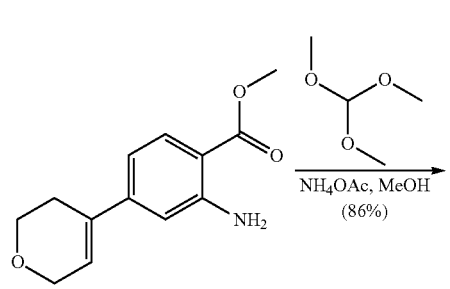

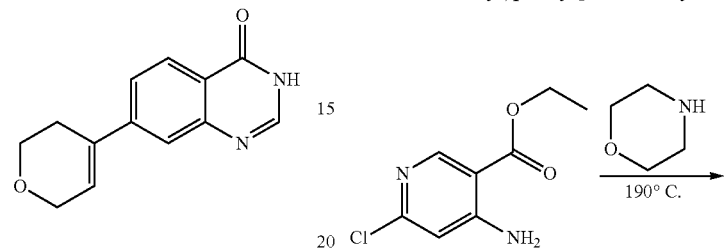

Methyl 2-amino-4-(3,6-dihydro-2H-pyran-4-yl)benzoate (620 mg, 2.66 mmol), trimethyl orthoformate (564.1 mg, 5.32 mmol) and ammonium acetate (410 mg, 5.32 mmol) dissolved in methanol (20 ml) was initially introduced in a glass vessel with stirrer bar. The substance mixture was stirred overnight at 80° C. Water (10 ml) was subsequently added, and the solid which precipitated out was filtered off with suction, washed with a little water and subsequently dried in vacuo, giving 7-(3,6-dihydro-2H-pyran-4-yl)-3H-quinazolin-4-one (520 mg, 2.28 mmol, MS: 229.1 [M+H⁺], 86% yield) as solid.

{3-[7-(3,6-Dihydro-2H-pyran-4-yl)quinazolin-4-yl]-4-fluorophenyl}thiazol-2-ylmethanol (EXAMPLE 139) was obtained analogously to the synthetic processes for the preparation of 1-[5-(7-morpholin-4-ylquinazolin-4-yl)pyridin-3-yl]-1-thiazol-2-ylethanol (EXAMPLE 138).

Example 140

[4-Fluoro-3-(7-morpholin-4-ylpyrido[4,3-d]pyrimidin-4-yl)phenyl]thiazol-2-ylmethanol (140)

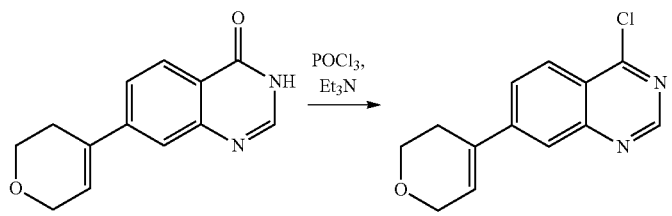

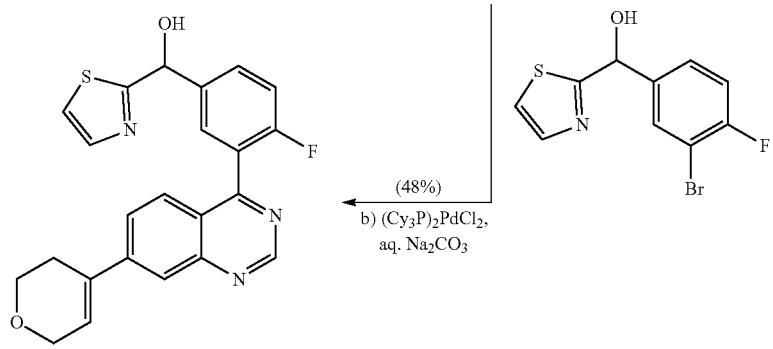

Ethyl 4-amino-6-chloronicotinate (8.38 g, 39.7 mmol) were dissolved in morpholine (40 ml). The substance mixture was heated at 120° C. for 4 h. When the reaction was terminated, the cooled reaction solution was decanted into water (400 ml). The aqueous suspension was stirred for 10 min, and the precipitate was subsequently filtered off. The filter cake was rinsed with a little water and dried overnight at 60° C. in vacuo, giving pure ethyl 4-amino-6-morpholin-4-ylnicotinate (8.55 g, 34.03 mmol, MS: 252.2 [M+H⁺], 85% yield) as colourless solid.

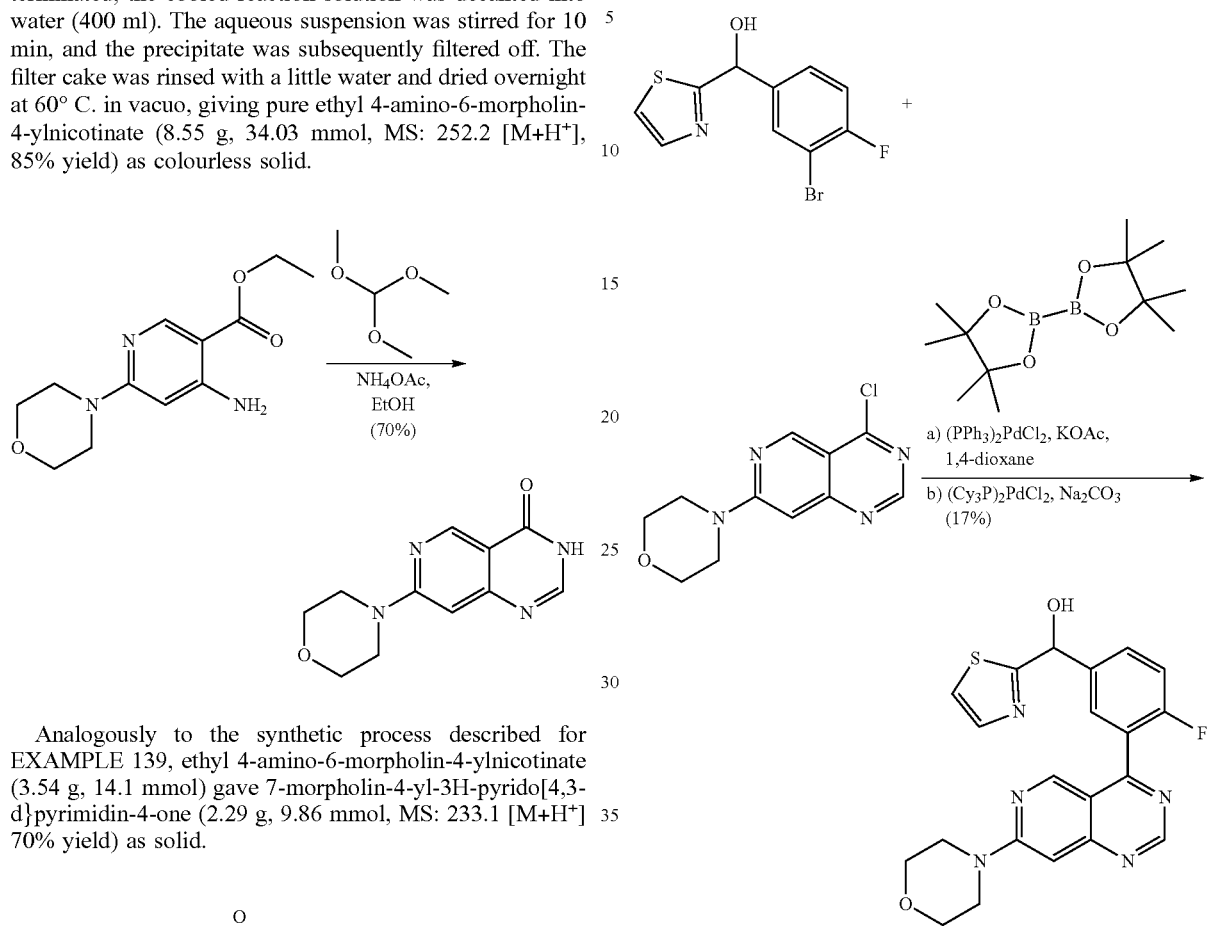

Analogously to the synthetic process described for EXAMPLE 139, ethyl 4-amino-6-morpholin-4-ylnicotinate (3.54 g, 14.1 mmol) gave 7-morpholin-4-yl-3H-pyrido[4,3-d]pyrimidin-4-one (2.29 g, 9.86 mmol, MS: 233.1 [M+H⁺] 70% yield) as solid.

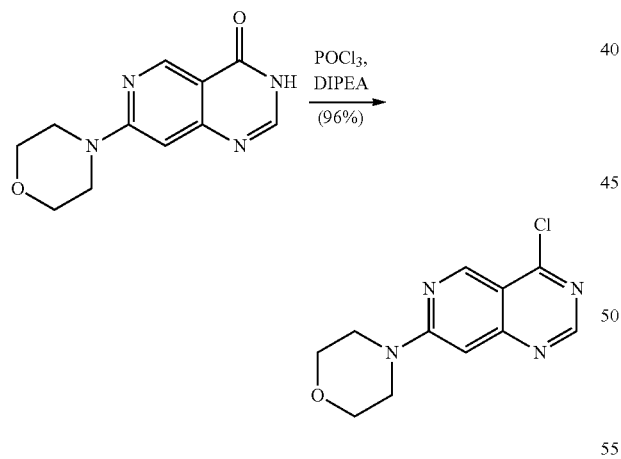

7-Morpholin-4-yl-3H-pyrido[4,3-d]pyrimidin-4-one (600 mg, 2.58 mmol) was suspended in 1,4-dioxane (10 ml). Phosphoryl chloride (POCl₃, 546 μl, 5.9 mmol) and Hünig's base (N-ethyldiisopropylamine, 220 μl, 1.29 mmol) were added to the reaction mixture. The mixture was subsequently stirred at a temperature of 100° C. for 3 h. After termination of the reaction, the reaction solution was decanted into a semi-saturated sodium hydrogencarbonate solution (80 ml). The aqueous phase was extracted three times with dichloromethane (40 ml in each case). The combined organic phases were dried over sodium sulfate, filtered and evaporated in vacuo in a rotary evaporator, giving 4-chloro-7-morpholin-4-ylpyrido[4,3-d]pyrimidine (627 mg, 2.50 mmol, MS: 251.0/253.0 [M+H⁺], 96% yield) as solid.

[4-Fluoro-3-(7-morpholin-4-ylpyrido[4,3-d]pyrimidin-4-yl)phenyl]thiazol-2-ylmethanol (EXAMPLE 140) was obtained analogously to the synthetic processes for the preparation of 1-[5-(7-morpholin-4-ylquinazolin-4-yl)pyridin-3-yl]-1-thiazol-2-ylethanol (EXAMPLE 138).

Example 141

[2-Chloro-4-fluoro-5-(7-morpholin-4-ylpyrido[4,3-d]pyrimidin-4-yl)phenyl]-(4-hydroxymethylthiazol-2-yl)methanol (141)

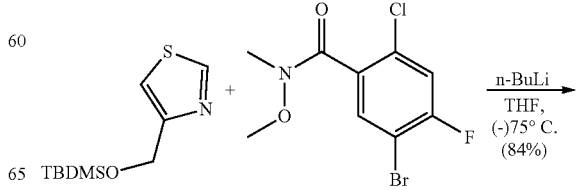

-continued

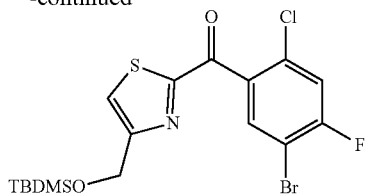

4-(tert-Butyldimethylsilanyloxymethyl)thiazole (10.15 g, 43.5 mmol) dissolved in dry tetrahydrofuran (78 ml) was initially introduced in a two-necked flask with stirrer bar, internal thermometer and septum under argon. The reaction solution was cooled to (−)75° C. by means of an acetone/dry-ice bath. n-Butyllithium (15% solution in n-hexane, 29.3 ml, 46.6 mmol) was subsequently slowly added dropwise to the reaction solution at constant temperature. The reaction solution was stirred at (−)75° C. for a further 30 min, subsequently warmed to 0° C. Then re-cooled to (−)50° C. A solution, pre-cooled to (−)50° C., of 5-bromo-2-chloro-4-fluoro-N-methoxy-N-methylbenzamide (5.58 g, 12.4 mmol), dissolved in dry tetrahydrofuran (21 ml), was slowly added dropwise to the reaction solution at (−)50° C. over a period of 1.5 h. The reaction solution was stirred at (−)50° C. for a further 30 min. When the reaction was complete, water (20 ml) was added to the reaction solution. The reaction solution was then allowed to warm to room temperature with stirring. The reaction solution was diluted with ethyl acetate (400 ml) and saturated sodium chloride solution (100 ml). The phases were separated, and the aqueous phase was extracted with ethyl acetate. The combined organic phases were dried over sodium sulfate, filtered and evaporated in vacuo in a rotary evaporator. The residue was purified by means of flash chromatography (gradient: cyclohexane/0-7% by vol. of ethyl acetate, CombiFlash Rf 200). The suitable product fractions were combined, and the organic solvents were removed in a rotary evaporator, giving (5-bromo-2-chloro-4-fluorophenyl)-[4-(tert-butyldimethylsilanyloxymethyl)thiazol-2-yl]methanone (4.94 g, 10.39 mmol, MS: main peak 466 [M+H$^+$], 84% yield) as oil.

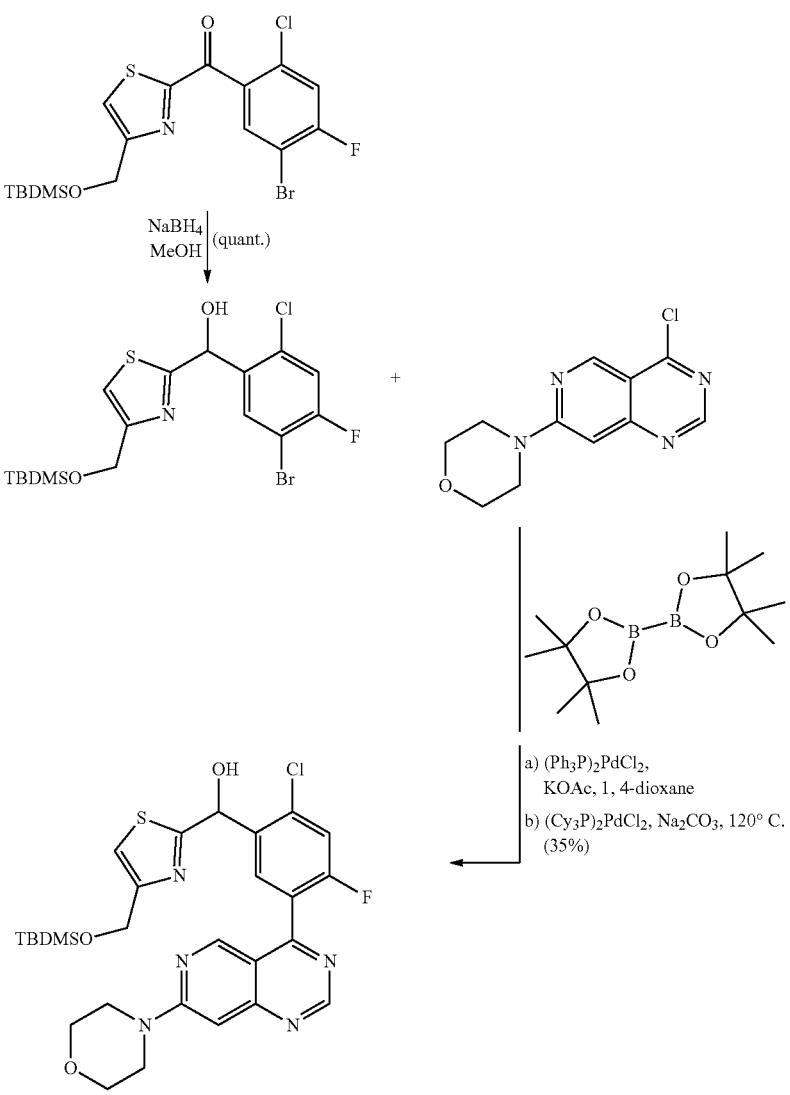

[4-[[tert-Butyl(dimethyl)silyl]oxymethyl]thiazol-2-yl]-[2-chloro-4-fluoro-5-(7-morpholinopyrido-[4,3-d}pyrimidin-4-yl)phenyl]methanol was prepared analogously to the synthetic processes of EXAMPLES 1 and 2 and 138 from (5-bromo-2-chloro-4-fluorophenyl)-[4-(tert-butyldimethylsilanyloxymethyl)thiazol-2-yl]methanone and 4-chloro-7-morpholin-4-ylpyrido[4,3-d]-pyrimidine.

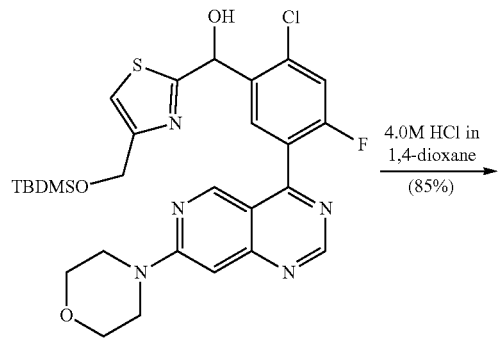

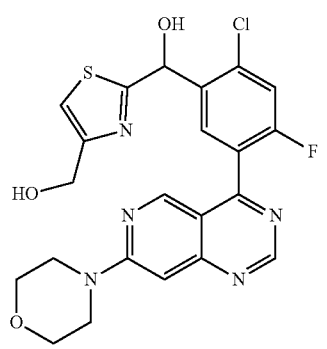

EXAMPLE 141

[4-(tert-Butyldimethylsilanyloxymethyl)thiazol-2-yl]-[2-chloro-4-fluoro-5-(7-morpholin-4-ylpyrido[4,3-d]pyrimidin-4-yl)phenyl]methanol (333 mg, 0.55 mmol) was dissolved in 1,4-dioxane (7 ml). 4.0 M HCl dissolved in 1,4-dioxane (1.38 ml, 5.53 mmol) was added, and the reaction solution was subsequently stirred at room temperature for 30 min. When the reaction was complete, the reaction solution was filtered, and solvents were removed in a rotary evaporator. The residue was purified by means of flash chromatography (gradient: dichloromethane/0-15% by vol. of ethanol, CombiFlash Rf 200). The suitable product fractions were combined, and the solvents were removed in vacuo. The residue was taken up in dichloromethane, extracted with saturated sodium hydrogencarbonate solution, dried over sodium sulfate, filtered, and the filtrate was evaporated to dryness, where [2-chloro-4-fluoro-5-(7-morpholin-4-ylpyrido[4,3-d]pyrimidin-4-yl)phenyl]-(4-hydroxymethylthiazol-2-yl)methanol (EXAMPLE 141, 229 mg, 0.47 mmol, MS: 488.0/490.0 [M+H⁺], 85% yield) as solid.

Examples 142 and 143

2-Chloro-4-fluoro-5-(7-morpholin-4-ylquinazolin-4-yl)phenyl]-(4-hydroxymethylthiazol-2-yl)methanol (142)

[2-Chloro-4-fluoro-5-(7-morpholin-4-ylquinazolin-4-yl)phenyl]-(4-methylaminomethylthiazol-2-yl)methanol (143)

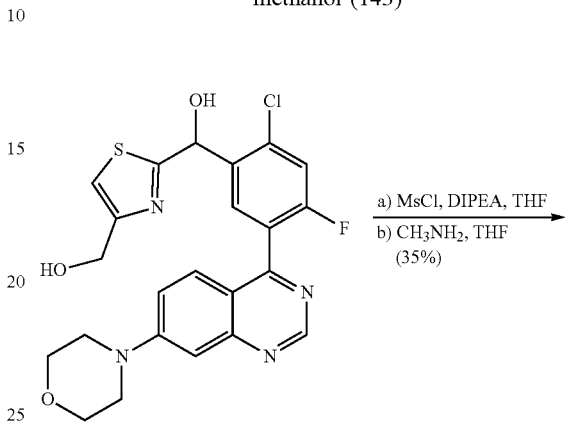

EXAMPLE 142

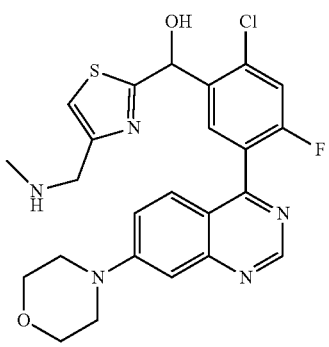

EXAMPLE 143

[2-Chloro-4-fluoro-5-(7-morpholin-4-ylpyrido[4,3-d]pyrimidin-4-yl)phenyl]-(4-hydroxymethylthiazol-2-yl)methanol (46.6 mg, 96 μmop was dissolved in dry tetrahydrofuran (3.1 ml) under argon. N-Ethyldiisopropylamine (98 μl, 57.4 μmop and methanesulfonyl chloride (14.8 μl, 191 μmol) were added. The reaction solution was stirred at room temperature for 30 min. Methylamine (40% solution in water, 183 μl, 1.91 mol) was subsequently added, and the mixture was stirred at room temperature for a further 2 h. After termination of the reaction, ethyl acetate (15 ml) and saturated sodium chloride solution (10 ml) were added to the reaction solution. The phases were separated, and the aqueous phase was extracted with ethyl acetate. The combined organic phases were dried over sodium sulfate and filtered. The filtrate was evaporated in a rotary evaporator, and the residue was purified by means of preparative RP-HPLC (gradient water+0.1% of trifluoroacetic acid/acetonitrile+ 0.1% of trifluoroacetic acid, Sunfire Prep C-18 150-21 mm, flow rate: 50 ml/min., λ=220 nm). The suitable product fractions were combined, and the solvents were removed in vacuo in a rotary evaporator, and the residue was freeze-dried from dioxane/water, where [2-chloro-4-fluoro-5-(7-morpholin-4-ylquinazolin-4-yl)phenyl]-(4-methylaminomethylthiazol-2-yl)methanol (EXAMPLE 143, 14.8 mg, 0.030 mmol, MS: 500.1/502.0 [M+H⁺], 31% yield) as solid.

Examples 144, 145 and 146

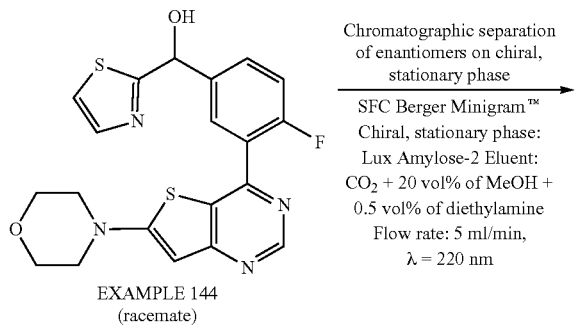

EXAMPLE 144
(racemate)

Chromatographic separation of enantiomers on chiral, stationary phase
SFC Berger Minigram™ Chiral, stationary phase: Lux Amylose-2 Eluent: $CO_2$ + 20 vol% of MeOH + 0.5 vol% of diethylamine
Flow rate: 5 ml/min,
λ = 220 nm

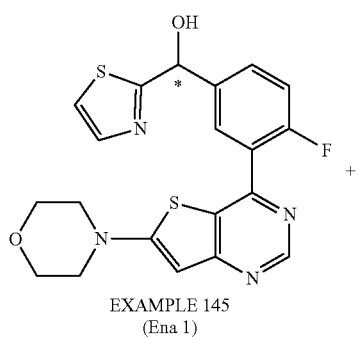

EXAMPLE 145
(Ena 1)

+

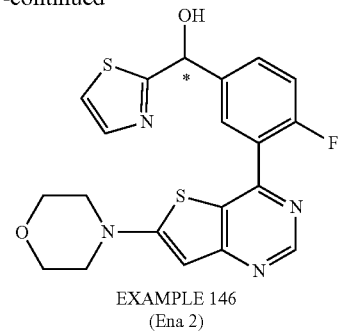

EXAMPLE 146
(Ena 2)

Racemic [4-fluoro-3-(6-morpholin-4-ylthieno[3,2-d}pyrimidin-4-yl)phenyl]thiazol-2-ylmethanol (EXAMPLE 144, 35 mg, 0.082 mmol) was separated by chromatography into its enantiomers on a chiral stationary phase using preparative SFC: after analytic column screening for identification of the most suitable chiral phase having the highest selectivity, the Lux amylose-2 phase from Phenomex was selected. SFC conditions: apparatus: SFC Berger minigram; column: Lux amylose-2, 250×4.6 mm; eluent: carbon dioxide+20% by vol. of methanol+0.5% by vol. of diethylamine, flow rate: 5 ml/min, wavelength: 220 nm. The preparative separation into the enantiomers was carried out under the same conditions in SFC Berger minigram Stacked Injection Mode. The suitable fractions were collected, and the solvents were removed in vacuo in a rotary evaporator, giving enantiomerically pure [4-fluoro-3-(6-morpholin-4-ylthieno[3,2-d}pyrimidin-4-yl)phenyl]thiazol-2-ylmethanol (EXAMPLE 145, $R_t$=7.85 min 12 mg, 0.028 mmol, >99% ee Ena 1) and [4-fluoro-3-(6-morpholin-4-ylthieno[3,2-d}pyrimidin-4-yl)phenyl]thiazol-2-ylmethanol (EXAMPLE 146, $R_t$=8.82 min, 12.0 mg, 0.028 mmol, 92% ee, Ena 2) as solids.

Compounds which were prepared analogously to EXAMPLES 138-146 can be found in Table 5 below.

TABLE 5

Compounds of the formula (I)

| No. | Structural formula | Name | $IC_{50}$ DNA-PK | $IC_{50}$ pDNA-PK | $K_i$ [Kv1.11 hERG] |
|---|---|---|---|---|---|
| 138 | MS: 420.2 (M + H⁺) | 1-[5-(7-Morpholin-4-ylquinazolin-4-yl)-pyridin-3-yl]-1-thiazol-2-ylethanol | D | | B |
| | | 1H NMR (400 MHz, DMSO-d6) ppm = 9.11 (s, 1H), 8.97 (d, J = 2.2, 1H), 8.83 (d, J = 2.1, 1H), 8.30 (t, J = 2.2, 1H), 7.82 (d, J = 9.5, 1H), 7.79 (d, J = 3.2, 1H), 7.65 (d, J = 3.3, 1H), 7.57 (dd, J = 9.5, 2.6, 1H), 7.22 (d, J = 2.5, 1H), 7.09 (s, 1H), 3.82-3.75 (m, 4H), 3.50-3.43 (m, 4H), 2.02 (s, 3H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 139 | | {3-[7-(3,6-Dihydro-2H-pyran-4-yl)-quinazolin-4-yl]-4-fluoro-phenyl}-thiazol-2-ylmethanol | C | D | A |
| | MS: 420.0 (M + H$^+$) | 1H NMR (500 MHz, DMSO-d6) ppm = 9.36 (s, 1H), 8.02 (d, J = 1.8, 1H), 7.94 (dd, J = 8.9, 1.9, 1H), 7.76-7.69 (m, 4H), 7.65 (d, J = 3.2, 1H), 7.49-7.43 (m, 1H), 7.00-6.96 (m, 1H), 6.71-6.67 (m, 1H), 6.11-6.08 (m, 1H), 4.33-4.30 (m, 2H), 3.89 (t, J = 5.5, 2H), 2.65-2.60 (m, 2H) | | | |
| 140 | | [4-Fluoro-3-(7-morpholin-4-yl-pyrido[4,3-d]-pyrimidin-4-yl)-phenyl]thiazol-2-yl-methanol | D | D | B |
| | MS: 424.2 (M + H$^+$) | 1H NMR (400 MHz, DMSO-d6) ppm = 9.16 (s, 1H), 8.80 (d, J = 3.6, 1H), 7.77-7.70 (m, 3H), 7.65 (d, J = 3.2, 1H), 7.48-7.42 (m, 1H, 7.08-6.94 (m, 2H), 6.10 (s, 1H), 3.78-3.66 (m, 8H) | | | |
| 141 | | [2-Chloro-4-fluoro-5-(7-morpholin-4-yl-pyrido[4,3-d]-pyrimidin-4-yl)-phenyl]-(4-hydroxymethyl-thiazol-2-yl)-methanol | D | D | B |
| | MS: 488.0/490.0 (M + H$^+$) (Cl isotopy, rel. peak intensity ratio [%] 100:38) | 1H NMR (400 MHz, DMSO-d6) ppm = 9.15 (s, 1H), 8.84 (d, J = 3.4, 1H), 7.83 (d, J = 7.6, 1H), 7.74 (d, J = 9.7, 1H), 7.39-7.35 (m, 1H), 7.04 (s, 1H), 6.99 (s, 1H), 6.28 (s, 1H), 5.24 (s, 1H), 4.50 (s, 2H), 3.77-3.69 (m, 8H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 142 | MS: 487.1/489.0 (M + H$^+$) (Cl isotopy, rel. peak intensity ratio [%] 100:41) | [2-Chloro-4-fluoro-5-(7-morpholin-4-yl-quinazolin-4-yl)-phenyl]-(4-hydroxymethyl-thiazol-2-yl)-methanol | A | B | D |

1H NMR (400 MHz, DMSO-d6) ppm = 9.10 (s, 1H), 7.75-7.69 (m, 2H), 7.59-7.49 (m, 2H), 7.36 (t, J = 1.1, 1H), 7.23-7.17 (m, 1H), 7.00 (d, J = 5.1, 1H), 6.27 (d, J = 5.0, 1H), 5.24 (t, J = 5.7, 1H), 4.52-4.45 (m, 2H), 3.81-3.74 (m, 4H), 3.49-3.41 (m, 4H)

| 143 | MS: 500.1/502.0 (M + H$^+$) (Cl isotopy, rel. peak intensity ratio [%] 100:34) | [2-Chloro-4-fluoro-5-(7-morpholin-4-yl-quinazolin-4-yl)-phenyl]-(4-methylaminomethyl-thiazol-2-yl)-methanol | C | C | C |

1H NMR (500 MHz, DMSO-d6) ppm = 9.10 (s, 1H), 8.26 (s, 1H), 7.76-7.69 (m, 2H), 7.58-7.50 (m, 2H), 7.48-7.43 (m, 1H), 7.24-7.16 (m, 1H), 6.97 (s, 1H), 6.28 (s, 1H), 3.80 (s, 2H), 3.79-3.74 (m, 4H), 3.48-3.42 (m, 4H), 2.33 (s, 3H)

| 144 | MS: 429.0 (M + H$^+$) | [4-Fluoro-3-(6-morpholin-4-yl-thieno[3,2-d]-pyrimidin-4-yl)-phenyl]thiazol-2-yl-methanol | A | B | B |

1H NMR (500 MHz, DMSO-d6) ppm = 8.89 (s, 1H), 7.76 (dd, J = 7.0, 2.3, 1H), 7.73 (d, J = 3.2, 1H), 7.69-7.64 (m, 2H), 7.43-7.38 (m, 1H), 6.96 (d, J = 4.6, 1H), 6.53 (s, 1H), 6.07 (d, J = 4.6, 1H), 3.77-3.71 (m, 4H), 3.44-3.38 (m, 4H)

TABLE 5-continued

Compounds of the formula (I)

| No. | Structural formula | Name | IC₅₀ DNA-PK | IC₅₀ pDNA-PK | $K_i$ [Kv1.11 hERG] |
|---|---|---|---|---|---|
| 145 | 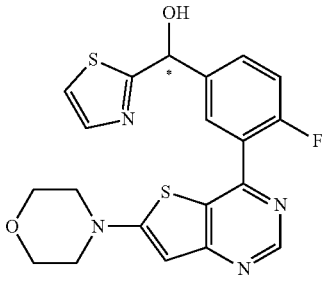 [SMILES: OC(c1ccc(F)c(-c2ncnc3cc(N4CCOCC4)sc23)c1)c1nccs1]<br>MS: 429.0 (M + H⁺); R_t 7.85 min, (SFC, Lux amylose, CO2/0.5% by vol. of methanol) | [4-Fluoro-3-(6-morpholin-4-yl-thieno[3,2-d}-pyrimidin-4-yl)-phenyl]thiazol-2-yl-methanol (Ena 1)<br><br>see racemate | A | B | A |
| 146 | 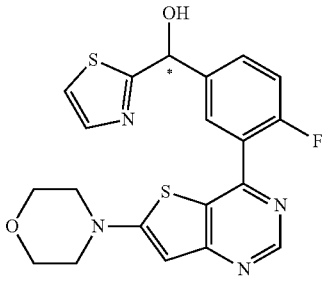 [SMILES: OC(c1ccc(F)c(-c2ncnc3cc(N4CCOCC4)sc23)c1)c1nccs1]<br>MS: 429.0 (M + H⁺); R_t 8.82 min, (SFC, Lux amylose-2, CO2/0.5% by vol. of methanol) | [4-Fluoro-3-(6-morpholin-4-yl-thieno[3,2-d}-pyrimidin-4-yl)-phenyl]thiazol-2-yl-methanol (Ena 2)<br><br>see racemate | A | B | A |
| 147 | 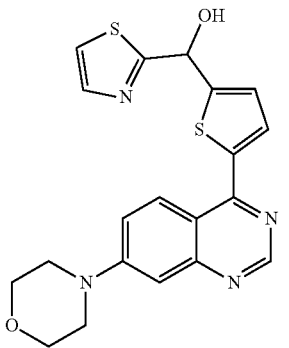 [SMILES: OC(c1ccc(-c2ncnc3cc(N4CCOCC4)ccc23)s1)c1nccs1]<br>MS: 411.0 (M + H⁺) | [5-(7-Morpholin-4-ylquinazolin-4-yl)-thiophen-2-yl]-thiazol-2-ylmethanol<br><br>1H NMR (500 MHz, DMSO-d6) ppm = 8.93 (s, 1H), 8.34 (d, J = 9.5, 1H), 7.83 (d, J = 3.9, 1H), 7.79 (d, J = 3.2, 1H), 7.71 (d, J = 3.2, 1H), 7.56 (dd, J = 9.5, 2.7, 1H), 7.32 (d, J = 4.8, 1H), 7.26-7.24 (m, 1H), 7.16 (d, J = 2.6, 1H), 6.31-6.29 (m, 1H), 3.81-3.75 m, 4H), 3.47-3.41 (m, 4H) | D |  | C |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 148 | MS: 405.2 (M + H$^+$) | [3-(7-Morpholin-4-ylquinazolin-4-yl)-phenyl]thiazol-2-yl-methanol | C | D | C |
|  |  | 1H NMR (500 MHz, DMSO-d6) ppm = 9.07 (s, 1H), 7.86 (d, J = 9.4, 1H), 7.83-7.81 (m, 1H), 7.74 (d, J = 3.2, 1H), 7.68-7.64 (m, 3H), 7.59-7.55 (m, 1H), 7.52 (dd, J = 9.5, 2.6, 1H), 7.20 (d, J = 2.6, 1H), 6.93 (d, J = 4.5, 1H), 6.10 (d, J = 4.0, 1H), 3.80-3.76 (m, 4H), 3.46-3.42 (m, 4H) |  |  |  |
| 149 | MS: 405.2 (M + H$^+$); R$_t$ 10.57 min, (HPLC, Chiralpak AD-H, heptane/ethanol 40/60) | [3-(7-Morpholin-4-ylquinazolin-4-yl)-phenyl]thiazol-2-yl-methanol (Ena 1) | D | | A |
|  |  | see racemate |  |  |  |
| 150 | MS: 405.2 (M + H$^+$); R$_t$ 13.55 min, (HPLC, Chiralpak AD-H, heptane/ethanol 40/60) | [3-(7-Morpholin-4-ylquinazolin-4-yl)-phenyl]thiazol-2-yl-methanol (Ena 2) | C | C | A |
|  |  | see racemate |  |  |  |

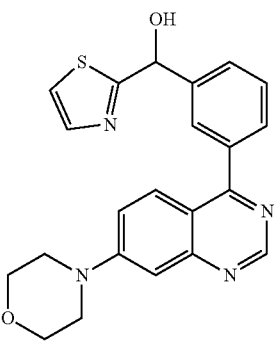 [SMILES: OC(c1cccc(-c2ncnc3cc(N4CCOCC4)ccc23)c1)c1nccs1]

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 151 | | 1-[5-(7-Morpholin-4-ylquinazolin-4-yl)-pyridin-3-yl]-1-thiazol-2-ylethanol (Ena 1) | D | | |
| | MS: 420.2 (M + H$^+$); R$_t$ 8.95 min, (SFC, Chiralpak AS-H, CO2/10% by vol. of methanol, 0.5% by vol. of diethylamine) | | | see racemate | |
| 152 | | 1-[5-(7-Morpholin-4-ylquinazolin-4-yl)-pyridin-3-yl]-1-thiazol-2-ylethanol (Ena 2) | C | D | A |
| | MS: 420.2 (M + H$^+$), R$_t$ 10.45 min, (SFC, Chiralpak AS-H, CO2/10% by vol. of methanol, 0.5% by vol. of diethylamine) | | | see racemate | |
| 153 | | 1-[4-(7-Morpholin-4-ylquinazolin-4-yl)-pyridin-2-yl]-1-thiazol-2-ylethanol | D | | |
| | MS: 420.2 (M + H$^+$) | 1H NMR (400 MHz, DMSO-d6) ppm = 9.11 (s, 1H), 8.73 (dd, J = 5.0, 0.8, 1H), 7.99-7.97 (m, 1H), 7.79 (d, J = 9.4, 1H), 7.72 (d, J = 3.2, 1H), 7.64 (dd, J = 5.0, 1.6, 1H), 7.62 (d, J = 3.2, 1H), 7.56 (dd, J = 9.5, 2.6, 1H), 7.23 (d, J = 2.5, 1H), 6.84 (s, 1H), 3.81-3.75 (m, 4H), 3.49-3.44 (m, 4H), 2.04 (s, 3H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 154 | 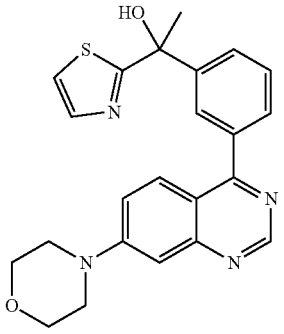 [SMILES: CC(O)(c1cccc(-c2ncnc3cc(N4CCOCC4)ccc23)c1)c1nccs1]<br>MS: 419.2 (M + H$^+$) | 1-[3-(7-Morpholin-4-ylquinazolin-4-yl)-phenyl]-1-thiazol-2-ylethanol | D | | B |
| | | 1H NMR (500 MHz, DMSO-d6) ppm = 9.07 (s, 1H), 7.96-7.93 (m, 1H), 7.83 (d, J = 9.4, 1H), 7.79-7.76 (m, 1H), 7.74 (d, J = 3.2, 1H), 7.63-7.61 (m, 1H), 7.60 (d, J = 3.3, 1H), 7.55 (d, J = 7.7, 1H), 7.53-7.50 (m, 1H), 7.20 (d, J = 2.6, 1H), 6.82 (s, 1H), 3.81-3.75 (m, 4H), 3.47-3.42 (m, 4H), 1.98 (s, 3H) | | | |
| 155 | 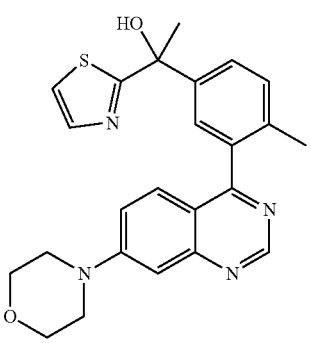 [SMILES: Cc1ccc(C(C)(O)c2nccs2)cc1-c1ncnc2cc(N3CCOCC3)ccc12]<br>MS: 433.2 (M + H$^+$) | 1-[4-methyl-3-(7-morpholin-4-yl-quinazolin-4-yl)-phenyl]-1-thiazol-2-ylethanol | D | | |
| | | 1H NMR (500 MHz, DMSO-d6) ppm = 9.07 (s, 1H), 7.70 (d, J = 3.2, 1H), 7.61 (dd, J = 8.0, 2.1, 1H), 7.57 (d, J = 3.2, 1H), 7.48-7.44 (m, 2H), 7.34 (d, J = 8.1, 1H), 7.32 (d, J = 9.3, 1H), 7.19 (d, J = 2.5, 1H), 6.70 (s, 1H), 3.79-3.76 (m, 4H), 3.44-3.41 (m, 4H), 2.03 (s, 3H), 1.92 (s, 3H) | | | |
| 156 | 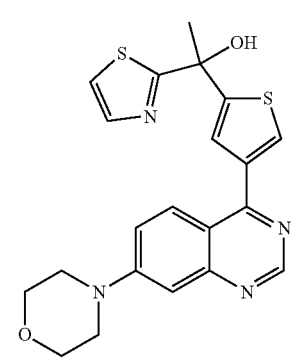 [SMILES: CC(O)(c1cc(-c2ncnc3cc(N4CCOCC4)ccc23)cs1)c1nccs1]<br>MS: 425.0 (M + H$^+$) | 1-[4-(7-Morpholin-4-ylquinazolin-4-yl)-thiophen-2-yl]-1-thiazol-2-ylethanol | D | | |
| | | 1H NMR (400 MHz, DMSO-d6) ppm = 8.99 (s, 1H), 8.13 (d, J = 9.5, 1H), 8.04 (d, J = 1.5, 1H), 7.76 (d, J = 3.2, 1H), 7.64 (d, J = 3.2, 1H), 7.54 (dd, J = 9.5, 2.6, 1H), 7.52 (d, J = 1.5, 1H), 7.20 (s, 1H), 7.16 (d, J = 2.6, 1H), 3.82-3.75 (m, 4H), 3.47-3.40 (m, 4H), 2.04 (s, 3H) | | | |

TABLE 5-continued

Compounds of the formula (I)

| No. | Structural formula | Name | IC₅₀ DNA-PK | IC₅₀ pDNA-PK | $K_i$ [Kv1.11 hERG] |
|---|---|---|---|---|---|
| 157 | MS: 420.2 (M + H⁺); R$_t$ 22.14 min, (HPLC, Chiralpak AD-H, heptane/ethanol 70/30, 0.5% by vol. of diethylamine) | 1-[4-(7-Morpholin-4-ylquinazolin-4-yl)-pyridin-2-yl]-1-thiazol-2-ylethanol (Ena 1) | D | see racemate | |
| 158 | MS: 420.2 (M + H⁺); R$_t$ 27.88 min, (HPLC, Chiralpak AD-H, heptane/ethanol 70/30, 0.5% by vol. of diethylamine) | 1-[4-(7-Morpholin-4-ylquinazolin-4-yl)-pyridin-2-yl]-1-thiazol-2-ylethanol (Ena 2) | D | see racemate | |
| 159 | MS: 473.0 (M + H⁺) | 2,2,2-Trifluoro-1-[3-(7-morpholin-4-yl-quinazolin-4-yl)-phenyl]-1-thiazol-2-ylethanol | C | D | D |

1H NMR (500 MHz, DMSO-d6) ppm = 9.08 (s, 1H), 8.54 (s, 1H), 8.15-8.13 (m, 1H), 7.98-7.95 (m, 1H), 7.94 (d, J = 3.3, 1H), 7.87 (d, J = 3.2, 1H), 7.83-7.79 (m, 2H), 7.67 (t, J = 7.8, 1H), 7.53 (dd, J = 9.5, 2.6, 1H), 7.21 (d J = 2.6, 1H), 3.80-3.76 (m, 4H), 3.47-3.43 (m, 4H)

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 160 | MS: 409.0 (M − H$^+$); O-TBDPS ether derivative: R$_t$ 4.78 min (SFC, Chiralpak AD-H, CO$_2$/30% by vol. of 2-propanol, 0.5% by vol. of diethylamine | [5-(7-Morpholin-4-ylquinazolin-4-yl)-thiophen-2-yl]-thiazol-2-yl-methanol (Ena 1) | D | see racemate | |
| 161 | MS: 409.0 (M − H$^+$); O-TBDPS ether derivative: R$_t$ 7.20 min (SFC, Chiralpak AD-H, CO$_2$/30% by vol. of 2-propanol, 0.5% by vol. of diethylamine | [5-(7-Morpholin-4-ylquinazolin-4-yl)-thiophen-2-yl]-thiazol-2-yl-methanol (Ena 2) | D | see racemate | |
| 162 | MS: 437.2 (M + H$^+$) | 1-[2-Fluoro-3-(7-morpholin-4-yl-quinazolin-4-yl)-phenyl]-1-thiazol-2-ylethanol  1H NMR (500 MHz, DMSO-d6) ppm = 9.07 (s, 1H), 7.94-7.87 (m, 1H), 7.71 (d, J = 3.2, 1H), 7.63 (d, J = 3.3, 1H), 7.55-7.40 (m, 4H), 7.17 (d, J = 2.4, 1H), 6.75 (s, 1H), 3.79-3.74 (m, 4H), 3.46-3.40 (m, 4H), 2.01 (s, 3H) | D | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 163 | | 1-[4-Fluoro-3-(7-morpholin-4-yl-quinazolin-4-yl)-phenyl]-1-thiazol-2-ylethanol | C | D | C |
| | MS: 437.2 (M + H$^+$) | 1H NMR (400 MHz, DMSO-d6) ppm = 9.11 (s, 1H), 7.82-7.75 (m, 2H), 7.73 (d, J = 3.2, 1H), 7.61 (d, J = 3.2, 1H), 7.53-7.50 (m, 2H), 7.41-7.36 (m, 1H), 7.20 (d, J = 1.9, 1H), 6.90 (s, 1H), 3.80-3.75 (m, 4H), 3.46-3.41 (m, 4H), 1.95 (s, 3H) | | | |
| 164 | | [5-(7-Morpholin-4-ylquinazolin-4-yl)-thiophen-3-yl]-thiazol-2-yl-methanol | D | | |
| | MS: 411.0 (M + H$^+$) | 1H NMR (500 MHz, DMSO-d6) ppm = 8.95 (s, 1H), 8.30 (d, J = 9.5, 1H), 7.93 (d, J = 1.3, 1H), 7.80-7.78 (m, 1H), 7.76 (d, J = 3.2, 1H), 7.67 (d, J = 3.2, 1H), 7.62 (dd, J = 9.5, 2.7, 1H), 7.17 (d, J = 2.6, 1H), 6.93 (d, J = 5.0, 1H), 6.14-6.11 (m, 1H), 3.81-3.76 (m, 4H), 3.48-3.43 (m, 4H) | | | |
| 165 | | 1-[4-(7-Morpholin-4-ylquinazolin-4-yl)-thiophen-2-yl]-1-thiazol-2-ylethanol (Ena 1) | D | | |
| | MS: 425.0 (M + H$^+$); R$_t$ 5.32 min, (SFC, Chiralcel OJ-H, CO2/25% by vol. of 2-propanol, 0.5% by vol. of diethylamine) | 1H NMR (500 MHz, DMSO-d6) ppm = 8.99 (s, 1H), 8.13 (d, J = 9.4, 1H), 8.05 (d, J = 1.5, 1H), 7.76 (d, J = 3.2, 1H), 7.64 (d, J = 3.2, 1H), 7.54 (dd, J = 9.5, 2.6, 1H), 7.52 (d, J = 1.5, 1H), 7.20 (s, 1H), 7.16 (d, J = 2.6, 1H), 3.81-3.74 (m, 4H), 3.46-3.39 (m, 4H), 2.04 (s, 3H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 166 | | 1-[4-(7-Morpholin-4-ylquinazolin-4-yl)-thiophen-2-yl]-1-thiazol-2-ylethanol (Ena 2) | D | | |
| | MS: 425.0 (M + H$^+$); R$_t$ 7.18 min, (SFC, Chiralcel OJ-H, CO2/25% by vol. of 2-propanol, 0.5% by vol. of diethylamine) | 1H NMR (500 MHz, DMSO-d6) ppm = 8.99 (s, 1H), 8.13 (d, J = 9.4, 1H), 8.05 (d, J = 1.5, 1H), 7.76 (d, J = 3.2, 1H), 7.64 (d, J = 3.2, 1H), 7.54 (dd, J = 9.5, 2.7, 1H), 7.52 (d, J = 1.5, 1H), 7.20 (s, 1H), 7.16 (d, J = 2.6, 1H), 3.81-3.75 (m, 4H), 3.46-3.40 (m, 4H), 2.03 (s, 3H) | | | |
| 167 | | [5-(7-Morpholin-4-ylquinazolin-4-yl)-thiophen-3-yl]-thiazol-2-yl-methanol (Ena 1) | D | | |
| | MS: 411.0 (M + H$^+$); O-TBDPS-Etherderivat: R$_t$ 13.11 min (SFC, Chiralpak IA, CO$_2$/20% by vol. of 2-methanol, 0.5% by vol. of diethylamine | 1H NMR (500 MHz, DMSO-d6) ppm = 8.95 (s, 1H), 8.30 (d, J = 9.5, 1H), 7.94-7.92 (m, 1H), 7.79-7.78 (m, 1H), 7.76 (d, J = 3.2, 1H), 7.67 (d, J = 3.2, 1H), 7.62 (dd, J = 9.5, 2.7, 1H), 7.17 (d, J = 2.6, 1H), 6.93 (d, J = 5.0, 1H), 6.12 (d, J = 4.9, 1H), 3.81-3.77 (m, 4H), 3.47-3.44 (m, 4H) | | | |
| 168 | | [5-(7-Morpholin-4-ylquinazolin-4-yl)-thiophen-3-yl]-thiazol-2-yl-methanol (Ena 2) | D | | |
| | MS: 411.0 (M + H$^+$); O-TBDPS ether derivative: R$_t$ 16.82 min (SFC, Chiralpak IA, CO$_2$/20% by vol. of 2-methanol, 0.5% by vol. of diethylamine | 1H NMR (500 MHz, DMSO-d6) ppm = 8.95 (s, 1H), 8.30 (d, J = 9.5, 1H), 7.94-7.92 (m, 1H), 7.79-7.78 (m, 1H), 7.76 (d, J = 3.2, 1H), 7.67 (d, J = 3.2, 1H), 7.62 (dd, J = 9.5, 2.7, 1H), 7.17 (d, J = 2.6, 1H), 6.93 (s, 1H), 6.12 (s, 1H), 3.82-3.74 (m, 4H), 3.50-3.42 (m, 4H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 169 | MS: 423.0 (M + H$^+$) | [3-Fluoro-5-(7-morpholin-4-yl-quinazolin-4-yl)-phenyl]thiazol-2-yl-methanol | C | D | |
| | | 1H NMR (500 MHz, DMSO-d6) ppm = 9.08 (s, 1H), 7.86 (d, J = 9.4, 1H), 7.77 (d, J = 3.2, 1H), 7.68-7.66 (m, 2H), 7.54 (dd, J = 9.4, 2.6, 1H), 7.51-7.46 (m, 2H), 7.21 (d, J = 2.6, 1H), 7.08 (d, J = 4.7, 1H), 6.14 (d, J = 4.7, 1H), 3.80-3.76 (m, 4H), 3.47-3.43 (m, 4H) | | | |
| 170 | MS: 423.0 (M + H$^+$) | [2-Fluoro-5-(7-morpholin-4-yl-quinazolin-4-yl)-phenyl]thiazol-2-yl-methanol | C | C | |
| | | 1H NMR (500 MHz, DMSO-d6) ppm = 9.04 (s, 1H), 7.85-7.81 (m, 2H), 7.77-7.73 (m, 1H), 7.72 (d, J = 3.2, 1H), 7.66 (d, J = 3.2, 1H), 7.52 (dd, J = 9.5, 2.6, 1H), 7.44-7.39 (m, 1H), 7.18 (d, J = 2.5, 1H), 7.05 (d, J = 4.9, 1H), 6.28 (d, J = 3.8, 1H), 3.79-3.75 (m, 4H), 3.33-3.29 (m, 4H) | | | |
| 171 | MS: 441.0 (M + H$^+$) | [3,4-Difluoro-5-(7-morpholin-4-yl-quinazolin-4-yl)-phenyl]thiazol-2-yl-methanol | A | B | D |
| | | 1H NMR (500 MHz, DMSO-d6) ppm = 9.11 (s, 1H), 7.75 (d, J = 3.2, 1H), 7.72-7.66 (m, 2H), 7.61-7.57 (m, 1H), 7.56-7.49 (m, 2H), 7.21 (d, J = 2.4, 1H), 7.10 (d, J = 4.8, 1H), 6.10 (d, J = 4.8, 1H), 3.81-3.75 (m, 4H), 3.48-3.43 (m, 4H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 172 | 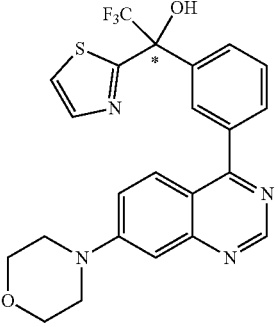 [SMILES: OC(c1cccc(-c2ncnc3cc(N4CCOCC4)ccc23)c1)(c1nccs1)C(F)(F)F] MS: 473.0 (M + H$^+$); R$_t$ 12.21 min, (HPLC, Chiralpak AD-H, n-heptane/ethanol, 70:30, vol.:vol) | 2,2,2-Trifluoro-1-[3-(7-morpholin-4-yl-quinazolin-4-yl)-phenyl]-1-thiazol-2-ylethanol (Ena 1) | C | D see racemate | |
| 173 | 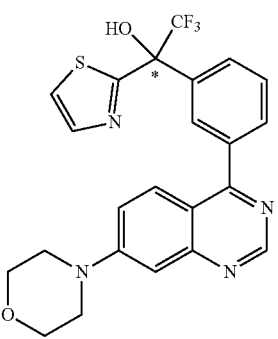 [SMILES: OC(c1cccc(-c2ncnc3cc(N4CCOCC4)ccc23)c1)(c1nccs1)C(F)(F)F] MS: 473.0 (M + H$^+$); R$_t$ 16.91 min, (HPLC, Chiralpak AD-H, n-heptane/ethanol, 70:30, vol.:vol.) | 2,2,2-Trifluoro-1-[3-(7-morpholin-4-yl-quinazolin-4-yl)-phenyl]-1-thiazol-2-ylethanol (Ena 2) | A | C see racemate | D |
| 174 | 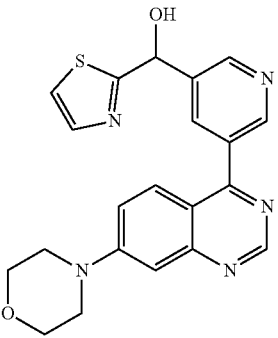 [SMILES: OC(c1cncc(-c2ncnc3cc(N4CCOCC4)ccc23)c1)c1nccs1] MS: 305.2 (M + H$^+$) | 7-Morpholin-4-yl-4-piperidin-1-yl-thieno[3,2-d]-pyrimidine 1H NMR (500 MHz, DMSO-d6) ppm = 9.10 (s, 1H), 8.88-8.85 (m, 2H), 8.19-8.17 (m, 1H), 7.84 (d, J = 9.4, 1H), 7.78 (d, J = 3.2, 1H), 7.69 (d, J = 3.2, 1H), 7.56 (dd, J = 9.5, 2.6, 1H), 7.22 (d, J = 2.6, 1H), 7.14 (d, J = 4.8, 1H), 6.23 (d, J = 4.8, 1H), 3.81-3.76 (m, 4H), 3.48-3.43 (m, 4H) | C | D | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 175 | | 4-[2-Fluoro-5-(methoxy-thiazol-2-ylmethyl)phenyl]-7-morpholin-4-yl-quinazoline | D | | |
| | MS: 337.2 (M + H$^+$) | 1H NMR (500 MHz, DMSO-d6) ppm = 9.11 (s, 1H), 7.78 (d, J = 3.2, 1H), 7.73 (d, J = 3.2, 1H), 7.67-7.62 (m, 2H), 7.54-7.52 (m, 2H), 7.49-7.44 (m, 1H), 7.21-7.19 (m, 1H), 5.84 (s, 1H), 3.80-3.75 (m, 4H), 3.46-3.43 (m, 4H), 3.43 (s, 3H) | | | |
| 176 | | 4-[2-Fluoro-5-(-methoxy-thiazol-2-ylmethyl)phenyl]-7-morpholin-4-yl-quinazoline (Ena 1) | C | | |
| | MS: 437.2 (M + H$^+$); R$_t$ 8.47 min, (SFC, Chiralcel OD-H, CO2/20% by vol. of 2-propanol, 0.5% by vol. of diethylamine) | see racemate | | | |
| 177 | | 4-[2-Fluoro-5-(-methoxythiazol-2-ylmethyl)phenyl]-7-morpholin-4-yl-quinazoline (Ena 2) | B | D | A |
| | MS: 437.2 (M + H$^+$); R$_t$ 9.90 min, (SFC, Chiralcel OD-H, CO2/20% by vol. of 2-propanol, 0.5% by vol. of diethylamine) | see racemate | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 178 | 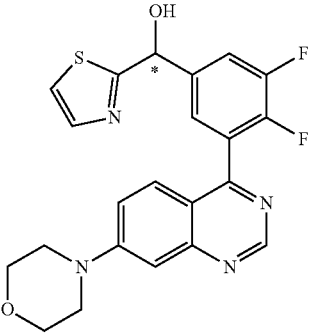 [SMILES: OC(c1cc(F)c(F)c(-c2ncnc3cc(N4CCOCC4)ccc23)c1)c1nccs1] MS: 441.0 (M + H$^+$); R$_t$ 8.34 min, (SFC, Chiralcel OD-H, CO2/20% by vol. of 2-propanol, 0.5% by vol. of diethylamine) | [3,4-Difluoro-5-(7-morpholin-4-yl-quinazolin-4-yl)-phenyl]thiazol-2-yl-methanol (Ena 1)<br><br>see racemate | A | B | A |
| 179 | 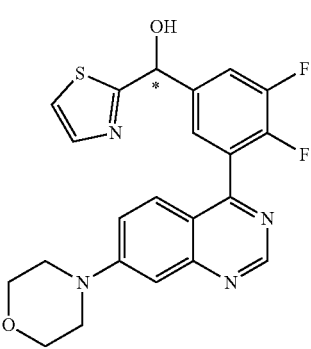 [SMILES: OC(c1cc(F)c(F)c(-c2ncnc3cc(N4CCOCC4)ccc23)c1)c1nccs1] MS: 441.0 (M + H$^+$); R$_t$ 9.68 min, (SFC, Chiralcel OD-H, CO2/20% by vol. of 2-propanol, 0.5% by vol. of diethylamine) | [3,4-Difluoro-5-(7-morpholin-4-yl-quinazolin-4-yl)-phenyl]thiazol-2-yl-methanol (Ena 2)<br><br>see racemate | B | B | D |
| 180 | 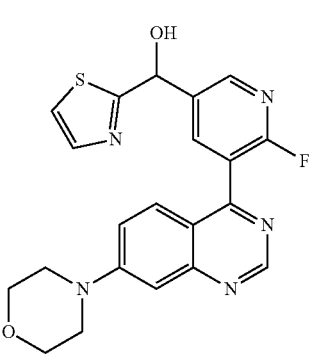 [SMILES: OC(c1cnc(F)c(-c2ncnc3cc(N4CCOCC4)ccc23)c1)c1nccs1] MS: 424.2 (M + H$^+$) | [6-Fluoro-5-(7-morpholin-4-yl-quinazolin-4-yl)-pyridin-3-yl]thiazol-2-ylmethanol<br><br>1H NMR (400 MHz, DMSO-d6) ppm = 9.11 (s, 1H), 8.56-8.52 (m, 1H), 8.21 (dd, J = 9.0, 2.3, 1H), 7.77 (d, J = 3.2, 1H), 7.69 (d, J = 3.2, 1H), 7.59-7.52 (m, 2H), 7.23-7.20 (m, 1H), 7.18 (d, J = 4.7, 1H), 6.23 (d, J = 4.5, 1H), 3.82-3.73 (m, 4H), 3.50-3.42 (m, 4H) | A | C | D |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 181 | MS: 471.1/473.1 (M + H$^+$) (Cl isotopy, rel. peak intensity ratio [%] 100:42) | [2-Chloro-4-fluoro-5-(7-morpholin-4-yl-quinazolin-4-yl)-phenyl]-(4-methyl-thiazol-2-yl)-methanol | A | B | D |
| | 1H NMR (500 MHz, DMSO-d6) ppm = 9.10 (s, 1H), 7.73 (dd, J = 10.5, 8.6, 2H), 7.57-7.51 (m, 2H), 7.22-7.18 (m, 2H), 6.97 (s, 1H), 6.26 (s, 1H), 3.80-3.74 (m, 4H), 3.49-3.41 (m, 4H), 2.30 (d, J = 1.0, 3H) | | | | |
| 182 | MS: 411.0 (M + H$^+$) | [3-(6-Morpholin-4-ylthieno[3,2-d]-pyrimidin-4-yl)-phenyl]thiazol-2-yl-methanol | C | C | |
| | 1H NMR (400 MHz, DMSO-d6) ppm = 8.90 (s, 1H), 8.14 (t, J = 1.8, 1H), 7.97-7.93 (m, 1H), 7.73 (d, J = 3.2, 1H), 7.68-7.64 (m, 2H), 7.61-7.54 (m, 1H), 6.93 (d, J = 4.4, 1H), 6.54 (s, 1H), 6.09 (d, J = 4.4, 1H), 3.81-3.74 (m, 4H), 3.47-3.41 (m, 4H) | | | | |
| 183 | MS: 406.0 (M + H$^+$); R$_t$ 20.67 min, (HPLC, Chiralcel OD-H, 2-propanol) | [5-(7-Morpholin-4-ylquinazolin-4-yl)-pyridin-3-yl]thiazol-2-ylmethanol (Ena 1) | C | | |
| | see racemate | | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 184 | MS: 406.0 (M + H$^+$); Rt 24.19 min, (HPLC, Chiralcel OD-H, 2-propanol) | [5-(7-Morpholin-4-ylquinazolin-4-yl)-pyridin-3-yl]thiazol-2-ylmethanol (Ena 2) see racemate | C | | |
| 185 | MS: 487.1/489.1 (M + H$^+$) (Cl isotopy, rel. peak intensity ratio [%] 100:41); R$_t$ 2.83 min (SFC, Chiralpak AD-H, CO$_2$/40% by vol. of methanol, 0.5% by vol. of diethylamine) | (S)-[2-Chloro-4-fluoro-5-(7-morpholin-4-yl-quinazolin-4-yl)-phenyl]-(4-hydroxymethyl-thiazol-2-yl)-methanol<br>1H NMR (500 MHz, DMSO-d6) ppm = 9.10 (s, 1H), 7.73 (dd, J = 8.6, 4.8, 2H), 7.58-7.50 (m, 2H), 7.39-7.34 (m, 1H), 7.22-7.18 (m, 1H), 7.02 (d, J = 5.0, 1H), 6.27 (d, J = 5.0, 1H), 5.27 (t, J = 5.7, 1H), 4.51-4.47 (m, 2H), 3.80-3.74 (m, 4H), 3.48-3.40 m, 4H) | A | B | A |
| 186 | MS: 487.1/489.1 (M + H$^+$) (Cl isotopy, rel. peak intensity ratio [%] 100:41); R$_t$ 5.77 min (SFC, Chiralpak AD-H, CO$_2$/40% by vol. of methanol, 0.5% by vol. of diethylamine) | (R)-[2-Chloro-4-fluoro-5-(7-morpholin-4-yl-quinazolin-4-yl)-phenyl]-(4-hydroxymethyl-thiazol-2-yl)-methanol<br>1H NMR (500 MHz, DMSO-d6) ppm = 9.10 (s, 1H), 7.73 (dd, J = 8.6, 4.5, 2H), 7.57-7.52 (m, 2H), 7.38-7.35 (m, 1H), 7.22-7.19 (m, 1H), 7.03 (d, J = 5.0, 1H), 6.27 (d, J = 5.0, 1H), 5.27 (t, J = 5.7, 1H), 4.50-4.46 (m, 2H), 3.80-3.74 (m, 4H), 3.48-3.42 (m, 4H) | C | C | D |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 187 | | {2-Chloro-4-fluoro-5-[7-(3-oxa-8-aza-bicyclo[3.2.1]oct-8-yl)quinazolin-4-yl]-phenyl}-(4-hydroxy-methylthiazol-2-yl)-methanol | D | D | B |
| | MS: 513.1/515.0 (M + H$^+$) (Cl isotopy, rel. peak intensity ratio [%] 100:41) | 1H NMR (500 MHz, DMSO-d6) ppm = 9.03 (s, 1H), 7.71 (t, J = 8.5, 2H), 7.50 (dd, J = 9.3, 3.2, 1H), 7.40 (dd, J = 9.4, 2.5, 1H), 7.37-7.35 (m, 1H), 7.13 (d, J = 2.4, 1H), 7.01 (d, J = 5.1, 1H), 6.27 (d, J = 5.0, 1H), 5.26 (t, J = 5.7, 1H), 4.52-4.50 (m, 2H), 4.50-4.47 (m, 2H), 3.69 (d, J = 10.9, 2H), 3.57-3.50 (m, 2H), 2.09-1.94 (m, 4H) | | | |
| 188 | | [6-Fluoro-5-(7-morpholin-4-yl-quinazolin-4-yl)-pyridin-3-yl]thiazol-2-ylmethanol (Ena 1) | A | C | A |
| | MS: 424.0 (M + H$^+$); R$_t$ 44.51 min, (HPLC, Chiralcel OD-H, hexane/2-propanol 80/20) | see racemate | | | |
| 189 | | [6-Fluoro-5-(7-morpholin-4-yl-quinazolin-4-yl)-pyridin-3-yl]thiazol-2-ylmethanol (Ena 2) | B | B | B |
| | MS: 424.0 (M + H$^+$); R$_t$ 49.66 min, (HPLC, Chiralcel OD-H, hexane/2-propanol 80/20) | see racemate | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 190 | 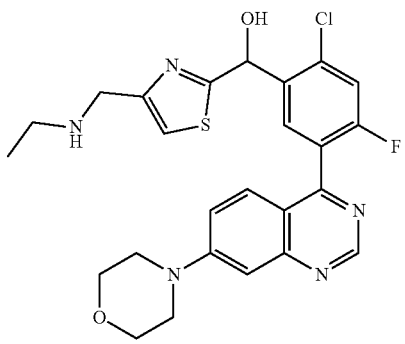 [SMILES: CCNCc1csc(C(O)c2cc(-c3ncnc4cc(N5CCOCC5)ccc34)c(F)cc2Cl)n1]<br>MS: 514.2/516.1 (M + H$^+$)<br>(Cl isotopy, rel. peak intensity ratio [%] 100:41) | [2-Chloro-4-fluoro-5-(7-morpholin-4-yl-quinazolin-4-yl)-phenyl]-(4-ethyl-aminomethyl-thiazol-2-yl)-methanol<br>1H NMR (500 MHz, DMSO-d6) ppm = 9.09 (s, 1H), 8.25 (s, 1H), 7.73 (d, J = 1.6, 1H), 7.71 (s, 1H), 7.58-7.49 (m, 2H), 7.44-7.40 (m, 1H), 7.23-7.18 (m, 1H), 7.05 (s, 1H), 6.27 (s, 1H), 3.80-3.76 (m, 6H), 3.48-3.40 (m, 4H), 2.60 (q, J = 7.1, 2H), 1.01 (t, J = 7.1, 3H) | C | B | B |
| 190 | 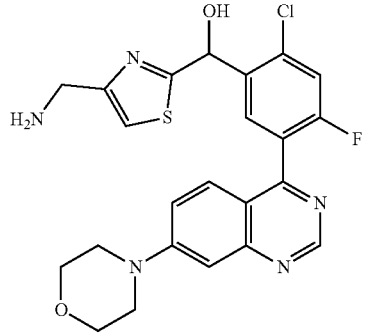 [SMILES: NCc1csc(C(O)c2cc(-c3ncnc4cc(N5CCOCC5)ccc34)c(F)cc2Cl)n1]<br>MS: 486.0/488.1 (M + H$^+$)<br>(Cl isotopy, rel. peak intensity ratio [%] 100:38) | (4-Aminomethyl-thiazol-2-yl)-[2-chloro-4-fluoro-5-(7-morpholin-4-yl-quinazolin-4-yl)-phenyl]methanol<br>1H NMR (400 MHz, DMSO-d6) ppm = 9.09 (s, 1H), 8.30 (s, 1H), 7.76-7.69 (m, 2H), 7.57-7.50 (m, 2H), 7.48-7.43 (m, 1H), 7.23-7.17 (m, 1H), 6.28 (s, 1H), 3.86 (s, 2H), 3.81-3.74 (m, 4H), 3.47-3.44 (m, 4H) | C | B | B |
| 191 | 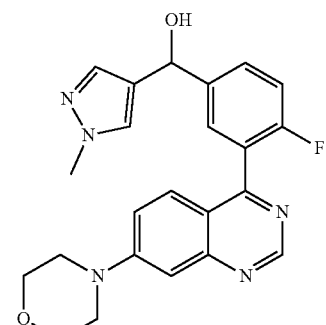<br>MS: 420.1 (M + H$^+$) | [4-Fluoro-3-(7-morpholin-4-yl-quinazolin-4-yl)-phenyl]-(1-methyl-1H-pyrazol-4-yl)-methanol<br>1H NMR (400 MHz, DMSO-d6) ppm = 9.10 (s, 1H), 7.68-7.33 (m, 6H), 7.31-7.15 (m, 2H), 5.76 (s, 2H), 3.90-3.64 (m, 7H), 3.51-3.39 (m, 4H) | A | D | A |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 192 | 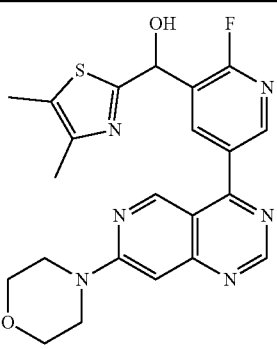<br>MS: 453.0 (M + H$^+$) | (4,5-Dimethyl-thiazol-2-yl)-[2-fluoro-5-(7-morpholin-4-yl-pyrido[4,3-d]-pyrimidin-4-yl)-pyridin-3-yl]-methanol<br><br>1H NMR (400 MHz, DMSO-d6) ppm = 9.14 (s, 1H), 9.09 (s, 1H), 8.67-8.65 (m, 1H), 8.46 (dd, J = 9.0, 2.4, 1H), 7.03-6.99 (m, 2H), 6.11 (d, J = 5.2, 1H), 3.77-3.68 (m, 8H), 2.31 (s, 3H), 2.19 (s, 3H) | D | | C |
| 194 | 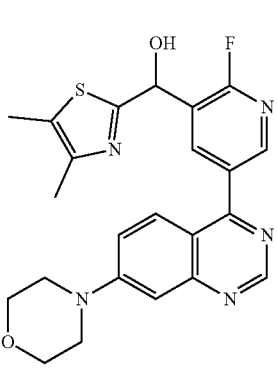 [SMILES: Cc1nc(C(O)c2cc(-c3ncnc4cc(N5CCOCC5)ccc34)cnc2F)sc1C]<br>MS: 452.2 (M + H$^+$) | (4,5-Dimethyl-thiazol-2-yl)-[2-fluoro-5-(7-morpholin-4-yl-quinazolin-4-yl)-pyridin-3-yl]-methanol<br><br>1H NMR (400 MHz, DMSO-d6) ppm = 9.10 (s, 1H), 8.58-8.56 (m, 1H), 8.37 (dd, J = 9.0, 2.4, 1H), 7.87 (d, J = 9.4, 1H), 7.57 (dd, J = 9.4, 2.6, 1H), 7.22 (d, J = 2.5, 1H), 6.99 (d, J = 5.1, 1H), 6.11 (d, J = 5.1, 1H), 3.80-3.76 (m, 4H), 3.49-3.43 (m, 4H), 2.30 (s, 3H), 2 19 (s, 3H) | C | | A |
| 195 | 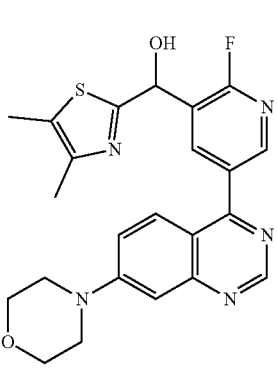<br>MS: 439.0 (M + H$^+$) | [6-Fluoro-5-(7-morpholin-4-yl-pyrido[4,3-d]-pyrimidin-4-yl)-pyridin-3-yl]-(4-methyl-thiazol-2-yl)-methanol<br><br>1H NMR (400 MHz, DMSO-d6) ppm = 9.17 (s, 1H), 8.90 (d, J = 2.5, 1H), 8.57-8.53 (m, 1H), 8.29 (dd, J = 9.1, 2.4, 1H), 7.24-7.21 (m, 1H), 7.10 (d, J = 4.9, 1H), 7.00 (s, 1H), 6.16 (d, J = 4.9, 1H), 3.79-3.67 (m, 8H), 2.33 (d, J = 1.0, 3H) | D | | B |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 196 | 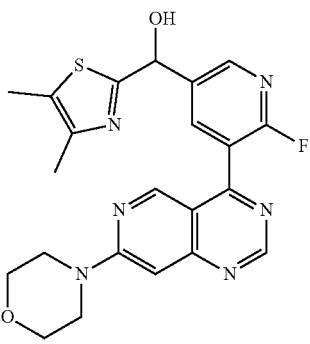<br>MS: 407.2 (M + H$^+$) | (4,5-Dimethyl-thiazol-2-yl)-[6-fluoro-5-(7-morpholin-4-yl-pyrido[4,3-d]-pyrimidin-4-yl)-pyridin-3-yl]-methanol | C | D | A |
| | | 1H NMR (500 MHz, DMSO-d6) ppm = 9.16 (s, 1H), 8.90 (d, J = 2.4, 1H), 8.53 (d, J = 2.3, 1H), 8.27 (dd, J = 9.1, 2.4, 1H), 7.06 (d, J = 4.9, 1H), 6.99 (s, 1H), 6.08 (d J = 4.9, 1H), 3.76-3.69 (m, 8H), 2.30 (s, 3H), 2.21 (s, 3H) | | | |
| 197 | 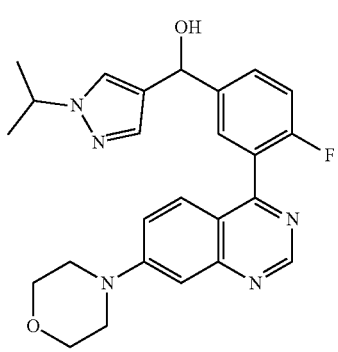 [SMILES: CC(C)n1cc(C(O)c2ccc(F)c(-c3ncnc4cc(N5CCOCC5)ccc34)c2)cn1]<br>MS: 448.2 (M + H$^+$) | [4-Fluoro-3-(7-morpholin-4-yl-quinazolin-4-yl)-phenyl]-(1-isopropyl-1H-pyrazol-4-yl)-methanol | B | C | D |
| | | 1H NMR (500 MHz, DMSO-d6) ppm = 9.10 (s, 1H), 7.64-7.60 (m, 1H), 7.60-7.57 (m, 2H), 7.56-7.50 (m, 2H), 7.41-7.35 (m, 1H), 7.28 (s, 1H), 7.20 (d, J = 2.2, 1H), 5.76 (s, 2H), 4.42 (h, J = 6.6, 1H), 3.80-3.76 (m, 4H), 3.46-3.42 (m, 4H), 1.36 (d, J = 6.7, 6H) | | | |
| 198 | 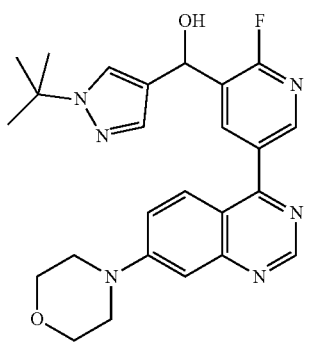 [SMILES: CC(C)(C)n1cc(C(O)c2cc(-c3ncnc4cc(N5CCOCC5)ccc34)cnc2F)cn1]<br>MS: 463.2 (M + H$^+$) | (1-tert-Butyl-1H-pyrazol-4-yl)-[2-fluoro-5-(7-morpholin-4-yl-quinazolin-4-yl)-pyridin-3-yl]-methanol | C | | A |
| | | 1H NMR (500 MHz, DMSO-d6) ppm = 9.10 (s, 1H), 8.54-8.49 (m, 1H), 8.46 (dd, J = 9.4, 2.6, 1H), 7.89 (d, J = 9.4, 1H), 7.73 (s, 1H), 7.57 (dd, J = 9.5, 2.6, 1H), 7.36 (s, 1H), 7.23 (d, J = 2.5, 1H), 6.02 (d, J = 4.8, 1H), 5.95 (d, J = 4.6, 1H), 3.82-3.75 (m, 4H), 3.50-3.42 (m, 4H), 1.48 (s, 9H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 199 | MS: 473.0 (M + H⁺) | 4-[5-(Difluoro-methoxy-thiazol-2-ylmethyl)-2-fluoro-phenyl]-7-morpholin-4-yl-quinazoline | B | D | D |
| | | 1H NMR (400 MHz, DMSO-d6) ppm = 9.11 (s, 1H), 7.85 (d, J = 3.2, 1H), 7.81 (d, J = 3.2, 1H), 7.73-7.71 (m, 2H), 7.55-7.52 (m, 2H), 7.52-7.48 (m, 1H), 7.22-6.82 (m, 3H), 3.80-3.75 (m, 4H), 3.48-3.42 (m, 4H) | | | |
| 200 | MS: 467.2 (M + H⁺) | [4-Fluoro-3-(7-morpholin-4-yl-quinazolin-4-yl)-phenyl]-(5-hydroxy-methyl-4-methyl-thiazol-2-yl)-methanol | B | C | A |
| | | 1H NMR (500 MHz, DMSO-d6) ppm = 9.11 (s, 1H), 7.70-7.63 (m, 2H), 7.55-7.50 (m, 2H), 7.44-7.39 (m, 1H), 7.22-7.19 (m, 1H), 6.81 (d, J = 4.5, 1H), 5.95 (d, J = 4.3, 1H), 5.35 (t, J = 5.6, 1H), 4.54 (d, J = 5.4, 2H), 3.80-3.75 (m, 4H), 3.47-3.42 (m, 4H), 2.22 (s, 3H) | | | |
| 201 | MS: 501.0/503.0 (M + H⁺) (Cl isotopy, rel. peak intensity ratio [%] 100:39) | 1-(2-{[2-Chloro-4-fluoro-5-(7-morpholin-4-yl-quinazolin-4-yl)-phenyl]hydroxy-methyl}thiazol-4-yl)-ethanol | B | B | B |
| | | 1H NMR (500 MHz, DMSO-d6) ppm = 9.11-9.09 (m, 1H), 7.75-7.70 (m, 2H), 7.55-7.52 (m, 2H), 7.34-7.32 (m, 1H), 7.21-7.19 (m, 1H), 7.00-6.96 (m, 1H), 6.28-6.25 (m, 1H), 5.26-5.18 (m, 1H), 4.77-4.70 (m, 1H), 3.79-3.75 (m, 4H), 3.47-3.43 (m, 4H), 1.36-1.30 (m, 3H) | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 202 | MS: 468.0/470.0 (M + H⁺) (Cl isotopy, rel. peak intensity ratio [%] 100:35) | [2-Chloro-4-fluoro-5-(7-morpholin-4-ylquinazolin-4-yl)-phenyl]-(1-ethyl-1H-pyrazol-4-yl)-methanol | C | B | B |
| | | 1H NMR (500 MHz, DMSO-d6) ppm = 9.12 (s, 1H), 7.91-7.88 (m, 1H), 7.64 (d, J = 9.6, 1H), 7.59 (dd, J = 9.4, 3.2, 1H), 7.57-7.52 (m, 2H), 7.29 (s, 1H), 7.22-7.20 (m, 1H), 5.98 (d, J = 4.8, 1H), 5.93 (d, J = 4.8, 1H), 4.08-4.02 (m, 2H), 3.80-3.76 (m, 4H), 3.48-3.43 (m, 4H), 1.34-1.28 (m, 3H) | | | |
| 203 | MS: 453.2 (M + H⁺); R$_t$ 73.58 min, (HPLC, Chiralcel OD-H, hexane/2-propanol 90/10) | (4,5-Dimethyl-thiazol-2-yl)-[6-fluoro-5-(7-morpholin-4-yl-pyrido[4,3-d]-pyrimidin-4-yl)-pyridin-3-yl]-methanol (Ena 2) | D | D | A |
| | | see racemate | | | |
| 204 | MS: 453.2 (M + H⁺); R$_t$ 68.00 min, (HPLC, Chiralcel OD-H, hexane/2-propanol 90/10) | (R)-(4,5-Dimethyl-thiazol-2-yl)-[6-fluoro-5-(7-morpholin-4-yl-pyrido[4,3-d]-pyrimidin-4-yl)-pyridin-3-yl]-methanol (Ena 1) | D | D | C |
| | | see racemate | | | |

TABLE 5-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 205 | | (4,5-Dimethyl-thiazol-2-yl)-[2-fluoro-5-(7-morpholin-4-yl-quinazolin-4-yl)-pyridin-3-yl]-methanol (Ena 1) MS: 452.2 (M + H$^+$); Rt 24.50 min, (HPLC, Chiralpak AD-H, ethanol) | C | D see racemate | C |
| 206 | | (4,5-Dimethyl-thiazol-2-yl)-[2-fluoro-5-(7-morpholin-4-yl-quinazolin-4-yl)-pyridin-3-yl]-methanol (Ena 2) MS: 452.2 (M + H$^+$); Rt 27.44 min, (HPLC, Chiralpak AD-H, ethanol) | D | B see racemate | B |

Example 207

[4-Fluoro-2-methyl-5-(7-morpholinylquinazolin-4-yl)phenyl]thiazol-2-ylmethanol (EXAMPLE 207)

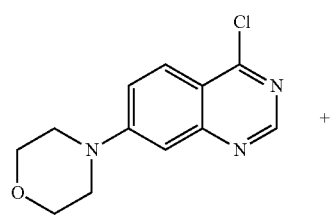

+

-continued

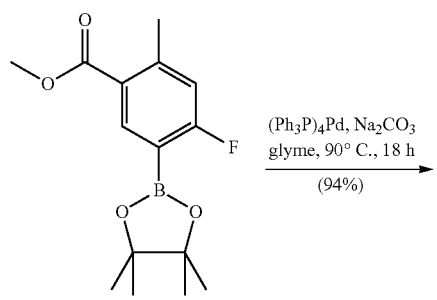

(Ph$_3$P)$_4$Pd, Na$_2$CO$_3$
glyme, 90° C., 18 h
(94%)

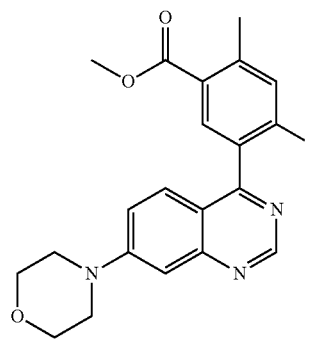

Methyl 4-fluoro-2-methyl-5-(7-morpholinylquinazolin-4-yl)benzoate was prepared analogously to the synthetic processes described under EXAMPLES 1 and 2 starting from 4-chloro-7-morpholin-4-ylquinazoline and methyl 4-fluoro-2-methyl-5-(4,4,5,5-tetramethyl-1,3,2-dioxaborolan-2-yl)benzoate.

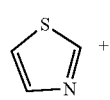

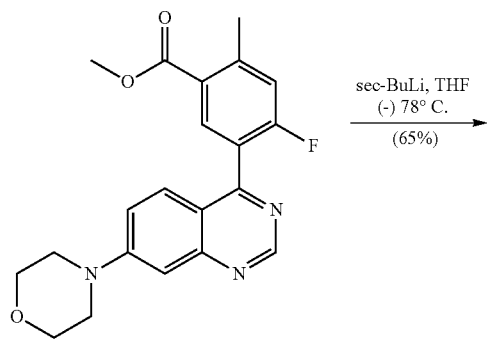

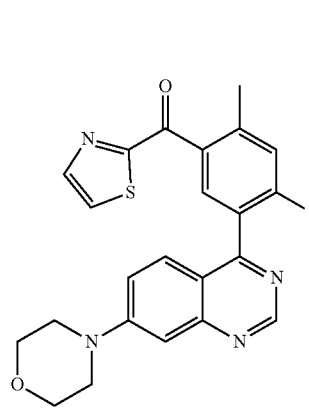

[4-Fluoro-2-methyl-5-(7-morpholinylquinazolin-4-yl)phenyl]thiazol-2-ylmethanone was prepared analogously to the synthetic processes described under EXAMPLE 138 starting from thiazole and methyl 4-fluoro-2-methyl-5-(7-morpholinylquinazolin-4-yl)benzoate.

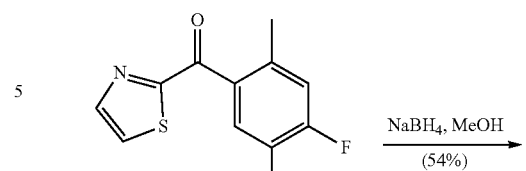

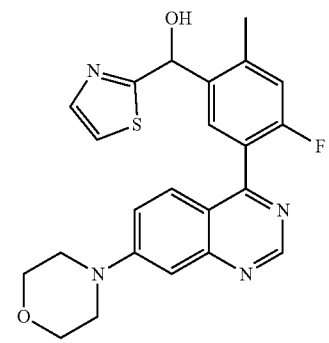

EXAMPLE 207

[4-Fluoro-2-methyl-5-(7-morpholinylquinazolin-4-yl)phenyl]thiazol-2-ylmethanol (EXAMPLE 207) was prepared analogously to the synthetic processes described under EXAMPLES 1 and 2 starting from [4-fluoro-2-methyl-5-(7-morpholinylquinazolin-4-yl)phenyl]thiazol-2-ylmethanone.

Example 208

[3-(2-Ethynyl-7-morpholinylquinazolin-4-yl)-4-fluorophenyl]thiazol-2-ylmethanol (EXAMPLE 208)

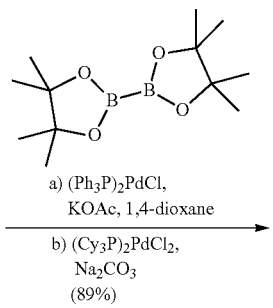

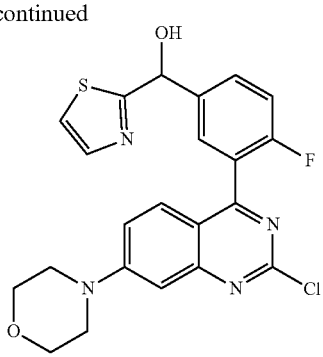

[3-(2-Chloro-7-morpholinylquinazolin-4-yl)-4-fluorophenyl]thiazol-2-ylmethanol was prepared analogously to the synthetic processes described under EXAMPLE 138 starting from (3-bromo-4-fluorophenyl)thiazol-2-ylmethanol and 4-(2,4-dichloroquinazolin-7-yl)morpholine.

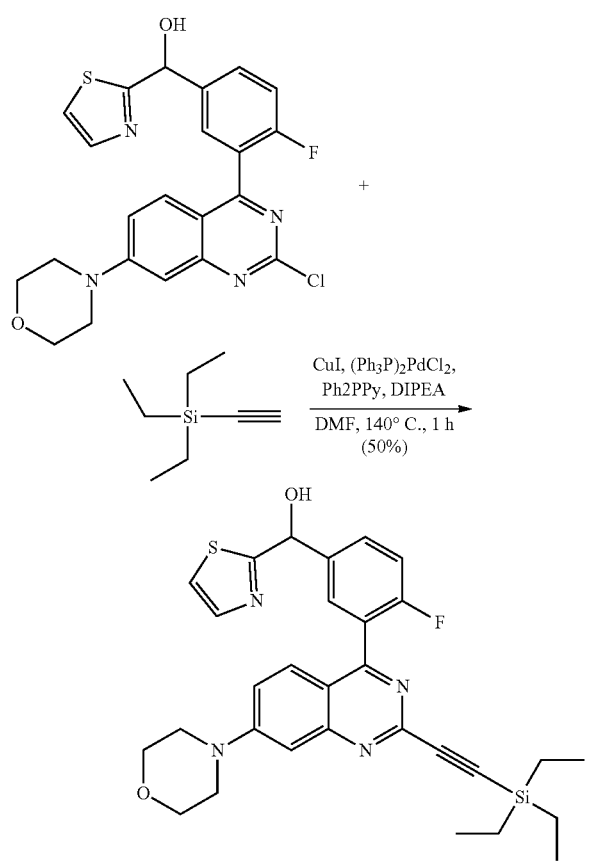

[3-(2-Chloro-7-morpholinylquinazolin-4-yl)-4-fluorophenyl]thiazol-2-ylmethanol (102 mg, 0.225 mmol) was dissolved in oxygen-free N,N-dimethylformamide (4 ml) in an argon atmosphere. CuI (17 mg, 90 μmol), (Ph₃P)₂PdCl₂ (63 mg, 90 μmol), 2-diphenylphosphanylpyridine (95 mg, 0.359 mmol), DIPEA (765 μl, 4.49 mmol) and triethylethynylsilane (275 μl, 1.48 mmol) were subsequently added. The reaction mixture was then heated at a temperature of 140° C. for 1 h. For work-up, ethyl acetate (50 ml), water (10 ml) and saturated sodium chloride solution (15 ml) were added. The aqueous phase was separated off and extracted with ethyl acetate (20 ml). The combined organic phases were dried over sodium sulfate, filtered, and the filtrate was evaporated to dryness in vacuo. The residue was dissolved in dimethyl sulfoxide (2 ml) purified by means of RP chromatography (solvent: acetonitrile/water/0.1% by vol. of HCOOH, CombiFlash Rf 200). The suitable product fractions were combined, and the solvents were removed in a rotary evaporator, giving [4-fluoro-3-[7-morpholinyl-2-(2-triethylsilylethynyl)quinazolin-4-yl]phenyl]thiazol-2-ylmethanol (64 mg, 0.114 mmol, MS: 561.2 [M+H⁺], 50% yield) as wax-like solid.

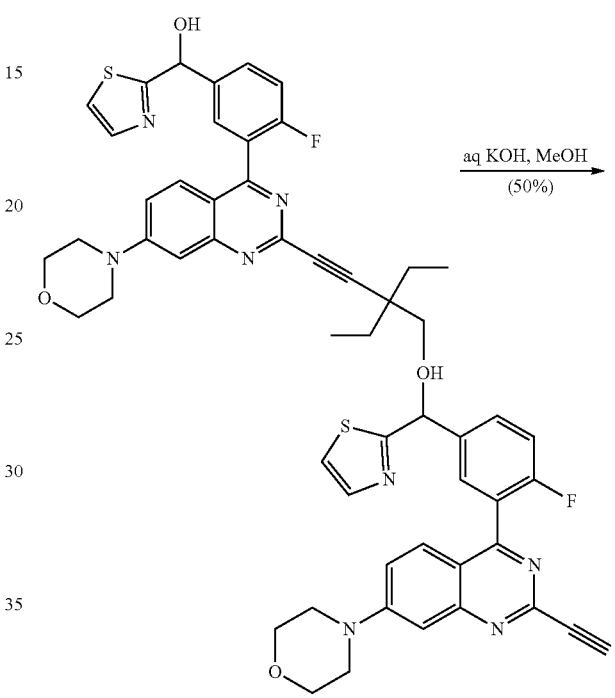

EXAMPLE 208

[4-Fluoro-3-[7-morpholinyl-2-(2-triethylsilylethynyl)quinazolin-4-yl]phenyl]thiazol-2-ylmethanol (552 mg, 0.985 mmol) was dissolved in methanol (102 ml). Potassium hydroxide solution (1.0 M, 15 ml, 15 mmol) was subsequently added, and the mixture was stirred at room temperature for 90 min. When the reaction was complete, the mixture was carefully neutralised using hydrochloric acid (1.0 M, 15 ml, 15 mmol). Ethyl acetate (500 ml), water (100 ml) and saturated sodium chloride solution (150 ml) were subsequently added. The phases were separated, and the aqueous phase was extracted with ethyl acetate (100 ml). The combined organic phases were dried over sodium sulfate, filtered, and the filtrate was evaporated to dryness in vacuo. The residue, dissolved in dimethyl sulfoxide (8 ml), was purified by means of flash column chromatography (gradient: dichloromethane/0-5% by vol. of ethanol, CombiFlash Rf 200). The suitable product fractions were combined, and the solvents were removed in a rotary evaporator, giving [3-(2-ethynyl-7-morpholinylquinazolin-4-yl)-4-fluorophenyl]-thiazol-2-ylmethanol (EXAMPLE 208, 221 mg, 0.495 mmol, MS: 447.1 [M+H⁺], 50% yield) as solid.

Compounds which were prepared analogously to EXAMPLES 207 and 208 can be found in Table 6 below.

TABLE 6

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 207 | 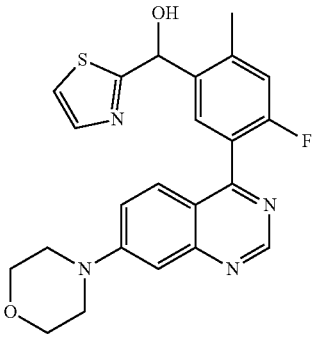 [SMILES: Cc1cc(F)c(-c2ncnc3cc(N4CCOCC4)ccc23)cc1C(O)c1nccs1]<br>MS: 437.1 (M + H$^+$) | [4-Fluoro-2-methyl-5-(7-morpholin-4-yl-quinazolin-4-yl)-phenyl]thiazol-2-ylmethanol<br><br>1H NMR (500 MHz, DMSO-d6) ppm = 9.09 (s, 1H), 7.71 (d, J = 3.2, 1H), 7.64 (d, J = 3.2, 1H), 7.62 (d, J = 7.5, 1H), 7.58-7.51 (m, 2H), 7.28 (d, J = 10.9, 1H), 7.19 (d, J = 2.1, 1H), 6.84 (s, 1H), 6.20 (s, 1H), 3.80-3.75 (m, 4H), 3.48-3.43 (m, 4H), 2.49 (s, 3H) | A | B | B |
| 208 | 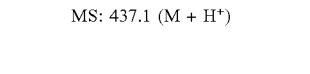<br>MS: 447.0 (M + H$^+$) | [3-(2-Ethynyl-7-morpholin-4-yl-quinazolin-4-yl)-4-fluoro-phenyl]-thiazol-2-yl-methanol<br><br>1H NMR (500 MHz, DMSO-d6) ppm = 7.81-7.47 (m, 6H), 7.46-7.36 (m, 1H), 7.18 (d, J = 2.4, 1H), 6.99 (d, J = 4.6, 1H), 6.08 (d, J = 4.3, 1H), 4.30 (s, 1H), 3.80-3.74 (m, 4H), 3.49-3.41 (m, 4H) | B | B | D |
| 209 | 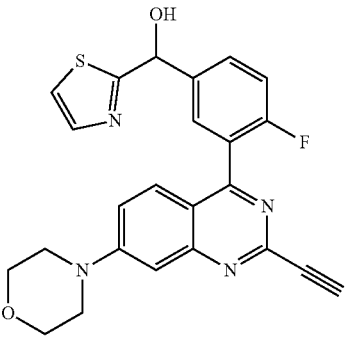<br>MS: 437.1 (M + H$^+$); R$_t$ 4.77 min (SFC, Chiracel OJ-H, CO$_2$/15% by vol. of methanol, 0.5% by vol. of diethylamine) | [4-Fluoro-2-methyl-5-(7-morpholin-4-yl-quinazolin-4-yl)-phenyl]thiazol-2-ylmethanol (Ena 1)<br><br>1H NMR (400 MHz, DMSO-d6) ppm = 9.09 (s, 1H), 7.72 (d, J = 3.3, 1H), 7.68-7.59 (m, 2H), 7.60-7.47 (m, 2H), 7.28 (d, J = 10.9, 1H), 7.19 (s, 1H), 6.99-6.71 (m, 1H) 6.20 (s, 1H), 3.82-3.73 (m, 4H), 3.48-3.42 (m, 4H), 2.58-2.50 (m, 3H) | D | D | A |

TABLE 6-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 210 | | [4-Fluoro-2-methyl-5-(7-morpholin-4-yl-quinazolin-4-yl)-phenyl]thiazol-2-ylmethanol (Ena 2) | B | B | A |
| | MS: 437.1 (M + H$^+$); R$_t$ 6.01 min (SFC, Chiracel OJ-H, CO$_2$/15% by vol. of methanol, 0.5% by vol. of diethylamine) | 1H NMR (400 MHz, DMSO-d6) ppm = 9.09 (s, 1H), 7.72 (d, J = 3.3, 1H), 7.68-7.59 (m, 2H), 7.60-7.47 (m, 2H), 7.28 (d, J = 10.9, 1H), 7.19 (s, 1H), 6.99-6.71 (m, 1H), 6.20 (s, 1H), 3.82-3.73 (m, 4H), 3.48-3.42 (m, 4H), 2.58-2.50 (m, 3H) | | | |
| 211 | | [4-Fluoro-3-(7-morpholin-4-yl-quinazolin-4-yl)-phenyl]thiazol-2-ylmethanol | B | B | A |
| | MS: 423.1 (M + H$^+$) | 1H NMR (400 MHz, DMSO-d6) ppm = 9.10 (s, 1H), 7.78-7.61 (m, 4H), 7.57-7.49 (m, 2H), 7.46-7.37 (m, 1H), 7.23-7.17 (m, 1H), 6.95 (s, 1H), 6.08 (s, 1H), 3.81-3.74 (m, 4H), 3.48-3.41 (m, 4H) | | | |
| 212 | | [4-Fluoro-3-(7-morpholin-4-yl-quinazolin-4-yl)-phenyl]thiazol-2-ylmethanol (Ena 1) | A | D | A |
| | MS: 423.1 (M + H$^+$); R$_t$ 15.65 min (SFC, Chiracel OJ-H, CO$_2$/10% by vol. of methanol, 0.5% by vol. of diethylamine) | 1H NMR (400 MHz, DMSO-d6) ppm = 9.10 (s, 1H), 7.73 (d, J = 3.2, 1H), 7.71-7.63 (m, 3H), 7.55-7.49 (m, 2H), 7.44-7.38 (m, 1H), 7.22-7.18 (m, 1H), 6.95 (d, J = 4.6, 1H), 6.08 (d, J = 4.5, 1H), 3.81-3.75 (m, 4H), 3.47-3.42 (m, 4H) | | | |

TABLE 6-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 213 | 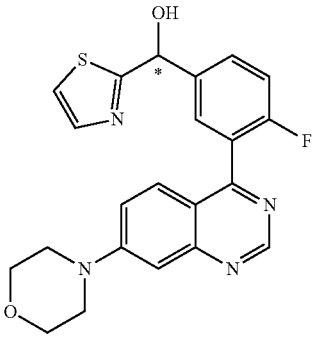 [SMILES: OC(c1ccc(F)c(-c2ncnc3cc(N4CCOCC4)ccc23)c1)c1nccs1] MS: 423.1 (M + H$^+$); R$_t$ 18.36 min (SFC, Chiracel OJ-H, CO$_2$/10% by vol. of methanol, 0.5% by vol. of diethylamine) | [4-Fluoro-3-(7-morpholin-4-yl-quinazolin-4-yl)-phenyl]thiazol-2-ylmethanol (Ena 2)  1H NMR (400 MHz, DMSO-d6) ppm = 9.10 (s, 1H), 7.73 (d, J = 3.2, 1H), 7.72-7.65 (m, 2H), 7.65-7.64 (m, 1H), 7.54-7.52 (m, 2H), 7.44-7.39 (m, 1H), 7.21-7.19 (m, 1H), 6.96 (d, J = 4.6, 1H), 6.08 (d, J = 4.6, 1H), 3.80-3.75 (m, 4H), 3.46-3.42 (m, 4H) | A | C | A |
| 214 | 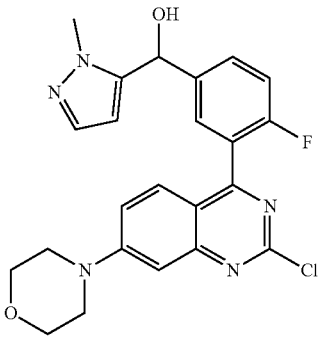 [SMILES: Cn1nccc1C(O)c1ccc(F)c(-c2nc(Cl)nc3cc(N4CCOCC4)ccc23)c1] MS: 454.1/456.1 (M + H$^+$) (Cl isotopy, rel. peak intensity ratio [%] 100:35) | [3-(2-Chloro-7-morpholin-4-yl-quinazolin-4-yl)-4-fluoro-phenyl]-(2-methyl-2H-pyrazol-3-yl)-methanol  1H NMR (500 MHz, DMSO-d6) ppm = 7.71-7.59 (m, 3H), 7.58-7.51 (m, 2H), 7.50-7.41 (m, 1H), 7.31-7.26 (m, 1H), 7.18-7.12 (m, 1H), 5.99 (s, 1H), 5.95-5.90 (m, 1H), 3.78 (s, 3H), 3.78-3.73 (m, 4H), 3.52-3.45 (m, 4H) | B | D | B |
| 215 | 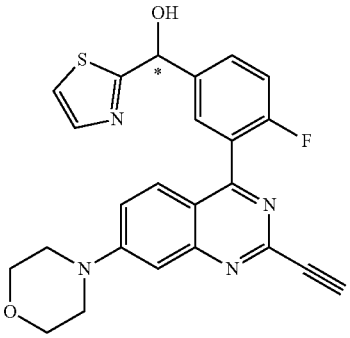 [SMILES: C#Cc1nc(-c2cc(C(O)c3nccs3)ccc2F)c2ccc(N3CCOCC3)cc2n1] MS: 447.1 (M + H$^+$); R$_t$ 10.67 min (HPLC, Chiralpak AD-H, n-heptane/40% by vol. of 2-propanol | [3-(2-Ethynyl-7-morpholin-4-yl-quinazolin-4-yl)-4-fluorophenyl]-thiazol-2-yl-methanol (Ena 1)  1H NMR (500 MHz, DMSO-d6) ppm = 7.73 (d, J = 3.2, 1H), 7.72-7.65 (m, 2H), 7.65 (d, J = 3.2, 1H), 7.53 (qd, J = 9.4, 2.7, 2H), 7.46-7.38 (m, 1H), 7.18 (d, J = 2.3, 1H), 6.97 (d, J = 4.6, 1H), 6.09 (d, J = 4.6, 1H), 4.30 (s, 1H), 3.80-3.74 (m, 4H), 3.49-3.43 (m, 4H) | A | C | D |

TABLE 6-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 216 | 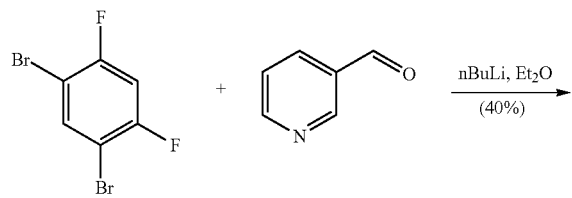<br>MS: 447.1 (M + H$^+$); R$_t$ 13.14 min (HPLC, Chiralpak AD-H, n-heptane/40% by vol. of 2-propanol | [3-(2-Ethynyl-7-morpholin-4-yl-quinazolin-4-yl)-4-fluorophenyl]-thiazol-2-yl-methanol (Ena 2) | A | D | C |

1H NMR (500 MHz, DMSO-d6) ppm = 7.73 (d, J = 3.2, 1H), 7.72-7.65 (m, 2H), 7.65 (d, J = 3.2, 1H), 7.53 (qd, J = 9.4, 2.7, 2H), 7.46-7.38 (m, 1H), 7.18 (d, J = 2.3, 1H), 6.97 (d, J = 4.6, 1H), 6.09 (d, J = 4.6, 1H), 4.30 (s, 1H), 3.80-3.74 (m, 4H), 3.49-3.43 (m, 4H)

Example 217

[2,4-Difluoro-5-(7-morpholin-4-ylquinazolin-4-yl)phenyl]pyridin-3-ylmethanol (217)

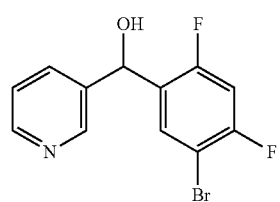

1,5-Dibromo-2,4-difluorobenzene (500 mg, 1.78 mmol) was dissolved in dry diethyl ether (10 ml) under argon. The reaction solution was cooled to (−)65° C. by means of an acetone/dry-ice bath. n-Butyllithium (15% solution in n-hexane, 1.23 ml, 1.96 mmol) was added dropwise over the course of 15 min at a constant temperature of (−)65° C., and the reaction solution was stirred at (−)65° C. for a further 30 min. A pre-prepared solution of nicotinaldehyde (201 µl, 2.14 mmol) in dry diethyl ether (5 ml) was subsequently added dropwise over a period of 15 min at (−)65° C., and the reaction mixture was stirred for a further 10 min and then warmed slowly to 0° C. over a period of one hour. After termination of the reaction, saturated ammonium chloride solution (5 ml) and water (30 ml) were added to the reaction solution. The aqueous phase was extracted three times with t-butyl methyl ether. The combined organic phases were washed with saturated sodium chloride solution, dried over sodium sulfate, filtered and evaporated in a rotary evaporator. The crude product (oil) was purified by means of preparative RP column chromatography (solvent gradient water/acetonitrile/0.1% by vol. of trifluoroacetic acid [5.5 min], CombiFlash Rf 200). The suitable product fractions were combined and evaporated in vacuo. The aqueous residue was neutralised using saturated sodium hydrogencarbonate solution and extracted three times with ethyl acetate. The combined organic phases were washed with saturated sodium chloride solution, dried over sodium sulfate, filtered and evaporated to dryness in vacuo in a rotary evaporator, giving (5-bromo-2,4-difluorophenyl)-(3-pyridyl)methanol (215 mg, 0.717 mmol, MS: 300.0/302.0 [M+H+$^+$], 40% yield) as colourless oil.

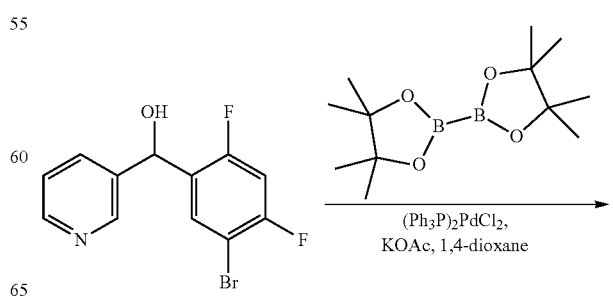

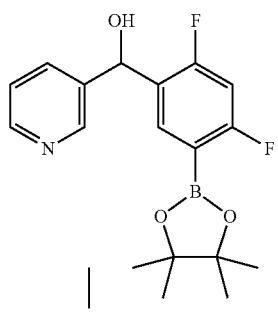

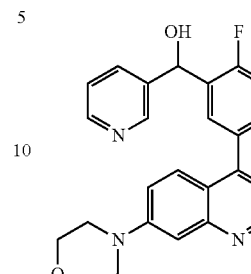

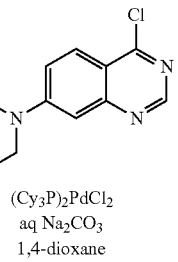

(Cy₃P)₂PdCl₂
aq Na₂CO₃
1,4-dioxane (73%)

EXAMPLE 217

[2,4-Difluoro-5-(7-morpholin-4-ylquinazolin-4-yl)phenyl]pyridin-3-ylmethanol (EXAMPLE 217) was obtained analogously to the synthetic processes for the preparation of 1-[5-(7-morpholin-4-ylquinazolin-4-yl)pyridin-3-yl]-1-thiazol-2-ylethanol (EXAMPLE 138) starting from (5-bromo-2,4-difluorophenyl)-(3-pyridyl)methanol.

Compounds which were prepared analogously to EXAMPLE 217 can be found in Table 7 below.

TABLE 7

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 217 | (structure shown) MS: 435.2 (M + H⁺) | [2,4-Difluoro-5-(7-morpholin-4-yl-quinazolin-4-yl)-phenyl]pyridin-3-yl-methanol | B | A | A |

1H NMR (500 MHz, DMSO-d6) ppm = 9.11 (s, 1H), 8.62-8.59 (m, 1H), 8.47 (dd, J = 4.8, 1.6, 1H), 7.84 (t, J = 8.2, 1H), 7.77-7.72 (m, 1H), 7.55 (qd, J = 9.4, 2.8, 2H), 7.46 (t, J = 10.1, 1H), 7.39-7.34 (m, 1H), 7.21 (d, J = 2.4, 1H), 6.36 (d, J = 4.5, 1H), 6.06 (d, J = 4.5, 1H), 3.81-3.74 (m, 4H), 3.48-3.42 (m, 4H)

TABLE 7-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 218 | MS: 435.2 (M + H⁺) | [2,4-Difluoro-5-(7-morpholin-4-yl-quinazolin-4-yl)-phenyl]pyridin-2-yl-methanol | B | A | B |
| | | 1H NMR (500 MHz, DMSO-d6) ppm = 9.09 (s, 1H), 8.50-8.46 (m, 1H), 7.82 (td, J = 7.7, 1.8, 1H), 7.68 (t, J = 8.1, 1H), 7.64-7.59 (m, 1H), 7.57-7.50 (m, 2H), 7.43 (t, J = 10.1, 1H), 7.29-7.24 (m, 1H), 7.21-7.17 (m, 1H), 6.34 (d, J = 5.0, 1H), 6.02 (d, J = 5.0, 1H), 3.82-3.72 (m, 4H), 3.48-3.41 (m, 4H). | | | |
| 219 | MS: 466.2 (M + H⁺) | 6-{[2,4-Difluoro-5-(7-morpholin-4-yl-quinazolin-4-yl)-phenyl]hydroxy-methyl}-2-methyl-2H-pyridazin-3-one | B | B | B |
| | | 1H NMR (500 MHz, DMSO-d6) ppm = 9.11 (s, 1H), 7.85 (t, J = 8.1, 1H), 7.61-7.51 (m, 3H), 7.47 (t, J = 10.1, 1H), 7.21 (d, J = 2.3, 1H), 6.94 (d, J = 9.6, 1H), 6.56 (d, J = 4.8, 1H), 5.85 (d, J = 4.8, 1H), 3.81-3.75 (m, 4H), 3.60 (s, 3H), 3.48-3.42 (m, 4H) | | | |
| 220 | MS: 466.2 (M + H⁺) | 6-{[2,4-Difluoro-3-(7-morpholin-4-yl-quinazolin-4-yl)-phenyl]hydroxy-methyl}-2-methyl-2H-pyridazin-3-one | D | C | A |
| | | 1H NMR (500 MHz, DMSO-d6) ppm = 9.10 (s, 1H), 7.75 (d, J = 9.6, 1H), 7.67-7.61 (m, 1H), 7.51 (qd, J = 9.4, 2.6, 2H), 7.32 (t, J = 8.8, 1H), 7.20 (d, J = 2.3, 1H), 6.99 (d, J = 9.7, 1H), 6.64 (d, J = 5.1, 1H), 6.02 (d, J = 5.1, 1H), 3.78 (t, J = 4.9, 4H), 3.57 (s, 3H), 3.45 (t, J = 4.9, 4H) | | | |

TABLE 7-continued

Compounds of the formula (I)

| No. | Structural formula | Name | IC$_{50}$ DNA-PK | IC$_{50}$ pDNA-PK | K$_i$ [Kv1.11 hERG] |
|---|---|---|---|---|---|
| 221 | MS: 465.2 (M + H$^+$) | [2,4-Difluoro-5-(7-morpholin-4-yl-quinazolin-4-yl)-phenyl]-(6-methoxy-pyridin-3-yl)methanol | B | B | B |
| | | 1H NMR (500 MHz, DMSO-d6) ppm = 9.11 (s, 1H), 8.17 (d, J = 2.4, 1H), 7.84 (t, J = 8.2, 1H), 7.63 (dd, J = 8.6, 2.5, 1H), 7.60-7.52 (m, 2H), 7.44 (t, J = 10.2, 1H), 7.21 (d, J = 2.3, 1H), 6.79 (d, J = 8.6, 1H), 6.22 (d, J = 4.0, 1H), 5.99 (d, J = 3.7, 1H), 3.83 (s, 3H), 3.80-3.76 (m, 4H), 3.47-3.43 (m, 4H) | | | |
| 222 | MS: 475.2 (M + H$^+$) | [2,4-Difluoro-5-(7-morpholin-4-yl-quinazolin-4-yl)-phenyl]-[1,2,4]-triazolo[1,5-a]pyridin-6-ylmethanol | B | B | A |
| | | 1H NMR (500 MHz, DMSO-d6) ppm = 9.10 (s, 1H), 8.98-8.95 (m, 1H), 8.49 (s, 1H), 7.88 (t, J = 8.1, 1H), 7.83-7.80 (m, 1H), 7.62-7.56 (m, 2H), 7.53 (dd, J = 9.5, 2.5, 1H), 7.48 (t, J = 10.1, 1H), 7.20 (d, J = 2.4, 1H), 6.52 (s, 1H), 6.17 (s, 1H), 3.82-3.74 (m, 4H), 3.49-3.41 (m, 4H) | | | |
| 223 | MS: 475.2 (M + H$^+$) | [2,4-Difluoro-5-(7-morpholin-4-yl-quinazolin-4-yl)-phenyl]imidazo-[1,2-a]pyrazin-6-yl-methanol | C | B | A |
| | | 1H NMR (500 MHz, DMSO-d6) ppm = 9.13 (s, 1H), 9.06-9.02 (m, 1H), 8.83 (t, J = 1.3, 1H), 8.25-8.22 (m, 1H), 7.86 (d, J = 1.0, 1H), 7.76 (t, J = 8.1, 1H), 7.63-7.56 (m, 2H), 7.52 (t, J = 10.1, 1H), 7.24 (d, J = 2.1, 1H), 6.53 (d, J = 4.7, 1H), 6.16 (d, J = 4.5, 1H), 3.87-3.80 (m, 4H), 3.54-3.46 (m, 4H) | | | |

TABLE 7-continued
Compounds of the formula (I)
| No. | Structural formula | Name | IC$_{50}$ DNA-PK | IC$_{50}$ pDNA-PK | K$_i$ [Kv1.11 hERG] |
|---|---|---|---|---|---|
| 224 | 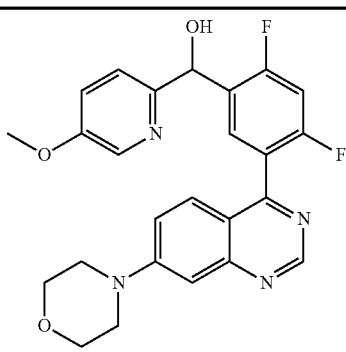<br>MS: 465.2 (M + H$^+$) | [2,4-Difluoro-5-(7-morpholin-4-yl-quinazolin-4-yl)-phenyl]-(5-methoxy-pyridin-2-yl)methanol<br>1H NMR (500 MHz, DMSO-d6) ppm = 9.09 (s, 1H), 8.20-8.17 (m, 1H), 7.68 (t, J = 8.1, 1H), 7.55-7.51 (m, 3H), 7.43-7.37 (m, 2H), 7.21-7.18 (m, 1H), 6.23 (d, J = 4.9, 1H), 5.98 (d, J = 4.6, 1H), 3.80 (s, 3H), 3.80-3.74 (m, 4H), 3.48-3.41 (m, 4H) | B | B | B |
Example 225
[2-Chloro-5-(5,6-dideuterio-7-morpholinylquinazolin-4-yl)-4-fluorophenyl]-(6-methoxypyridazin-3-yl)methanol (225)
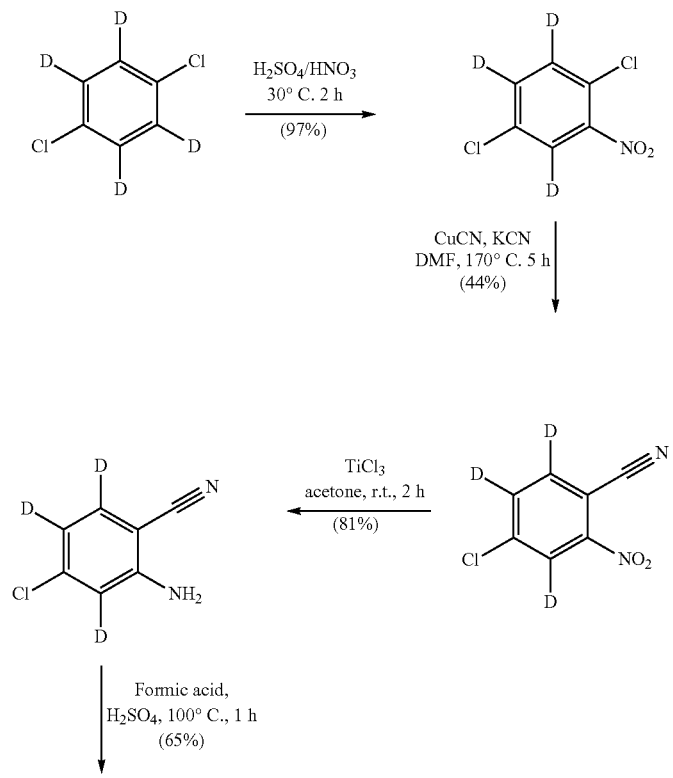

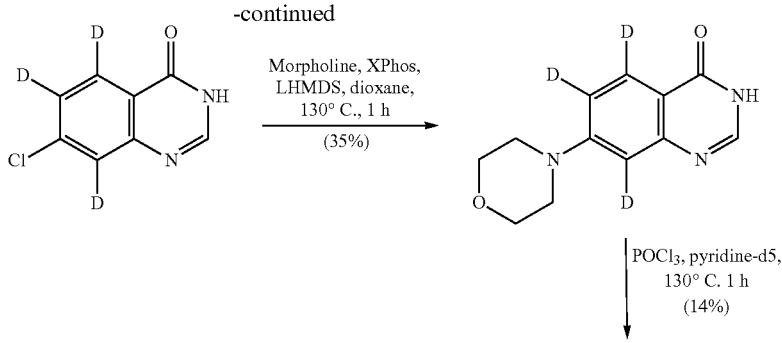
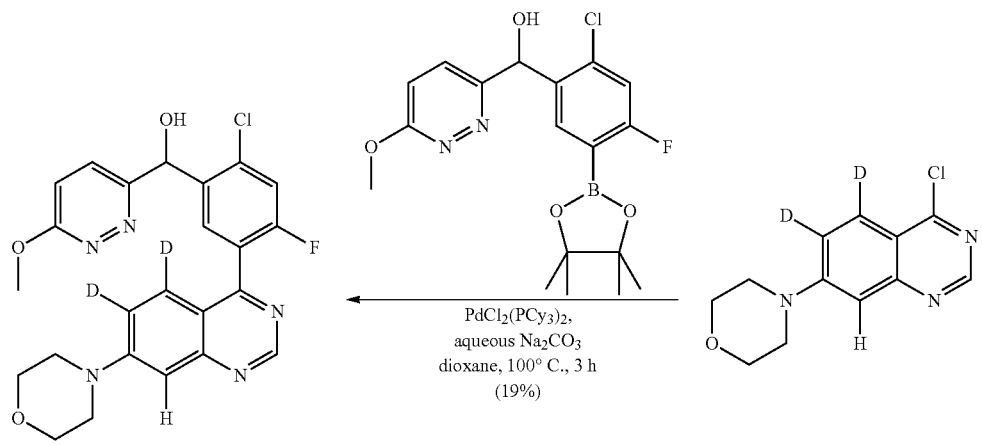
EXAMPLE 225
Reaction of 5,6,8-trideuterio-7-morpholinyl-3H-quinazolin-4-one with phosphorus oxychloride gave 4-chloro-5,6-dideuterio-7-N-morpholinylquinazoline.
Example 237
[4-Fluoro-3-(7-morpholin-4-ylpyrido[3,2-d}pyrimidin-4-yl)phenyl]-(3-methylpyrazin-2-yl)methanol (237)
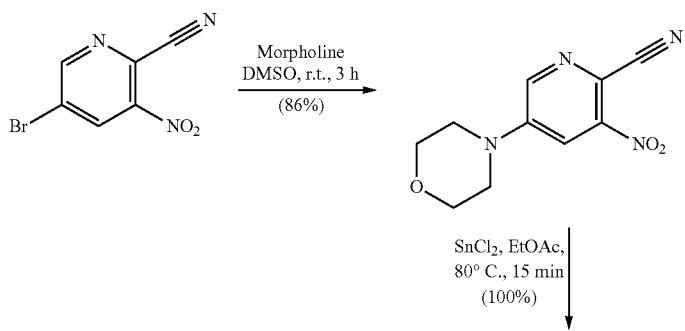

-continued
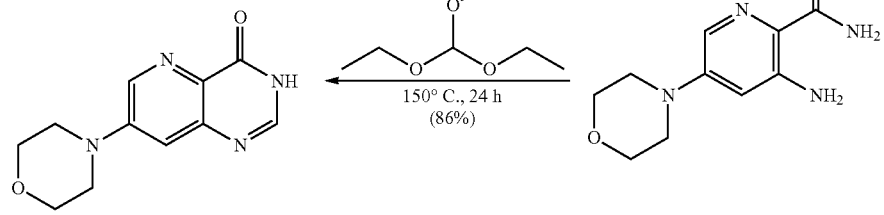
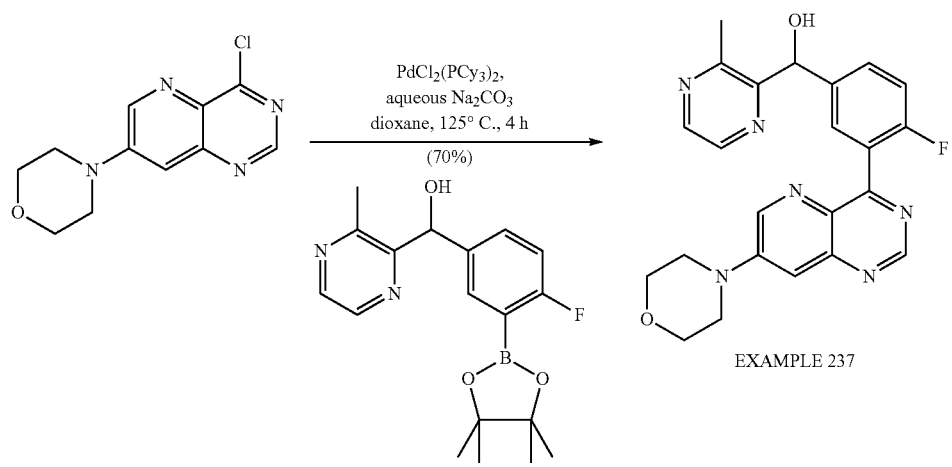
EXAMPLE 237
Example 258
[2-Chloro-4-fluoro-5-[7-(2,2,3,3,5,5,6,6-octadeuteriomorpholin-4-yl)quinazolin-4-yl]phenyl]-(3-methoxypyrazin-2-yl)methanol (258)
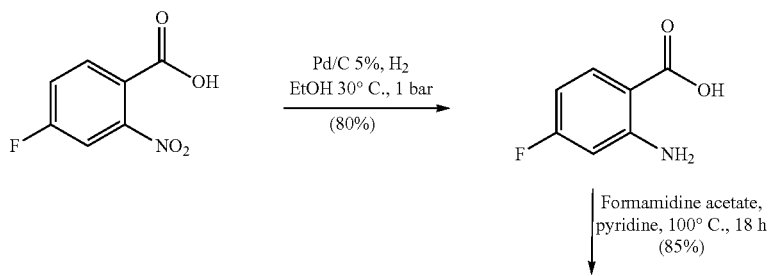

-continued
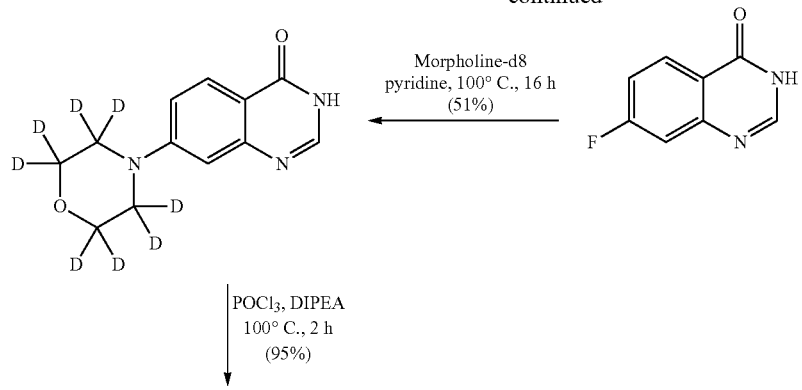
Examples 268 and 278
[4-Fluoro-3-(5-fluoro-7-morpholin-4-ylquinazolin-4-yl)phenyl]-(3-methylpyrazin-2-yl)methanol (268), [2-chloro-4-fluoro-5-(5-fluoro-7-morpholin-4-ylquinazolin-4-yl)phenyl]-(6-methoxypyridazin-3-yl)methanol (278)
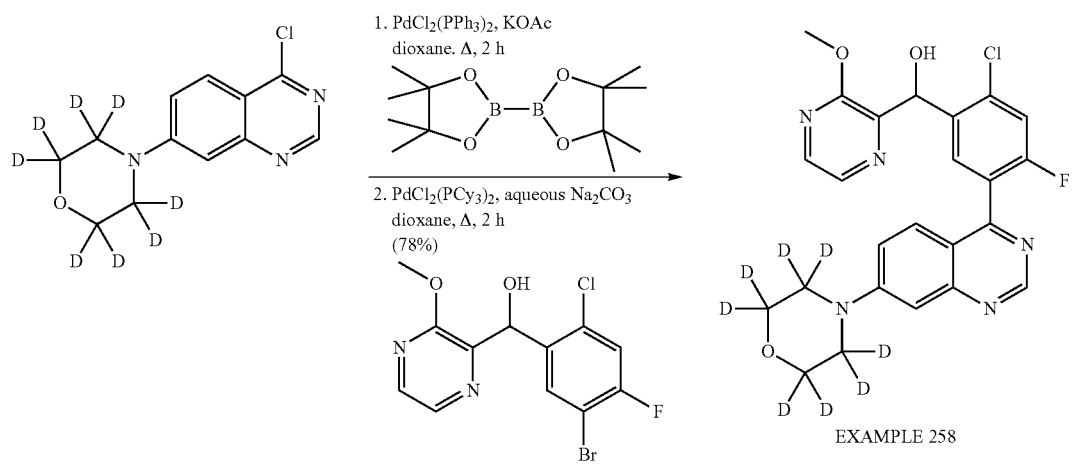
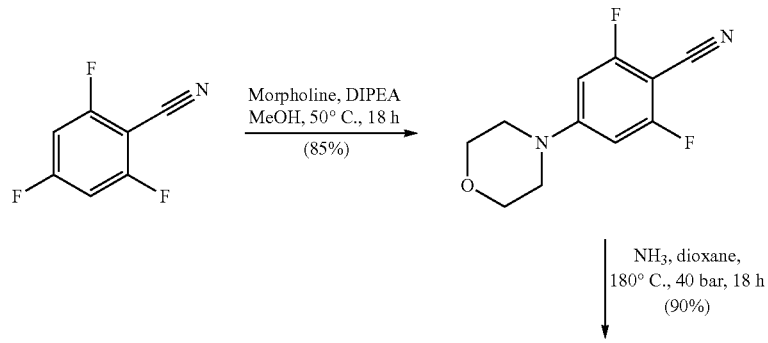

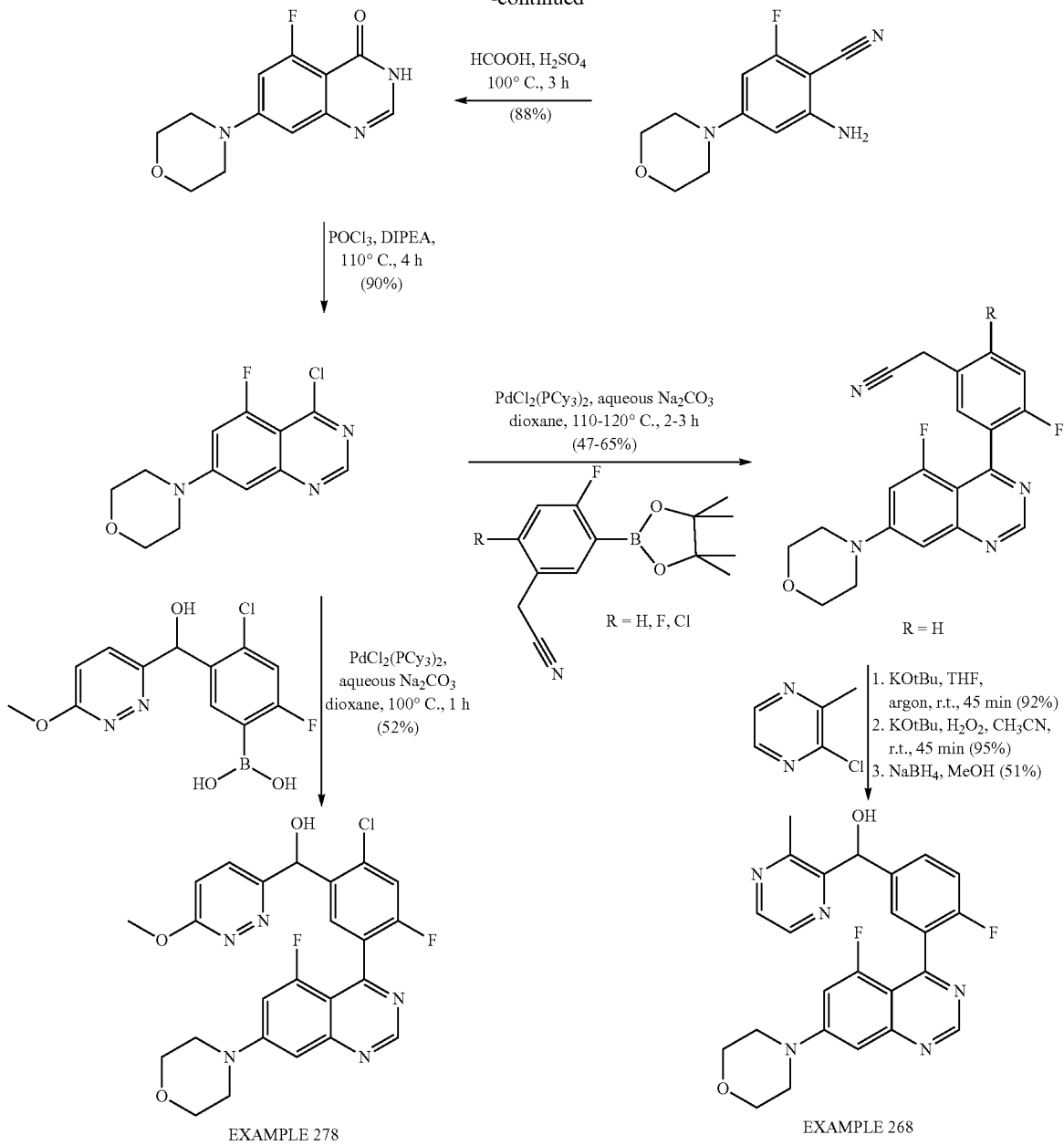
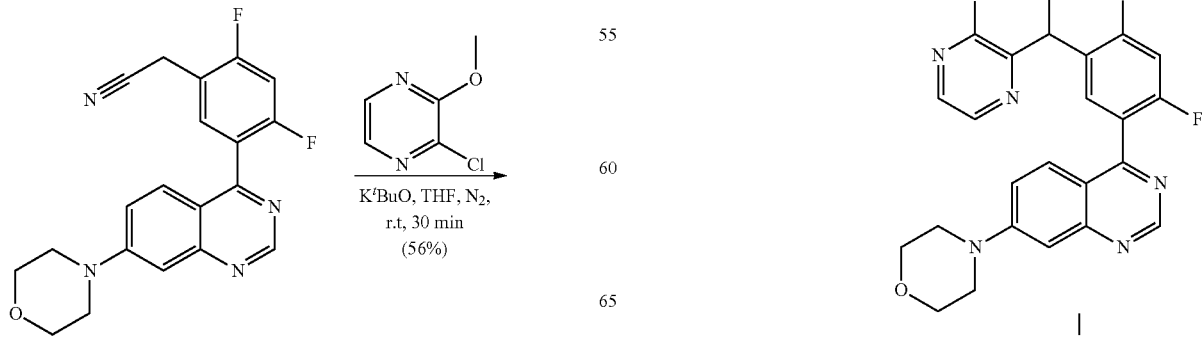
Example 319
2-[2,4-Difluoro-5-(7-morpholin-4-ylquinazolin-4-yl)phenyl]-2-(3-methoxypyrazin-2-yl)acetamide (319)

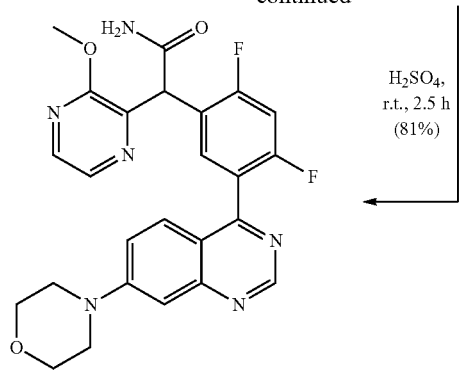

EXAMPLE 319

[2,4-Difluoro-5-(7-morpholin-4-ylquinazolin-4-yl)phenyl]acetonitrile (300 mg, 0.82 mmol) and 2-chloro-3-methoxypyrazine (297 mg, 1.97 mmol) were dissolved in tetrahydrofuran. Nitrogen was subsequently passed into the solution for a period of 10 min. Potassium tert-butoxide (193 mg, 1.72 mmol) was then added to the reaction solution, and the mixture was stirred at room temperature under an argon atmosphere for a period of 30 min. When the reaction was complete, the reaction mixture was neutralised using saturated $NH_4Cl$ solution, diluted with distilled water (30 ml) and extracted three times with dichloromethane (30 ml in each case). The organic phase was dried over $NaSO_4$, filtered off with suction and evaporated to dryness in vacuo. The residue was purified by means of flash column chromatography (gradient: dichloromethane/0-5% by vol. of ethanol, CombiFlash Rf 200, 40 g silica column, λ=220 nm). The suitable product fractions were combined, and solvents were removed in a rotary evaporator, giving [2,4-difluoro-5-(7-morpholin-4-ylquinazolin-4-yl)phenyl]-(3-methoxypyrazin-2-yl)acetonitrile (218 mg, 0.46 mmol; MS: 475.2 [M+H$^+$], 56% yield) as solid.

[2,4-Difluoro-5-(7-morpholin-4-ylquinazolin-4-yl)phenyl]-(3-methoxypyrazin-2-yl)acetonitrile (218 mg, 0.46 mmol) was initially introduced in the reaction flask and subsequently dissolved with $H_2SO_4$ (95-98%, 3.53 ml, 64 mmol). The reaction solution was stirred at room temperature for 2.5 h. When the reaction was complete, ice (80 g) was added to the reaction solution. The mixture was subsequently carefully neutralised using NaOH solution (32%, 10.6 ml). The suspension obtained was diluted with distilled water (50 ml) and extracted three times with dichloromethane (100 ml in each case). The organic phase was dried over over a $SO_4$, filtered off with suction and evaporated to dryness in vacuo. The residue was purified by means of flash column chromatography (gradient: dichloromethane/0-12% by vol. of ethanol, CombiFlash Rf 200, 40 g silica column, λ=220 nm). The suitable product fractions were combined, and solvents were removed in a rotary evaporator, giving 2-[2,4-difluoro-5-(7-morpholin-4-ylquinazolin-4-yl)phenyl]-2-(3-methoxypyrazin-2-yl)acetamide (182 mg, 0.37 mmol, MS: 493.4 [M+H$^+$], 81% yield) as solid.

Compounds which were prepared corresponding to EXAMPLES 225, 237, 258, 268, 278 and 319 and analogously to the synthesis sequences of EXAMPLES 1, 2, 37, 137, 121, 217 can be found in Table 8 below:

| No. | Structural formula | Name | IC$_{50}$ DNA-PK | IC$_{50}$ pDNA-PK | K$_i$ [Kv1.11 hERG] |
|---|---|---|---|---|---|
| 225 | OH, Cl, D, D, F, N, O, N, H (structure) MS: 484.3/486.3 (M + H$^+$) (Cl isotopy, rel. peak intensity ratio [%] 100:37) | [2-Chloro-5-(5,6-dideuterio-7-morpholinoquinazolin-4-yl)-4-fluorophenyl]-(6-methoxypyridazin-3-yl)methanol | B | A | A |

1H NMR (500 MHz, DMSO-d6) ppm = 9.12 (s, 1H), 7.91 (d, J = 7.8, 1H), 7.72-7.64 (m, 2H), 7.27-7.17 (m, 2H), 6.61 (d, J = 5.0, 1H), 6.23 (d, J = 5.0, 1H), 4.00 (s, 3H), 3.81-3.72 (m, 4H), 3.49-3.36 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 226 | | [3-(5,6-Dideuterio-7-morpholino-quinazolin-4-yl)-4-fluorophenyl]-(3-methylpyrazin-2-yl)-methanol | B | A | A |

MS: 434.4/436.4 (M + H⁺) (Cl isotopy, rel. peak intensity ratio [%] 100:40)

1H NMR (500 MHz, DMSO-d6) ppm = 9.09 (s, 1H), 8.43 (s, 2H), 7.64-7.55 (m, 2H), 7.42-7.34 (m, 1H), 7.19 (s, 1H), 6.34-6.20 (m, 1H), 6.08 (s, 1H), 3.86-3.68 (m, 4H), 3.50-3.36 (m, 4H), 2.55 (s, 3H).

| 227 | | [2-Chloro-4-fluoro-5-(7-morpholin-4-yl-pyrido[3,2-d]-pyrimidin-4-yl)-phenyl]-(6-methoxy-pyridazin-3-yl)-methanol (Ena 1) | B | B | A |

MS: 483.2/485.1 (M + H⁺) (Cl isotopy, rel. peak intensity ratio [%] 100:33); R$_t$ 8.37 min (HPLC, Chiralpak AD-H, n-heptane/90% by vol. of 2-propanol)

see racemate

| 228 | | [2-Chloro-4-fluoro-5-(7-morpholin-4-yl-pyrido[3,2-d]-pyrimidin-4-yl)-phenyl]-(6-methoxy-pyridazin-3-yl)-methanol (Ena 2) | D | D | A |

MS: 483.2/485.1 (M + H⁺) (Cl isotopy, rel. peak intensity ratio [%] 100:33); R$_t$ 12.45 min (HPLC, Chiralpak AD-H, n-heptane/90% by vol. of 2-propanol)

see racemate

| No. | Structural formula | Name | IC₅₀ DNA-PK | IC₅₀ pDNA-PK | $K_i$ [Kv1.11 hERG] |
|---|---|---|---|---|---|
| 229 | | 2-[2-Chloro-4-fluoro-5-(7-morpholin-4-yl-quinazolin-4-yl)-phenyl]-2-(3-methoxypyrazin-2-yl)-N-methyl-acetamide | C | B | A |

MS: 523.3/525.2 (M + H⁺) (Cl isotopy, rel. peak intensity ratio [%] 100:40)

1H NMR (500 MHz, DMSO-d6) ppm = 9.09 (s, 1H), 8.26 (q, J = 4.5, 1H), 8.13 (d, J = 2.8, 1H), 8.11 (d, J = 2.8, 1H), 7.73 (d, J = 9.6, 1H), 7.59 (dd, J = 9.4, 2.6, 1H), 7.56 (dd, J = 9.5, 2.3, 1H), 7.47 (d, J = 7.7, 1H), 7.20 (d, J = 2.2, 1H), 5.66 (s, 1H), 3.94 (s, 3H), 3.80-3.71 (m, 4H), 3.48-3.42 (m, 4H), 2.61 (d, J = 4.6, 3H).

| No. | Structural formula | Name | IC₅₀ DNA-PK | IC₅₀ pDNA-PK | $K_i$ [Kv1.11 hERG] |
|---|---|---|---|---|---|
| 230 | | 2-(3-Chloro-pyridin-2-yl)-2-[4-fluoro-3-(7-morpholin-4-yl-quinazolin-4-yl)-phenyl]-N-methyl-acetamide | C | C | B* |

MS: 492.3/494.2 (M + H⁺) (Cl isotopy, rel. peak intensity ratio [%] 100:40)

1H NMR (500 MHz, DMSO-d6) ppm = 9.09 (s, 1H), 8.51 (dd, J = 4.7, 1.4, 1H), 8.03 (q, J = 4.4, 1H), 7.92 (dd, J = 8.1, 1.5, 1H), 7.63 (dd, J = 9.4, 2.7, 1H), 7.58-7.54 (m, 3H), 7.41-7.33 (m, 2H), 7.20 (d, J = 2.4, 1H), 5.52 (s, 1H), 3.85-3.71 (m, 4H), 3.51-3.40 (m, 4H), 2.60 (d, J = 4.6, 3H).

| No. | Structural formula | Name | IC₅₀ DNA-PK | IC₅₀ pDNA-PK | $K_i$ [Kv1.11 hERG] |
|---|---|---|---|---|---|
| 231 | | [2-Chloro-4-fluoro-5-(7-morpholin-4-yl-pyrido[3,2-d]-pyrimidin-4-yl)-phenyl]-(3-methoxy-pyrazin-2-yl)-methanol (Ena 2) | C | B | A |

MS: 483.1/485.1 (M + H⁺) (Cl isotopy, rel. peak intensity ratio [%] 100:38); R, 8.72 min (SFC, Chiralpak AD-H, CO₂/40% by vol. of methanol)

see racemate

| No. | Structural formula | Name | IC$_{50}$ DNA-PK | IC$_{50}$ pDNA-PK | K$_i$ [Kv1.11 hERG] |
|---|---|---|---|---|---|
| 232 | | [2-Chloro-4-fluoro-5-(7-morpholin-4-yl-pyrido[3,2-d]-pyrimidin-4-yl)-phenyl]-(3-methoxy-pyrazin-2-yl)-methanol (Ena 1) | C | D | A |
| | MS: 483.1/485.1 (M + H$^+$) (Cl isotopy, rel. peak intensity ratio [%] 100:38); R$_t$ 7.27 min (SFC, Chiralpak AD-H, CO$_2$/40% by vol. of methanol) | | see racemate | | |
| 233 | | (S)-[4-Fluoro-3-(7-morpholin-4-yl-pyrido[3,2-d]-pyrimidin-4-yl)-phenyl]-(3-methyl-pyrazin-2-yl)-methanol | C | D | A |
| | MS: 433.1 (M + H$^+$); R$_t$ 4.40 min (SFC, Chiralcel OD-H, CO$_2$/40% by vol. of 2-propanol, 0.5% by vol. of diethylamine) | | see racemate | | |
| 234 | | (R)-[4-Fluoro-3-(7-morpholin-4-yl-pyrido[3,2-d]-pyrimidin-4-yl)-phenyl]-(3-methyl-pyrazin-2-yl)-methanol | A | A | A |
| | MS: 433.1 (M + H$^+$); R$_t$ 3.01 min (SFC, Chiralcel OD-H, CO$_2$/40% by vol. of 2-propanol, 0.5% by vol. of diethylamine) | | see racemate | | |

| No. | Structural formula | Name | IC₅₀ DNA-PK | IC₅₀ pDNA-PK | K_i [Kv1.11 hERG] |
|---|---|---|---|---|---|
| 235 | | 4-(4-Chloro-2-fluoro-5-imidazo[1,2-b]-pyridazin-6-ylmethyl-phenyl)-7-morpholin-4-ylquinazoline | A | A | A* |

MS: 475.1/477.1 (M + H⁺) (Cl isotopy, rel. peak intensity ratio [%] 100:35)

1H NMR (500 MHz, DMSO-d6) ppm = 9.10 (s, 1H), 8.22 (s, 1H), 8.07 (d, J = 9.4, 1H), 7.78-7.74 (m, 2H), 7.74-7.71 (m, 1H), 7.60 (dd, J = 9.4, 3.1, 1H), 7.54 (dd, J = 9.4, 2.5, 1H), 7.20 (d, J = 2.5, 1H), 7.16 (d, J = 9.4, 1H), 4.42 (s, 2H), 3.80-3.75 (m, 4H), 3.47-3.43 (m, 4H).

| 236 | | 2-[2-Chloro-4-fluoro-5-(7-morpholin-4-yl-quinazolin-4-yl)-phenyl]-2-imidazo-[1,2-b]pyridazin-6-yl-N-methylacetamide | D | C | A* |

MS: 532.2/534.2 (M + H⁺) (Cl isotopy, rel. peak intensity ratio [%] 100:35)

1H NMR (500 MHz, DMSO-d6) ppm = 9.11 (s, 1H), 8.56 (q, J = 4.5, 1H), 8.26 (s, 1H), 8.10 (d, J = 9.5, 1H), 7.81 (d, J = 9.5, 1H), 7.77 (d, J = 1.2, 1H), 7.74 (d, J = 7.6, 1H), 7.60 (dd, J = 9.4, 3.0, 1H), 7.55 (dd, J = 9.4, 2.5, 1H), 7.21 (d, J = 2.4, 1H), 7.12 (d, J = 9.5, 1H), 5.62 (s 1H), 3.81-3.75 (m, 4H), 3.48-3.40 (m, 4H), 2.65 (d, J = 4.6, 3H).

| 237 | | [4-Fluoro-3-(7-morpholin-4-yl-pyrido[3,2-d]-pyrimidin-4-yl)-phenyl]-(3-methyl-pyrazin-2-yl)-methanol | A | A | C |

MS: 433.3 (M + H⁺)

1H NMR (500 MHz, DMSO-d6) ppm = 9.18 (s, 1H), 9.02 (d, J = 2.9, 1H), 8.47-8.39 (m, 2H), 7.64 (dd, J = 6.7, 2.2, 1H), 7.59-7.50 (m, 1H), 7.45 (d, J = 2.9, 1H), 7.31 (dd, J = 9.7, 8.6, 1H), 6.28 (d, J = 5.4, 1H), 6.06 (d, J = 5.4, 1H), 3.81-3.76 (m, 4H), 3.56-3.50 (m, 4H), 2.55 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 238 | 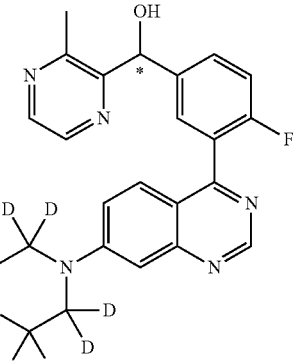 MS: 440.4 (M + H$^+$); R$_t$ 10.58 min (SFC, Chiralpak AD-H, CO$_2$/30% by vol. of 2-propanol, 0.5% by vol. of diethylamine) | [4-Fluoro-3-[7-(2,2,3,3,5,5,6,6-octadeuteriomorpholin-4-yl)quinazolin-4-yl]phenyl]-(3-methyl-pyrazin-2-yl)-methanol (Ena 2) S. Racemat | A | A | B |
| 239 | 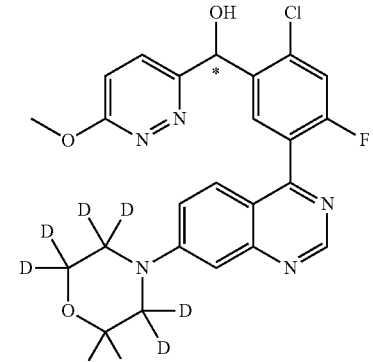 MS: 490.3/492.2 (M + H$^+$) (Cl isotopy, rel. peak intensity ratio [%] 100:38); R$_t$ 5.20 min (SFC, Chiralpak AD-H, CO$_2$/40% by vol. of methanol, 0.5% by vol. of diethylamine) | [2-Chloro-4-fluoro-5-[7-(2,2,3,3,5,5,6,6-octadeuteriomorpholin-4-yl)quinazolin-4-yl]phenyl]-(6-methoxypyridazin-3-yl)methanol (Ena 2) see racemate | C | D | B |
| 240 | 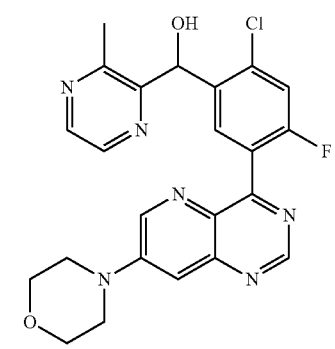 MS: 467.3/469.2 (M + H$^+$) (Cl isotopy, rel. peak intensity ratio [%] 100:38) | [2-Chloro-4-fluoro-5-(7-morpholin-4-yl-pyrido[3,2-d]-pyrimidin-4-yl)-phenyl]-(3-methyl-pyrazin-2-yl)-methanol 1H NMR (500 MHz, DMSO-d6) ppm = 9.23 (s, 1H), 9.06 (d, J = 2.9, 1H), 8.43 (d, J = 2.5, 1H), 8.33 (d, J = 2.5, 1H), 8.05 (d, J = 7.5, 1H), 7.54 (d, J = 9.2, 1H), 7.48 (d, J = 2.9, 1H), 6.65-6.27 (m, 1H), 6.25-6.22 (m, 1H), 3.82-3.77 (m, 4H), 3.58-3.52 (m, 4H), 2.74 (s, 3H). | C | B | A |

| No. | Structural formula | Name | IC$_{50}$ DNA-PK | IC$_{50}$ pDNA-PK | K$_i$ [Kv1.11 hERG] |
|---|---|---|---|---|---|
| 241 | 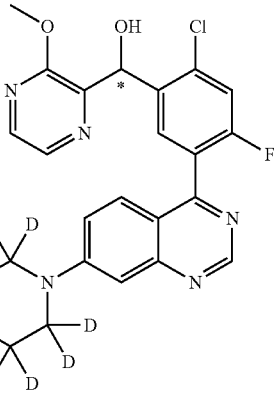 MS: 490.2/492.2 (M + H$^+$) (Cl isotopy, rel. peak intensity ratio [%] 100:38); R$_t$ 6.47 min (SFC, Chiralpak AD-H, CO$_2$/40% by vol. of methanol, 0.5% by vol. of diethylamine) | [2-Chloro-4-fluoro-5-[7-(2,2,3,3,5,5,6,6-octadeuteriomorpholin-4-yl)quinazolin-4-yl]phenyl]-(3-methoxypyrazin-2-yl)methanol (Ena 2) | A | A see racemate | C |
| 242 | 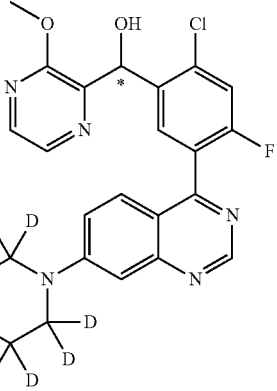 MS: 490.2/492.2 (M + H$^+$) (Cl isotopy, rel. peak intensity ratio [%] 100:35); R$_t$ 2.91 min (SFC, Chiralpak AD-H, CO$_2$/40% by vol. of methanol, 0.5% by vol. of diethylamine) | [2-Chloro-4-fluoro-5-[7-(2,2,3,3,5,5,6,6-octadeuteriomorpholin-4-yl)quinazolin-4-yl]phenyl]-(3-methoxypyrazin-2-yl)methanol (Ena 1) | A | A see racemate | B |
| 243 | 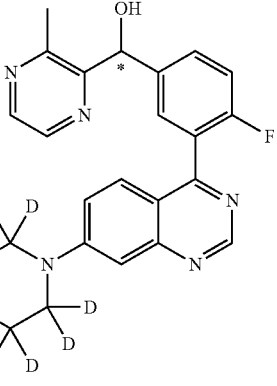 MS: 440.4 (M + H$^+$); R$_t$ 8.16 min (SFC, Chiralpak AD-H, CO$_2$/30% by vol. of 2-propanol, 0.5% by vol. of diethylamine) | (S)-[4-Fluoro-3-[7-(2,2,3,3,5,5,6,6-octadeuteriomorpholin-4-yl)quinazolin-4-yl]phenyl]-(3-methylpyrazin-2-yl)methanol (Ena 1) | C | B see racemate | B |

-continued

| No. | Structural formula | Name | IC$_{50}$ DNA-PK | IC$_{50}$ pDNA-PK | K$_i$ [Kv1.11 hERG] |
| --- | --- | --- | --- | --- | --- |
| 244 | | [2-Chloro-4-fluoro-5-[7-(2,2,3,3,5,5,6,6-octadeuteriomorpholin-4-yl)quinazolin-4-yl]phenyl]-(6-methoxypyridazin-3-yl)methanol (Ena 1) | A | A | B |
| | MS: 490.1/492.1 (M + H$^+$) (Cl isotopy, rel. peak intensity ratio [%] 100:33); R$_t$ 3.39 min (SFC, Chiralpak AD-H, CO$_2$/40% by vol. of methanol, 0.5% by vol. of diethylamine) | | see racemate | | |
| 245 | | [4-Fluoro-3-(6-morpholin-4-yl-thieno[3,2-d]-pyrimidin-4-yl)-phenyl]-(3-methyl-pyrazin-2-yl)-methanol (Ena 1) | A | A | A* |
| | MS: 438.1 (M + H$^+$); R$_t$ 4.70 min (SFC, Chiralcel OD-H, CO$_2$/30% by vol. of 2-propanol, 0.5% by vol. of diethylamine) | | see racemate | | |
| 246 | | [4-Fluoro-3-(6-morpholin-4-yl-thieno[3,2-d]-pyrimidin-4-yl)-phenyl]-(3-methyl-pyrazin-2-yl)-methanol (Ena 2) | B | B | A* |
| | MS: 438.1 (M + H$^+$); R$_t$ 7.04 min (SFC, Chiralcel OD-H, CO$_2$/30% by vol. of 2-propanol, 0.5% by vol. of diethylamine) | | see racemate | | |

| No. | Structural formula | Name | IC$_{50}$ DNA-PK | IC$_{50}$ pDNA-PK | K$_i$ [Kv1.11 hERG] |
|---|---|---|---|---|---|
| 247 | | [2-Chloro-4-fluoro-5-(7-morpholin-4-yl-pyrido[3,2-d]-pyrimidin-4-yl)-phenyl]-(3-methoxy-pyrazin-2-yl)-methanol | C | C | B |

MS: 483.1/485.1 (M + H$^+$) (Cl isotopy, rel. peak intensity ratio [%] 100:35)

1H NMR (500 MHz, DMSO-d6) ppm = 9.22 (s, 1H), 9.04 (d, J = 2.9, 1H), 8.16 (d, J = 2.7, 1H), 8.08 (d, J = 2.7, 1H), 8.02 (d, J = 7.6, 1H), 7.51 (d, J = 9.3, 1H), 7.47 (d, J = 2.8, 1H), 6.32-6.28 (m, 2H), 4.00 (s, 3H), 3.82-3.77 (m, 4H), 3.57-3.52 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 248 | | (R)-[4-Fluoro-3-(5-fluoro-7-morpholin-4-ylquinazolin-4-yl)-phenyl]-(3-methyl-pyrazin-2-yl)-methanol | A | A | A |

MS: 450.1 (M + H$^+$); R$_t$ 7.18 min (SFC, Chiralcel OD-H, CO$_2$/25% by vol. of 2-propanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 249 | | [2-Chloro-4-fluoro-5-(5-fluoro-7-morpholin-4-yl-quinazolin-4-yl)-phenyl]-(3-methoxy-pyrazin-2-yl)-methanol (Ena 2) | A | A | A* |

MS: 500.2/502.1 (M + H$^+$) (Cl isotopy, rel. peak intensity ratio [%] 100:35); R$_t$ 7.94 min (SFC, Chiralpak AD-H, CO$_2$/40% by vol. of methanol)

see racemate

-continued

| No. | Structural formula | Name | IC$_{50}$ DNA-PK | IC$_{50}$ pDNA-PK | K$_i$ [Kv1.11 hERG] |
|---|---|---|---|---|---|
| 250 | | [2-Chloro-4-fluoro-5-(5-fluoro-7-morpholin-4-yl-quinazolin-4-yl)-phenyl]-(3-methoxy-pyrazin-2-yl)-methanol (Ena 1) | A | A | A* |
| | MS: 500.2/502.1 (M + H$^+$) (Cl isotopy, rel. peak intensity ratio [%] 100:35); R$_t$ 3.46 min (SFC, Chiralpak AD-H, CO$_2$/40% by vol. of methanol) | | see racemate | | |
| 251 | | (S)-[4-fluoro-3-(5-fluoro-7-morpholin-4-ylquinazolin-4-yl)-phenyl]-(3-methyl-pyrazin-2-yl)-methanol | B | B | A* |
| | MS: 450.1 (M + H$^+$); R$_t$ 8.84 min (SFC, Chiralcel OD-H, CO$_2$/25% by vol. of 2-propanol, 0.5% by vol. of diethylamine) | | see racemate | | |
| 252 | | [4-Fluoro-3-(5-fluoro-7-morpholin-4-yl-quinazolin-4-yl)-phenyl]-(3-methoxy-pyrazin-2-yl)-methanol (Ena 2) | A | A | A* |
| | MS: 466.2 (M + H$^+$); R$_t$ 10.46 min (SFC, Chiralcel OD-H, CO$_2$/25% by vol. of 2-propanol, 0.5% by vol. of diethylamine) | | see racemate | | |

| No. | Structural formula | Name | IC$_{50}$ DNA-PK | IC$_{50}$ pDNA-PK | K$_i$ [Kv1.11 hERG] |
|---|---|---|---|---|---|
| 253 | | [4-Fluoro-3-(5-fluoro-7-morpholin-4-yl-quinazolin-4-yl)-phenyl]-(3-methoxy-pyrazin-2-yl)-methanol (Ena 1) | C | C | A* |

MS: 466.2 (M + H$^+$); R$_t$ 7.37 min (SFC, Chiralcel OD-H, CO$_2$/25% by vol. of 2-propanol, 0.5% by vol. of diethylamine)

see racemate

| 254 | | 2-[2-Chloro-4-fluoro-5-(7-morpholin-4-yl-quinazolin-4-yl)-phenyl]-N-methyl-2-(3-methyl-pyrazin-2-yl)acetamide | C | D | A* |

MS: 507.2/509.2 (M + H$^+$) (Cl isotopy, rel. peak intensity ratio [%] 100:35)

1H NMR (500 MHz, DMSO-d6) ppm = 9.08 (s, 1H), 8.41 (d, J = 2.6, 1H), 8.39 (d, J = 2.5, 1H), 8.30 (q, J = 4.5, 1H), 7.74 (d, J = 9.5, 1H), 7.59 (dd, J = 9.4, 2.6, 1H), 7.55 (dd, J = 9.5, 2.4, 1H), 7.47 (d, J = 7.7, 1H), 7.20 (d, J = 2.3, 1H), 5.66 (s, 1H), 3.78 (t, J = 5.8, 3.9, 4H), 3.46 (t, J = 4.9, 4H), 2.63 (d, J = 4.5, 3H), 2.52 (s, 3H).

| 255 | | [4-Fluoro-3-(5-fluoro-7-morpholin-4-yl-quinazolin-4-yl)-phenyl]-(6-methoxy-pyridazin-3-yl)-methanol (Ena 2) | C | A | A* |

MS: 466.2 (M + H$^+$); R$_t$ 10.43 min (SFC, Chiralpak AS-H, CO$_2$/15% by vol. of methanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 256 | MS: 466.2 (M + H$^+$); R$_t$ 7.26 min (SFC, Chiralpak AS-H, CO$_2$/15% by vol. of methanol, 0.5% by vol. of diethylamine) | [4-Fluoro-3-(5-fluoro-7-morpholin-4-yl-quinazolin-4-yl)-phenyl]-(6-methoxy-pyridazin-3-yl)-methanol (Ena 1) | A | A | A* |
| | | see racemate | | | |
| 257 | MS: 483.2/485.1 (M + H$^+$) (Cl isotopy, rel. peak intensity ratio [%] 100:33) | [2-Chloro-4-fluoro-5-(7-morpholin-4-yl-pyrido[3,2-d}-pyrimidin-4-yl)-phenyl]-(6-methoxy-pyridazin-3-yl)-methanol | B | B | A |
| | | 1H NMR (500 MHz, DMSO-d6) ppm = 9.21 (s, 1H), 9.04 (d, J = 2.9, 1H), 7.96 (d, J = 7.5, 1H), 7.68 (d, J = 9.2, 1H), 7.58 (d, J = 9.3, 1H), 7.46 (d, J = 2.9, 1H), 7.22 (d, J = 9.1, 1H), 6.60 (d, J = 4.9, 1H), 6.23 (d, J = 4.9, 1H), 4.00 (s 3H), 3.84-3.76 (m, 4H), 3.57-3.51 (m, 4H). | | | |
| 258 | MS: 490.1/492.3 (M + H$^+$) (Cl isotopy, rel. peak intensity ratio [%] 100:36) | [2-Chloro-4-fluoro-5-[7-(2,2,3,3,5,5,6,6-octadeuterio-morpholin-4-yl)-quinazolin-4-yl-]phenyl]-(3-methoxy-pyrazin-2-yl)-methanol | B | A | A* |
| | | 1H NMR (500 MHz, DMSO-d6) ppm = 9.13 (s, 1H), 8.17 (d, J = 2.7, 1H), 8.11 (d, J = 2.7, 1H), 7.97 (d, J = 7.8, 1H), 7.67-7.58 (m, 2H), 7.56 (dd, J = 9.4, 2.6, 1H), 7.21 (d, J = 2.5, 1H), 6.34 (d, J = 5.9, 1H), 6.31 (d, J = 5.9, 1H), 4.00 (s, 3H). | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 259 | MS: 440.4 (M + H$^+$) | [4-Fluoro-3-[7-(2,2,3,3,5,5,6,6-octadeuteriomorpholin-4-yl)quinazolin-4-yl]phenyl]-(3-methyl-pyrazin-2-yl)-methanol | A | A | A* |
| | 1H NMR (500 MHz, DMSO-d6) ppm = 9.09 (s, 1H), 8.44 (s, 2H), 7.63-7.55 (m, 2H), 7.53 (s, 2H), 7.42-7.34 (m, 1H), 7.19 (s, 1H), 6.30 (d, J = 5.3, 1H), 6.08 (d, J = 4.6, 1H), 2.55 (s, 3H). | | | | |
| 260 | MS: 466.2 (M + H$^+$) | [4-Fluoro-3-(5-fluoro-7-morpholin-4-yl-quinazolin-4-yl)-phenyl]-(6-methoxy-pyridazin-3-yl)-methanol | A | A | A |
| | 1H NMR (500 MHz, DMSO-d6) ppm = 9.09 (d, J = 6.1, 1H), 7.69 (d, J = 9.2, 1H), 7.66-7.48 (m, 2H), 7.37 (dt, J = 15.3, 2.7, 1H), 7.29 (ddd, J = 9.8, 8.5, 3.1, 1H), 7.21 (t, J = 9.2, 1H), 7.08 (d, J = 2.4, 1H), 6.57-6.43 (m, 1H), 6.00 (d, J = 4.4, 1H), 4.00 (d, J = 2.9, 3H), 3.81-3.69 (m, 4H), 3.53-3.40 (m, 4H). | | | | |
| 261 | MS: 527.2/529.2 (M + H$^+$) (Cl isotopy, rel. peak intensity ratio [%] 100:35) | 2-[2-Chloro-4-fluoro-5-(5-fluoro-7-morpholin-4-yl-quinazolin-4-yl)-phenyl]-2-(3-methoxy-pyrazin-2-yl)acetamide | C | B | B |
| | 1H NMR (400 MHz, DMSO-d6) ppm = 9.07 (s, 1H), 8.10 (d, J = 2.8, 1H), 8.07 (d, J = 2.8, 1H), 7.56 (d, J = 7.7, 1H), 7.51 (d, J = 9.7, 1H), 7.41-6.85 (m, 5H), 3.96 (s, 3H), 3.82-3.74 (m, 4H), 3.52-3.45 (m, 4H). | | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 262 | 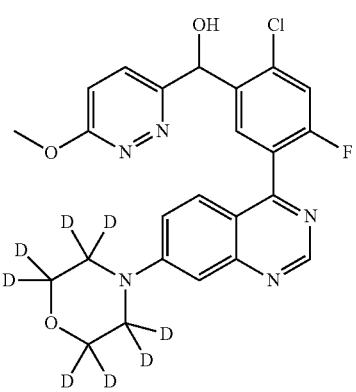 [SMILES: [2H]C1([2H])OC([2H])([2H])C([2H])([2H])N(c2ccc3c(-c4cc(C(O)c5ccc(OC)nn5)c(Cl)cc4F)ncnc3c2)C1([2H])[2H]] MS: 490.2/492.2 (M + H⁺) (Cl isotopy, rel. peak intensity ratio [%] 100:36) | [2-Chloro-4-fluoro-5-[7-(2,2,3,3,5,5,6,6-octadeuteriomorpholin-4-yl)quinazolin-4-yl]phenyl]-(6-methoxypyridazin-3-yl)methanol  1H NMR (500 MHz, DMSO-d6) ppm = 9.12 (s, 1H), 7.91 (d, J = 7.8, 1H), 7.71-7.64 (m, 2H), 7.59 (dd, J = 9.4, 3.4, 1H), 7.54 (dd, J = 9.4, 2.6, 1H), 7.23-7.19 (m, 2H), 6.63 (d, J = 5.0, 1H), 6.23 (d, J = 5.0, 1H), 4.00 (s, 3H). | A | A | A* |
| 263 | 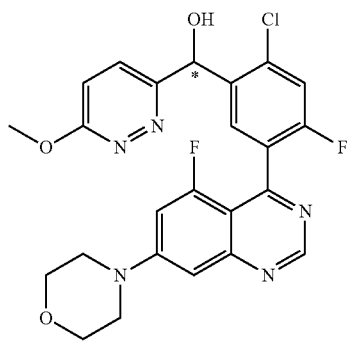 [SMILES: COc1ccc(C(O)c2cc(-c3ncnc4cc(N5CCOCC5)cc(F)c34)c(F)cc2Cl)nn1] MS: 500.1/502.1 (M + H⁺) (Cl isotopy, rel. peak intensity ratio [%] 100:30); R$_t$ 6.17 min (SFC, Chiralpak AD-H, CO$_2$/40% by vol. of methanol, 0.5% by vol. of diethylamine) | [2-Chloro-4-fluoro-5-(5-fluoro-7-morpholin-4-yl-quinazolin-4-yl)-phenyl]-(6-methoxy-pyridazin-3-yl)-methanol (Ena 2)  see racemate | C | D | A* |
| 264 | 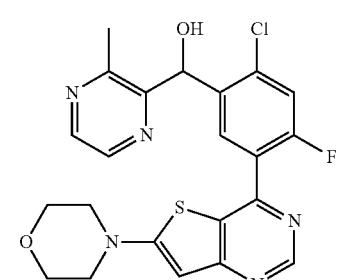 MS: 472.1/474.0 (M + H⁺) (Cl isotopy, rel. peak intensity ratio [%] 100:40) | [2-Chloro-4-fluoro-5-(6-morpholin-4-yl-thieno[3,2-d]-pyrimidin-4-yl)-phenyl]-(3-methyl-pyrazin-2-yl)-methanol  1H NMR (500 MHz, DMSO-d6) ppm = 8.93 (s, 1H), 8.43 (d, J = 2.5, 1H), 8.33 (d, J = 2.4, 1H), 8.11 (d, J = 7.9, 1H), 7.63 (d, J = 9.9, 1H), 6.56 (s, 1H), 6.47 (d, J = 6.0, 1H), 6.23 (d, J = 4.6, 1H), 3.79-3.71 (m, 4H), 3.48-3.39 (m, 4H), 2.73 (s, 3H). | A | A | A* |

-continued

| No. | Structural formula | Name | IC₅₀ DNA-PK | IC₅₀ pDNA-PK | $K_i$ [Kv1.11 hERG] |
|---|---|---|---|---|---|
| 265 | 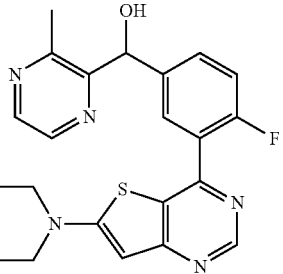<br>MS: 438.1 (M + H⁺) | [4-Fluoro-3-(6-morpholin-4-yl-thieno[3,2-d]-pyrimidin-4-yl)-phenyl]-(3-methyl-pyrazin-2-yl)-methanol | A | A | A* |
| | | 1H NMR (500 MHz, DMSO-d6) ppm = 8.88 (s, 1H), 8.46-8.42 (m, 2H), 7.67 (dd, J = 7.0, 2.3, 1H), 7.60-7.55 (m, 1H), 7.38 (dd, J = 10.3, 8.6, 1H), 6.52 (s, 1H), 6.32 (d, J = 5.4, 1H), 6.08-6.05 (m, 1H), 3.79-3.70 (m, 4H), 3.44-3.37 (m, 4H), 2.54 (s, 3H). | | | |
| 266 | 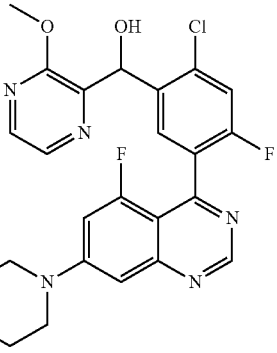<br>MS: 500.2/502.1 (M + H⁺) (Cl isotopy, rel. peak intensity ratio [%] 100:35) | [2-Chloro-4-fluoro-5-(5-fluoro-7-morpholin-4-yl-quinazolin-4-yl)-phenyl]-(3-methoxy-pyrazin-2-yl)-methanol | A | A | A* |
| | | 1H NMR (400 MHz, 90° C., DMSO-d6) ppm = 9.08 (s, 1H), 8.11 (d, J = 2.7, 1H), 8.07 (d, J = 2.7, 1H), 7.90 (d, J = 8.0, 1H), 7.39 (d, J = 9.7, 1H), 7.29 (dd, J = 15.2, 2.3, 1H), 7.07 (d, J = 2.3, 1H), 6.30 (s, 1H), 3.96 (s, 3H), 3.80-3.72 (m, 4H), 3.51-3.44 (m, 4H). | | | |
| 267 | 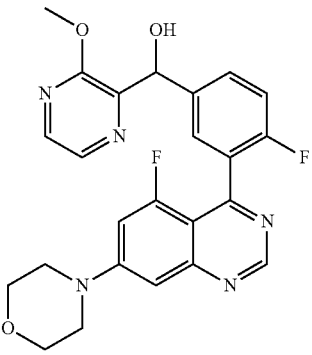<br>MS: 466.2 (M + H⁺) | [4-Fluoro-3-(5-fluoro-7-morpholin-4-yl-quinazolin-4-yl)-phenyl]-(3-methoxy-pyrazin-2-yl)-methanol | A | A | A* |
| | | 1H NMR (400 MHz, 90° C., DMSO-d6) ppm = 9.05 (s, 1H), 8.15 (d, J = 2.5, 1H), 8.11 (d, J = 2.5, 1H), 7.62-7.44 (m, 2H), 7.30-7.12 (m, 2H), 7.05 (d, J = 2.2, 1H), 6.09-5.95 (m, 2H), 3.91 (s, 3H), 3.81-3.70 (m, 4H), 3.52-3.41 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 268 | MS: 450.1 (M + H$^+$) | [4-Fluoro-3-(5-fluoro-7-morpholin-4-yl-quinazolin-4-yl)-phenyl]-(3-methyl-pyrazin-2-yl)-methanol | A | A | A* |

1H NMR (500 MHz, DMSO-d6) ppm = 9.08 (s, 1H), 8.45 (s, 2H), 7.63-7.56 (m, 1H), 7.56-7.46 (m, 1H), 7.46-7.34 (m, 1H), 7.34-7.22 (m, 1H), 7.08 (s, 1H), 6.36-6.27 (m, 1H), 6.06 (d, J = 5.4, 1H), 3.81-3.73 (m, 4H), 3.53-3.43 (m, 4H), 2.53 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 269 | MS: 499.1/501.1 (M + H$^+$) (Cl isotopy, rel. peak intensity ratio [%] 100:39) | 2-[2-Chloro-4-fluoro-5-(6-morpholin-4-yl-thieno[3,2-d]-pyrimidin-4-yl)-phenyl]-2-(3-methyl-pyrazin-2-yl)-acetamide | B | B | A* |

1H NMR (500 MHz, DMSO-d6) ppm = 8.87 (s, 1H), 8.43 (d, J = 2.6, 1H), 8.40 (d, J = 2.7, 1H), 7.82-7.78 (m, 1H), 7.74 (d, J = 10.0, 1H), 7.55 (d, J = 7.8, 1H), 7.41-7.36 (m, 1H), 6.53 (s, 1H), 5.63 (s, 1H), 3.79-3.73 (m, 4H), 3.43-3.38 (m, 4H), 2.51 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 270 | MS: 465.1 (M + H$^+$) | 2-[4-Fluoro-3-(6-morpholin-4-yl-thieno[3,2-d]-pyrimidin-4-yl)-phenyl]-2-(3-methyl-pyrazin-2-yl)-acetamide | B | C | A* |

1H NMR (500 MHz, DMSO-d6) ppm = 8.88 (s, 1H), 8.42-8.37 (m, 2H), 7.67 (dd, J = 7.1, 2.3, 1H), 7.61-7.55 (m, 2H), 7.41-7.34 (m, 1H), 7.25-7.19 (m, 1H), 6.53 (s, 1H), 5.40 (s, 1H), 3.79-3.71 (m, 4H), 3.44-3.39 (m, 4H), 2.53 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 271 | | [2-Chloro-4-fluoro-5-(5-fluoro-7-morpholin-4-yl-quinazolin-4-yl)-phenyl]-(6-methoxy-pyridazin-3-yl)-methanol (Ena 1) | A | A | A |

MS: 500.1/502.1 (M + H$^+$) (Cl isotopy, rel. peak intensity ratio [%] 100:32); R$_t$ 4.25 min (SFC, Chiralpak AD-H, CO$_2$/40% by vol. of methanol, 0.5% by vol. of diethylamine)

1H NMR (400 MHz, DMSO-d6/DMSO, 120° C.) ppm = 9.05 (s, 1H), 7.84 (d, J = 7.7 Hz, 1H), 7.60 (d, J = 9.0 Hz, 1H), 7.40 (d, J = 9.5 Hz, 1H), 7.23 (d, J = 14.5 Hz, 1H), 7.11 (d, J = 9.1 Hz, 1H), 7.06 (s, 1H), 6.24 (d, J = 4.7 Hz, 1H), 6.16 (d, J = 4.7 Hz, 1H), 4.02 (s, 3H), 3.80-3.72 (m, 4H), 3.51-3.43 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 272 | | 2-[2-Chloro-4-fluoro-5-(6-morpholin-4-yl-thieno[3,2-d]-pyrimidin-4-yl)-phenyl]-2-(6-methoxy-pyridazin-3-yl)acetamide | B | B | A* |

MS: 515.2/517.2 (M + H$^+$) (Cl isotopy, rel. peak intensity ratio [%] 100:41)

1H NMR (400 MHz, DMSO-d6) ppm = 8.89 (s, 1H), 7.94 (s, 1H), 7.81 (d, J = 7.7, 1H), 7.74 (d, J = 10.0, 1H), 7.47 (d, J = 9.2, 1H), 7.40 (s, 1H), 7.19 (d, J = 9.2, 1H), 6.53 (s, 1H), 5.65 (s, 1H), 4.00 (s, 3H), 3.79-3.71 (m, 4H), 3.45-3.39 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 278 | | [2-Chloro-4-fluoro-5-(5-fluoro-7-morpholin-4-yl-quinazolin-4-yl)-phenyl]-(6-methoxy-pyridazin-3-yl)-methanol | A | A | A* |

MS: 500.2/502.2 (M + H$^+$) (Cl isotopy, rel. peak intensity ratio [%] 100:35)

1H NMR (400 MHz, 120° C., DMSO-d6) ppm = 9.05 (s, 1H), 7.84 (d, J = 7.8, 1H), 7.60 (d, J = 9.1, 1H), 7.40 (d, J = 9.6, 1H), 7.23 (dd, J = 15.2, 2.5, 1H), 7.11 (d, J = 9.1, 1H), 7.06 (d, J = 2.5, 1H), 6.25 (d, J = 5.1, 1H), 6.16 (d, J = 5.1, 1H), 4.03 (s, 3H), 3.80-3.73 (m, 4H), 3.49-3.43 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 279 | MS: 458.2 (M + H$^+$) | [4-Fluoro-3-(7-morpholin-4-yl-quinazolin-4-yl)-phenyl]-[1,2,4]-triazolo[1,5-a]-pyrazin-8-ylmethanol | B | C | A* |
| | | 1H NMR (400 MHz, DMSO-d6) ppm = 9.10 (s, 1H), 9.03 (d, J = 4.5, 1H), 8.76 (s, 1H), 8.25 (d, J = 4.5, 1H), 7.84-7.76 (m, 2H), 7.59-7.51 (m, 2H), 7.39 (dd, J = 9.9, 8.5, 1H), 7.20 (d, J = 2.1, 1H), 6.48 (s, 1H), 3.82-3.75 (m, 4H), 3.51-3.43 (m, 4H). | | | |
| 280 | MS: 485.2 (M + H$^+$) | 2-[4-Fluoro-3-(7-morpholin-4-yl-quinazolin-4-yl)-phenyl]-2-[1,2,4]-triazolo[1,5-a]-pyrazin-8-yl-acetamide | C | D | A* |
| | | 1H NMR (500 MHz, DMSO-d6) ppm = 9.10 (s, 1H), 9.02 (d, J = 4.5, 1H), 8.74 (s, 1H), 8.21 (d, J = 4.5, 1H), 7.79-7.75 (m, 1H), 7.74-7.69 (m, 2H), 7.64 (dd, J = 9.4, 2.9, 1H), 7.56 (dd, J = 9.5, 2.5, 1H), 7.45-7.40 (m, 1H), 7.31-7.27 (m, 1H), 7.20 (d, J = 2.4, 1H), 5.89 (s, 1H), 3.81-3.74 (m, 4H), 3.49-3.41 (m, 4H). | | | |
| 282 | MS: 466.2 (M + H$^+$) DELETE | [4-Fluoro-3-(6-fluoro-7-morpholin-4-yl-quinazolin-4-yl)-phenyl]-(6-methoxy-pyridazin-3-yl)-methanol | D | D | A* |
| | | 1H NMR (500 MHz, DMSO-d6) ppm = 9.24 (s, 1H), 7.74-7.63 (m, 3H), 7.48-7.39 (m, 2H), 7.34 (dd, J = 13.6, 3.1, 1H), 7.21 (d, J = 9.2, 1H), 6.53 (d, J = 4.3, 1H), 6.03 (d, J = 4.4, 1H), 4.00 (s, 3H), 3.83-3.77 (m, 4H), 3.36-3.27 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 283 | MS: 450.2 (M + H$^+$) DELETE | [4-Fluoro-3-(6-fluoro-7-morpholin-4-yl-quinazolin-4-yl)-phenyl]-(3-methyl-pyrazin-2-yl)-methanol | C | D | A |
| | | 1H NMR (400 MHz, DMSO-d6) ppm = 9.23 (s, 1H), 8.46-8.41 (m, 2H), 7.66-7.58 (m, 2H), 7.49-7.31 (m, 3H), 6.32 (d, J = 5.5, 1H), 6.10 (d, J = 5.5, 1H), 3.84-3.78 (m, 4H), 3.36-3.27 (m, 4H), 2.57 (s, 3H). | | | |
| 284 | MS: 501.1 (M + H$^+$) | 2-[4-Fluoro-3-(7-morpholin-4-yl-quinazolin-4-yl)-phenyl]-2-thieno-[2,3-d]pyridazin-7-yl-acetamide | B | D | A* |
| | | 1H NMR (500 MHz, DMSO-d6) ppm = 9.59 (s, 1H), 9.09 (s, 1H), 8.24 (d, J = 5.3, 1H), 7.92 (s, 1H), 7.73-7.65 (m, 3H), 7.57 (dd, J = 9.4, 3.1, 1H), 7.50 (dd, J = 9.5, 2.5, 1H), 7.47-7.36 (m, 2H), 7.19 (d, J = 2.5, 1H), 5.72 (s, 1H), 3.84-3.73 (m, 4H), 3.46-3.41 (m, 4H), 9.09-9.09 (m, 0H). | | | |
| 285 | MS: 501.1 (M + H$^+$) | 2-[4-Fluoro-3-(7-morpholin-4-yl-quinazolin-4-yl)-phenyl]-2-thieno-[2,3-d]pyridazin-4-yl-acetamide | B | D | B |
| | | 1H NMR (500 MHz, DMSO-d6) ppm = 9.83-9.79 (m, 1H), 9.08 (s, 1H), 8.30 (d, J = 5.4, 1H), 7.81-7.75 (m, 2H), 7.75-7.68 (m, 2H), 7.56 (dd, J = 9.4, 3.1, 1H), 7.49 (dd, J = 9.4, 2.6, 1H), 7.40 (dd, J = 9.8, 8.4, 1H), 7.32 (s, 1H), 7.19 (d, J = 2.5, 1H), 5.90 (s, 1H), 3.81-3.74 (m, 4H), 3.47-3.40 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 286 | | (6-Chloro-3-methoxy-pyridazin-4-yl)-[4-fluoro-3-(7-morpholin-4-yl-quinazolin-4-yl)-phenyl]methanol (Ena 1) | C | C | A* |
| | MS: 482.1/484.2 (M + H⁺) (Cl isotopy, rel. peak intensity ratio [%] 100:36); R$_t$ 5.83 min (SFC, Chiralpak AS-H, CO$_2$/20% by vol. of methanol, 0.5% by vol. of diethylamine) | see racemate | | | |
| 288 | | 6-{[2-Chloro-4-fluoro-5-(7-morpholin-4-yl-quinazolin-4-yl)-phenyl]hydroxymethyl}-2-methyl-4,5-dihydro-2H-pyridazin-3-one | C | C | A* |
| | MS: 484.2/486.2 (M + H⁺) (Cl isotopy, rel. peak intensity ratio [%] 100:35) | 1H NMR (500 MHz, DMSO-d6) ppm = 9.12 (s, 1H), 7.84 (d, J = 7.8, 1H), 7.68 (d, J = 9.5, 1H), 7.57 (dd, J = 9.4, 2.8, 1H), 7.54 (dd, J = 9.5, 2.4, 1H), 7.21 (d, J = 2.3, 1H), 6.42 (s, 1H), 5.57 (s, 1H), 3.81-3.75 (m, 4H), 3.47-3.43 (m, 4H), 3.16 (s, 3H), 2.61-2.51 (m, 1H), 2.43-2.28 (m, 3H). | | | |
| 289 | | 2-[2-Chloro-4-fluoro-5-(7-morpholin-4-yl-quinazolin-4-yl)-phenyl]-2-(3-chloro-pyridin-2-yl)-acetamide | A | B | B |
| | MS: 512.2/514.2/516.2 (M + H⁺) (Cl$_2$ isotopy, rel. peak intensity ratio [%] 100:71:21) | 1H NMR (500 MHz, DMSO-d6) ppm = 9.08 (s, 1H), 8.44 (dd, J = 4.7, 1.5, 1H), 7.95 (dd, J = 8.1, 1.5, 1H), 7.76 (s, 1H), 7.72 (d, J = 9.6, 1H), 7.58 (dd, J = 9.4, 2.9, 1H), 7.54 (dd, J = 9.5, 2.5, 1H), 7.41 (d, J = 7.6, 1H), 7.35 (dd, J = 8.1, 4.7, 1H), 7.28 (s, 1H), 7.19 (d, J = 2.4, 1H), 5.81 (s, 1H), 3.80-3.75 (m, 4H), 3.48-3.42 (m, 4H). | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 290 | | 2-(4-Chlorothieno-[2,3-d]pyridazin-7-yl)-2-[4-fluoro-3-(7-morpholin-4-yl-quinazolin-4-yl)-phenyl]acetamide | B | C | D |

MS: 535.3/537.2 (M + H$^+$) (Cl isotopy, rel. peak intensity ratio [%] 100:41)

1H NMR (500 MHz, DMSO-d6) ppm = 9.09 (s, 1H), 8.41 (d, J = 5.4, 1H), 7.94 (s, 1H), 7.71-7.65 (m, 3H), 7.56 (dd, J = 9.4, 3.1, 1H), 7.51 (dd, J = 9.4, 2.5, 1H), 7.48-7.40 (m, 2H), 7.20 (d, J = 2.4, 1H), 5.75 (s, 1H), 3.82-3.73 (m, 4H), 3.48-3.40 (m, 4H).

| 291 | | 2-(7-Chlorothieno-[2,3-d]pyridazin-4-yl)-2-[4-fluoro-3-(7-morpholin-4-yl-quinazolin-4-yl)-phenyl]acetamide | B | C | D |

MS: 535.2/537.2 (M + H$^+$) (Cl isotopy, rel. peak intensity ratio [%] 100:41)

1H NMR (500 MHz, DMSO-d6) ppm = 9.09 (s, 1H), 8.43 (d, J = 5.4, 1H), 7.86 (d, J = 5.4, 1H), 7.77 (s, 1H), 7.74-7.67 (m, 2H), 7.56 (dd, J = 9.4, 3.1, 1H), 7.50 (dd, J = 9.5, 2.5, 1H), 7.44-7.35 (m, 2H), 7.19 (d, J = 2.4, 1H), 5.92 (s, 1H), 3.81-3.74 (m, 4H), 3.47-3.40 (m, 4H).

| 292 | | 6-{Carbamoyl-[4-fluoro-3-(7-morpholin-4-yl-quinazolin-4-yl)-phenyl]methyl}-pyrazine-2-carboxylic acid amide | C | D | A |

MS: 488.2 (M + H$^+$)

1H NMR (500 MHz, DMSO-d6) ppm = 9.12 (s, 1H), 9.06 (s, 1H), 8.90 (s, 1H), 8.08-8.01 (m, 1H), 7.99-7.93 (m, 1H), 7.85-7.77 (m, 2H), 7.77-7.71 (m, 1H), 7.59 (dd, J = 9.4, 3.6, 1H), 7.52 (dd, J = 9.5, 2.5, 1H), 7.46-7.39 (m, 1H), 7.38-7.32 (m, 1H), 7.20 (d, J = 2.5, 1H), 5.39 (s, 1H), 3.80-3.75 (m, 4H), 3.47-3.42 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 293 | | 2-[2-Chloro-4-fluoro-5-(7-morpholin-4-yl-quinazolin-4-yl)-phenyl]-2-pyridin-3-ylacetamide | B | C | A |
| | MS: 478.2/480.2 (M + H$^+$) (Cl isotopy, rel. peak intensity ratio [%] 100:30) | 1H NMR (500 MHz, DMSO-d6) ppm = 9.09 (s, 1H), 8.49 (s, 1H), 8.46 (d, J = 3.9, 1H), 7.94 (s, 1H), 7.74 (d, J = 9.5, 1H), 7.67 (d, J = 7.7, 1H), 7.66-7.63 (m, 1H), 7.56 (dd, J = 9.4, 3.2, 1H), 7.53 (dd, J = 9.5, 2.4, 1H), 7.37 (dd, J = 7.9, 4.8, 1H), 7.33 (s, 1H), 7.20 (d, J = 2.3, 1H), 5.41 (s, 1H), 3.81-3.74 (m, 4H), 3.49-3.42 (m, 4H). | | | |
| 294 | | 2-[2,4-Difluoro-5-(7-morpholin-4-yl-quinazolin-4-yl)-phenyl]-2-pyridin-3-ylacetamide | B | D | A |
| | MS: 462.3 (M + H$^+$) | 1H NMR (500 MHz, DMSO-d6) ppm = 9.08 (s, 1H), 8.53 (d, J = 2.3, 1H), 8.48 (dd, J = 4.8, 1.6, 1H), 7.89 (s, 1H), 7.72 (dt, J = 8.0, 2.0, 1H), 7.61 (t, J = 8.2, 1H), 7.59-7.48 (m, 3H), 7.38 (dd, J = 7.9, 4.7, 1H), 7.32 (s, 1H), 7.19 (d, J = 2.3, 1H), 5.31 (s, 1H), 3.82-3.73 (m, 4H), 3.47-3.42 (m, 4H). | | | |
| 295 | | 2-[4-Fluoro-3-(7-morpholin-4-yl-quinazolin-4-yl)-phenyl]-2-pyridin-3-ylacetamide | C | D | A |
| | MS: 444.2 (M + H$^+$) | 1H NMR (500 MHz, DMSO-d6) ppm = 9.09 (s, 1H), 8.55 (s, 1H), 8.47 (s, 1H), 7.82 (s, 1H), 7.79 (d, J = 8.0, 1H), 7.62-7.56 (m, 2H), 7.56-7.49 (m, 2H), 7.45-7.35 (m, 2H), 7.25 (s, 1H), 7.20 (d, J = 2.0, 1H), 5.12 (s, 1H), 3.80-3.74 (m, 4H), 3.47-3.41 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 296 | 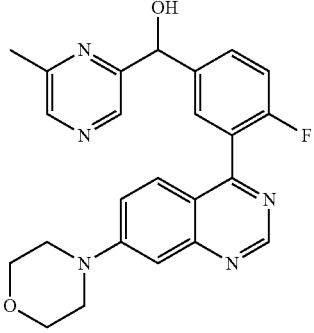 [SMILES: Cc1cncc(C(O)c2ccc(F)c(-c3ncnc4cc(N5CCOCC5)ccc34)c2)n1]<br>MS: 432.2 (M + H$^+$) | [4-Fluoro-3-(7-morpholin-4-yl-quinazolin-4-yl)-phenyl]-(6-methyl-pyrazin-2-yl)-methanol | C | C | A |

1H NMR (500 MHz, DMSO-d6) ppm = 9.10 (s, 1H), 8.66 (s, 1H), 8.43 (s, 1H), 7.68-7.63 (m, 2H), 7.54-7.49 (m, 2H), 7.42-7.35 (m, 1H), 7.21-7.18 (m, 1H), 6.40 (d, J = 4.3, 1H), 5.87 (d, J = 4.3, 1H), 3.81-3.74 (m, 4H), 3.47-3.41 (m, 4H), 2.46 (s, 3H).

| 297 | 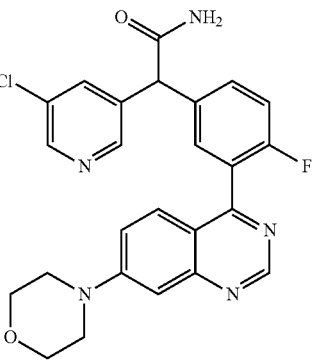<br>MS: 478.3/480.2 (M + H$^+$) (Cl isotopy, rel. peak intensity ratio [%] 100:38) | 2-(5-Chloro-pyridin-3-yl)-2-[4-fluoro-3-(7-morpholin-4-yl-quinazolin-4-yl)-phenyl]acetamide | C | D | C |

1H NMR (500 MHz, DMSO-d6) ppm = 9.10 (s, 1H), 8.54 (d, J = 2.4, 1H), 8.52 (d, J = 1.9, 1H), 7.90-7.87 (m, 1H), 7.85 (s, 1H), 7.61 (tt, J = 6.9, 2.3, 2H), 7.53 (qd, J = 9.4, 2.8, 2H), 7.47-7.39 (m, 1H), 7.33 (s, 1H), 7.20 (d, J = 2.3, 1H), 5.16 (s, 1H), 3.82-3.73 (m, 4H), 3.48-3.40 (m, 4H).

| 298 | 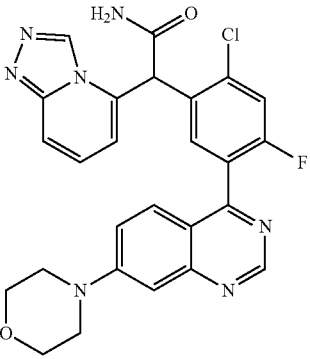 [SMILES: NC(=O)C(c1cc(-c2ncnc3cc(N4CCOCC4)ccc23)c(F)cc1Cl)c1cccc2nncn12]<br>MS: 518.2/520.2 (M + H$^+$) (Cl isotopy, rel. peak intensity ratio [%] 100:35) | 2-[2-Chloro-4-fluoro-5-(7-morpholin-4-yl-quinazolin-4-yl)-phenyl]-2-[1,2,4]-triazolo[4,3-a]pyridin-5-ylacetamide | C | D | A |

1H NMR (500 MHz, DMSO-d6) ppm = 9.21 (d, J = 0.8, 1H), 9.08 (s, 1H), 8.13 (s, 1H), 7.88 (d, J = 9.5, 1H), 7.79 (d, J = 9.2, 1H), 7.73 (s, 1H), 7.57-7.48 (m, 3H), 7.38 (dd, J = 9.2, 6.9, 1H), 7.19 (d, J = 2.3, 1H), 6.57 (d, J = 6.9, 1H), 5.84 (s, 1H), 3.80-3.75 (m, 4H), 3.48-3.42 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 299 | | 2-[4-Fluoro-3-(7-morpholin-4-yl-quinazolin-4-yl)-phenyl]-2-pyrrolo-[2,1-f][1,2,4]triazin-4-ylacetamide | C | D | D |
| | MS: 484.2 (M + H⁺) | 1H NMR (500 MHz, DMSO-d6) ppm = 13.68 (d, J = 4.0, 1H), 9.09 (s, 1H), 7.84-7.74 (m, 2H), 7.57-7.46 (m, 3H), 7.46-7.39 (m, 1H), 7.31-7.25 (m, 1H), 7.24-7.16 (m, 1H), 7.02 (s, 1H), 6.21 (dd, J = 4.4, 2.7, 1H), 6.08 (s, 1H), 4.81 (dd, J = 4.3, 1.7, 1H), 3.90-3.70 (m, 4H), 3.53-3.38 (m, 4H). | | | |
| 300 | | 2-[2-Chloro-4-fluoro-5-(7-morpholin-4-yl-quinazolin-4-yl)-phenyl]-2-pyridazin-3-ylacetamide | C | D | A |
| | MS: 479.2/481.2 (M + H⁺) (Cl isotopy, rel. peak intensity ratio [%] 100:33) | 1H NMR (500 MHz, DMSO-d6) ppm = 9.14 (dd, J = 4.9, 1.6, 1H), 9.10 (s, 1H), 8.03 (s, 1H), 7.76 (d, J = 9.6, 1H), 7.71 (d, J = 7.6, 1H), 7.65 (dd, J = 8.5, 4.9, 1H), 7.60 (dd, J = 9.4, 3.4, 1H), 7.53 (dd, J = 5.6, 2.1, 1H), 7.52 (dd, J = 4.7, 2.0, 1H), 7.43 (s, 1H), 7.20 (d, J = 2.5, 1H), 5.78 (s, 1H), 3.78 (dd, J = 5.8, 4.0, 4H), 3.46 (dd, J = 6.0, 3.9, 4H). | | | |
| 301 | | 2-[2-Chloro-4-fluoro-5-(7-morpholin-4-yl-quinazolin-4-yl)-phenyl]-2-(3,5-dimethyl-pyrazin-2-yl)acetamide | C | B | A |
| | MS: 507.2/509.2 (M + H⁺) (Cl isotopy, rel. peak intensity ratio [%] 100:35) | 1H NMR (500 MHz, DMSO-d6) ppm = 9.08 (s, 1H), 8.25 (s, 1H), 7.75-7.69 (m, 2H), 7.58 (dd, J = 9.4, 3.0, 1H), 7.54 (dd, J = 9.5, 2.5, 1H), 7.47 (d, J = 7.7, 1H), 7.28 (s, 1H), 7.19 (d, J = 2.4, 1H), 5.60 (s, 1H), 3.81-3.74 (m, 4H), 3.49-3.42 (m, 4H), 2.49 (s, 3H), 2.41 (s, 3H). | | | |

| No. | Structural formula | Name | IC$_{50}$ DNA-PK | IC$_{50}$ pDNA-PK | K$_i$ [Kv1.11 hERG] |
|---|---|---|---|---|---|
| 302 | 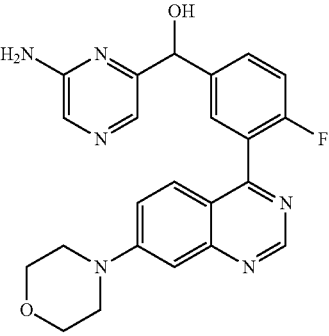 [SMILES: Nc1cncc(C(O)c2ccc(F)c(-c3ncnc4cc(N5CCOCC5)ccc34)c2)n1]<br>MS: 433.1 (M + H$^+$) | (6-Amino-pyrazin-2-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 7.91 (s, 1H), 7.74 (s, 1H), 7.63-7.56 (m, 2H), 7.54-7.51 (m, 2H), 7.39-7.34 (m, 1H), 7.21-7.19 (m, 1H), 6.36 (s, 2H), 6.10 (d, J = 4.3, 1H), 5.60 (d, J = 4.3, 1H), 3.81-3.74 (m, 4H), 3.47-3.41 (m, 4H). | B | C | A |
| 303 | 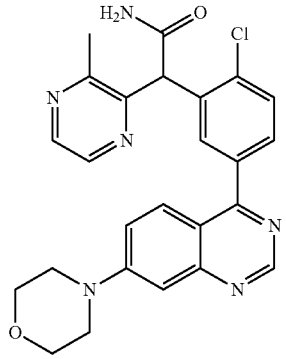<br>MS: 475.2/477.2 (M + H$^+$) (Cl isotopy, rel. peak intensity ratio [%] 100:38) | 2-[2-Chloro-5-(7-morpholin-4-yl-quinazolin-4-yl)-phenyl]-2-(3-methyl-pyrazin-2-yl)-acetamide<br><br>1H NMR (500 MHz, DMSO-d6) ppm = 9.05 (s, 1H), 8.43-8.37 (m, 2H), 7.87 (d, J = 9.4, 1H), 7.80 (s, 1H), 7.75-7.65 (m, 3H), 7.51 (dd, J = 9.5, 2.6, 1H), 7.33 (s, 1H), 7.19 (d, J = 2.5, 1H), 5.71 (s, 1H), 3.85-3.74 (m, 4H), 3.52-3.39 (m, 4H), 2.55 (s, 3H). | C | C | B |
| 304 | 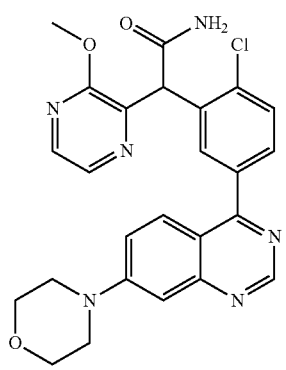 [SMILES: COc1nccnc1C(C(N)=O)c1cc(-c2ncnc3cc(N4CCOCC4)ccc23)ccc1Cl]<br>MS: 491.3/493.2 (M + H$^+$) (Cl isotopy, rel. peak intensity ratio [%] 100:38) | 2-[2-Chloro-5-(7-morpholin-4-yl-quinazolin-4-yl)-phenyl]-2-(3-methoxy-pyrazin-2-yl)acetamide<br><br>1H NMR (500 MHz, DMSO-d6) ppm = 9.06 (s, 1H), 8.12 (d, J = 2.8, 1H), 8.10 (d, J = 2.8, 1H), 7.89 (d, J = 9.4, 1H), 7.79-7.75 (m, 1H), 7.73-7.69 (m, 2H), 7.67 (d, J = 8.1, 1H), 7.52 (dd, J = 9.5, 2.6, 1H), 7.27-7.23 (m, 1H), 7.20 (d, J = 2.6, 1H), 5.71 (s, 1H), 3.95 (s, 3H), 3.81-3.75 (m, 4H), 3.49-3.41 (m, 4H). | C | C | A |

-continued

| No. | Structural formula | Name | IC$_{50}$ DNA-PK | IC$_{50}$ pDNA-PK | K$_i$ [Kv1.11 hERG] |
|---|---|---|---|---|---|
| 305 | MS: 475.3 (M + H$^+$) | 2-[4-Fluoro-3-(7-morpholin-4-yl-quinazolin-4-yl)-phenyl]-2-(3-methoxy-pyrazin-2-yl)acetamide | C | C | A |
| | | 1H NMR (500 MHz, DMSO-d6) ppm = 9.09 (s, 1H), 8.13 (d, J = 2.8, 1H), 8.10 (d, J = 2.8, 1H), 7.63 (dd, J = 9.4, 2.8, 1H), 7.61-7.52 (m, 4H), 7.41-7.35 (m, 1H), 7.20 (d, J = 2.4, 1H), 7.11 (s, 1H), 5.34 (s, 1H), 3.93 (s, 3H), 3.82-3.74 (m, 4H), 3.48-3.41 (m, 4H). | | | |
| 306 | MS: 493.3 (M + H$^+$) | 2-[2,4-Difluoro-5-(7-morpholin-4-yl-quinazolin-4-yl)-phenyl]-2-(6-methoxy-pyridazin-3-yl)acetamide | C | D | A |
| | | 1H NMR (500 MHz, DMSO-d6) ppm = 9.10 (s, 1H), 7.90 (s, 1H), 7.71 (t, J = 8.2, 1H), 7.61-7.49 (m, 4H), 7.37 (s, 1H), 7.20 (d, J = 2.4, 1H), 7.18 (d, J = 9.2, 1H), 5.57 (s, 1H), 4.00 (s, 3H), 3.81-3.74 (m, 4H), 3.49-3.41 (m, 4H). | | | |
| 307 | MS: 509.2/511.1 (M + H$^+$) (Cl isotopy, rel. peak intensity ratio [%] 100:39) | 2-[2-Chloro-4-fluoro-5-(7-morpholin-4-yl-quinazolin-4-yl)-phenyl]-2-(3-methoxypyridazin-4-yl)acetamide | B | C | A |
| | | 1H NMR (500 MHz, DMSO-d6) ppm = 9.09 (s, 1H), 8.80 (d, J = 4.7, 1H), 8.02 (s, 1H), 7.80 (d, J = 9.5, 1H), 7.59 (dd, J = 9.4, 3.3, 1H), 7.53 (dd, J = 9.5, 2.5, 1H), 7.46 (d, J = 7.5, 1H), 7.42 (s, 1H), 7.20 (d, J = 2.4, 1H), 7.08 (dd, J = 4.7, 0.5, 1H), 5.46 (s, 1H), 4.07 (s, 3H), 3.80-3.76 (m, 4H), 3.49-3.43 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 308 | MS: 475.3 (M + H$^+$) | 2-[4-Fluoro-3-(7-morpholin-4-yl-quinazolin-4-yl)-phenyl]-2-(6-methoxypyridazin-3-yl)acetamide | C | D | A |
| | | 1H NMR (500 MHz, DMSO-d6) ppm = 9.10 (s, 1H), 7.87 (s, 1H), 7.67 (d, J = 9.2, 1H), 7.64-7.57 (m, 2H), 7.57-7.49 (m, 2H), 7.46-7.38 (m, 1H), 7.31 (s, 1H), 7.20 (d, J = 2.2, 1H), 7.18 (d, J = 9.2, 1H), 5.40 (s, 1H), 4.00 (s, 3H), 3.78 (dd, J = 5.8, 3.9, 4H), 3.44 (dd, J = 5.8, 4.1, 4H). | | | |
| 309 | MS: 518.2/520.2 (M + H$^+$) (Cl isotopy, rel. peak intensity ratio [%] 100:37) | 2-[2-Chloro-4-fluoro-5-(7-morpholin-4-yl-quinazolin-4-yl)-phenyl]-2-[3H-pyrrolo[2,1-f][1,2,4]-triazin-(4E)-ylidene]-acetamide | D | D | D |
| | | 1H NMR (500 MHz, DMSO-d6) ppm = 13.76 (d, J = 3.9, 1H), 9.07 (s, 1H), 7.86 (d, J = 9.7, 1H), 7.84-7.76 (m, 2H), 7.56 (d, J = 7.8, 1H), 7.51 (dd, J = 9.5, 2.5, 1H), 7.32 (dd, J = 2.7, 1.7, 1H), 7.18 (d, J = 2.4, 1H), 6.99 (s, 1H), 6.37 (s, 1H), 6.26 (dd, J = 4.4, 2.7, 1H), 4.87 (dd, J = 4.4, 1.7, 1H), 3.81-3.74 (m, 4H), 3.49-3.42 (m, 4H). | | | |
| 310 | MS: 491.2/493.2 (M + H$^+$) (Cl isotopy, rel. peak intensity ratio [%] 100:35) | 2-[2-Chloro-5-(7-morpholin-4-yl-quinazolin-4-yl)-phenyl]-2-(6-methoxy-pyridazin-3-yl)acetamide | D | D | B |
| | | 1H NMR (500 MHz, DMSO-d6) ppm = 9.07 (s, 1H), 7.97 (s, 1H), 7.89-7.85 (m, 2H), 7.73 (dd, J = 8.2, 2.1, 1H), 7.70 (d, J = 8.2, 1H), 7.52 (dd, J = 9.5, 2.6, 1H), 7.46 (d, J = 9.2, 1H), 7.39 (s, 1H), 7.21 (d, J = 2.5, 1H), 7.18 (d, J = 9.2, 1H), 5.72 (s, 1H), 4.01 (s, 3H), 3.82-3.75 (m, 4H), 3.48-3.42 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 311 | | 2-[2-Chloro-4-fluoro-5-(7-morpholin-4-yl-quinazolin-4-yl)-phenyl]-2-(1-methyl-6-oxo-1,6-dihydro-pyridazin-3-yl)-acetamide | D | D | A |
| | MS: 509.3/511.3 (M + H⁺) (Cl isotopy, rel. peak intensity ratio [%] 100:38) | 1H NMR (500 MHz, DMSO-d6) ppm = 9.11 (s, 1H), 7.92 (s, 1H), 7.76 (d, J = 9.5, 1H), 7.68 (d, J = 7.5, 1H), 7.58 (dd, J = 9.4, 3.1, 1H), 7.54 (dd, J = 9.5, 2.5, 1H), 7.41 (s, 1H), 7.33 (d, J = 9.6, 1H), 7.21 (d, J = 2.4, 1H), 6.90 (d, J = 9.6, 1H), 5.33 (s, 1H), 3.81-3.75 (m, 4H), 3.59 (s, 3H), 3.49-3.42 (m, 4H). | | | |
| 312 | | 2-[2-Chloro-4-fluoro-5-(7-morpholin-4-yl-quinazolin-4-yl)-phenyl]-2-(1-methyl-6-oxo-1,6-dihydro-pyridin-2-yl)-acetamide | D | D | A |
| | MS: 508.3/510.2 (M + H⁺) (Cl isotopy, rel. peak intensity ratio [%] 100:38) | 1H NMR (500 MHz, DMSO-d6) ppm = 9.09 (s, 1H), 8.04 (s, 1H), 7.83 (d, J = 9.4, 1H), 7.62-7.44 (m, 3H), 7.42-7.27 (m, 2H), 7.19 (d, J = 2.4, 1H), 6.36 (dd, J = 9.1, 1.3, 1H), 5.90 (dd, J = 7.1, 1.3, 1H), 5.48 (s, 1H), 3.77 (dd, J = 5.8, 4.0, 4H), 3.52-3.42 (m, 4H), 3.40 (s, 3H). | | | |
| 313 | | 2-(3-Chloro-pyridin-2-yl)-2-[4-fluoro-3-(7-morpholin-4-yl-quinazolin-4-yl)-phenyl]acetamide | C | C | B |
| | MS: 478.2/480.2 (M + H⁺) (Cl isotopy, rel. peak intensity ratio [%] 100:36) | 1H NMR (500 MHz, DMSO-d6) ppm = 9.10 (s, 1H), 8.51 (dd, J = 4.7, 1.5, 1H), 7.93 (dd, J = 8.1, 1.5, 1H), 7.64 (dd, J = 9.4, 2.9, 1H), 7.61-7.53 (m, 4H), 7.39 (dd, J = 9.9, 8.7, 1H), 7.36 (dd, J = 8.1, 4.7, 1H), 7.21 (d, J = 2.5, 1H), 7.17 (s, 1H, 5.53 (s, 1H), 3.84-3.73 (m, 4H), 3.50-3.41 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 314 | 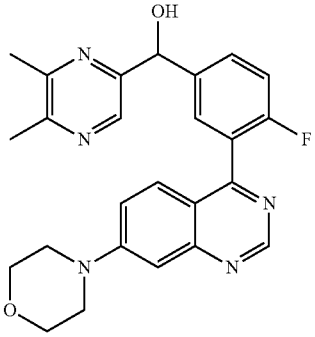 [SMILES: Cc1ncc(C(O)c2ccc(F)c(-c3ncnc4cc(N5CCOCC5)ccc34)c2)nc1C]<br>MS: 446.2 (M + H⁺) | (5,6-Dimethyl-pyrazin-2-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 8.51 (s, 1H), 7.66-7.61 (m, 2H), 7.54-7.49 (m, 2H), 7.40-7.35 (m, 1H), 7.21-7.19 (m, 1H), 6.32 (d, J = 4.2, 1H), 5.84 (d, J = 4.0, 1H), 3.80-3.75 (m, 4H), 3.46-3.42 (m, 4H), 2.45 (s, 3H), 2.44 (s, 3H). | C | B | B |
| 315 | 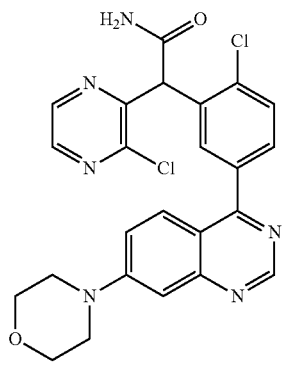 [SMILES: NC(=O)C(c1cc(-c2ncnc3cc(N4CCOCC4)ccc23)ccc1Cl)c1nccnc1Cl]<br>MS: 495.0/497.1/499.1 (M + H⁺) (Cl$_2$ isotopy, rel. peak intensity ratio [%] 100:75:20) | 2-[2-Chloro-5-(7-morpholin-4-yl-quinazolin-4-yl)-phenyl]-2-(3-chloro-pyrazin-2-yl)-acetamide<br><br>1H NMR (500 MHz, DMSO-d6) ppm = 9.07 (s, 1H), 8.60 (d, J = 2.5, 1H), 8.45 (d, J = 2.5, 1H), 7.97-7.91 (m, 1H), 7.88 (d, J = 9.5, 1H), 7.75 (dd, J = 8.3, 2.1, 1H), 7.71 (d, J = 8.2, 1H), 7.66 (d, J = 2.1, 1H), 7.53 (dd, J = 9.5, 2.6, 1H), 7.47-7.42 (m, 1H), 7.22-7.19 (m, 1H), 5.87 (s, 1H), 3.81-3.76 (m, 4H), 3.47-3.42 (m, 4H). | D | D | C |
| 316 | 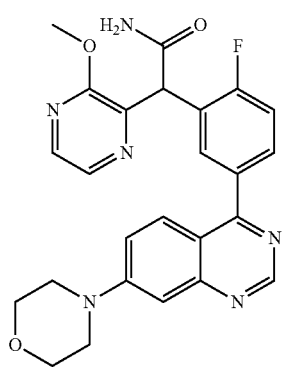 [SMILES: COc1nccnc1C(C(N)=O)c1cc(-c2ncnc3cc(N4CCOCC4)ccc23)ccc1F]<br>MS: 475.4 (M + H⁺) | 2-[2-Fluoro-5-(7-morpholin-4-yl-quinazolin-4-yl)-phenyl]-2-(3-methoxy-pyrazin-2-yl)acetamide<br><br>1H NMR (500 MHz, DMSO-d6) ppm = 9.05 (s, 1H), 8.13 (d, J = 2.9, 2H), 7.94 (d, J = 9.4, 1H), 7.78-7.70 (m, 3H), 7.53 (dd, J = 9.5, 2.6, 1H), 7.41 (dd, J = 9.6, 8.6, 1H), 7.23 (s, 1H), 7.19 (d, J = 2.5, 1H), 5.59 (s, 1H), 3.95 (s, 3H), 3.82-3.74 (m, 4H), 3.48-3.40 (m, 4H). | D | C | B |

| No. | Structural formula | Name | IC$_{50}$ DNA-PK | IC$_{50}$ pDNA-PK | K$_i$ [Kv1.11 hERG] |
|---|---|---|---|---|---|
| 317 | MS: 475.3 (M + H⁺) | 2-[4-Fluoro-3-(7-morpholin-4-yl-quinazolin-4-yl)-phenyl]-2-(1-methyl-6-oxo-1,6-dihydro-pyridazin-3-yl)-acetamide | D | D | B |

1H NMR (500 MHz, DMSO-d6) ppm = 9.10 (s, 1H), 7.86 (s, 1H), 7.64-7.50 (m, 4H), 7.47 (d, J = 9.6, 1H), 7.44 (dd, J = 9.8, 8.5, 1H), 7.34 (s, 1H), 7.20 (d, J = 2.2, 1H), 6.90 (d, J = 9.6, 1H), 5.05 (s, 1H), 3.83-3.73 (m, 4H), 3.61 (s, 3H), 3.44 (t, J = 4.9, 4H).

| No. | Structural formula | Name | IC$_{50}$ DNA-PK | IC$_{50}$ pDNA-PK | K$_i$ [Kv1.11 hERG] |
|---|---|---|---|---|---|
| 318 | MS: 473.4 (M + H⁺) | 2-(3,5-Dimethyl-pyrazin-2-yl)-2-[4-fluoro-3-(7-morpholin-4-yl-quinazolin-4-yl)-phenyl]acetamide | C | D | A |

1H NMR (500 MHz, DMSO-d6) ppm = 9.09 (s, 1H), 8.29 (s, 1H), 7.60 (dd, J = 9.5, 2.9, 1H), 7.59-7.55 (m, 2H), 7.54 (dd, J = 9.5, 2.5, 1H), 7.50 (s, 1H), 7.42-7.33 (m, 1H), 7.20 (d, J = 2.5, 1H), 7.15 (s, 1H), 5.35 (s, 1H), 3.78 (dd, J = 5.8, 4.0, 4H), 3.44 (dd, J = 6.0, 3.9, 4H), 2.49 (s, 3H), 2.41 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 319 | MS: 493.4 (M + H⁺) | 2-[2,4-Difluoro-5-(7-morpholin-4-yl-quinazolin-4-yl)-phenyl]-2-(3-methoxy-pyrazin-2-yl)acetamide | C | C | A |

1H NMR (500 MHz, DMSO-d6) ppm = 9.08 (s, 1H), 8.13 (d, J = 2.8, 1H), 8.11 (d, J = 2.8, 1H), 7.73 (s, 1H), 7.61 (dd, J = 9.4, 3.2, 1H), 7.58-7.46 (m, 3H), 7.24 (s, 1H), 7.20 (d, J = 2.4, 1H), 5.53 (s, 1H), 3.95 (s, 3H), 3.78 (dd, J = 5.8, 4.0, 4H), 3.45 (dd, J = 6.0, 3.9, 4H).

| No. | Structural formula | Name | IC$_{50}$ DNA-PK | IC$_{50}$ pDNA-PK | K$_i$ [Kv1.11 hERG] |
|---|---|---|---|---|---|
| 320 | | 2-[2-Chloro-4-fluoro-5-(7-morpholin-4-yl-quinazolin-4-yl)-phenyl]-2-(3-methoxy-pyrazin-2-yl)acetamide | C | B | A |
| | MS: 509.3/511.3 (M + H⁺) (Cl isotopy, rel. peak intensity ratio [%] 100:38) | 1H NMR (500 MHz, DMSO-d6) ppm = 9.09 (s, 1H), 8.12 (d, J = 2.8, 1H), 8.09 (d, J = 2.8, 1H), 7.78 (s, 1H), 7.72 (d, J = 9.6, 1H), 7.60 (dd, J = 9.4, 3.1, 1H), 7.55 (dd, J = 9.5, 2.5, 1H), 7.51 (d, J = 7.6, 1H), 7.26 (s, 1H), 7.20 (d, J = 2.4, 1H), 5.65 (s, 1H), 3.95 (s, 3H), 3.86-3.66 (m, 4H), 3.56-3.37 (m, 4H). | | | |
| 321 | | 2-(3,5-Difluoro-pyridin-4-yl)-2-[4-fluoro-3-(7-morpholin-4-yl-quinazolin-4-yl)-phenyl]acetamide | C | B | B |
| | MS: 480.2 (M + H⁺) | 1H NMR (500 MHz, DMSO-d6) ppm = 9.09 (s, 1H), 8.50 (s, 2H), 7.59 (s, 1H), 7.58-7.49 (m, 4H), 7.46-7.37 (m, 2H), 7.20 (d, J = 2.2, 1H), 5.42 (s, 1H), 3.87-3.64 (m, 4H), 3.59-3.40 (m, 4H). | | | |
| 322 | | 2-(4-Chloro-5-fluoro-pyridin-3-yl)-2-[4-fluoro-3-(7-morpholin-4-yl-quinazolin-4-yl)-phenyl]acetamide | B | B | C |
| | MS: 496.2/498.1 (M + H⁺) (Cl isotopy, rel. peak intensity ratio [%] 100:37) | 1H NMR (500 MHz, DMSO-d6) ppm = 9.09 (d, J = 2.3, 1H), 8.65 (s, 1H), 8.33 (s, 1H), 7.94 (s, 1H), 7.61-7.50 (m, 4H), 7.44 (dt, J = 20.5, 9.0, 2H), 7.20 (d, J = 2.1, 1H), 5.44 (s, 1H), 3.80-3.75 (m, 4H), 3.47-3.42 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 323 | | 2-[2-Chloro-4-fluoro-5-(7-morpholin-4-yl-quinazolin-4-yl)-phenyl]-2-imidazo-[1,2-b]pyridazin-6-yl-acetamide | B | B | B |

MS: 518.2/520.2 (M + H⁺) (Cl isotopy, rel. peak intensity ratio [%] 100:35)

1H NMR (500 MHz, DMSO-d6) ppm = 9.10 (d, J = 10.0, 1H), 8.24 (s, 1H), 8.08 (d, J = 9.5, 1H), 8.02 (s, 1H), 7.79 (d, J = 9.5, 1H), 7.76 (d, J = 1.2, 1H), 7.72 (d, J = 7.6, 1H), 7.60 (dd, J = 9.5, 3.2, 1H), 7.53 (dd, J = 9.5, 2.5, 1H), 7.47 (s, 1H), 7.22 (d, J = 2.5, 1H), 7.11 (d, J = 9.5, 1H), 5.61 (s, 1H), 3.81-3.74 (m, 4H), 3.49-3.42 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 324 | | 2-[2-Chloro-4-fluoro-5-(7-morpholin-4-yl-quinazolin-4-yl)-phenyl]-2-(3-methyl-pyrazin-2-yl)-acetamide | B | B | A |

MS: 493.3/495.3 (M + H⁺) (Cl isotopy, rel. peak intensity ratio [%] 100:38)

1H NMR (500 MHz, DMSO-d6) ppm = 9.08 (s, 1H), 8.40 (d, J = 2.5, 1H), 8.38 (d, J = 2.5, 1H), 7.80 (s, 1H), 7.73 (d, J = 9.5, 1H), 7.59 (dd, J = 9.4, 3.0, 1H), 7.54 (dd, J = 9.5, 2.5, 1H), 7.48 (d, J = 7.6, 1H), 7.34 (s, 1H), 7.19 (d, J = 2.4, 1H), 5.66 (s, 1H), 3.78 (dd, J = 5.8, 4.0, 4H), 3.45 (dd, J = 5.9, 3.9, 4H), 2.55 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 325 | | 2-[2-Chloro-4-fluoro-5-(7-morpholin-4-yl-quinazolin-4-yl)-phenyl]-2-(6-methoxypyridazin-3-yl)acetamide | D | D | B |

MS: 509.2/511.1 (M + H⁺) (Cl isotopy, rel. peak intensity ratio [%] 100:37)

1H NMR (500 MHz, DMSO-d6) ppm = 9.11 (s, 1H), 7.96 (s, 1H), 7.75 (d, J = 9.5, 1H), 7.71 (d, J = 7.6, 1H), 7.63-7.51 (m, 2H), 7.47 (d, J = 9.2, 1H), 7.39 (s, 1H), 7.21 (d, J = 2.4, 1H), 7.17 (d, J = 9.2, 1H), 5.67 (s, 1H), 4.00 (s, 3H), 3.82-3.74 (m, 4H), 3.50-3.42 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 326 | MS: 448.2 (M + H$^+$) | 6-{[4-Fluoro-3-(7-morpholin-4-yl-quinazolin-4-yl)-phenyl]hydroxy-methyl}-2-methyl-2H-pyridazin-3-one | C | B | A |
| | | 1H NMR (500 MHz, DMSO-d6) ppm = 9.10 (s, 1H), 7.66-7.60 (m, 2H), 7.55-7.49 (m, 2H), 7.47 (d, J = 9.6, 1H), 7.44-7.39 (m, 1H), 7.21-7.19 (m, 1H), 6.93 (d, J = 9.6, 1H), 6.46 (d, J = 4.3, 1H), 5.66 (d, J = 4.3, 1H), 3.80-3.75 (m, 4H), 3.62 (s, 3H), 3.46-3.42 (m, 4H). | | | |
| 327 | MS: 459.3 (M + H$^+$) | 2-[4-Fluoro-3-(7-morpholin-4-yl-quinazolin-4-yl)-phenyl]-2-(3-methyl-pyrazin-2-yl)-acetamide | C | D | A |
| | | 1H NMR (500 MHz, DMSO-d6) ppm = 9.09 (s, 1H), 8.41 (d, J = 2.4, 1H), 8.38 (d, J = 2.6, 1H), 7.64-7.51 (m, 5H), 7.38 (dd, J = 10.6, 8.5, 1H), 7.21-7.16 (m, 2H), 5.41 (s, 1H), 3.83-3.74 (m, 4H), 3.46-3.40 (m, 4H), 2.54 (s, 3H). | | | |
| 328 | MS: 457.2 (M + H$^+$) | [4-Fluoro-3-(7-morpholin-4-yl-quinazolin-4-yl)-phenyl]furo[2,3-c]-pyridin-7-ylmethanol | A | A | D |
| | | 1H NMR (500 MHz, DMSO-d6) ppm = 9.08 (s, 1H), 8.32 (d, J = 5.2, 1H), 8.21 (d, J = 2.2, 1H), 7.74-7.67 (m, 2H), 7.64 (d, J = 5.2, 1H), 7.52-7.49 (m, 2H), 7.36 (dd, J = 9.9, 8.4, 1H), 7.22-7.16 (m, 1H), 7.06 (d, J = 2.2, 1H), 6.32 (d, J = 5.0, 1H), 6.25 (d, J = 5.0, 1H), 3.80-3.75 (m, 4H), 3.46-3.41 (m, 4H). | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 329 | MS: 477.2 (M + H⁺) | 2-[2,4-Difluoro-5-(7-morpholin-4-yl-quinazolin-4-yl)-phenyl]-2-(3-methyl-pyrazin-2-yl)-acetamide | C | C | A |
| | 1H NMR (500 MHz, DMSO-d6) ppm = 9.08 (s, 1H), 8.41 (d, J = 2.6, 1H), 8.39 (d, J = 2.7, 1H), 7.77-7.68 (m, 1H), 7.61 (dd, J = 9.4, 3.1, 1H), 7.59-7.47 (m, 3H), 7.32 (s, 1H), 7.19 (d, J = 2.5, 1H), 5.57 (s, 1H), 3.84-3.74 (m, 4H), 3.48-3.41 (m, 4H), 2.55 (s, 3H). | | | | |
| 330 | MS: 484.1/486.1/488.1 (M + H⁺) (Cl$_2$ isotopy, rel. peak intensity ratio [%] 100:70:18) | 5-Chloro-6-{[2-chloro-5-(7-morpholin-4-yl-quinazolin-4-yl)-phenyl]hydroxy-methyl}pyrimidin-4-ol | C | D | A |
| | 1H NMR (500 MHz, DMSO-d6) ppm = 13 06 (s, 1H), 9.09 (s, 1H), 8.22-8.14 (m, 2H), 7.97 (d, J = 9.4, 1H), 7.71 (dd, J = 8.2, 2.2, 1H), 7.62-7.56 (m, 2H), 7.22 (d, J = 2.6, 1H), 6.46 (d, J = 5.5, 1H), 6.31 (d, J = 5.5, 1H), 3.83-3.77 (m, 4H), 3.48-3.43 (m, 4H). | | | | |
| 331 | MS: 456.2 (M + H⁺) | (3-methyl-pyrazin-2-yl)-[3-(7-morpholin-4-ylquinazolin-4-yl)-4-oxocyclohexa-2,5-dien-(E)-ylidene]-acetic acid | C | C | A |
| | 1H NMR (500 MHz, DMSO-d6) ppm = 9.06 (s, 1H), 8.70 (d, J = 2.5, 1H), 8.56 (d, J = 2.6, 1H), 8.01 (dd, J = 8.8, 2.3, 1H), 7.84 (d, J = 2.3, 1H), 7.48 (d, J = 1.4, 2H), 7.38 (d, J = 8.8, 1H), 7.17-7.14 (m, 1H), 3.81-3.74 (m, 4H), 3.45-3.39 (m, 4H), 2.55 (s, 3H). | | | | |

| No. | Structural formula | Name | IC$_{50}$ DNA-PK | IC$_{50}$ pDNA-PK | K$_i$ [Kv1.11 hERG] |
|---|---|---|---|---|---|
| 332 | MS: 474.1 (M + H$^+$) | [4-Fluoro-3-(7-morpholin-4-yl-quinazolin-4-yl)-phenyl]thieno[2,3-d}-pyridazin-7-yl-methanol | A | A | B |

1H NMR (500 MHz, DMSO-d6) ppm = 9.56 (s, 1H), 9.08 (s, 1H), 8.26 (d, J = 5.4, 1H), 7.79-7.72 (m, 2H), 7.70 (d, J = 5.4, 1H), 7.51-7.44 (m, 2H), 7.43-7.35 (m, 1H), 7.21-7.16 (m, 1H), 7.10 (d, J = 3.8, 1H), 6.38 (d, J = 3.9, 1H), 3.82-3.74 (m, 4H), 3.47-3.40 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 333 | MS: 474.2 (M + H$^+$) | [4-Fluoro-3-(7-morpholin-4-yl-quinazolin-4-yl)-phenyl]thieno[2,3-d}-pyridazin-4-yl-methanol | A | A | B |

1H NMR (500 MHz, DMSO-d6) ppm = 9.84 (d, J = 0.6, 1H), 9.08 (s, 1H), 8.28 (d, J = 5.3, 1H), 7.89 (dd, J = 5.4, 0.7, 1H), 7.75-7.67 (m, 2H), 7.49 (dd, J = 9.4, 2.4, 1H), 7.45 (dd, J = 9.4, 2.9, 1H), 7.42-7.34 (m, 1H), 7.19 (d, J = 2.3, 1H), 6.82 (s, 1H), 6.42 (s, 1H), 3.81-3.75 (m, 4H), 3.47-3.41 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 334 | MS: 522.1/524.1 (M + H$^+$) (Cl isotopy, rel. peak intensity ratio [%] 100:35) | 2-[2-Chloro-4-fluoro-5-(7-morpholin-4-yl-quinazolin-4-yl)-phenyl]-2-(1,4-dimethyl-6-oxo-1,6-dihydropyridin-2-yl)-acetamide | D | D | A |

1H NMR (500 MHz, DMSO-d6) ppm = 9.10 (s, 1H), 8.10-7.99 (m, 1H), 7.85 (d, J = 9.4, 1H), 7.58-7.49 (m, 3H), 7.34 (d, J = 7.4, 1H), 7.24-7.17 (m, 1H), 6.22-6.15 (m, 1H), 5.79-5.77 (m, 1H), 5.47 (s, 1H), 3.82-3.75 (m, 4H), 3.46 (t, J = 5.0, 4H), 3.36 (s, 3H), 2.05 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 335 | MS: 458.2 (M + H$^+$) | [4-Fluoro-3-(7-morpholin-4-yl-quinazolin-4-yl)-phenyl]furo[2,3-d}-pyridazin-7-yl-methanol | A | A | A |
| | | 1H NMR (500 MHz, DMSO-d6) ppm = 9.59 (s, 1H), 9.09 (s, 1H), 8.37 (d, J = 2.1, 1H), 7.82-7.70 (m, 2H), 7.54-7.47 (m, 2H), 7.40 (dd, J = 9.8, 8.6, 1H), 7.23-7.16 (m, 2H), 6.69 (d, J = 4.6, 1H), 6.40 (d, J = 4.6, 1H), 3.81-3.75 (m, 4H), 3.47-3.41 (m, 4H). | | | |
| 336 | MS: 475.7 (M + H$^+$) | [2,4-Difluoro-5-(7-morpholin-4-yl-quinazolin-4-yl)-phenyl]furo[2,3-d}-pyridazin-7-yl-methanol | A | A | A |
| | | 1H NMR (500 MHz, DMSO-d6) ppm = 9.63 (s, 1H), 9.14 (s, 1H), 8.41 (d, J = 2.1, 1H), 8.10 (t, J = 8.1, 1H), 7.63 (dd, J = 9.4, 3.0, 1H), 7.58 (dd, J = 9.4, 2.5, 1H), 7.45 (t, J = 10.1, 1H), 7.27-7.19 (m, 2H), 6.82 (d, J = 5.3, 1H), 6.63 (d, J = 5.3, 1H), 3.83-3.77 (m, 4H), 3.50-3.45 (m, 4H). | | | |
| 337 | MS: 490.1 (M + H$^+$) | 7-[[4-Fluoro-3-(7-morpholino-quinazolin-4-yl)-phenyl]hydroxy-methyl]-5H-thieno-[2,3-d}pyridazin-4-one | A | B | B |
| | | 1H NMR (500 MHz, DMSO-d6) ppm = 12.73 (s, 1H), 9.10 (s, 1H), 8.04 (d, J = 5.3, 1H), 7.74-7.63 (m, 2H), 7.59 (d, J = 5.2, 1H), 7.53-7.45 (m, 2H), 7.44-7.37 (m, 1H), 7.23-7.13 (m, 1H), 6.88 (s, 1H), 5.94 (s, 1H), 3.82-3.71 (m, 4H), 3.46-3.41 (m, 4H). | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 338 | MS: 490.1 (M + H$^+$) | 4-[[4-Fluoro-3-(7-morpholino-quinazolin-4-yl)-phenyl]hydroxy-methyl]-6H-thieno[2,3-d]-pyridazin-7-one<br><br>1H NMR (500 MHz, DMSO-d6) ppm = 12.82 (s, 1H), 9.09 (s, 1H), 8.18 (d, J = 5.2, 1H), 7.70-7.64 (m, 2H), 7.62 (d, J = 5.2, 1H), 7.50 (dd, J = 9.4, 2.4, 1H), 7.47 (dd, J = 9.4, 2.8, 1H), 7.44-7.36 (m, 1H), 7.19 (d, J = 2.3, 1H), 6.62 (s, 1H), 6.01 (s, 1H), 3.81-3.73 (m, 4H), 3.48-3.40 (m, 4H). | A | B | A |
| 339 | MS: 494.7/496.7 (M + H$^+$) (Cl isotopy, rel. peak intensity ratio [%] 100:37) | 6-{[2-Chloro-4-fluoro-5-(7-morpholin-4-yl-quinazolin-4-yl)-phenyl]hydroxy-methyl}-1,4-dimethyl-1H-pyridin-2-one<br><br>1H NMR (500 MHz, DMSO-d6) ppm = 9.13 (s, 1H), 7.79 (d, J = 9.5, 1H), 7.71 (d, J = 7.6, 1H), 7.60 (dd, J = 9.4, 3.2, 1H), 7.54 (dd, J = 9.4, 2.5, 1H), 7.22 (d, J = 2.4, 1H), 6.60 (d, J = 6.2, 1H), 6.27-6.15 (m, 1H), 6.05 (d, J = 6.2, 1H), 5.84-5.68 (m, 1H), 3.81-3.75 (m, 4H), 3.52-3.43 (m, 7H), 2.05 (s, 3H). | C | B | A |
| 340 | MS: 461.2 (M + H$^+$) | 6-{[4-Fluoro-3-(7-morpholin-4-yl-quinazolin-4-yl)-phenyl]hydroxy-methyl}-1,4-dimethyl-1H-pyridin-2-one<br><br>1H NMR (500 MHz, DMSO-d6) ppm = 9.10 (s, 1H), 7.62-7.54 (m, 2H), 7.54-7.49 (m, 2H), 7.49-7.41 (m, 1H), 7.22-7.18 (m, 1H), 6.50 (d, J = 5.1, 1H), 6.21-6.15 (m, 2H), 5.90 (d, J = 5.1, 1H), 3.81-3.74 (m, 4H), 3.48-3.41 (m, 4H), 3.30 (s, 3H), 2.12 (s, 3H). | A | B | A |

| No. | Structural formula | Name | IC$_{50}$ DNA-PK | IC$_{50}$ pDNA-PK | K$_i$ [Kv1.11 hERG] |
|---|---|---|---|---|---|
| 341 | MS: 492.2 (M + H$^+$) | [2,4-Difluoro-5-(7-morpholin-4-yl-quinazolin-4-yl)-phenyl]thieno[2,3-d}-pyridazin-4-yl-methanol | A | A | B |
| | 1H NMR (500 MHz, DMSO-d6) ppm = 9.85 (d, J = 0.8, 1H), 9.12 (s, 1H), 8.33 (d, J = 5.3, 1H), 8.01 (t, J = 8.1, 1H), 7.91 (dd, J = 5.4, 0.8, 1H), 7.66-7.50 (m, 2H), 7.43 (t, J = 10.1, 1H), 7.21 (d, J = 2.4, 1H), 6.84 (s, 1H), 6.63 (s, 1H), 3.86-3.70 (m, 4H), 3.54-3.40 (m, 4H). | | | | |
| 342 | MS: 492.2 (M + H$^+$) | [2,4-Difluoro-5-(7-morpholin-4-yl-quinazolin-4-yl)-phenyl]thieno[2,3-d}-pyridazin-7-yl-methanol | A | A | A |
| | 1H NMR (500 MHz, DMSO-d6) ppm = 9.57 (s, 1H), 9.09 (s, 1H), 8.27 (d, J = 5.4, 1H), 7.86 (t, J = 8.0, 1H), 7.71 (d, J = 5.4, 1H), 7.61-7.42 (m, 3H), 7.19 (d, J = 2.4, 1H), 7.16 (d, J = 4.8, 1H), 6.54 (d, J = 4.8, 1H), 3.85-3.69 (m, 4H), 3.50-3.38 (m, 4H). | | | | |
| 343 | MS: 457.2 (M + H$^+$); R$_t$ 11.36 min (SFC, Chiralpak AS-H, CO$_2$/20% by vol. of methanol, 0.5% by vol. of diethylamine) | [4-Fluoro-3-(7-morpholin-4-yl-quinazolin-4-yl)-phenyl]-[1,2,4]-triazolo[4,3-a]pyridin-3-ylmethanol (Ena 2) | A | B | B |
| | see racemate | | | | |

| No. | Structural formula | Name | IC$_{50}$ DNA-PK | IC$_{50}$ pDNA-PK | K$_i$ [Kv1.11 hERG] |
|---|---|---|---|---|---|
| 344 | | [4-Fluoro-3-(7-morpholin-4-yl-quinazolin-4-yl)-phenyl]-[1,2,4]-triazolo[4,3-a]pyridin-3-ylmethanol (Ena 1) | A | C | A |

MS: 457.2 (M + H⁺); R$_t$ 8.65 min (SFC, Chiralpak AS-H, CO$_2$/20% by vol. of methanol, 0.5% by vol. of diethylamine)

see racemate

| 345 | | [4-Fluoro-3-(7-morpholin-4-yl-quinazolin-4-yl)-phenyl]pyrrolo[2,1-f]-[1,2,4]triazin-4-yl-methanol | A | A | D |

MS: 457.2 (M + H⁺)

1H NMR (500 MHz, DMSO-d6) ppm = 9.09 (s, 1H), 8.49 (s, 1H), 8.08 (dd, J = 2.6, 1.4, 1H), 7.84-7.76 (m, 2H), 7.53-7.45 (m, 2H), 7.42-7.36 (m, 1H), 7.29 (dd, J = 4.6, 1.4, 1H), 7.19 (d, J = 2.0, 1H), 7.02 (dd, J = 4.6, 2.6, 1H), 6.62 (s, 1H), 6.07 (s, 1H), 3.80-3.74 (m, 4H), 3.46-3.41 (m, 4H).

| 346 | | [2,4-Difluoro-5-(7-morpholin-4-yl-quinazolin-4-yl)-phenyl]-(9-methyl-9H-purin-6-yl)-methanol (Ena 2) | C | D | B |

MS: 490.2 (M + H⁺); R$_t$ 7.65 min (SFC, Chiralpak AD-H, CO$_2$/40% by vol. of methanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 347 | | [2,4-Difluoro-5-(7-morpholin-4-yl-quinazolin-4-yl)-phenyl]-(9-methyl-9H-purin-6-yl)-methanol (Ena 1) | B | B | A |

MS: 490.2 (M + H$^+$); R$_t$ 4.59 min (SFC, Chiralpak AD-H, CO$_2$/40% by vol. of methanol, 0.5% by vol. of diethylamine)

see racemate

| 348 | | 2-[2,4-Difluoro-5-(7-morpholin-4-yl-quinazolin-4-yl)-phenyl]-2-pyrrolo-[1,2-a]pyrazin-1-yl-acetamide | A | B | C |

MS: 501.3 (M + H$^+$)

1H NMR (500 MHz, DMSO-d6) ppm = 9.10 (s, 1H), 8.23-8.19 (m, 1H), 7.93 (s, 1H), 7.80 (t, J = 8.2, 1H), 7.77 (dd, J = 2.4, 1.4, 1H), 7.63 (dd, J = 9.4, 3.1, 1H), 7.55 (dd, J = 12.3, 2.8, 1H), 7.50 (d, J = 10.0, 1H), 7.44 (d, J = 4.8, 1H), 7.33 (s, 1H), 7.21 (d, J = 2.5, 1H), 6.94-6.89 (m, 2H), 5.75 (s, 1H), 3.82-3.77 (m, 4H), 3.49-3.45 (m, 4H).

| 349 | | 4-[2-Fluoro-5-(3-methyl-pyrazin-2-ylmethyl)phenyl]-7-morpholin-4-yl-quinazoline | B | A | A |

MS: 416.3 (M + H$^+$)

1H NMR (500 MHz, DMSO-d6) ppm = 9.09 (s, 1H), 8.43-8.36 (m, 2H), 7.56-7.49 (m, 2H), 7.46 (dd, J = 7.8, 5.5, 2H), 7.39-7.33 (m, 1H), 7.22-7.16 (m, 1H), 4.28 (s, 2H), 3.81-3.75 (m, 4H), 3.46-3.41 (m, 4H), 2.53 (s, 3H).

| No. | Structural formula | Name | IC$_{50}$ DNA-PK | IC$_{50}$ pDNA-PK | K$_i$ [Kv1.11 hERG] |
|---|---|---|---|---|---|
| 350 | | [2,4-Difluoro-5-(7-morpholin-4-yl-quinazolin-4-yl)-phenyl]-[1,2,4]-triazolo[4,3-a]pyridin-5-ylmethanol | B | C | A |
| | MS: 475.2 (M + H⁺) | 1H NMR (500 MHz, DMSO-d6) ppm = 9.33 (s, 1H), 9.13 (s, 1H), 7.94 (t, J = 8.1, 1H), 7.80 (d, J = 9.2, 1H), 7.61-7.50 (m, 3H), 7.42 (dd, J = 9.2, 6.8, 1H), 7.22 (d, J = 2.4, 1H), 6.93 (d, J = 5.7, 1H), 6.87 (d, J = 6.8, 1H), 6.49 (d, J = 5.6, 1H), 3.83-3.75 (m, 4H), 3.49-3.43 (m, 4H). | | | |
| 351 | | [4-Fluoro-3-(7-morpholin-4-yl-quinazolin-4-yl)-phenyl]-[1,2,4]-triazolo[4,3-a]-pyrazin-8-ylmethanol | C | D | A |
| | MS: 458.1 (M + H⁺) | 1H NMR (500 MHz, DMSO-d6) ppm = 9.44 (s, 1H), 9.09 (s, 1H), 8.52 (d, J = 4.7, 1H), 7.91 (d, J = 4.7, 1H), 7.85-7.78 (m, 2H), 7.53 (dd, J = 9.4, 2.9, 1H), 7.50 (dd, J = 9.4, 2.4, 1H), 7.41-7.35 (m, 1H), 7.20 (d, J = 2.3, 1H), 6.51 (s, 1H), 6.43 (s, 1H), 3.82-3.74 (m, 4H), 3.47-3.41 (m, 4H). | | | |
| 352 | | 4-{2-Fluoro-5-[methoxy-(3-methyl-pyrazin-2-yl)methyl]-phenyl}-7-morpholin-4-ylquinazoline (Ena 1) | | D | A* |
| | MS: 446.2 (M + H⁺); R$_t$ 3.08 min (SFC, Chiralcel OJ-H, CO$_2$/20% by vol. of 2-propanol, 0.5% by vol. of diethylamine) | 1H NMR (500 MHz, DMSO-d6) ppm = 9.11 (s, 1H), 8.53-8.42 (m, 2H), 7.69-7.58 (m, 2H), 7.58-7.48 (m, 2H), 7.48-7.38 (m, 1H), 7.21 (d, J = 1.9, 1H), 5.80 (s, 1H), 3.81-3.70 (m, 4H), 3.48-3.39 (m, 4H), 3.36 (s, 3H), 2.59 (s, 3H). | | | |

| No. | Structural formula | Name | IC$_{50}$ DNA-PK | IC$_{50}$ pDNA-PK | K$_i$ [Kv1.11 hERG] |
|---|---|---|---|---|---|
| 353 | 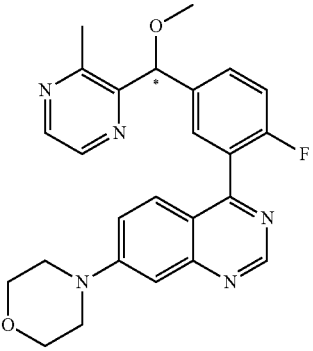 [SMILES: COC(c1ccc(F)c(-c2ncnc3cc(N4CCOCC4)ccc23)c1)c1nccnc1C] MS: 446.2 (M + H$^+$); R$_t$ 3.78 min (SFC, Chiralcel OJ-H, CO$_2$/20% by vol. of 2-propanol, 0.5% by vol. of diethylamine) | 4-{2-Fluoro-5-[methoxy-(3-methyl-pyrazin-2-yl)methyl]-phenyl}-7-morpholin-4-ylquinazoline (Ena 2) <br><br> 1H NMR (500 MHz, DMSO-d6) ppm = 9.11 (s, 1H), 8.52-8.43 (m, 2H), 7.69-7.58 (m, 2H), 7.58-7.51 (m, 2H), 7.49-7.39 (m, 1H), 7.28-7.15 (m, 1H), 5.81 (s, 1H), 3.84-3.74 (m, 4H), 3.49-3.42 (m, 4H), 3.36 (s, 3H), 2.59 (s, 3H). | C | D | A |
| 354 | 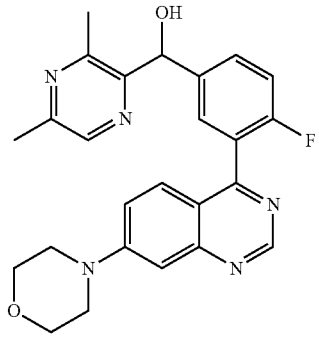 [SMILES: Cc1cnc(C(O)c2ccc(F)c(-c3ncnc4cc(N5CCOCC5)ccc34)c2)c(C)n1] MS: 446.2 (M + H$^+$) | (3,5-Dimethyl-pyrazin-2-yl)-[4-fluoro-3-(7-morpholin-4-yl-quinazolin-4-yl)-phenyl]methanol <br><br> 1H NMR (500 MHz, DMSO-d6) ppm = 9.09 (s, 1H), 8.30 (s, 1H), 7.60-7.50 (m, 4H), 7.41-7.33 (m, 1H), 7.23-7.17 (m, 1H), 6.20 (d, J = 5.4, 1H), 6.04 (d, J = 5.2, 1H), 3.81-3.76 (m, 4H), 3.47-3.42 (m, 4H), 2.50 (s, 3H), 2.43 (s, 3H). | A | A | A |
| 355 | 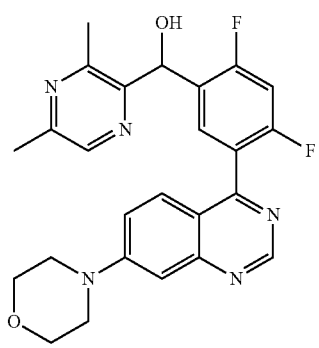 [SMILES: Cc1cnc(C(O)c2cc(-c3ncnc4cc(N5CCOCC5)ccc34)c(F)cc2F)c(C)n1] MS: 464.3 (M + H$^+$) | [2,4-Difluoro-5-(7-morpholin-4-yl-quinazolin-4-yl)-phenyl]-(3,5-dimethyl-pyrazin-2-yl)methanol <br><br> 1H NMR (500 MHz, DMSO-d6) ppm = 9.12 (s, 1H), 8.26 (s, 1H), 7.89 (t, J = 8.2, 1H), 7.61 (dd, J = 9.4, 3.2, 1H), 7.56 (dd, J = 9.4, 2.5, 1H), 7.39 (t, J = 10.1, 1H), 7.21 (d, J = 2.4, 1H), 6.28 (d, J = 6.0, 1H), 6.23 (d, J = 6.0, 1H), 3.82-3.75 (m, 4H), 3.49-3.41 (m, 4H), 2.62 (s, 3H), 2.43 (s, 3H). | B | B | B |

-continued

| No. | Structural formula | Name | IC$_{50}$ DNA-PK | IC$_{50}$ pDNA-PK | K$_i$ [Kv1.11 hERG] |
|---|---|---|---|---|---|
| 356 | MS: 456.2 (M + H⁺) | [4-Fluoro-3-(7-morpholin-4-yl-quinazolin-4-yl)-phenyl]pyrrolo[1,2-a]-pyrazin-1-ylmethanol | A | A | D |
| 357 | MS: 448.2 (M + H⁺) | [2-Fluoro-5-(7-morpholin-4-yl-quinazolin-4-yl)-phenyl]-(6-methoxy-pyridazin-3-yl)-methanol | B | B | A |
| 358 | MS: 474.2 (M + H⁺) | [2,4-Difluoro-5-(7-morpholin-4-yl-quinazolin-4-yl)-phenyl]pyrrolo[1,2-a]-pyrazin-1-ylmethanol | A | A | C |

356: 1H NMR (500 MHz, DMSO-d6) ppm = 9.10 (s, 1H), 8.20 (dd, J = 4.8, 1.0, 1H), 7.79-7.72 (m, 3H), 7.53-7.45 (m, 3H), 7.40-7.34 (m, 1H), 7.20 (d, J = 2.1, 1H), 7.02 (dt, J = 4.1, 1.2, 1H), 6.87 (dd, J = 4.1, 2.5, 1H), 6.33 (d, J = 4.9, 1H), 6.06 (d, J = 4.8, 1H), 3.82-3.76 (m, 4H), 3.48-3.42 (m, 4H).

357: 1H NMR (500 MHz, DMSO-d6) ppm = 9.08 (s, 1H), 8.00 (dd, J = 7.1, 2.3, 1H), 7.89 (d, J = 9.4, 1H), 7.80-7.71 (m, 2H), 7.55 (dd, J = 9.5, 2.6, 1H), 7.38 (dd, J = 10.0, 8.4, 1H), 7.27-7.18 (m, 2H), 6.57 (d, J = 4.8, 1H), 6.24 (d, J = 4.8, 1H), 4.01 (s, 3H), 3.85-3.71 (m, 4H), 3.51-3.40 (m, 4H).

358: 1H NMR (500 MHz, DMSO-d6) ppm = 9.12 (s, 1H), 8.25-8.19 (m, 1H), 7.94 (t, J = 8.2, 1H), 7.78 (dd, J = 2.5, 1.3, 1H), 7.58 (dd, J = 9.3, 3.0, 1H), 7.55 (dd, J = 9.4, 2.4, 1H), 7.47-7.39 (m, 2H), 7.22 (d, J = 2.3, 1H), 6.97-6.93 (m, 1H), 6.91 (dd, J = 4.1, 2.5, 1H), 6.43 (d, J = 5.9, 1H), 6.30 (d, J = 5.9, 1H), 3.82-3.76 (m, 4H), 3.49-3.44 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 359 | | [2-Chloro-4-fluoro-5-(7-morpholin-4-yl-quinazolin-4-yl)-phenyl]pyrrolo[1,2-a]-pyrazin-1-ylmethanol | A | A | D |
| | MS: 490.2/492.2 (M + H$^+$) (Cl isotopy, rel. peak intensity ratio [%] 100:31) | 1H NMR (500 MHz, DMSO-d6) ppm = 9.12 (s, 1H), 8.20 (dd, J = 4.7, 1.0, 1H), 7.97 (d, J = 7.8, 1H), 7.76 (dd, J = 2.5, 1.3, 1H), 7.63 (d, J = 9.5, 1H), 7.60 (dd, J = 9.4, 3.2, 1H), 7.55 (dd, J = 9.4, 2.6, 1H), 7.40 (d, J = 4.8, 1H), 7.21 (d, J = 2.5, 1H), 7.00-6.95 (m, 1H), 6.91 (dd, J = 4.1, 2.5, 1H), 6.48 (d, J = 6.2, 1H), 6.36 (d, J = 6.1, 1H), 3.81-3.75 (m, 4H), 3.48-3.43 (m, 4H). | | | |
| 360 | | 2-{[4-Fluoro-3-(7-morpholin-4-yl-quinazolin-4-yl)-phenyl]hydroxy-methyl}-3-methyl-3H-pyrimidin-4-one | B | B | A |
| | MS: 448.3 (M + H$^+$) | 1H NMR (400 MHz, DMSO-d6) ppm = 9.10 (s, 1H), 7.91 (d, J = 6.5, 1H), 7.67-7.60 (m, 2H), 7.60-7.50 (m, 2H), 7.44 (t, J = 9.5, 1H), 7.20 (d, J = 1.7, 1H), 6.72 (s, 1H), 6.38 (d, J = 6.5, 1H), 6.00 (s, 1H), 3.82-3.73 (m, 4H), 3.48 (s, 3H), 3.47-3.42 (m, 4H). | | | |
| 361 | | [2-Chloro-5-(7-morpholin-4-yl-quinazolin-4-yl)-phenyl]pyrrolo[1,2-a]-pyrazin-1-ylmethanol | B | B | D |
| | MS: 472.2/474.2 (M + H$^+$) (Cl isotopy, rel. peak intensity ratio [%] 100:33) | 1H NMR (500 MHz, DMSO-d6) ppm = 9.08 (s, 1H), 8.22-8.19 (m, 1H), 8.14 (d, J = 2.2, 1H), 7.89 (d, J = 9.4, 1H), 7.76 (dd, J = 2.5, 1.3, 1H), 7.70 (dd, J = 8.2, 2.2, 1H), 7.61 (d, J = 8.2, 1H), 7.53 (dd, J = 9.5, 2.6, 1H), 7.43 (d, J = 4.8, 1H), 7.21 (d, J = 2.6, 1H), 7.00-6.97 (m, 1H), 6.93-6.90 (m, 1H), 6.45-6.40 (m, 2H), 3.81-3.76 (m, 4H), 3.48-3.42 (m, 4H). | | | |

| No. | Structural formula | Name | IC₅₀ DNA-PK | IC₅₀ pDNA-PK | K$_i$ [Kv1.11 hERG] |
|---|---|---|---|---|---|
| 362 | 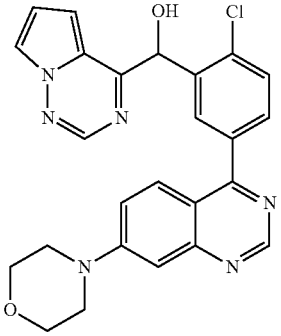 [SMILES: OC(c1cc(-c2ncnc3cc(N4CCOCC4)ccc23)ccc1Cl)c1ncnn2cccc12]<br>MS: 473.2/475.2 (M + H⁺) (Cl isotopy, rel. peak intensity ratio [%] 100:38) | [2-Chloro-5-(7-morpholin-4-yl-quinazolin-4-yl)-phenyl]pyrrolo[2,1-f]-[1,2,4]triazin-4-yl-methanol<br><br>1H NMR (500 MHz, DMSO-d6) ppm = 9.08 (s, 1H), 8.49 (s, 1H), 8.16 (d, J = 2.2, 1H), 8.12 (dd, J = 2.6, 1.4, 1H), 7.88 (d, J = 9.4, 1H), 7.74 (dd, J = 8.2, 2.2, 1H), 7.64 (d, J = 8.2, 1H), 7.54 (dd, J = 9.5, 2.6, 1H), 7.23-7.19 (m, 2H), 7.06 (dd, J = 4.6, 2.6, 1H), 6.80 (d, J = 5.7, 1H), 6.44 (d, J = 5.7, 1H), 3.81-3.76 (m, 4H), 3.48-3.43 (m, 4H). | B | B | D |
| 363 | 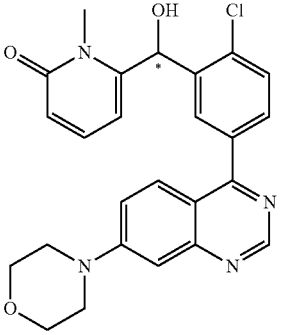<br>MS: 463.2/465.1 (M + H⁺) (Cl isotopy, rel. peak intensity ratio [%] 100:42); R$_t$ 4.63 min (SFC, Chiralcel OJ-H, CO₂/20% by vol. of methanol, 0.5% by vol. of diethylamine) | 6-{[2-Chloro-5-(7-morpholin-4-yl-quinazolin-4-yl)-phenyl]hydroxy-methyl}-1-methyl-1H-pyridin-2-one (Ena 2)<br><br>see racemate | C | C | B |
| 364 | 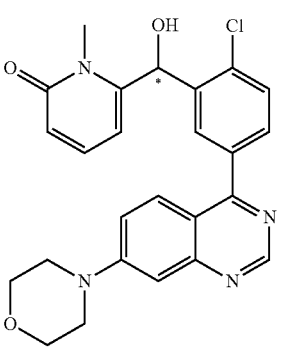 [SMILES: Cn1c(C(O)c2cc(-c3ncnc4cc(N5CCOCC5)ccc34)ccc2Cl)cccc1=O]<br>MS: 463.2/465.2 (M + H⁺) (Cl isotopy, rel. peak intensity ratio [%] 100:41); R$_t$ 2.74 min (SFC, Chiralcel OJ-H, CO₂/20% by vol. of methanol, 0.5% by vol. of diethylamine) | 6-{[2-Chloro-5-(7-morpholin-4-yl-quinazolin-4-yl)-phenyl]hydroxy-methyl}-1-methyl-1H-pyridin-2-one (Ena 1)<br><br>see racemate | A | A | A |

-continued

| No. | Structural formula | Name | IC₅₀ DNA-PK | IC₅₀ pDNA-PK | K_i [Kv1.11 hERG] |
|---|---|---|---|---|---|
| 365 | | 6-{[2-Fluoro-5-(7-morpholin-4-yl-quinazolin-4-yl)-phenyl]hydroxy-methyl}-1-methyl-1H-pyridin-2-one (Ena 2) | B | B | A |
| | MS: 447.2 (M + H⁺); R_t 7.64 min (SFC, Chiralpak AS-H, CO₂/25% by vol. of methanol) | see racemate | | | |
| 366 | | 6-{[2-Fluoro-5-(7-morpholin-4-yl-quinazolin-4-yl)-phenyl]hydroxy-methyl}-1-methyl-1H-pyridin-2-one (Ena 1) | C | C | A |
| | MS: 447.2 (M + H⁺); R_t 4.61 min (SFC, Chiralpak AS-H, CO₂/25% by vol. of methanol) | see racemate | | | |
| 367 | | 6-{[4-Fluoro-3-(7-morpholin-4-yl-quinazolin-4-yl)-phenyl]hydroxy-methyl}-2H-pyridazin-3-one (Ena 1) | A | B | A |
| | MS: 434.1 (M + H⁺); Rt 13.79 min, (SFC, Chiralcel OJ-H, OJ-H, CO₂/15% by vol. of methanol, 0.5% by vol. of diethylamine) Ena 2 to this compound: Example 76 | see enantiomer | | | |

| No. | Structural formula | Name | IC$_{50}$ DNA-PK | IC$_{50}$ pDNA-PK | K$_i$ [Kv1.11 hERG] |
|---|---|---|---|---|---|
| 368 | MS: 482.2/484.2 (M + H$^+$) (Cl isotopy, rel. peak intensity ratio [%] 100:41) | 2-{[2-Chloro-4-fluoro-5-(7-morpholin-4-yl-quinazolin-4-yl)-phenyl]hydroxy-methyl}-3-methyl-3H-pyrimidin-4-one | C | C | A |
| | 1H NMR (500 MHz, DMSO-d6) ppm = 9.14 (s, 1H), 7.88 (d, J = 7.7, 1H), 7.83 (d, J = 6.5, 1H), 7.70 (d, J = 9.4, 1H), 7.63 (dd, J = 9.4, 3.2, 1H), 7.57 (dd, J = 9.5, 2.5, 1H), 7.23 (d, J = 2.4, 1H), 6.91 (d, J = 7.0, J = 7.0, 1H), 6.39 (d, J = 6.5, 1H), 6.15 (d, 1H), 3.83-3.76 (m, 4H), 3.72 (s, 3H), 3.50-3.44 (m, 4H). | | | | |
| 369 | MS: 473.1/475.2 (M + H$^+$) (Cl isotopy, rel. peak intensity ratio [%] 100:25) | [2-Chloro-5-(7-morpholin-4-yl-quinazolin-4-yl)-phenyl]imidazo-[1,2-a]pyrazin-8-yl-methanol | C | C | B |
| | 1H NMR (500 MHz, DMSO-d6) ppm = 9.11 (s, 1H), 8.57 (d, J = 4.5, 1H), 8.27 (d, J = 2.2, 1H), 8.18 (d, J = 1.1, 1H), 8.04 (d, J = 9.4, 1H), 7.88 (d, J = 1.1, 1H), 7.83 (d, J = 4.5, 1H), 7.72 (dd, J = 8.2, 2.3, 1H), 7.62-7.55 (m, 2H), 7.23 (d, J = 2.6, 1H), 6.87 (d, J = 5.8, 1H), 6.50 (d, J = 5.9, 1H), 3.83-3.78 (m, 4H), 3.50-3.45 (m, 4H). | | | | |
| 370 | MS: 472.2 (M + H$^+$) | [2-Fluoro-5-(7-morpholin-4-yl-quinazolin-4-yl)-phenyl]-(9-methyl-9H-purin-6-yl)-methanol | C | B | A |
| | 1H NMR (500 MHz, DMSO-d6) ppm = 9.07 (s, 1H), 8.91 (s, 1H), 8.58 (s, 1H), 8.28 (dd, J = 7.0, 2.3, 1H), 8.05 (d, J = 9.4, 1H), 7.72 (ddd, J = 8.3, 5.0, 2.4, 1H), 7.58 (dd, J = 9.5, 2.6, 1H), 7.30 (dd, J = 10.0, 8.5, 1H), 7.21 (d, J = 2.5, 1H), 6.66 (d, J = 5.5, 1H), 6.44 (d, J = 5.6, 1H), 3.85 (s, 3H), 3.82-3.78 (m, 4H), 3.49-3.45 (m, 4H). | | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 371 | | [2-Chloro-5-(7-morpholin-4-yl-quinazolin-4-yl)-phenyl]-(9-methyl-9H-purin-6-yl)-methanol | C | B | C |

MS: 488.2/490.2 (M + H⁺) (Cl isotopy, rel. peak intensity ratio [%] 100:33)

1H NMR (500 MHz, DMSO-d6) ppm = 9.10 (s, 1H), 8.90 (s, 1H), 8.59 (s, 1H), 8.38 (d, J = 2.2, 1H), 8.12 (d, J = 9.4, 1H), 7.70 (dd, J = 8.2, 2.3, 1H), 7.60 (dd, J = 9.5, 2.6, 1H), 7.56 (d, J = 8.2, 1H), 7.23 (d, J = 2.6, 1H), 6.71 (d, J = 5.4, 1H), 6.53 (d, J = 5.4, 1H), 3.86 (s, 3H), 3.82-3.77 (m, 4H), 3.49-3.45 (m, 4H).

| 372 | | [2-Fluoro-5-(7-morpholin-4-yl-quinazolin-4-yl)-phenyl]imidazo-[1,2-a]pyrazin-8-yl-methanol | C | B | A |

MS: 457.2 (M + H⁺)

1H NMR (500 MHz, DMSO-d6) ppm = 9.08 (s, 1H), 8.58 (d, J = 4.5, 1H), 8.24-8.16 (m, 2H), 8.00 (d, J = 9.4, 1H), 7.91-7.83 (m, 2H), 7.74 (ddd, J = 8.1, 5.0, 2.4, 1H), 7.57 (dd, J = 9.5, 2.6, 1H), 7.33 (dd, J = 10.0, 8.5, 1H), 7.22 (d, J = 2.5, 1H), 6.80 (d, J = 5.9, 1H), 6.39 (d, J = 6.0, 1H), 3.86-3.75 (m, 4H), 3.52-3.43 (m, 4H).

| 373 | | [2-Fluoro-5-(7-morpholin-4-yl-quinazolin-4-yl)-phenyl]-[1,2,4]-triazolo[4,3-a]pyridin-5-ylmethanol | B | B | B |

MS: 457.2 (M + H⁺)

1H NMR (500 MHz, DMSO-d6) ppm = 9.36-9.30 (m, 1H), 9.07 (s, 1H), 8.03 (dd, J = 7.2, 2.3, 1H), 7.86-7.76 (m, 3H), 7.52-7.38 (m, 3H), 7.21 (d, J = 2.6, 1H), 6.91 (d, J = 5.6, 1H), 6.87-6.80 (m, 1H), 6.53 (d, J = 5.6, 1H), 3.83-3.74 (m, 4H), 3.48-3.40 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 374 | 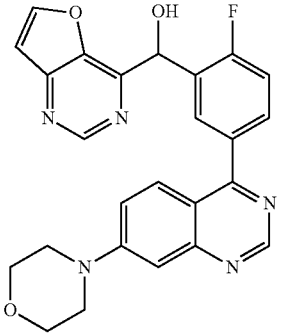 [SMILES: OC(c1cc(-c2ncnc3cc(N4CCOCC4)ccc23)ccc1F)c1ncnc2ccoc12]<br>MS: 458.2 (M + H⁺) | [2-Fluoro-5-(7-morpholin-4-yl-quinazolin-4-yl)-phenyl]furo[3,2-d]-pyrimidin-4-yl-methanol<br><br>1H NMR (500 MHz, DMSO-d6) ppm = 9.08 (s, 1H), 9.02 (s, 1H), 8.59 (d, J = 2.2, 1H), 8.20 (dd, J = 7.0, 2.3, 1H), 7.92 (d, J = 9.4, 1H), 7.77 (ddd, J = 8.4, 5.0, 2.4, 1H), 7.57 (dd, J = 9.5, 2.6, 1H), 7.37 (dd, J = 10.0, 8.5, 1H), 7.27 (d, J = 2.3, 1H), 7.22 (d, J = 2.5, 1H), 6.73 (d, J = 5.2, 1H), 6.48 (d, J = 5.1, 1H), 3.82-3.76 (m, 4H), 3.49-3.44 (m, 4H). | A | B | B |
| 375 | 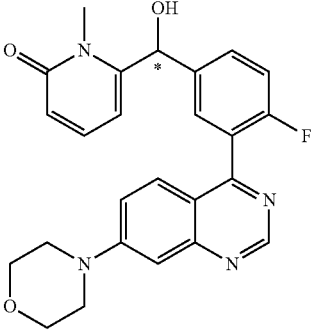<br>MS: 447.3 (M + H⁺); R$_t$ 4.15 min (SFC, Chiralcel OJ-H, CO$_2$/20% by vol. of methanol, 0.5% by vol. of diethylamine) | 6-{[4-Fluoro-3-(7-morpholin-4-yl-quinazolin-4-yl)-phenyl]hydroxy-methyl}-1-methyl-1H-pyridin-2-one (Ena 2)<br><br>see racemate | A | B | A |
| 376 | 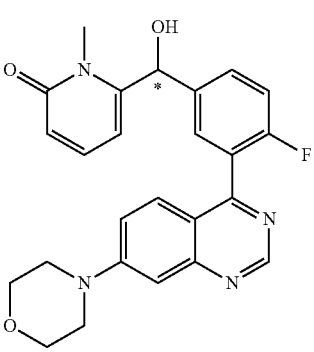<br>MS: 447.3 (M + H⁺); R$_t$ 3.23 min (SFC, Chiralcel OJ-H, CO$_2$/20% by vol. of methanol, 0.5% by vol. of diethylamine) | 6-{[4-Fluoro-3-(7-morpholin-4-yl-quinazolin-4-yl)-phenyl]hydroxy-methyl}-1-methyl-1H-pyridin-2-one (Ena 1)<br><br>see racemate | A | A | A |

-continued

| No. | Structural formula | Name | IC$_{50}$ DNA-PK | IC$_{50}$ pDNA-PK | K$_i$ [Kv1.11 hERG] |
|---|---|---|---|---|---|
| 377 | MS: 475.1/477.1 (M + H$^+$) (Cl isotopy, rel. peak intensity ratio [%] 100:34); R$_t$ 6.14 min (SFC, Chiralpak AD-H, CO$_2$/40% by vol. of methanol, 0.5% by vol. of diethylamine) | 2-[2-Chloro-5-(7-morpholin-4-yl-quinazolin-4-yl)-phenyl]-2-(5-methyl-pyrimidin-4-yl)-acetamide (Ena 2) | B | B | B |
| | | see racemate | | | |
| 378 | MS: 475.1/477.1 (M + H$^+$) (Cl isotopy, rel. peak intensity ratio [%] 100:34); R$_t$ 3.81 min (SFC, Chiralpak AD-H, CO$_2$/40% by vol. of methanol, 0.5% by vol. of diethylamine) | 2-[2-Chloro-5-(7-morpholin-4-yl-quinazolin-4-yl)-phenyl]-2-(5-methyl-pyrimidin-4-yl)-acetamide (Ena 1) | B | B | A |
| | | see racemate | | | |
| 379 | MS: 475.2 (M + H$^+$) | [2,4-Difluoro-5-(7-morpholin-4-yl-quinazolin-4-yl)-phenyl]-[1,2,4]-triazolo[4,3-a]pyridin-3-ylmethanol | B | B | A |
| | | 1H NMR (500 MHz, DMSO-d6) ppm = 9.14 (s, 1H), 8.63 (dt, J = 7.1, 1.2, 1H), 8.02 (t, J = 8.1, 1H), 7.81 (dt, J = 9.3, 1.1, 1H), 7.64 (dd, J = 9.4, 3.3, 1H), 7.60-7.50 (m, 2H), 7.44 (ddd, J = 9.3, 6.6, 1.1, 1H), 7.23 (d, J = 2.5, 1H), 7.06 (td, J = 6.8, 1.0, 1H), 6.87 (d, J = 6.0, 1H), 6.69 (d, J = 6.0, 1H), 3.82-3.77 (m, 4H), 3.49-3.45 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 380 | | 6-{[2,4-Difluoro-5-(7-morpholin-4-yl-quinazolin-4-yl)-phenyl]hydroxy-methyl}-1-methyl-1H-pyridin-2-one (Ena 2) | B | B | A |
| | MS: 465.2 (M + H$^+$); R$_t$ 10.95 min (SFC, Chiralpak AD-H, CO$_2$/20% by vol. of methanol, 0.5% by vol. of diethylamine) | see racemate | | | |
| 381 | | 6-{[2,4-Difluoro-5-(7-morpholin-4-yl-quinazolin-4-yl)-phenyl]hydroxy-methyl}-1-methyl-1H-pyridin-2-one (Ena 1) | A | B | A |
| | MS: 465.2 (M + H$^+$); R$_t$ 7.49 min (SFC, Chiralpak AD-H, CO$_2$/20% by vol. of methanol, 0.5% by vol. of diethylamine) | see racemate | | | |
| 382 | | 6-{[2-Chloro-4-fluoro-5-(7-morpholin-4-yl-quinazolin-4-yl)-phenyl]hydroxy-methyl}-1-methyl-1H-pyridin-2-one (Ena 2) | C | B | B |
| | MS: 481.1/483.1 (M + H$^+$) (Cl isotopy, rel. peak intensity ratio [%] 100:35); R$_t$ 4.55 min (SFC, Chiralpak AD-H, CO$_2$/40% by vol. of methanol, 0.5% by vol. of diethylamine) | see racemate | | | |

| No. | Structural formula | Name | IC$_{50}$ DNA-PK | IC$_{50}$ pDNA-PK | K$_i$ [Kv1.11 hERG] |
|---|---|---|---|---|---|
| 383 | | 6-{[2-Chloro-4-fluoro-5-(7-morpholin-4-yl-quinazolin-4-yl)-phenyl]hydroxy-methyl}-1-methyl-1H-pyridin-2-one (Ena 1) | A | A | A |
| | MS: 481.1/483.1 (M + H$^+$) (Cl isotopy, rel. peak intensity ratio [%] 100:35); R$_t$ 2.24 min (SFC, Chiralpak AD-H, CO$_2$/40% by vol. of methanol, 0.5% by vol. of diethylamine) | see racemate | | | |
| 384 | | (R)-[2,4-Difluoro-5-(7-morpholin-4-yl-quinazolin-4-yl)-phenyl]-(7-methyl-7H-purin-6-yl)-methanol (Ena 2) | C | D | A |
| | MS: 490.2 (M + H$^+$); R$_t$ 5.77 min (SFC, Chiralpak AD-H, CO$_2$/40% by vol. of methanol, 0.5% by vol. of diethylamine) | see racemate | | | |
| 385 | | [2-Chloro-5-(7-morpholin-4-yl-quinazolin-4-yl)-phenyl]-(1-methyl-1H-pyrazolo[3,4-d]-pyrimidin-4-yl)-methanol | C | B | A |
| | MS: 488.2/490.2 (M + H$^+$) (Cl isotopy, rel. peak intensity ratio [%] 100:31) | 1H NMR (500 MHz, DMSO-d6) ppm = 9.05 (s, 1H), 8.92 (s, 1H), 8.44 (s, 1H), 7.95 (d, J = 2.2, 1H), 7.80 (d, J = 9.4, 1H), 7.72 (dd, J = 8.2, 2.2, 1H), 7.66 (d, J = 8.2, 1H), 7.50 (dd, J = 9.5, 2.6, 1H), 7.19 (d, J = 2.5, 1H), 6.90 (d, J = 4.9, 1H), 6.49 (d, J = 4.9, 1H), 4.05 (s, 3H), 3.82-3.76 (m, 4H), 3.47-3.41 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 386 | | [2,4-Difluoro-5-(7-morpholin-4-yl-quinazolin-4-yl)-phenyl]-(7-methyl-7H-purin-6-yl)-methanol (Ena 1) | B | C | A |

MS: 490.2 (M + H$^+$); R$_t$ 3.50 min (SFC, Chiralpak AD-H, CO$_2$/40% by vol. of methanol, 0.5% by vol. of diethylamine)

see racemate

| 387 | | [2,4-Difluoro-5-(7-morpholin-4-yl-quinazolin-4-yl)-phenyl]-(5,6,7,8-tetrahydropyrido-[3,4-d]pyrimidin-4-yl)-methanol | C | B | B |

MS: 491.2 (M + H$^+$)

1H NMR (500 MHz, DMSO-d6) ppm = 9.11 (s, 1H), 8.83 (s, 1H), 7.87 (t, J = 8.2, 1H), 7.60 (dd, J = 9.4, 3.0, 1H), 7.56 (dd, J = 9.4, 2.5, 1H), 7.42 (t, J = 10.1, 1H), 7.21 (d, J = 2.4, 1H), 6.33 (d, J = 6.3, 1H), 6.16 (d, J = 6.3, 1H), 3.86 (s, 2H), 3.82-3.75 (m, 4H), 3.49-3.42 (m, 4H), 3.09-2.94 (m, 2H), 2.94-2.72 (m, 2H).

| 388 | | [4-Fluoro-3-(7-morpholin-4-yl-quinazolin-4-yl)-phenyl]-(5,6,7,8-tetrahydropyrido-[3,4-d]pyrimidin-4-yl)-methanol | C | B | C |

MS: 473.2 (M + H$^+$)

1H NMR (500 MHz, DMSO-d6) ppm = 9.09 (s, 1H), 8.88 (s, 1H), 7.64-7.56 (m, 2H), 7.55-7.50 (m, 2H), 7.38 (dd, J = 10.5, 8.1, 1H), 7.23-7.16 (m, 1H), 6.20 (d, J = 5.8, 1H), 5.96 (d, J = 5.8, 1H), 3.83 (s, 2H), 3.81-3.72 (m, 4H), 3.49-3.39 (m, 4H), 3.05-2.84 (m, 2H), 2.77-2.72 (m, 2H).

-continued

| No. | Structural formula | Name | IC$_{50}$ DNA-PK | IC$_{50}$ pDNA-PK | K$_i$ [Kv1.11 hERG] |
|---|---|---|---|---|---|
| 389 | | [2-Chloro-5-(7-morpholin-4-yl-quinazolin-4-yl)-phenyl]-(5-fluoro-pyrimidin-4-yl)-methanol (Ena 2) | C | C | C |
| | MS: 452.1/454.1 (M + H$^+$) (Cl isotopy, rel. peak intensity ratio [%] 100:34); R$_t$ 3.98 min (SFC, Chiralpak AD-H, CO$_2$/40% by vol. of 2-propanol, 0.5% by vol. of diethylamine) | see racemate | | | |
| 390 | | [2-Chloro-5-(7-morpholin-4-yl-quinazolin-4-yl)-phenyl]-(5-fluoro-pyrimidin-4-yl)-methanol (Ena 1) | B | B | B |
| | MS: 452.1/454.1 (M + H$^+$) (Cl isotopy, rel. peak intensity ratio [%] 100:34); R$_t$ 2.20 min (SFC, Chiralpak AD-H, CO$_2$/40% by vol. of 2-propanol, 0.5% by vol. of diethylamine) | see racemate | | | |
| 391 | | [2-Fluoro-5-(7-morpholin-4-yl-quinazolin-4-yl)-phenyl]-(1-methyl-1H-pyrazolo[3,4-d]-pyrimidin-4-yl)-methanol | C | B | B |
| | MS: 472.2 (M + H$^+$) | 1H NMR (500 MHz, DMSO-d6) ppm = 9.05 (s, 1H), 8.90 (s, 1H), 8.49 (s, 1H), 7.93 (dd, J = 6.9, 2.3, 1H), 7.81 (d, J = 9.4, 1H), 7.74 (ddd, J = 8.4, 4.9, 2.3, 1H), 7.52 (dd, J = 9.5, 2.6, 1H), 7.40 (dd, J = 9.9, 8.5, 1H), 7.19 (d, J = 2.6, 1H), 6.88 (s, 1H), 6.37 (s, 1H), 4.05 (s, 3H), 3.81-3.75 (m, 4H), 3.51-3.42 (m, 4H). | | | |

| No. | Structural formula | Name | IC₅₀ DNA-PK | IC₅₀ pDNA-PK | $K_i$ [Kv1.11 hERG] |
|---|---|---|---|---|---|
| 392 | MS: 432.2 (M + H⁺) | [2-Fluoro-5-(7-morpholin-4-yl-quinazolin-4-yl)-phenyl]-(5-methyl-pyrimidin-4-yl)-methanol | B | B | B |

1H NMR (500 MHz, DMSO-d6) ppm = 9.08 (s, 1H), 8.98 (s, 1H), 8.64 (s, 1H), 8.07 (dd, J = 7.1, 2.3, 1H), 7.93 (d, J = 9.4, 1H), 7.74 (ddd, J = 8.3, 5.0, 2.3, 1H), 7.57 (dd, J = 9.5, 2.6, 1H), 7.35 (dd, J = 10.1, 8.4, 1H), 7.21 (d, J = 2.6, 1H), 6.38 (d, J = 6.0, 1H), 6.25 (d, J = 6.0, 1H), 3.82-3.76 (m, 4H), 3.51-3.43 (m, 4H), 2.41 (s, 3H).

| 393 | MS: 432.2 (M + H⁺) | [2-Fluoro-5-(7-morpholin-4-yl-quinazolin-4-yl)-phenyl]-(3-methyl-pyrazin-2-yl)-methanol | B | C | B |

1H NMR (500 MHz, DMSO-d6) ppm = 9.08 (s, 1H), 8.45 (d, J = 2.5, 1H), 8.41 (d, J = 2.5, 1H), 8.09 (dd, J = 7.1, 2.3, 1H), 7.94 (d, J = 9.4, 1H), 7.74 (ddd, J = 7.9, 5.0, 2.3, 1H), 7.56 (dd, J = 9.5, 2.6, 1H), 7.33 (dd, J = 10.1, 8.4, 1H), 7.21 (d, J = 2.5, 1H), 6.35 (d, J = 5.8, 1H), 6.32 (d, J = 5.9, 1H), 3.83-3.76 (m, 4H), 3.45 (t, J = 4.9, 4H), 2.68 (s, 3H).

| 394 | MS: 448.2 (M + H⁺) | [2-Fluoro-5-(7-morpholin-4-yl-quinazolin-4-yl)-phenyl]-(3-methoxy-pyrazin-2-yl)-methanol | B | B | D |

1H NMR (500 MHz, DMSO-d6) ppm = 9.08 (s, 1H), 8.19 (d, J = 2.7, 1H), 8.17 (d, J = 2.7, 1H), 8.07 (dd, J = 7.1, 2.3, 1H), 7.93 (d, J = 9.4, 1H), 7.73 (ddd, J = 8.3, 5.0, 2.4, 1H), 7.57 (dd, J = 9.5, 2.6, 1H), 7.33 (dd, J = 10.1, 8.4, 1H), 7.22 (d, J = 2.5, 1H), 6.35 (d, J = 6.0, 1H), 6.21 (d, J = 6.0, 1H), 3.98 (s, 3H), 3.82-3.76 (m, 4H), 3.46 (dd, J = 5.9, 3.9, 4H).

| No. | Structural formula | Name | IC$_{50}$ DNA-PK | IC$_{50}$ pDNA-PK | K$_i$ [Kv1.11 hERG] |
|---|---|---|---|---|---|
| 395 | | [2-Chloro-4-fluoro-5-(7-morpholin-4-yl-quinazolin-4-yl)-phenyl]imidazo-[1,2-a]pyrazin-8-yl-methanol (Ena 2) | C | C | B |
| | MS: 491.2/493.2 (M + H$^+$) (Cl isotopy, rel. peak intensity ratio [%] 100:37); R$_t$ 14.57 min (SFC, Chiralpak AD-H, CO$_2$/40% by vol. of methanol, 0.5% by vol. of diethylamine) | see racemate | | | |
| 396 | | (S)-[2-Chloro-4-fluoro-5-(7-morpholin-4-yl-quinazolin-4-yl)-phenyl]imidazo-[1,2-a]pyrazin-8-yl-methanol (Ena 1) | B | A | A |
| | MS: 491.2/493.1 (M + H$^+$) (Cl isotopy, rel. peak intensity ratio [%] 100:35); R$_t$ 4.27 min (SFC, Chiralpak AD-H, CO$_2$/40% by vol. of methanol, 0.5% by vol. of diethylamine) | see racemate | | | |
| 397 | | [2-Chloro-4-fluoro-5-(7-morpholin-4-yl-quinazolin-4-yl)-phenyl]imidazo-[1,2-a]pyrazin-8-yl-methanol | B | A | A |
| | MS: 491.2/493.1 (M + H$^+$) (Cl isotopy, rel. peak intensity ratio [%] 100:35) | 1H NMR (500 MHz, DMSO-d6) ppm = 9.13 (s, 1H), 8.55 (d, J = 4.5, 1H), 8.17 (d, J = 1.1, 1H), 8.06 (d, J = 7.8, 1H), 7.85 (d, J = 1.1, 1H), 7.80 (d, J = 4.5, 1H), 7.67 (dd, J = 9.4, 3.1, 1H), 7.61 (d, J = 9.5, 1H), 7.57 (dd, J = 9.5, 2.6, 1H), 7.22 (d, J = 2.5, 1H), 6.81 (d, J = 5.3, 1H), 6.52 (d, J = 6.1, 1H), 3.81-3.77 (m, 4H), 3.49-3.45 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 398 | MS: 461.2 (M + H$^+$) | 1-Ethyl-6-{[4-fluoro-3-(7-morpholin-4-yl-quinazolin-4-yl)-phenyl]hydroxy-methyl}-1H-pyridin-2-one | B | B | A |

1H NMR (500 MHz, DMSO-d6) ppm = 9.10 (s, 1H), 7.63-7.56 (m, 2H), 7.54 (dd, J = 9.4, 2.5, 1H), 7.52-7.43 (m, 2H), 7.41 (dd, J = 9.1, 6.9, 1H), 7.20 (d, J = 2.4, 1H), 6.58 (d, J = 5.0, 1H), 6.35 (dd, J = 9.1, 1.4, 1H), 6.31 (dd, J = 7.0, 1.4, 1H), 5.91 (d, J = 5.0, 1H), 4.05-3.88 (m, 2H), 3.81-3.74 (m, 4H), 3.48-3.39 (m, 4H), 0.95 (t, J = 6.9, 3H).

| No. | Structural formula | Name | IC$_{50}$ DNA-PK | IC$_{50}$ pDNA-PK | K$_i$ [Kv1.11 hERG] |
|---|---|---|---|---|---|
| 399 | MS: 457.2 (M + H$^+$) | [4-Fluoro-3-(7-morpholin-4-yl-quinazolin-4-yl)-phenyl]-[1,2,4]-triazolo[4,3-a]pyridin-3-ylmethanol | A | B | A |

1H NMR (500 MHz, DMSO-d6) ppm = 9.10 (s, 1H), 8.51-8.39 (m, 1H), 7.83-7.74 (m, 1H), 7.74-7.64 (m, 2H), 7.55 (dd, J = 9.4, 3.0, 1H), 7.51 (dd, J = 9.4, 2.4, 1H), 7.48-7.42 (m, 1H), 7.42-7.35 (m, 1H), 7.20 (d, J = 2.3, 1H), 7.04-6.94 (m, 1H), 6.83 (d, J = 5.2, 1H), 6.52 (d, J = 4.8, 1H), 3.88-3.72 (m, 4H), 3.49-3.37 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 400 | MS: 463.1/465.1 (M + H$^+$) (Cl isotopy, rel. peak intensity ratio [%] 100:37) | 6-{[2-Chloro-5-(7-morpholin-4-yl-quinazolin-4-yl)-phenyl]hydroxy-methyl}-1-methyl-1H-pyridin-2-one | A | A | B |

1H NMR (500 MHz, DMSO-d6) ppm = 9.08 (s, 1H), 7.90 (d, J = 2.1, 1H), 7.84 (d, J = 9.4, 1H), 7.79 (dd, J = 8.2, 2.2, 1H), 7.72 (d, J = 8.2, 1H), 7.51 (dd, J = 9.5, 2.6, 1H), 7.33 (dd, J = 9.1, 7.0, 1H), 7.21 (d, J = 2.5, 1H), 6.60 (d, J = 6.2, 1H), 6.38 (dd, J = 9.1, 1.3, 1H), 6.10 (d, J = 6.1, 1H), 5.88 (dd, J = 7.0, 1.4, 1H), 3.84-3.74 (m, 4H), 3.56 (s, 3H), 3.48-3.40 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 401 | 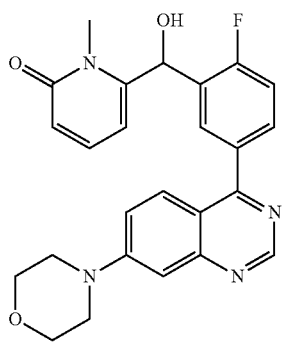 [SMILES: Cn1c(C(O)c2cc(-c3ncnc4cc(N5CCOCC5)ccc34)ccc2F)cccc1=O] MS: 447.2 (M + H$^+$) | 6-{[2-Fluoro-5-(7-morpholin-4-yl-quinazolin-4-yl)-phenyl]hydroxy-methyl}-1-methyl-1H-pyridin-2-one | B | B | C |

1H NMR (500 MHz, DMSO-d6) ppm = 9.06 (s, 1H), 7.85-7.75 (m, 3H), 7.51 (dd, J = 9.5, 2.6, 1H), 7.46 (dd, J = 10.1, 8.4, 1H), 7.38 (dd, J = 9.1, 7.0, 1H), 7.20 (d, J = 2.5, 1H), 6.59 (d, J = 5.9, 1H), 6.38 (dd, J = 9.1, 1.1, 1H), 6.21-6.15 (m, 1H), 6.14 (d, J = 5.8, 1H), 3.81-3.74 (m, 4H), 3.46 (s, 3H), 3.45-3.41 (m, 4H).

| 402 |  MS: 506.2/508.1 (M + H$^+$) (Cl isotopy, rel. peak intensity ratio [%] 100:38) | [2-Chloro-4-fluoro-5-(7-morpholin-4-yl-quinazolin-4-yl)-phenyl]-(1-methyl-1H-pyrazolo[3,4-d]-pyrimidin-4-yl)-methanol | B | B | B |

1H NMR (500 MHz, DMSO-d6) ppm = 9.08 (s, 1H), 8.90 (s, 1H), 8.44 (s, 1H), 7.81 (d, J = 7.6, 1H), 7.69 (d, J = 9.5, 1H), 7.56-7.48 (m, 2H), 7.22-7.16 (m, 1H), 6.92 (d, J = 5.0, 1H), 6.43 (d, J = 5.0, 1H), 4.04 (s, 3H), 3.81-3.74 (m, 4H), 3.48-3.40 (m, 4H).

| 403 | 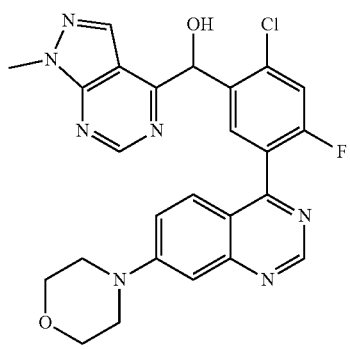 MS: 490.2 (M + H$^+$) | [2,4-Difluoro-5-(7-morpholin-4-yl-quinazolin-4-yl)-phenyl]-(1-methyl-1H-pyrazolo[3,4-d]-pyrimidin-4-yl)-methanol | B | B | B |

1H NMR (500 MHz, DMSO-d6) ppm = 9.07 (s, 1H), 8.89 (s, 1H), 8.49 (s, 1H), 7.79 (t, J = 8.0, 1H), 7.56-7.50 (m, 2H), 7.47 (t, J = 10.0, 1H), 7.19 (s, 1H), 6.88 (s, 1H), 6.32 (s, 1H), 4.04 (s, 3H), 3.81-3.74 (m, 4H), 3.48-3.40 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 404 | MS: 472.2 (M + H$^+$) | [4-Fluoro-3-(7-morpholin-4-yl-quinazolin-4-yl)-phenyl]-(1-methyl-1H-pyrazolo[3,4-d]-pyrimidin-4-yl)-methanol | B | A | A |
| | | 1H NMR (500 MHz, DMSO-d6) ppm = 9.09 (s, 1H), 8.91 (s, 1H), 8.53 (s, 1H), 7.79-7.72 (m, 2H), 7.54-7.44 (m, 2H), 7.38 (dd, J = 9.8, 8.4, 1H), 7.19 (d, J = 2.1, 1H), 6.79 (d, J = 4.0, 1H), 6.10 (d, J = 3.3, 1H), 4.03 (s, 3H), 3.80-3.75 (m, 4H), 3.46-3.41 (m, 4H). | | | |
| 405 | MS: 474.2 (M + H$^+$) | [2-Fluoro-5-(7-morpholin-4-yl-quinazolin-4-yl)-phenyl]thieno[3,2-d}-pyrimidin-4-yl-methanol | A | A | D |
| | | 1H NMR (500 MHz, DMSO-d6) ppm = 9.07 (s, 1H), 9.04 (s, 1H), 8.49 (d, J = 5.5, 1H), 7.91 (dd, J = 6.9, 2.3, 1H), 7.80 (d, J = 9.4, 1H), 7.79-7.74 (m, 1H), 7.63 (d, J = 5.5, 1H), 7.49 (dd, J = 9.5, 2.6, 1H), 7.43 (dd, J = 9.9, 8.5, 1H), 7.21-7.15 (m, 2H), 6.38 (d, J = 2.1, 1H), 3.83-3.76 (m, 4H), 3.47-3.42 (m, 4H). | | | |
| 406 | MS: 474.1 (M + H$^+$) | [2-Fluoro-5-(7-morpholin-4-yl-quinazolin-4-yl)-phenyl]thieno[2,3-d}-pyrimidin-4-yl-methanol | A | A | C |
| | | 1H NMR (500 MHz, DMSO-d6) ppm = 9.06 (s, 1H), 9.03 (s, 1H), 8.48 (d, J = 5.6, 1H), 7.90 (dd, J = 6.9, 2.3, 1H), 7.79 (d, J = 9.4, 1H), 7/8-7.73 (m, 1H), 7.62 (d, J = 5.6, 1H), 7.48 (dd, J = 9.5, 2.6, 1H), 7.41 (dd, J = 9.9, 8.5, 1H), 7.18 (d, J = 2.6, 1H), 7.16 (d, J = 4.7, 1H), 6.36 (d, J = 4.5, 1H), 3.82-3.74 (m, 4H), 3.48-3.40 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 407 | | 2-[2-Chloro-5-(7-morpholin-4-yl-quinazolin-4-yl)-phenyl]-2-(5-methyl-pyrimidin-4-yl)-acetamide | A | B | B |

MS: 475.2/477.2 (M + H⁺) (Cl isotopy, rel. peak intensity ratio [%] 100:36)

1H NMR (400 MHz, DMSO-d6) ppm = 9.06 (s, 1H), 8.95 (s, 1H), 8.64-8.60 (m, 1H), 7.89 (d, J = 9.5, 1H), 7.85-7.79 (m, 1H), 7.76-7.67 (m, 3H), 7.54 (dd, J = 9.4, 2.6, 1H), 7.42-7.34 (m, 1H), 7.20 (d, J = 2.5, 1H), 5.67 (s, 1H), 3.84-3.74 (m, 4H), 3.50-3.42 (m, 4H), 2.31 (s, 3H).

| 408 | | [2-Chloro-5-(7-morpholin-4-yl-quinazolin-4-yl)-phenyl]-(5-methoxy-pyrimidin-4-yl)-methanol (Ena 2) | B | B | C |

MS: 464.2/466.2 (M + H⁺) (Cl isotopy, rel. peak intensity ratio [%] 100:36); R$_t$ 5.41 min (SFC, Chiralpak AD-H, CO$_2$/40% by vol. of 2-propanol, 0.5% by vol. of diethylamine)

see racemate

| 409 | | [2-Chloro-5-(7-morpholin-4-yl-quinazolin-4-yl)-phenyl]-(5-methoxy-pyrimidin-4-yl)-methanol (Ena 1) | B | B | A |

MS: 464.1/466.1 (M + H⁺) (Cl isotopy, rel. peak intensity ratio [%] 100:35); R$_t$ 3.05 min (SFC, Chiralpak AD-H, CO$_2$/40% by vol. of 2-propanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 410 | | [2-Chloro-5-(7-morpholin-4-yl-quinazolin-4-yl)-phenyl]-(3-methoxy-pyrazin-2-yl)-methanol (Ena 2) | A | A | D |
| | MS: 464.2/466.2 (M + H$^+$) (Cl isotopy, rel. peak intensity ratio [%] 100:35); R$_t$ 5.47 min (SFC, Chiralpak AD-H, CO$_2$/40% by vol. of 2-propanol, 0.5% by vol. of diethylamine) | see racemate | | | |
| 411 | | (S)-[2-Chloro-5-(7-morpholin-4-yl-quinazolin-4-yl)-phenyl]-(3-methoxy-pyrazin-2-yl)-methanol (Ena 1) | B | B | C |
| | MS: 464.1/466.1 (M + H$^+$) (Cl isotopy, rel. peak intensity ratio [%] 100:35); R$_t$ 2.84 min (SFC, Chiralpak AD-H, CO$_2$/40% by vol. of 2-propanol, 0.5% by vol. of diethylamine) | see racemate | | | |
| 412 | | [2-Chloro-5-(7-morpholin-4-yl-quinazolin-4-yl)-phenyl]-(5-fluoro-pyrimidin-4-yl)-methanol | C | C | B |
| | MS: 452.1/454.1 (M + H$^+$) (Cl isotopy, rel. peak intensity ratio [%] 100:35) | 1H NMR (500 MHz, DMSO-d6) ppm = 9.10 (s, 1H), 9.03 (d, J = 2.9, 1H), 8.93 (d, J = 2.1, 1H), 8.24 (d, J = 2.2, 1H), 7.96 (d, J = 9.4, 1H), 7.74 (dd, J = 8.2, 2.3, 1H), 7.62 (d, J = 8.2, 1H), 7.59 (dd, J = 9.5, 2.6, 1H), 7.23 (d, J = 2.5, 1H), 6.77 (d, J = 5.5, 1H), 6.38 (d, J = 5.5, 1H), 3.82-3.76 (m, 4H), 3.49-3.44 (m, 4H). | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 413 | | [2-Chloro-5-(7-morpholin-4-yl-quinazolin-4-yl)-phenyl]-(5-methoxy-pyrimidin-4-yl)-methanol | B | B | B |
| | MS: 464.2/466.2 (M + H$^+$) (Cl isotopy, rel. peak intensity ratio [%] 100:36) | 1H NMR (500 MHz, DMSO-d6) ppm = 9.09 (s, 1H), 8.74 (s, 1H), 8.64 (s, 1H), 8.15 (d, J = 2.2, 1H), 7.95 (d, J = 9.4, 1H), 7.69 (dd, J = 8.2, 2.3, 1H), 7.57 (dd, J = 8.9, 2.8, 2H), 7.22 (d, J = 2.5, 1H), 6.43 (d, J = 6.0, 1H), 6.31 (d, J = 6.0, 1H), 4.01 (s, 3H), 3.83-3.74 (m, 4H), 3.50-3.41 (m, 4H). | | | |
| 414 | | [2-Chloro-5-(7-morpholin-4-yl-quinazolin-4-yl)-phenyl]furo[3,2-d}-pyrimidin-4-yl-methanol (Ena 2) | C | A | C |
| | MS: 474.1/476.1 (M + H$^+$) (Cl isotopy, rel. peak intensity ratio [%] 100:34); R$_t$ 6.16 min (SFC, Chiralpak AD-H, CO$_2$/40% by vol. of 2-propanol, 0.5% by vol. of diethylamine) | see racemate | | | |
| 415 | | [2-Chloro-5-(7-morpholin-4-yl-quinazolin-4-yl)-phenyl]furo[3,2-d}-pyrimidin-4-yl-methanol (Ena 1) | B | A | C |
| | MS: 474.1/476.1 (M + H$^+$) (Cl isotopy, rel. peak intensity ratio [%] 100:35); R$_t$ 3.19 min (SFC, Chiralpak AD-H, CO$_2$/40% by vol. of 2-propanol, 0.5% by vol. of diethylamine) | see racemate | | | |

| No. | Structural formula | Name | IC$_{50}$ DNA-PK | IC$_{50}$ pDNA-PK | K$_i$ [Kv1.11 hERG] |
|---|---|---|---|---|---|
| 416 | | [2-Chloro-5-(7-morpholin-4-yl-quinazolin-4-yl)-phenyl]furo[2,3-d}-pyrimidin-4-yl-methanol | B | B | C |

MS: 474.1/476.1 (M + H⁺) (Cl isotopy, rel. peak intensity ratio [%] 100:34)

1H NMR (500 MHz, DMSO-d6) ppm = 9.07 (s, 1H), 8.88 (s, 1H), 8.20 (d, J = 2.5, 1H), 8.03 (d, J = 2.2, 1H), 7.84 (d, J = 9.4, 1H), 7.72 (dd, J = 8.2, 2.2, 1H), 7.65 (d, J = 8.3, 1H), 7.52 (dd, J = 9.4, 2.6, 1H), 7.26 (d, J = 2.5, 1H), 7.20 (d, J = 2.5, 1H), 6.88-6.72 (m, 1H), 6.46 (s, 1H), 3.82-3.76 (m, 4H), 3.48-3.42 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 417 | | [2-Chloro-5-(7-morpholin-4-yl-quinazolin-4-yl)-phenyl]-(5-methyl-pyrimidin-4-yl)-methanol (Ena 2) | C | B | B |

MS: 448.1/450.1 (M + H⁺) (Cl isotopy, rel. peak intensity ratio [%] 100:36); R$_t$ 6.39 min (SFC, Chiralpak AD-H, CO$_2$/40% by vol. of methanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 418 | | [2-Chloro-5-(7-morpholin-4-yl-quinazolin-4-yl)-phenyl]-(5-methyl-pyrimidin-4-yl)-methanol (Ena 1) | C | B | A |

MS: 448.1/450.1 (M + H⁺) (Cl isotopy, rel. peak intensity ratio [%] 100:36); R$_t$ 4.95 min (SFC, Chiralpak AD-H, CO$_2$/40% by vol. of methanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 419 | | [2-Chloro-5-(7-morpholin-4-yl-quinazolin-4-yl)-phenyl]-(5-methyl-pyrimidin-4-yl)-methanol | C | B | B |
| | MS: 448.1/450.1 (M + H⁺) (Cl isotopy, rel. peak intensity ratio [%] 100:37 | 1H NMR (400 MHz, DMSO-d6) ppm = 9.10 (s, 1H), 8.94 (s, 1H), 8.67 (s, 1H), 8.16 (d, J = 2.2, 1H), 7.98 (d, J = 9.4, 1H), 7.72 (dd, J = 8.2, 2.2, 1H), 7.64-7.53 (m, 2H), 7.22 (d, J = 2.5, 1H), 6.47 (d, J = 6.0, 1H), 6.25 (d, J = 6.0, 1H), 3.84-3.73 (m, 4H), 3.51-3.42 (m, 4H), 2.49 (s, 3H). | | | |
| 420 | | [4-Fluoro-3-(7-morpholin-4-yl-quinazolin-4-yl)-phenyl]-(9-methyl-9H-purin-6-yl)-methanol | C | C | A |
| | MS: 472.3 (M + H⁺) | 1H NMR (500 MHz, DMSO-d6) ppm = 9.08 (s, 1H), 8.91 (s, 1H), 8.55 (s, 1H), 7.82-7.73 (m, 2H), 7.56-7.47 (m, 2H), 7.40-7.31 (m, 1H), 7.19 (d, J = 1.3, 1H), 6.43 (d, J = 3.0, 1H), 6.30 (d, J = 5.2, 1H), 3.83 (s, 3H), 3.81-3.75 (m, 4H), 3.47-3.40 (m, 4H). | | | |
| 421 | | [2,4-Difluoro-5-(7-morpholin-4-yl-quinazolin-4-yl)-phenyl]-(9-methyl-9H-purin-6-yl)-methanol | C | B | A |
| | MS: 490.3 (M + H⁺) | 1H NMR (500 MHz, DMSO-d6) ppm = 9.11 (s, 1H), 8.90 (s, 1H), 8.56 (s, 1H), 8.07 (t, J = 8.2, 1H), 7.66 (dd, J = 9.4, 2.9, 1H), 7.56 (dd, J = 9.4, 2.5, 1H), 7.38 (t, J = 10.1, 1H), 7.21 (d, J = 2.4, 1H), 6.61 (d, J = 4.8, 1H), 6.48 (d, J = 5.6, 1H), 3.85 (s, 3H), 3.82-3.75 (m, 4H), 3.52-3.43 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 422 | | [2-Chloro-5-(7-morpholin-4-yl-quinazolin-4-yl)-phenyl]-(3-methoxy-pyrazin-2-yl)-methanol | B | B | C |
| | MS: 464.1/466.1 (M + H$^+$) (Cl isotopy, rel. peak intensity ratio [%] 100:37) | 1H NMR (500 MHz, DMSO-d6) ppm = 9.09 (s, 1H), 8.19-8.14 (m, 2H), 8.11 (d, J = 2.7, 1H), 7.95 (d, J = 9.4, 1H), 7.69 (dd, J = 8.2, 2.3, 1H), 7.60-7.53 (m, 2H), 7.22 (d, J = 2.6, 1H), 6.38 (d, J = 5.8, 1H), 6.27 (d, J = 5.8, 1H), 4.00 (s, 3H), 3.82-3.75 (m, 4H), 3.49-3.42 (m, 4H). | | | |
| 423 | | [2-Chloro-4-fluoro-5-(7-morpholin-4-yl-quinazolin-4-yl)-phenyl]-(7-methyl-7H-purin-6-yl)-methanol | C | C | A |
| | MS: 506.2/4508.3 (M + H$^+$) (Cl isotopy, rel. peak intensity ratio [%] 100:40) | 1H NMR (500 MHz, DMSO-d6) ppm = 9.14 (s, 1H), 8.83 (s, 1H), 8.69 (s, 1H), 8.01 (d, J = 7.8, 1H), 7.71-7.63 (m, 2H), 7.59 (dd, J = 9.4, 2.5, 1H), 7.22 (d, J = 2.4, 1H), 6.87 (d, J = 6.3, 1H), 6.66 (d, J = 6.3, 1H), 4.25 (s, 3H), 3.84-3.73 (m, 4H), 3.52-3.42 (m, 4H). | | | |
| 424 | | 1-(3-{[4-Fluoro-3-(7-morpholin-4-yl-quinazolin-4-yl)-phenyl]hydroxymethyl}pyrazin-2-yl)-3-methyl-imidazolidin-2-one | D | D | A |
| | MS: 516.4 (M + H$^+$) | 1H NMR (500 MHz, DMSO-d6) ppm = 9.09 (s, 1H), 8.50 (d, J = 2.4, 1H), 8.43 (d, J = 2.4, 1H), 7.69-7.59 (m, 2H), 7.59-7.49 (m, 2H), 7.35 (t, J = 9.2, 1H), 7.19 (d, J = 1.9, 1H), 6.23 (d, J = 4.4, 1H), 5.95 (d, J = 5.3, 1H), 3.85 (t, J = 7.8, 2H), 3.82-3.73 (m, | | | |

| No. | Structural formula | Name | IC$_{50}$ DNA-PK | IC$_{50}$ pDNA-PK | K$_i$ [Kv1.11 hERG] |
|---|---|---|---|---|---|
| | | 4H), 3.52-3.40 (m, 6H), 2.78 (s, 3H). | | | |
| 425 | 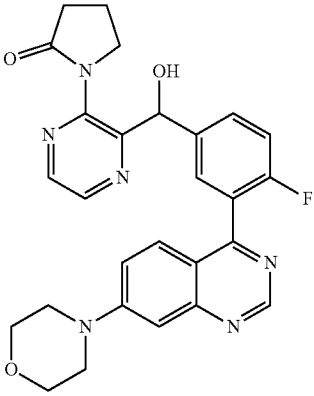 [SMILES: O=C1CCCN1c1nccnc1C(O)c1ccc(F)c(-c2ncnc3cc(N4CCOCC4)ccc23)c1] MS: 501.4 (M + H$^+$) | 1-(3-{[4-Fluoro-3-(7-morpholin-4-yl-quinazolin-4-yl)-phenyl]hydroxymethyl}pyrazin-2-yl)-pyrrolidin-2-one  1H NMR (500 MHz, DMSO-d6) ppm = 9.09 (s, 1H), 8.61 (d, J = 2.4, 1H), 8.52 (d, J = 2.4, 1H), 7.65-7.56 (m, 2H), 7.56-7.49 (m, 2H), 7.36 (t, J = 9.5, 1H), 7.19 (s, 1H), 6.02 (s, 2H), 3.89-3.82 (m, 1H), 3.81-3.74 (m, 4H), 3.74-3.64 (m, 1H), 3.50-3.39 (m, 4H), 2.57-2.41 (m, 2H), 2.17-2.08 (m, 1H), 2.07-1.98 (m, 1H). | D | D | A |
| 426 | 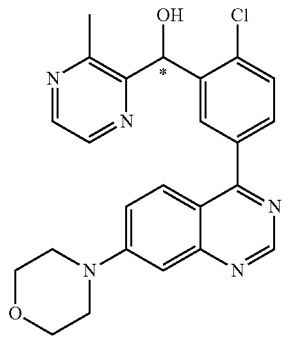 MS: 448.1/450.1 (M + H$^+$) (Cl isotopy, rel. peak intensity ratio [%] 100:36); R$_t$ 5.95 min (SFC, Chiralpak AD-H, CO$_2$/40% by vol. of methanol, 0.5% by vol. of diethylamine) | [2-Chloro-5-(7-morpholin-4-yl-quinazolin-4-yl)-phenyl]-(3-methyl-pyrazin-2-yl)-methanol (Ena 2)  see racemate | C | B | A |
| 427 | 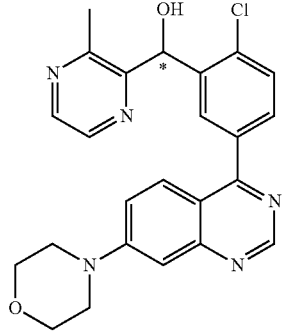 [SMILES: Cc1nccnc1C(O)c1cc(-c2ncnc3cc(N4CCOCC4)ccc23)ccc1Cl] MS: 448.1/450.2 (M + H$^+$) (Cl isotopy, rel. peak intensity ratio [%] 100:31); R$_t$ 3.91 min (SFC, Chiralpak AD-H, CO$_2$/40% by vol. of methanol, 0.5% by vol. of diethylamine) | [2-Chloro-5-(7-morpholin-4-yl-quinazolin-4-yl)-phenyl]-(3-methyl-pyrazin-2-yl)-methanol (Ena 1)  see racemate | C | B | B |

| No. | Structural formula | Name | IC$_{50}$ DNA-PK | IC$_{50}$ pDNA-PK | K$_i$ [Kv1.11 hERG] |
|---|---|---|---|---|---|
| 428 | | [2-Chloro-5-(7-morpholin-4-yl-quinazolin-4-yl)-phenyl]-(3-methyl-pyrazin-2-yl)-methanol | C | A | C |//
| | MS: 448.2/450.2 (M + H⁺) (Cl isotopy, rel. peak intensity ratio [%] 100:36) | 1H NMR (500 MHz, DMSO-d6) ppm = 9.10 (s, 1H), 8.43 (d, J = 2.5, 1H), 8.36 (d, J = 2.5, 1H), 8.18 (d, J = 2.2, 1H), 7.97 (d, J = 9.4, 1H), 7.71 (dd, J = 8.2, 2.3, 1H), 7.61-7.54 (m, 2H), 7.22 (d, J = 2.6, 1H), 6.41 (d, J = 5.8, 1H), 6.30 (d, J = 5.8, 1H), 3.81-3.75 (m, 4H), 3.49-3.42 (m, 4H), 2.76 (s, 3H). | | | |
| 429 | | [2-Chloro-4-fluoro-5-(7-morpholin-4-yl-quinazolin-4-yl)-phenyl]thieno[2,3-d]-pyrimidin-4-yl-methanol | A | A | D |
| | MS: 508.1/510.1 (M + H⁺) (Cl isotopy, rel. peak intensity ratio [%] 100:40) | 1H NMR (500 MHz, DMSO-d6) ppm = 9.07 (s, 1H), 9.05 (s, 1H), 8.46 (d, J = 5.6, 1H), 7.75 (d, J = 7.6, 1H), 7.72 (d, J = 9.6, 1H), 7.61 (d, J = 5.6, 1H), 7.55-7.49 (m, 2H), 7.20 (d, J = 5.0, 1H), 7.19-7.17 (m, 1H), 6.42 (d, J = 5.1, 1H), 3.80-3.75 (m, 4H), 3.46-3.42 (m, 4H). | | | |
| 430 | | [2-Chloro-5-(7-morpholin-4-yl-quinazolin-4-yl)-phenyl]thieno[2,3-d]-pyrimidin-4-yl-methanol | B | A | A |
| | MS: 490.2/492.1 (M + H⁺) (Cl isotopy, rel. peak intensity ratio [%] 100:40) | 1H NMR (500 MHz, DMSO-d6) ppm = 9.06 (s, 1H), 9.04 (s, 1H), 8.47 (d, J = 5.6, 1H), 7.89 (d, J = 2.1, 1H), 7.76 (d, J = 9.4, 1H), 7.73 (dd, J = 8.2, 2.2, 1H), 7.69 (d, J = 8.3, 1H), 7.62 (d, J = 5.5, 1H), 7.47 (dd, J = 9.5, 2.6, 1H), 7.20-7.16 (m, 2H), 6.47 (d, J = 4.9, 1H), 3.80-3.75 (m, 4H), 3.46-3.41 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 431 | MS: 490.2 (M + H$^+$) | [2,4-Difluoro-5-(7-morpholin-4-yl-quinazolin-4-yl)-phenyl]-(7-methyl-7H-purin-6-yl)-methanol | C | B | A |
| | 1H NMR (500 MHz, DMSO-d6) ppm = 9.12 (s, 1H), 8.85 (s, 1H), 8.67 (s, 1H), 7.91 (t, J = 8.1, 1H), 7.64 (dd, J = 9.4, 3.2, 1H), 7.58 (dd, J = 9.4, 2.5, 1H), 7.46 (t, J = 10.1, 1H), 7.21 (d, J = 2.5, 1H), 6.82 (d, J = 6.5, 1H), 6.65 (d, J = 6.5, 1H), 4.19 (s, 3H), 3.81-3.76 (m, 4H), 3.49-3.44 (m, 4H). | | | | |
| 432 | MS: 474.1/476.1 (M + H$^+$) (Cl isotopy, rel. peak intensity ratio [%] 100:34) | [2-Chloro-5-(7-morpholin-4-yl-quinazolin-4-yl)-phenyl]furo[3,2-d]-pyrimidin-4-yl-methanol | C | B | C |
| | 1H NMR (500 MHz, DMSO-d6) ppm = 9.10 (s, 1H), 9.02 (s, 1H), 8.59 (d, J = 2.3, 1H), 8.30 (d, J = 2.2, 1H), 7.96 (d, J = 9.4, 1H), 7.74 (dd, J = 8.2, 2.3, 1H), 7.62 (d, J = 8.2, 1H), 7.59 (dd, J = 9.5, 2.6, 1H), 7.28 (d, J = 2.3, 1H), 7.23 (d, J = 2.6, 1H), 6.79 (d, J = 5.2, 1H), 6.54 (d, J = 5.2, 1H), 3.83-3.75 (m, 4H), 3.50-3.42 (m, 4H). | | | | |
| 433 | MS: 472.2 (M + H$^+$) | [4-Fluoro-3-(7-morpholin-4-yl-quinazolin-4-yl)-phenyl]-(7-methyl-7H-purin-6-yl)-methanol | C | B | A |
| | 1H NMR (500 MHz, DMSO-d6) ppm = 9.08 (s, 1H), 8.90 (s, 1H), 8.60 (s, 1H), 7.68-7.60 (m, 2H), 7.56 (dd, J = 9.4, 2.8, 1H), 7.52 (dd, J = 9.4, 2.4, 1H), 7.44-7.38 (m, 1H), 7.19 (d, J = 2.3, 1H), 6.84 (d, J = 5.5, 1H), 6.37 (d, J = 5.4, 1H), 4.04 (s, 3H), 3.81-3.75 (m, 4H), 3.47-3.41 (m, 4H). | | | | |

| No. | Structural formula | Name | IC$_{50}$ DNA-PK | IC$_{50}$ pDNA-PK | K$_i$ [Kv1.11 hERG] |
|---|---|---|---|---|---|
| 434 | 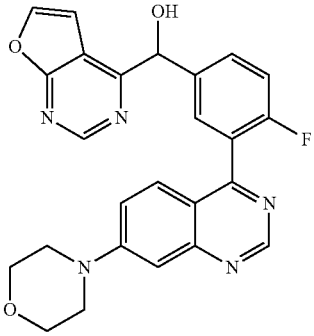 [SMILES: OC(c1ccc(F)c(-c2ncnc3cc(N4CCOCC4)ccc23)c1)c1ncnc2occc12]<br>MS: 458.2 (M + H$^+$) | [4-Fluoro-3-(7-morpholin-4-yl-quinazolin-4-yl)-phenyl]furo[2,3-d]-pyrimidin-4-yl-methanol<br><br>1H NMR (500 MHz, DMSO-d6) ppm = 9.10 (s, 1H), 8.89 (s, 1H), 8.18 (d, J = 2.5, 1H), 7.77-7.72 (m, 2H), 7.54-7.47 (m, 2H), 7.40 (t, J = 9.5, 1H), 7.36 (d, J = 2.5, 1H), 7.20 (d, J = 2.2, 1H), 6.71 (d, J = 4.2, 1H), 6.13 (d, J = 4.2, 1H), 3.81-3.76 (m, 4H), 3.47-3.42 (m, 4H). | A | A | A |
| 435 | 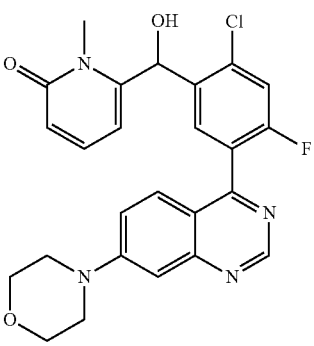<br>MS: 481.2/483.2 (M + H$^+$) (Cl isotopy, rel. peak intensity ratio [%] 100:38) | 6-{[2-Chloro-4-fluoro-5-(7-morpholin-4-yl-quinazolin-4-yl)-phenyl]hydroxy-methyl}-1-methyl-1H-pyridin-2-one<br><br>1H NMR (500 MHz, DMSO-d6) ppm = 9.11 (s, 1H), 7.77 (d, J = 9.5, 1H), 7.74 (d, J = 7.6, 1H), 7.60 (dd, J = 9.4, 3.3, 1H), 7.53 (dd, J = 9.4, 2.5, 1H), 7.33 (dd, J = 9.1, 7.0, 1H), 7.21 (d, J = 2.5, 1H), 6.62 (d, J = 6.3, 1H), 6.37 (dd, J = 9.1, 1.3, 1H), 6.06 (d, J = 6.2, 1H), 5.89-5.85 (m, 1H), 3.81-3.75 (m, 4H), 3.55 (s, 3H), 3.49-3.43 (m, 4H). | B | A | A |
| 436 | 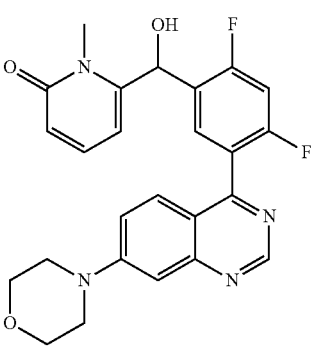<br>MS: 465.3 (M + H$^+$) | 6-{[2,4-Difluoro-5-(7-morpholin-4-yl-quinazolin-4-yl)-phenyl]hydroxy-methyl}-1-methyl-1H-pyridin-2-one<br><br>1H NMR (500 MHz, DMSO-d6) ppm = 9.09 (s, 1H), 7.63 (t, J = 8.1, 1H), 7.59-7.51 (m, 3H), 7.38 (dd, J = 9.1, 7.0, 1H), 7.20 (d, J = 2.3, 1H), 6.60 (d, J = 5.9, 1H), 6.39-6.35 (m, 1H), 6.20-6.16 (m, 1H), 6.09 (d, J = 5.9, 1H), 3.81-3.75 (m, 4H), 3.49-3.40 (m, 7H). | B | B | A |

| No. | Structural formula | Name | IC$_{50}$ DNA-PK | IC$_{50}$ pDNA-PK | K$_i$ [Kv1.11 hERG] |
|---|---|---|---|---|---|
| 437 | 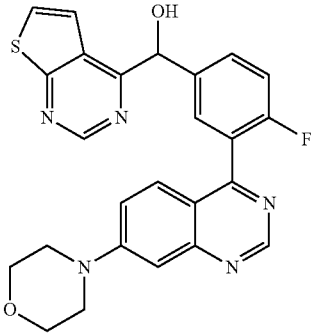<br>MS: 474.1 (M + H$^+$) | [4-Fluoro-3-(7-morpholin-4-yl-quinazolin-4-yl)-phenyl]thieno[2,3-d}-pyrimidin-4-yl-methanol | A | A | C |
| | 1H NMR (400 MHz, DMSO-d6) ppm = 9.09 (s, 1H), 9.08 (s, 1H), 8.47 (d, J = 5.6, 1H), 7.78-7.73 (m, 2H), 7.61 (d, J = 5.6, 1H), 7.54-7.46 (m, 2H), 7.43-7.36 (m, 1H), 7.21-7.18 (m, 1H), 7.13 (d, J = 3.9, 1H), 6.12 (d, J = 3.9, 1H), 3.82-3.73 (m, 4H), 3.48-3.40 (m, 4H). | | | | |
| 438 | 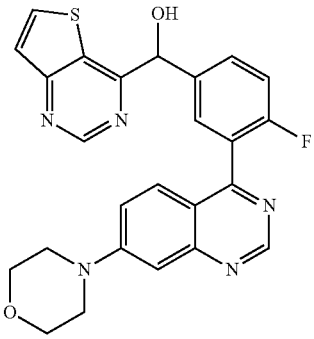 [SMILES: OC(c1ccc(F)c(-c2ncnc3cc(N4CCOCC4)ccc23)c1)c1ncnc2ccsc12]<br>MS: 474.2 (M + H$^+$) | [4-Fluoro-3-(7-morpholin-4-yl-quinazolin-4-yl)-phenyl]thieno[3,2-d}-pyrimidin-4-yl-methanol | A | A | C |
| | 1H NMR (500 MHz, DMSO-d6) ppm = 9.09 (s, 1H), 9.07 (s, 1H), 8.46 (s, 1H), 8.45 (s, 1H), 7.78-7.73 (m, 2H), 7.60 (d, J = 5.5, 1H), 7.52-7.46 (m, 2H), 7.41-7.36 (m, 1H), 7.20-7.18 (m, 1H), 7.11 (d, J = 3.9, 1H), 6.12 (d, J = 3.9, 1H), 3.80-3.75 (m, 4H), 3.46-3.41 (m, 4H). | | | | |
| 439 | 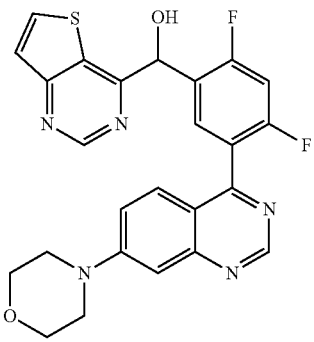 [SMILES: OC(c1cc(-c2ncnc3cc(N4CCOCC4)ccc23)c(F)cc1F)c1ncnc2ccoc12]<br>MS: 492.2 (M + H$^+$) | [2,4-Difluoro-5-(7-morpholin-4-yl-quinazolin-4-yl)-phenyl]thieno[3,2-d}-pyrimidin-4-yl-methanol | A | A | C |
| | 1H NMR (500 MHz, DMSO-d6) ppm = 9.07 (s, 1H), 9.05 (s, 1H), 8.47 (d, J = 5.6, 1H), 7.76 (t, J = 8.0, 1H), 7.61 (d, J = 5.6, 1H), 7.54-7.46 (m, 3H), 7.21-7.16 (m, 2H), 6.32 (d, J = 4.8, 1H), 3.80-3.74 (m, 4H), 3.46-3.41 (m, 4H). | | | | |

-continued

| No. | Structural formula | Name | IC$_{50}$ DNA-PK | IC$_{50}$ pDNA-PK | K$_i$ [Kv1.11 hERG] |
| --- | --- | --- | --- | --- | --- |
| 440 | | [2-Chloro-4-fluoro-5-(7-morpholin-4-yl-quinazolin-4-yl)-phenyl]furo[3,2-d}-pyrimidin-4-yl-methanol (Ena 2) | A | A | B |
| | MS: 492.1/494.1 (M + H$^+$) (Cl isotopy, rel. peak intensity ratio [%] 100:38); R$_t$ 8.33 min (SFC, Chiralpak AD-H, CO$_2$/40% by vol. of methanol, 0.5% by vol. of diethylamine) | | see racemate | | |
| 441 | | [2-Chloro-4-fluoro-5-(7-morpholin-4-yl-quinazolin-4-yl)-phenyl]furo[3,2-d}-pyrimidin-4-yl-methanol (Ena 1) | A | A | C |
| | MS: 492.1/494.1 (M + H$^+$) (Cl isotopy, rel. peak intensity ratio [%] 100:38); R$_t$ 3.83 min (SFC, Chiralpak AD-H, CO$_2$/40% by vol. of methanol, 0.5% by vol. of diethylamine) | | see racemate | | |
| 442 | | [4-Fluoro-3-(7-morpholin-4-yl-quinazolin-4-yl)-phenyl]furo[3,2-d}-pyrimidin-4-yl-methanol (Ena 2) | A | A | A |
| | MS: 458.2 (M + H+); R$_t$ 7.52 min (SFC, Chiralpak AD-H, CO$_2$/40% by vol. of 2-propanol, 0.5% by vol. of diethylamine) | | see racemate | | |

| No. | Structural formula | Name | IC$_{50}$ DNA-PK | IC$_{50}$ pDNA-PK | K$_i$ [Kv1.11 hERG] |
|---|---|---|---|---|---|
| 443 | | [4-fluoro-3-(7-morpholin-4-yl-quinazolin-4-yl)-phenyl]furo[3,2-d]-pyrimidin-4-yl-methanol (Ena 1) | B | B | A* |
| | MS: 458.1 (M + H$^+$); R$_t$ 3.43 min (SFC, Chiralpak AD-H, CO$_2$/40% by vol. of 2-propanol, 0.5% by vol. of diethylamine) | | see racemate | | |
| 444 | | [2,4-Difluoro-5-(7-morpholin-4-yl-quinazolin-4-yl)-phenyl]furo[3,2-d]-pyrimidin-4-yl-methanol (Ena 2) | A | B | A |
| | MS: 476.2 (M + H$^+$); R$_t$ 9.29 min (SFC, Chiralpak AD-H, CO$_2$/30% by vol. of methanol, 0.5% by vol. of diethylamine) | | see racemate | | |
| 445 | 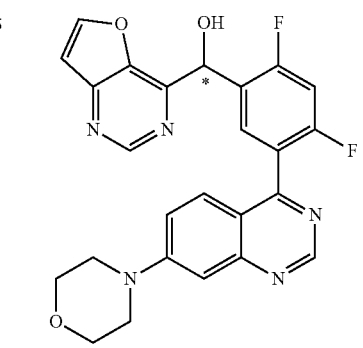 | [2,4-Difluoro-5-(7-morpholin-4-yl-quinazolin-4-yl)-phenyl]furo[3,2-d]-pyrimidin-4-yl-methanol (Ena 1) | B | A | A |
| | MS: 476.1 (M + H$^+$); R$_t$ 5.74 min (SFC, Chiralpak AD-H, CO$_2$/30% by vol. of methanol, 0.5% by vol. of diethylamine) | | see racemate | | |

| No. | Structural formula | Name | IC$_{50}$ DNA-PK | IC$_{50}$ pDNA-PK | K$_i$ [Kv1.11 hERG] |
|---|---|---|---|---|---|
| 446 | MS: 476.2 (M + H$^+$) | [2,4-Difluoro-5-(7-morpholin-4-yl-quinazolin-4-yl)-phenyl]furo[3,2-d]-pyrimidin-4-yl-methanol | A | B | A |

1H NMR (500 MHz, DMSO-d6) ppm = 9.12 (s, 1H), 9.00 (s, 1H), 8.57 (d, J = 2.3, 1H), 8.00 (t, J = 8.1, 1H), 7.59 (dd, J = 9.4, 2.8, 1H), 7.56 (dd, J = 9.4, 2.4, 1H), 7.45 (t, J = 10.1, 1H), 7.27 (d, J = 2.3, 1H), 7.21 (d, J = 2.3, 1H), 6.75 (d, J = 5.4, 1H), 6.43 (d, J = 5.3, 1H), 3.81-3.76 (m, 4H), 3.49-3.42 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 447 | MS: 482.2/484.1 (M + H$^+$) (Cl isotopy, rel. peak intensity ratio [%] 100:40) | [2-Chloro-4-fluoro-5-(7-morpholin-4-yl-quinazolin-4-yl)-phenyl]-(5-methoxy-pyrimidin-4-yl)-methanol | A | B | C |

1H NMR (400 MHz, DMSO-d6) ppm = 9.14 (s, 1H), 8.74 (s, 1H), 8.65 (s, 1H), 7.97 (d, J = 7.9, 1H), 7.69-7.52 (m, 3H), 7.23 (d, J = 2.4, 1H), 6.43-6.32 (m, 2H), 4.01 (s, 3H), 3.80 (dd, J = 5.9, 3.9, 4H), 3.47 (t, J = 4.9, 4H).

| No. | Structural formula | Name | IC$_{50}$ DNA-PK | IC$_{50}$ pDNA-PK | K$_i$ [Kv1.11 hERG] |
|---|---|---|---|---|---|
| 448 | MS: 466.2 (M + H$^+$) | [2,4-Difluoro-5-(7-morpholin-4-yl-quinazolin-4-yl)-phenyl]-(5-methoxy-pyrimidin-4-yl)-methanol | A | B | C |

1H NMR (400 MHz, DMSO-d6) ppm = 9.11 (s, 1H), 8.77 (s, 1H), 8.62 (s, 1H), 7.86 (t, J = 8.2, 1H), 7.66-7.50 (m, 2H), 7.41 (t, J = 10.1, 1H), 7.21 (d, J = 2.1, 1H), 6.32 (d, J = 6.2, 1H), 6.25 (d, J = 6.3, 1H), 3.97 (s, 3H), 3.78 (t, J = 4.9, 4H), 3.45 (t, J = 4.9, 4H).

| No. | Structural formula | Name | IC$_{50}$ DNA-PK | IC$_{50}$ pDNA-PK | K$_i$ [Kv1.11 hERG] |
|---|---|---|---|---|---|
| 449 | | (3-Difluoromethoxy-pyrazin-2-yl)-[2,4-difluoro-5-(7-morpholin-4-yl-quinazolin-4-yl)-phenyl]methanol (Ena 2) | A | B | A |
| | MS: 502.2 (M + H⁺); R$_t$ 3.40 min (SFC, Chiralpak AD-H, CO$_2$/40% by vol. of methanol, 0.5% by vol. of diethylamine) | see racemate | | | |
| 450 | | (3-Difluoromethoxy-pyrazin-2-yl)-[2,4-difluoro-5-(7-morpholin-4-yl-quinazolin-4-yl)-phenyl]methanol (Ena 1) | C | C | B |
| | MS: 502.2 (M + H⁺); R$_t$ 2.00 min (SFC, Chiralpak AD-H, CO$_2$/40% by vol. of methanol, 0.5% by vol. of diethylamine) | see racemate | | | |
| 451 | | (3-Difluoromethoxy-pyrazin-2-yl)-[2,4-difluoro-5-(7-morpholin-4-yl-quinazolin-4-yl)-phenyl]methanol | B | B | B |
| | MS: 502.2 (M + H⁺) | 1H NMR (500 MHz, DMSO-d6) ppm = 9.12 (s, 1H), 8.49 (d, J = 2.6, 1H), 8.32 (d, J = 2.6, 1H), 7.91 (t, J = 8.2, 1H), 7.77 (t, J = 71.7, 1H), 7.61-7.51 (m, 2H), 7.43 (t, J = 10.1, 1H), 7.21 (d, J = 2.4, 1H), 6.48 (d, J = 5.9, 1H), 6.29 (d, J = 4.7, 1H), 3.81-3.75 (m, 4H), 3.48-3.42 (m, 4H). | | | |

| No. | Structural formula | Name | IC$_{50}$ DNA-PK | IC$_{50}$ pDNA-PK | K$_i$ [Kv1.11 hERG] |
|---|---|---|---|---|---|
| 452 | | [2-Chloro-4-fluoro-5-(7-morpholin-4-yl-quinazolin-4-yl)-phenyl]furo[3,2-d]-pyrimidin-4-yl-methanol | A | A | C |

MS: 492.1/494.1 (M + H$^+$) (Cl isotopy, rel. peak intensity ratio [%] 100:41)

1H NMR (500 MHz, DMSO-d6) ppm = 9.15 (s, 1H), 9.01 (s, 1H), 8.59 (d, J = 2.3, 1H), 8.11 (d, J = 7.7, 1H), 7.67 (d, J = 9.4, 1H), 7.64 (dd, J = 9.4, 2.9, 1H), 7.59 (dd, J = 9.4, 2.5, 1H), 7.29 (d, J = 2.3, 1H), 7.24 (d, J = 2.4, 1H), 6.85 (d, J = 5.4, 1H), 6.50 (d, J = 5.3, 1H), 3.83-3.77 (m, 4H), 3.51-3.44 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 453 | | [2,4-Difluoro-5-(7-morpholin-4-yl-quinazolin-4-yl)-phenyl]-(3-methoxy-pyrazin-2-yl)-methanol (Ena 1) | B | A | C |

MS: 466.1 (M + H$^+$); R$_t$ 2.76 min (SFC, Chiralpak AD-H, CO$_2$/40% by vol. of methanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 454 | | [2,4-Difluoro-5-(7-morpholin-4-yl-quinazolin-4-yl)-phenyl]-(3-methoxy-pyrazin-2-yl)-methanol (Ena 2) | A | A | A |

MS: 466.2 (M + H$^+$); R$_t$ 4.60 min (SFC, Chiralpak AD-H, CO$_2$/40% by vol. of methanol, 0.5% by vol. of diethylamine)

see racemate

-continued

| No. | Structural formula | Name | IC$_{50}$ DNA-PK | IC$_{50}$ pDNA-PK | K$_i$ [Kv1.11 hERG] |
|---|---|---|---|---|---|
| 455 | 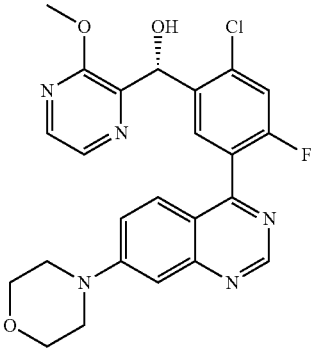 [SMILES: COc1nccnc1[C@H](O)c1cc(-c2ncnc3cc(N4CCOCC4)ccc23)c(F)cc1Cl] MS: 482.1/484.1 (M + H$^+$) (Cl isotopy, rel. peak intensity ratio [%] 100:36); R$_t$ 5.48 min (SFC, Chiralpak AD-H, CO$_2$/40% by vol. of methanol, 0.5% by vol. of diethylamine) | (R)-[2-Chloro-4-fluoro-5-(7-morpholin-4-yl-quinazolin-4-yl)-phenyl]-(3-methoxy-pyrazin-2-yl)-methanol<br><br>see racemate | A | A | B |
| 456 | 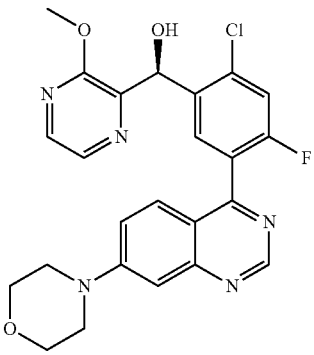 [SMILES: COc1nccnc1[C@@H](O)c1cc(-c2ncnc3cc(N4CCOCC4)ccc23)c(F)cc1Cl] MS: 482.1/484.1 (M + H$^+$) (Cl isotopy, rel. peak intensity ratio [%] 100:35); R$_t$ 2.58 min (SFC, Chiralpak AD-H, CO$_2$/40% by vol. of methanol, 0.5% by vol. of diethylamine) | (S)-[2-Chloro-4-fluoro-5-(7-morpholin-4-yl-quinazolin-4-yl)-phenyl]-(3-methoxy-pyrazin-2-yl)-methanol<br><br>see racemate | A | A | C |
| 457 | 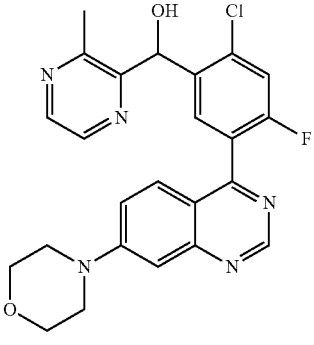 MS: 466.1/468.1 (M + H$^+$) (Cl isotopy, rel. peak intensity ratio [%] 100:36) | [2-Chloro-4-fluoro-5-(7-morpholin-4-yl-quinazolin-4-yl)-phenyl]-(3-methyl-pyrazin-2-yl)-methanol<br><br>1H NMR (500 MHz, DMSO-d6) ppm = 9.13 (s, 1H), 8.43 (d, J = 2.5, 1H), 8.36 (d, J = 2.5, 1H), 7.99 (d, J = 7.8, 1H), 7.67-7.60 (m, 2H), 7.57 (dd, J = 9.4, 2.5, 1H), 7.22 (d, J = 2.4, 1H), 6.44 (d, J = 5.9, 1H), 6.25 (d, J = 5.6, 1H), 3.86-3.72 (m, 4H), 3.52-3.42 (m, 4H), 2.74 (s, 3H). | B | A | A |

-continued

| No. | Structural formula | Name | IC$_{50}$ DNA-PK | IC$_{50}$ pDNA-PK | K$_i$ [Kv1.11 hERG] |
|---|---|---|---|---|---|
| 458 | | [2-Chloro-5-(7-morpholin-4-yl-quinazolin-4-yl)-phenyl]-(6-methoxy-pyridazin-3-yl)-methanol (Ena 1) | A | A | C |

MS: 464.1/466.1 (M + H$^+$) (Cl isotopy, rel. peak intensity ratio [%] 100:36); R$_t$ 11.22 min (SFC, Chiralcel OJ-H, CO$_2$/15% by vol. of 2-propanol, 0.5% by vol. of diethylamine)

1H NMR (400 MHz, DMSO-d6) ppm = 9.08 (s, 1H), 8.07 (d, J = 2.2, 1H), 7.89 (d, J = 9.5, 1H), 7.73-7.67 (m, 2H), 7.63 (d, J = 8.2, 1H), 7.54 (dd, J = 9.5, 2.6, 1H), 7.24-7.19 (m, 2H), 6.59 (d, J = 4.8, 1H), 6.28 (d, J = 4.8, 1H), 4.00 (s, 3H), 3.82-3.75 (m, 4H), 3.48-3.41 (m, 4H).

| No. | Structural formula | Name | IC$_{50}$ DNA-PK | IC$_{50}$ pDNA-PK | K$_i$ [Kv1.11 hERG] |
|---|---|---|---|---|---|
| 459 | | [2-Chloro-5-(7-morpholin-4-yl-quinazolin-4-yl)-phenyl]-(6-methoxy-pyridazin-3-yl)-methanol (Ena 2) | B | B | A* |

MS: 464.1/466.1 (M + H$^+$) (Cl isotopy, rel. peak intensity ratio [%] 100:36); R$_t$ 14.88 min (SFC, Chiralcel OJ-H, CO$_2$/15% by vol. of 2-propanol, 0.5% by vol. of diethylamine)

see racemate

| No. | Structural formula | Name | IC$_{50}$ DNA-PK | IC$_{50}$ pDNA-PK | K$_i$ [Kv1.11 hERG] |
|---|---|---|---|---|---|
| 460 | | [2-Chloro-5-(7-morpholin-4-yl-quinazolin-4-yl)-phenyl]-(6-methoxy-pyridazin-3-yl)-methanol | B | A | A* |

MS: 464.1/466.1 (M + H$^+$) (Cl isotopy, rel. peak intensity ratio [%] 100:36)

1H NMR (500 MHz, DMSO-d6) ppm = 9.09 (s, 1H), 8.08 (d, J = 2.2, 1H), 7.89 (d, J = 9.5, 1H), 7.73-7.67 (m, 2H), 7.63 (d, J = 8.2, 1H), 7.54 (dd, J = 9.4, 2.7, 1H), 7.23-7.19 (m, 2H), 6.59 (d, J = 4.9, 1H), 6.28 (d, J = 4.8, 1H), 4.00 (s, 3H), 3.81-3.75 (m, 4H), 3.48-3.42 (m, 4H).

-continued

| No. | Structural formula | Name | IC$_{50}$ DNA-PK | IC$_{50}$ pDNA-PK | K$_i$ [Kv1.11 hERG] |
|---|---|---|---|---|---|
| 461 | 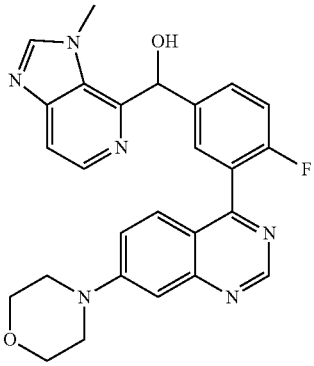 [SMILES: Cn1cnc2ccnc(C(O)c3ccc(F)c(-c4ncnc5cc(N6CCOCC6)ccc45)c3)c21]<br>MS: 471.2 (M + H$^+$) | [4-Fluoro-3-(7-morpholin-4-yl-quinazolin-4-yl)-phenyl]-(3-methyl-3H-imidazo[4,5-c]-pyridin-4-yl)methanol<br><br>1H NMR (500 MHz, DMSO-d6) ppm = 9.08 (s, 1H), 8.33 (s, 1H), 8.25 (d, J = 5.5, 1H), 7.62 (d, J = 5.5, 1H), 7.61-7.50 (m, 4H), 7.42-7.37 (m, 1H), 7.19 (d, J = 2.3, 1H), 6.61 (d, J = 5.5, 1H), 6.43 (d, J = 5.4, 1H), 4.01 (s, 3H), 3.80-3.74 (m, 4H), 3.46-3.41 (m, 4H). | A | A | A* |
| 462 | 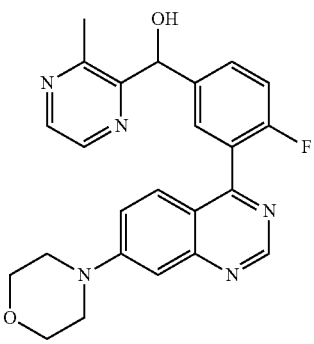<br>MS: 544.1 (M + H$^+$) | [4-Fluoro-3-(7-morpholin-4-yl-quinazolin-4-yl)-phenyl]-(3-iodo-pyrazin-2-yl)-methanol<br><br>1H NMR (500 MHz, DMSO-d6) ppm = 9.09 (s, 1H), 8.62 (d, J = 2.4, 1H), 8.37 (d, J = 2.4, 1H), 7.69-7.61 (m, 2H), 7.58-7.49 (m, 2H), 7.44-7.36 (m, 1H), 7.22-7.17 (m, 1H), 6.33 (d, J = 5.7, 1H), 6.17 (d, J = 5.7, 1H), 3.81-3.75 (m, 4H), 3.47-3.41 (m, 4H). | A | A | B |
| 463 | 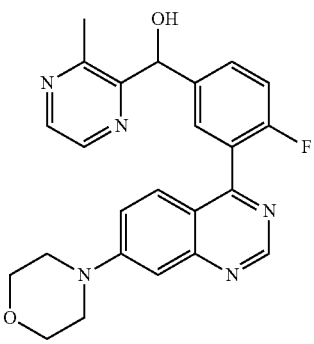<br>MS: 461.2 (M + H$^+$) | (3-Ethoxy-pyridin-2-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 8.14 (dd, J = 4.7, 1.2, 1H), 7.63-7.55 (m, 2H), 7.55-7.47 (m, 2H), 7.41 (dd, J = 8.3, 1.3, 1H), 7.38-7.31 (m, 1H), 7.29 (dd, J = 8.3, 4.7, 1H), 7.21-7.17 (m, 1H), 6.07 (d, J = 6.3, 1H), 5.79 (d, J = 6.6, 1H), 4.06 (q, J = 7.0, 2H), 3.81-3.75 (m, 4H), 3.47-3.41 (m, 4H), 1.28 (t, J = 6.9, 3H). | B | A | B |

-continued

| No. | Structural formula | Name | IC$_{50}$ DNA-PK | IC$_{50}$ pDNA-PK | K$_i$ [Kv1.11 hERG] |
|---|---|---|---|---|---|
| 464 | 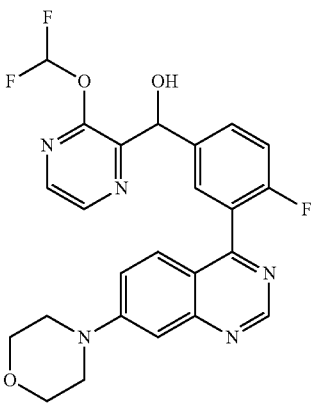 [SMILES: OC(c1ccc(F)c(-c2ncnc3cc(N4CCOCC4)ccc23)c1)c1nccnc1OC(F)F]<br>MS: 484.2 (M + H$^+$) | (3-Difluoromethoxy-pyrazin-2-yl)-[4-fluoro-3-(7-morpholin-4-yl-quinazolin-4-yl)-phenyl]methanol<br><br>1H NMR (500 MHz, DMSO-d6) ppm = 9.09 (s, 1H), 8.51 (d, J = 2.6, 1H), 8.28 (d, J = 2.6, 1H), 7.86-7.55 (m, 3H), 7.54-7.49 (m, 2H), 7.43-7.36 (m, 1H), 7.22-7.17 (m, 1H), 6.30 (d, J = 5.6, 1H), 6.10 (d, J = 4.9, 1H), 3.83-3.73 (m, 4H), 3.48-3.40 (m, 4H). | B | B | B |
| 465 | 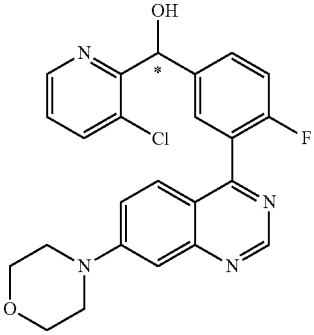 [SMILES: OC(c1ccc(F)c(-c2ncnc3cc(N4CCOCC4)ccc23)c1)c1ncccc1Cl]<br>MS: 451.1/453.1 (M + H$^+$) (Cl isotopy, rel. peak intensity ratio [%] 100:35); R$_t$ 6.63 min (SFC, Chiralpak AD-H, CO$_2$/40% by vol. of 2-propanol, 0.5% by vol. of diethylamine) | (3-Chloro-pyridin-2-yl)-[4-fluoro-3-(7-morpholin-4-yl-quinazolin-4-yl)-phenyl]methanol (Ena 2)<br><br>see racemate | A | A | B |
| 466 | 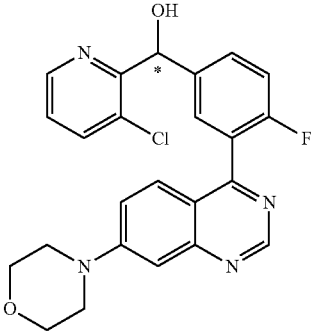 [SMILES: OC(c1ccc(F)c(-c2ncnc3cc(N4CCOCC4)ccc23)c1)c1ncccc1Cl]<br>MS: 451.1/453.1 (M + H$^+$) (Cl isotopy, rel. peak intensity ratio [%] 100:35); R$_t$ 3.98 min (SFC, Chiralpak AD-H, CO$_2$/40% by vol. of 2-propanol, 0.5% by vol. of diethylamine) | (3-Chloro-pyridin-2-yl)-[4-fluoro-3-(7-morpholin-4-yl-quinazolin-4-yl)-phenyl]methanol (Ena 1)<br><br>see racemate | C | B | B |

-continued

| No. | Structural formula | Name | IC$_{50}$ DNA-PK | IC$_{50}$ pDNA-PK | K$_i$ [Kv1.11 hERG] |
|---|---|---|---|---|---|
| 467 | 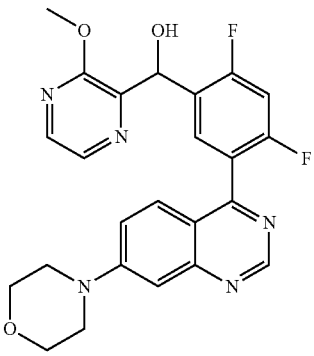 MS: 466.2 (M + H$^+$) | [2,4-Difluoro-5-(7-morpholin-4-yl-quinazolin-4-yl)-phenyl]-(3-methoxy-pyrazin-2-yl)-methanol | B | A | A |
| | | 1H NMR (500 MHz, DMSO-d6) ppm = 9.11 (s, 1H), 8.16 (dd, J = 16.4, 2.7, 2H), 7.87 (1, J = 8.2, 1H), 7.59 (dd, J = 9.4, 3.0, 1H), 7.56 (dd, J = 9.4, 2.4, 1H), 7.40 (t, J = 10.1, 1H), 7.21 (d, J = 2.5, 1H), 6.28 (s, 1H), 6.23 (s, 1H), 3.96 (s, 3H), 3.81-3.75 (m, 4H), 3.49-3.43 (m, 4H). | | | |
| 468 | 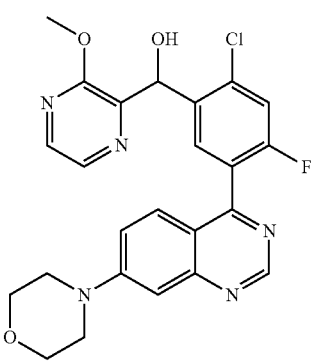 MS: 482.1/484.1 (M + H$^+$) (Cl isotopy, rel. peak intensity ratio [%] 100:37) | [2-Chloro-4-fluoro-5-(7-morpholin-4-yl-quinazolin-4-yl)-phenyl]-(3-methoxy-pyrazin-2-yl)-methanol | A | A | B |
| | | 1H NMR (500 MHz, DMSO-d6) ppm = 9.13 (s, 1H), 8.17 (d, J = 2.7, 1H), 8.11 (d, J = 2.7, 1H), 7.97 (d, J = 7.8, 1H), 7.65-7.58 (m, 2H), 7.56 (dd, J = 9.4, 2.5, 1H), 7.22 (d, J = 2.4, 1H), 6.31 (s, 2H), 4.00 (s, 3H), 3.81-3.76 (m, 4H), 3.48-3.43 (m, 4H). | | | |
| 469 | 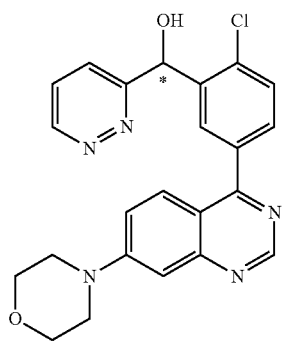 [SMILES: OC(c1cccnn1)c1cc(-c2ncnc3cc(N4CCOCC4)ccc23)ccc1Cl] MS: 434.1/436.1 (M + H$^+$) (Cl isotopy, rel. peak intensity ratio [%] 100:38); R$_t$ 4.70 min (SFC, Chiralcel OJ-H, CO$_2$/20% by vol. of methanol, 0.5% by vol. of diethylamine) | [2-Chloro-5-(7-morpholin-4-yl-quinazolin-4-yl)-phenyl]pyridazin-3-yl-methanol (Ena 2) | D | D | C |
| | | see racemate | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 470 | 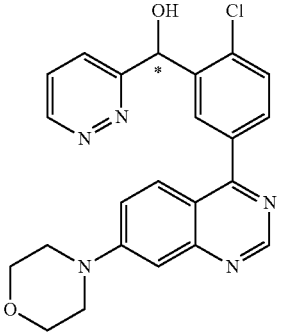 [SMILES: OC(c1cccnn1)c1cc(-c2ncnc3cc(N4CCOCC4)ccc23)ccc1Cl] MS: 434.1/436.1 (M + H$^+$) (Cl isotopy, rel. peak intensity ratio [%] 100:38); R$_t$ 2.52 min (SFC, Chiralcel OJ-H, CO$_2$/20% by vol. of methanol, 0.5% by vol. of diethylamine) | [2-Chloro-5-(7-morpholin-4-yl-quinazolin-4-yl)-phenyl]pyridazin-3-yl-methanol (Ena 1) see racemate | B | A | A |
| 471 | 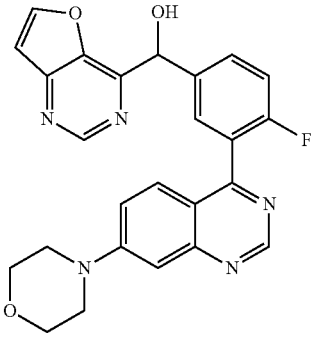 MS: 458.1 (M + H+) | [4-Fluoro-3-(7-morpholin-4-yl-quinazolin-4-yl)-phenyl]furo[3,2-d]-pyrimidin-4-yl-methanol 1H NMR (500 MHz, DMSO-d6) ppm = 9.10 (s, 1H), 9.01 (s, 1H), 8.55 (d, J = 2.3, 1H), 7.79-7.73 (m, 2H), 7.54-7.49 (m, 2H), 7.44-7.38 (m, 1H), 7.24 (d, J = 2.2, 1H), 7.22-7.18 (m, 1H), 6.62 (d, J = 4.6, 1H), 6.20 (d, J = 4.6, 1H), 3.80-3.75 (m, 4H), 3.47-3.42 (m, 4H). | A | A | A* |
| 472 | 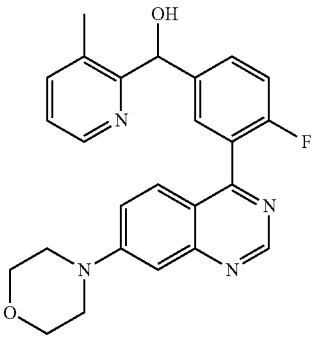 MS: 431.2 (M + H$^+$) | [4-Fluoro-3-(7-morpholin-4-yl-quinazolin-4-yl)-phenyl]-(3-methyl-pyridin-2-yl)methanol 1H NMR (400 MHz, DMSO-d6) ppm = 9.08 (s, 1H), 8.43-8.39 (m, 1H), 7.63-7.57 (m, 1H), 7.56-7.49 (m, 4H), 7.39-7.32 (m, 1H), 7.28-7.23 (m, 1H), 7.21-7.17 (m, 1H), 6.09 (s, 1H), 6.01 (s, 1H), 3.82-3.73 (m, 4H), 3.48-3.40 (m, 4H), 2.28 (s, 3H). | B | A | A |

-continued

| No. | Structural formula | Name | IC$_{50}$ DNA-PK | IC$_{50}$ pDNA-PK | K$_i$ [Kv1.11 hERG] |
|---|---|---|---|---|---|
| 473 | MS: 525.1/527.1 (M + H$^+$) (Br isotopy, rel. peak intensity ratio [%] 100:97) | (3-bromo-5-methoxy-pyridin-2-yl)-[4-fluoro-3-(7-morpholin-4-yl-quinazolin-4-yl)-phenyl]methanol | B | A | B |
| | 1H NMR (400 MHz, DMSO-d6) ppm = 9.09 (s, 1H), 8.31 (d, J = 2.6, 1H), 7.70 (d, J = 2.6, 1H), 7.62-7.56 (m, 2H), 7.54-7.50 (m, 2H), 7.39-7.33 (m, 1H), 7.21-7.18 (m, 1H), 6.16 (d, J = 6.1, 1H), 6.01 (d, J = 6.1, 1H), 3.84 (s, 3H), 3.80-3.75 (m, 4H), 3.46-3.41 (m, 4H). | | | | |
| 474 | MS: 480.1 (M + H$^+$) | [2,4-Difluoro-5-(7-morpholin-4-yl-quinazolin-4-yl)-phenyl]imidazo-[2,1-b]thiazol-6-yl-methanol | D | D | C |
| | 1H NMR (400 MHz, DMSO-d6) ppm = 9.09 (s, 1H), 7.85 (d, J = 4.5, 1H), 7.71-7.68 (m, 1H), 7.62-7.55 (m, 1H), 7.54-7.51 (m, 2H), 7.26 (t, J = 9.1, 1H), 7.21-7.17 (m, 2H), 6.18-6.13 (m, 2H), 3.80-3.75 (m, 4H), 3.47-3.41 (m, 4H). | | | | |
| 475 | MS: 501.2 (M + H$^+$) | [4-Fluoro-3-(7-morpholin-4-yl-quinazolin-4-yl)-phenyl]-(3-trifluoro-methoxypyridin-2-yl)-methanol | A | A | B |
| | 1H NMR (400 MHz, DMSO-d6) ppm = 9.11 (s, 1H), 8.61 (dd, J = 4.6, 1.3, 1H), 7.87 (dp, J = 8.4, 1.6, 1H), 7.69-7.57 (m, 2H), 7.57-7.46 (m, 3H), 7.40 (dd, J = 9.9, 8.4, 1H), 7.21 (d, J = 1.9, 1H), 6.26 (d, J = 5.9, 1H), 6.13 (d, J = 5.9, 1H), 3.89-3.65 (m, 4H), 3.54-3.38 (m, 4H). | | | | |

-continued

| No. | Structural formula | Name | IC$_{50}$ DNA-PK | IC$_{50}$ pDNA-PK | K$_i$ [Kv1.11 hERG] |
|---|---|---|---|---|---|
| 476 | 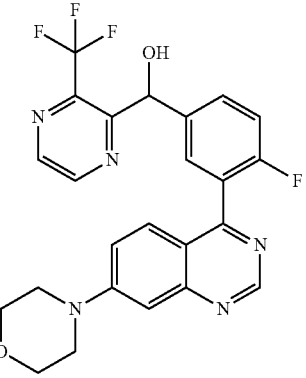<br>MS: 486.2 (M + H⁺) | [4-Fluoro-3-(7-morpholin-4-yl-quinazolin-4-yl)-phenyl]-(3-trifluoro-methylpyrazin-2-yl)-methanol<br><br>1H NMR (500 MHz, DMSO-d6) ppm = 9.10 (s, 1H), 9.00 (d, J = 2.3, 1H), 8.77 (d, J = 2.3, 1H), 7.66 (dd, J = 6.9, 2.3, 1H), 7.63-7.59 (m, 1H), 7.56-7.50 (m, 2H), 7.43-7.37 (m, 1H), 7.21-7.18 (m, 1H), 6.54 (d, J = 5.7, 1H), 6.21 (d, J = 4.3, 1H), 3.81-3.74 (m, 4H), 3.48-3.40 (m, 4H). | B | A | A |
| 478 | 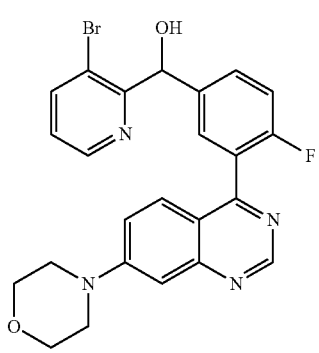<br>MS: 495.1/497.1 (M + H⁺) (Br isotopy, rel. peak intensity ratio [%] 100:96) | (3-bromo-pyridin-2-yl)-[4-fluoro-3-(7-morpholin-4-yl-quinazolin-4-yl)-phenyl]methanol<br><br>1H NMR (400 MHz, DMSO-d6) ppm = 9.09 (s, 1H), 8.60 (dd, J = 4.6, 1.4, 1H), 8.08 (dd, J = 8.1, 1.5, 1H), 7.65-7.59 (m, 2H), 7.54-7.50 (m, 2H), 7.41-7.34 (m, 1H), 7.29 (dd, J = 8.1, 4.6, 1H), 7.21-7.18 (m, 1H), 6.20 (d, J = 6.3, 1H), 6.12 (d, J = 6.3, 1H), 3.82-3.74 (m, 4H), 3.49-3.40 (m, 4H). | A | A | D |
| 479 | 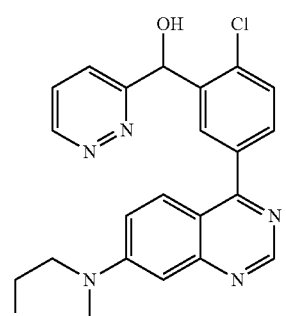<br>MS: 434.1/436.1 (M + H⁺) (Cl isotopy, rel. peak intensity ratio [%] 100:37) | [2-Chloro-5-(7-morpholin-4-yl-quinazolin-4-yl)-pyenyl]pyridazin-3-yl-methanol<br><br>1H NMR (500 MHz, DMSO-d6) ppm = 9.15 (dd, J = 4.9, 1.7, 1H), 9.08 (s, 1H), 8.04 (d, J = 2.2, 1H), 7.87 (d, J = 9.4, 1H), 7.80 (dd, J = 8.5, 1.7, 1H), 7.74-7.69 (m, 2H), 7.64 (d, J = 8.2, 1H), 7.52 (dd, J = 9.5, 2.6, 1H), 7.21 (d, J = 2.5, 1H), 6.69 (d, J = 4.9, 1H), 6.38 (d, J = 4.9, 1H), 3.83-3.72 (m, 4H), 3.49-3.40 (m, 4H). | B | A | B |

*In the second column: enantiomer isolated by chromatography which represents either the pure R or S configuration of the molecule
*In the final column: potassium channel activity measured using hERG binding assay instead of hERG patch clamp assay Example numbers 273-277, 281-283, 287 and 477 have intentionally been omitted.

The invention claimed is:
1. A compound of formula (III)

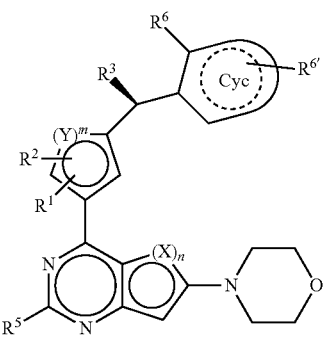

(III)

in which
R⁶ is Hal, LA, oxo, CN, NH₂ or Het²;
R⁶" is H, Hal, LA, oxo, CN, NH₂ or Het²;
- - - - denotes the presence or absence of double bonds in Cyc;
X is CH, CF, S or N,
Y is CH, S or N,
n is 1 or 2, where
  if n=1, X=S, and if n=2, both X=CH, or the X linked to the pyrimidine ring is CF and the X not linked to the pyrimidine ring is CH, or one X is CH and the other X is N;
m is 1 or 2, where
  if m=1, Y=S, and if m=2, both Y=CH, or one Y is CH and the other Y is N;
R¹ and R², independently of one another, are H, Hal, CN, OH, CONH₂, CONH(LA) or LA;
R³ is Hal, CN, OH, CONH₂, CONH(LA) or LA;
R⁵ is H, Hal, CN or C≡CH;
Cyc is phenyl, which may be mono- or disubstituted, independently of one another, by R⁶, or is Het¹;
Het¹ is a mono- or bicyclic, 5-10-membered heterocycle, having 1-3 N, O or S atoms, or 1-4 N atoms, which may be mono-, di- or trisubstituted, independently of one another, by R⁶, or may be monosubstituted by Het²;
LA is unbranched or branched alkyl having 1-5 C atoms, which may be saturated or partially unsaturated, in which 1-3 H atoms may be replaced by Hal, or one H atom may be replaced by CN or Het², or one or two CH₂ groups may be replaced by O, NH, N(CH₃) or CO;
Het² is a 3-5-membered aliphatic homo- or heterocycle having 0, 1, 2 or 3 N, O or S atoms, which is unsubstituted; and
Hal is F, Cl, Br or I;
wherein any H, C, N, O, P, F, and Cl can be in the form of a heavier isotope thereof;
or physiologically acceptable salts, tautomers or stereoisomers thereof, including mixtures thereof in all ratios.
2. The compound according to claim 1, wherein said compound is of formula (IIIa)

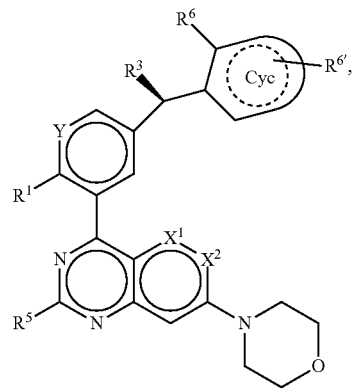

(IIIa)

in which
R³ is Hal, CN, OH, CONH₂, CON(LA) or LA;
R⁶ is Hal, LA, oxo, CN, NH₂ or Het²;
R⁶" is H, Hal, LA, oxo, CN, NH₂ or Het²;
X¹ is CH, CF or N;
X² is CH or N,
where X¹, X² are not simultaneously N;
Y is CH or N; and
- - - - denotes the presence or absence of double bonds in Cyc;
or physiologically acceptable salts, tautomers or stereoisomers thereof, including mixtures thereof in all ratios.
3. The compound according to claim 1, wherein said compound is of formula (IIIb)

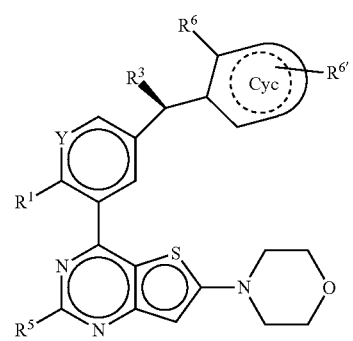

(IIIb)

in which
R³ is Hal, CN, OH, CONH₂, CON(LA) or LA;
R⁶ is Hal, LA, oxo, CN, NH₂ or Het²;
R⁶" is H, Hal, LA, oxo, CN, NH₂ or Het²;
Y is CH or N; and
- - - - denotes the presence or absence of double bonds in Cyc;
or physiologically acceptable salts, tautomers or stereoisomers thereof, including mixtures thereof in all ratios.
4. The compound according to claim 2, in which
in the case of sub-formula (IIIa-B)
  R¹ is F; or
in the case of sub-formula (IIIa-C)
  X¹, X² is CH; or
in the case of sub-formula (IIIa-D)
  X¹ is CH, and
  R⁵ is H; or in the case of sub-formula (IIIa-E)
R³ is OH; or
in the case of sub-formula (IIIa-F)
X¹ is CH, and
R³ is OH; or
in the case of sub-formula (IIIa-G)
X¹ is CH, and
Y is CH; or
in the case of sub-formula (IIIa-H)
X¹ is CH, and
Cyc is pyridine, pyrazine or pyridazine, or pyrazolo[1,5-a]pyrimidinyl or imidazo[1,2-b]pyridazinyl; or
in the case of the sub-formula (IIIa-J)
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}-pyridazinyl, thieno[2,3-d}pyrimidinyl or imidazo[4,5-c]pyridinyl, each of which may be mono- or disubstituted by methoxy, methyl, oxo, Cl or CHF₂O; or
in the case of sub-formula (IIIa-K)
R¹ is F or Cl,
R³ is OH,
R⁵ is H, and
X¹, X² is CH; or
in the case of sub-formula (IIIa-L)
R¹ is F,
R³ is OH, and
R⁵ is H; or
in the case of sub-formula (IIIa-M)
R¹ is F or Cl,
R³ is OH,
R⁵ is H,
X¹, X² is CH, and
Cyc is pyridine, pyrazine or pyridazine, or pyrazolo[1,5-a]pyrimidinyl or imidazo[1,2-b]pyridazinyl; or
in the case of sub-formula (IIIa-N)
R¹ is F,
R³ is OH,
R⁵ is H, and
Cyc is pyridine, pyrazine, pyridazine, pyrazolo[1,5-a]pyrimidinyl, imidazo[1,2-b]pyridazinyl, furo[2,3-c]pyridinyl, furo[2,3-d}pyridazinyl, thieno[2,3-d}-pyridazinyl, thieno[2,3-d}pyrimidinyl or imidazo[4,5-c]pyridinyl, each of which may be mono- or disubstituted by methoxy, methyl, oxo, Cl or CHF₂O; or
in the case of sub-formula (IIIa-O)
R¹ is F,
R³ is OH,
R⁵ is H, and
Cyc is 5-methoxypyridazin-3-yl, imidazo[1,2-b]pyridazin-6-yl, 3-chloro-6-methoxypyrazin-2-yl, 3-chloropyrazin-2-yl, pyridazin-4-yl, 3-methoxypyrazin-2-yl, 6-methoxypyridazin-3-yl, 3-difluoromethoxypyridin-2-yl, 3-methylpyrazin-2-yl, thieno[2,3-d}pyrimidin-4-yl, 1-methyl-1H-pyridin-2-one-6-yl, 1H-pyridazin-6-one-3-yl, furo[2,3-d}pyridazin-7-yl, thieno[2,3-d}pyridazin-7-yl, 3,5-dimethylpyrazin-2-yl, furo[2,3-d}pyrimidin-4-yl, 3-methyl-3H-imidazo[4,5-c]pyridin-4-yl,
or physiologically acceptable salts, tautomers or stereoisomers thereof, including mixtures thereof in all ratios.

5. The compound according to claim 3, in which
in the case of sub-formula (IIIb-Q)
R¹ is F or Cl,
R³ is OH,
R⁵ is H, and
Y is CH; or
in the case of sub-formula (IIIb-R)
R¹ is F,
R³ is OH,
R⁵ is H, and
Y is CH; or
in the case of sub-formula (IIIb-S)
Cyc is pyridine, pyrazine or pyridazine; or
in the case of sub-formula (IIIb-T)
R¹ is F or Cl,
R³ is OH,
R⁵ is H, and
Cyc is pyridine, pyrazine or pyridazine; or
in the case of sub-formula (IIIb-U)
R¹ is F,
R³ is OH,
R⁵ is H, and
Cyc is pyridine, pyrazine, pyridazine or 3-methylpyrazin-2-yl; or
or physiologically acceptable salts, tautomers or stereoisomers thereof, including mixtures thereof in all ratios.

6. The compound according to claim 1, wherein said compound is selected from the following:
(R)-(3-Chloropyrazin-2-yl)-[4-fluoro-3-(7-morpholin-4-ylquinazolin-4-yl)phenyl]methanol,
(R)-[4-Fluoro-3-(7-morpholin-4-ylquinazolin-4-yl)phenyl]-(3-methyl pyrazin-2-yl)methanol,
(R)-[4-Fluoro-3-(7-morpholin-4-ylpyrido[3,2-d}pyrimidin-4-yl)phenyl]-(3-methylpyrazin-2-yl)methanol, or
(R)-[4-Fluoro-3-(5-fluoro-7-morpholin-4-ylquinazolin-4-yl)phenyl]-(3-methylpyrazin-2-yl)methanol;
or physiologically acceptable salts, tautomers or stereoisomers thereof, including mixtures thereof in all ratios.

7. A pharmaceutical composition comprising, as active compound, an effective amount of at least one compound according to claim 1 or physiologically acceptable salts, tautomers or stereoisomers thereof, including mixtures thereof in all ratios, together with pharmaceutically tolerated adjuvants.

8. The pharmaceutical composition according to claim 7, further comprising an effective amount of at least one anticancer agent.

9. A kit comprising separate packs of (a) an effective amount of at least one compound according to claim 1 or physiologically acceptable salts, tautomers or stereoisomers thereof, including mixtures thereof in all ratios, and (b) an effective amount of at least one anticancer agent.

* * * * *